(12) United States Patent
Vicker et al.

(10) Patent No.: US 7,786,152 B2
(45) Date of Patent: Aug. 31, 2010

(54) COMPOUND

(75) Inventors: Nigel Vicker, Slough (GB); Su Xiangdon, Slough (GB); Dharshini Ganeshapillai, Slough (GB); Atul Purohit, Slough (GB); Michael John Reed, Slough (GB); Barry Victor Lloyd Potter, Slough (GB)

(73) Assignee: Sterix Limited, Slough (GB)

( * ) Notice: Subject to any disclaimer, the term of this patent is extended or adjusted under 35 U.S.C. 154(b) by 169 days.

(21) Appl. No.: 11/979,160

(22) Filed: Oct. 31, 2007

(65) Prior Publication Data

US 2008/0114042 A1 May 15, 2008

Related U.S. Application Data

(62) Division of application No. 10/690,708, filed on Oct. 23, 2003, now Pat. No. 7,309,715.

(60) Provisional application No. 60/436,635, filed on Dec. 30, 2002.

(30) Foreign Application Priority Data

Oct. 24, 2002 (GB) ................................. 0224830.0

(51) Int. Cl.
A61K 31/428 (2006.01)
(52) U.S. Cl. ...................... 514/367; 514/365
(58) Field of Classification Search ................ 514/367, 514/365
See application file for complete search history.

(56) References Cited

U.S. PATENT DOCUMENTS

| 5,185,361 | A | 2/1993 | Gilmore |
|---|---|---|---|
| 5,585,395 | A | 12/1996 | Lunkenheimer et al. |
| 5,721,246 | A | 2/1998 | Yoshino et al. |
| 6,114,532 | A | 9/2000 | Ries et al. |
| 6,143,747 | A | 11/2000 | Freskos et al. |
| 6,211,167 | B1 | 4/2001 | Houze |
| 6,316,474 | B1 | 11/2001 | McCauley et al. |
| 6,579,881 | B2 | 6/2003 | Kitazawa et al. |
| 6,638,965 | B2 | 10/2003 | Walter et al. |
| 7,250,442 | B2 * | 7/2007 | Brown et al. ............... 514/415 |

FOREIGN PATENT DOCUMENTS

| EP | 0976732 | 2/2000 |
|---|---|---|
| EP | 01325910 | 7/2003 |
| JP | 4-230661 | 8/1992 |
| WO | 98/43956 | 10/1998 |
| WO | 00/21927 | 4/2000 |
| WO | 01/90090 A1 | 11/2001 |
| WO | 01/90091 A1 | 11/2001 |
| WO | 01/90092 A1 | 11/2001 |
| WO | 01/90093 A1 | 11/2001 |
| WO | 01/90094 A1 | 11/2001 |
| WO | 02/30891 | 4/2002 |
| WO | 02/092585 A1 | 11/2002 |
| WO | 03/065983 A2 | 8/2003 |
| WO | 2004/103980 | 12/2004 |

OTHER PUBLICATIONS

Yoshino et al. (1995): STN International HCAPLUS database, Columbus (OH), accession No. 1995:713785.
Kitazawa et al. (1998): STN International HCAPLUS database, Columbus (OH), accession No. 1998:682229.
Arrhenius et al. (2002): STN International HCAPLUS database, Columbus (OH), accession No. 2002:657951.
Portnaya et al. (1960): STN International HCAPLUS database, Columbus (OH), accession No. 1962:469757.
English Abstract of JP 2002 249695 A.

* cited by examiner

*Primary Examiner*—Rei-tsang Shiao
(74) *Attorney, Agent, or Firm*—Steptoe & Johnson LLP

(57) ABSTRACT

A compound having Formula I

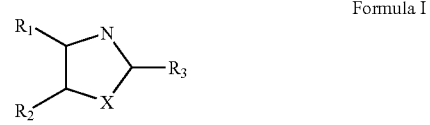

wherein one of $R_1$ and $R_2$ is a group of the formula

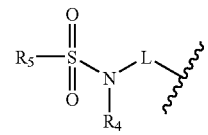

wherein $R_4$ is selected from H and hydrocarbyl, $R_5$ is a hydrocarbyl group and L is an optional linker group, or $R_1$ and $R_2$ together form a ring substituted with the group

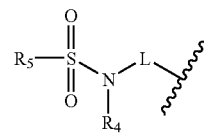

wherein $R_3$ is H or a substituent, and wherein X is selected from S, O, $NR_6$ and $C(R_7)(R_8)$, wherein $R_6$ is selected from H and hydrocarbyl groups, wherein each of $R_7$ and $R_8$ are independently selected from H and hydrocarbyl groups.

28 Claims, 27 Drawing Sheets

Graph 1, the amount of protein per μL of rat liver and rat kidney

Graph 2, enzyme concentration and time-dependency course, E to F, in rat liver 11 β-HSD type 1 activity

COMPOUND

This application is a divisional of U.S. application Ser. No. 10/690,708, filed Oct. 23, 2003, which claims the benefit of priority of U.S. Provisional Application 60/436,635, filed Dec. 30, 2002, and U.K. Application 0224830.0, filed Oct. 24, 2002, each of which is incorporated by reference in its entirety.

FIELD OF INVENTION

The present invention relates to a compound. In particular the present invention provides compounds capable of inhibiting 11β-hydroxysteroid dehydrogenase (11β-HSD).

INTRODUCTION

The Role of Glucocorticoids

Glucocorticoids are synthesised in the adrenal cortex from cholesterol. The principle glucocorticoid in the human body is cortisol, this hormone is synthesised and secreted in response to the adrenocortictrophic hormone (ACTH) from the pituitary gland in a circadian, episodic manner, but the secretion of this hormone can also be stimulated by stress, exercise and infection. Cortisol circulates mainly bound to transcortin (cortisol binding protein) or albumin and only a small fraction is free (5-10%) for biological processes [1].

Cortisol has a wide range of physiological effects, including regulation of carbohydrate, protein and lipid metabolism, regulation of normal growth and development, influence on cognitive function, resistance to stress and mineralocorticoid activity. Cortisol works in the opposite direction compared to insulin meaning a stimulation of hepatic gluconeogenesis, inhibition of peripheral glucose uptake and increased blood glucose concentration.

Glucocorticoids are also essential in the regulation of the immune response. When circulating at higher concentrations glucocorticoids are generally immunosuppressive and are used pharmacologically as anti-inflammatory agents.

binding affinities for glucocorticoids and mineralocorticoids [3]. Because the circulating concentration of cortisol is a 100 times higher than that of aldosterone and during times of stress or high activity even more, it was not clear how the MR remained mineralocorticoid specific and was not constantly occupied by glucocorticoids. Earlier Ulick et al. [4] had described the hypertensive condition known as, "apparent mineralocorticoid excess" (AME), and observed that whilst secretion of aldosterone from the adrenals was in fact low the peripheral metabolism of cortisol was disrupted. These discoveries lead to the suggestion of a protective. role for the enzymes. By converting cortisol to cortisone in mineralocorticoid dependent tissues 11β-HSD enzymes protects the MR from occupation by glucocorticoids and allows it to be mineralcorticoid specific. Aldosterone itself is protected from the enzyme by the presence of an aldehyde group at the C-18 position.

Congenital defects in the 11β-HSD enzyme results in over occupation of the MR by cortisol and hypertensive and hypokalemic symptoms seen in AME.

Localisation of the 11β-HSD showed that the enzyme and its activity is highly present in the MR dependent tissues, kidney and parotid. However in tissues where the MR is not mineralocorticoid specific and is normally occupied by glucocorticoids, 11 β-HSD is not present in these tissues, for example in the heart and hippocampus [5]. This research also showed that inhibition of 11 β-HSD caused a loss of the aldosterone specificity of the MR in these mineralocorticoid dependent tissues.

It has been shown that two iso-enzymes of 11 β-HSD exist. Both are members of the short chain alcohol dehydrogenase (SCAD) superfamily which have been widely conserved throughout evolution. 11 β-HSD type 2 acts as a dehydrogenase to convert the secondary alcohol group at the C-11 position of cortisol to a secondary ketone, so producing the less active metabolite cortisone. 11 β-HSD type 1 is thought to act mainly in vivo as a reductase, that is in the opposite direction to type 2 [6] [see below]. 11 β-HSD type 1 and type 2 have only a 30% amino acid homology.

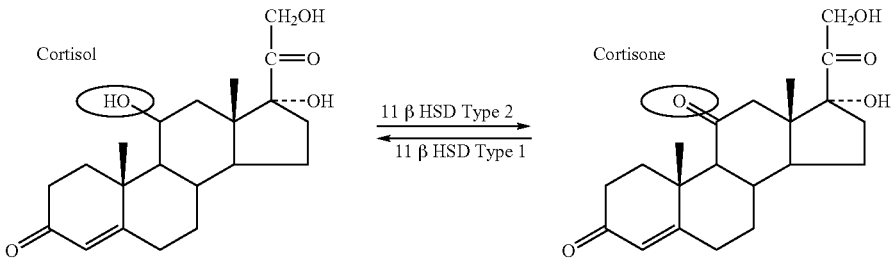

11 β-HSD Enzyme Activity

Glucocorticoids like other steroid hormones are generally lipophilic and penetrate the cell membrane freely. Cortisol binds, primarily, to the intracellular glucocorticoid receptor (GR) that then acts as a transcription factor to induce the expression of glucocorticoid responsive genes, and as a result of that protein synthesis.

The Role of the 11β-HSD Enzyme

The conversion of cortisol (F) to its inactive metabolite cortisone (E) by 11β-HSD was first described in the 1950's, however it was not until later that a biological importance for this conversion was suggested [2]. In 1983 Krozowski et al. showed that the mineralocorticoid receptor (MR) has equal The intracellular activity of cortisol is dependent on the concentration of glucocorticoids and can be modified and independently controlled without involving the overall secretion and synthesis of the hormone.

The Role of 11 β-HSD Type 1

The direction of 11 β-HSD type 1 reaction in vivo is generally accepted to be opposite to the dehydrogenation of type 2. In vivo homozygous mice with a disrupted type 1 gene are unable to convert cortisone to cortisol, giving further evidence for the reductive activity of the enzyme [7]. 11 β-HSD type 1 is expressed in many key glucocorticoid regulated tissues like the liver, pituitary, gonad, brain, adipose and adrenals, however, the function of the enzyme in many of these tissues is poorly understood [8].

The concentration of cortisone in the body is higher than that of cortisol, cortisone also binds poorly to binding globulins, making cortisone many times more biologically available. Although cortisol is secreted by the adrenal cortex, there is a growing amount of evidence that the intracellular conversion of E to F may be an important mechanism in regulating the action of glucocorticoids [9].

It may be that 11 β-HSD type 1 allows certain tissues to convert cortisone to cortisol to increase local glucocorticoid activity and potentiate adaptive response and counteracting the type 2 activity that could result in a fall in active glucocorticoids [10]. Potentiation of the stress response would be especially important in the brain and high levels of 11 β-HSD type 1 are found around the hippocampus, further proving the role of the enzyme. 11 β-HSD type 1 also seems to play an important role in hepatocyte maturation [8]. Another emerging role of the 11 β-HSD type 1 enzyme is in the detoxification process of many non-steroidal carbonyl compounds, reduction of the carbonyl group of many toxic compounds is a common way to increase solubility and therefore increase their excretion. The 11 β-HSD type 1 enzyme has recently been shown to be active in lung tissue [11]. Type 1 activity is not seen until after birth, therefore mothers who smoke during pregnancy expose their children to the harmful effects of tobacco before the child is able to metabolically detoxify this compound.

The Role of 11 β-HSD Type 2

As already stated earlier the 11 β-HSD type 2 converts cortisol to cortisone, thus protecting the MR in many key regulatory tissues of the body. The importance of protecting the MR from occupation by glucocorticoids is seen in patients with AME or liquorice intoxification. Defects or inactivity of the type 2 enzyme results in hypertensive syndromes and research has shown that patients with an hypertensive syndrome have an increased urinary excretion ratio of cortisol:cortisone. This along with a reported increase in the half life of radiolabelled cortisol suggests a reduction of 11 β-HSD type 2 activity [12].

Rationale for the Development of 11 βInhibitors

As said earlier cortisol opposes the action of insulin meaning a stimulation of hepatic gluconeogenesis, inhibition of peripheral glucose uptake and increased blood glucose concentration. The effects of cortisol appear to be enhanced in patients suffering from glucose intolerance or diabetes mellitus. Inhibition of the enzyme 11 β-HSD type 1 would increase glucose uptake and inhibit hepatic gluconeogenesis, giving a reduction in circulatory glucose levels. The development of a potent 11 β-HSD type 1 inhibitor could therefore have considerable therapeutic potential for conditions associated with elevated blood glucose levels.

An excess in glucocorticoids can result in neuronal dysfunctions and also impair cognitive functions. A specific 11 β-HSD type 1 inhibitor might be of some importance by reducing neuronal dysfunctions and the loss of cognitive functions associated with ageing, by blocking the conversion of cortisone to cortisol.

Glucocorticoids also have an important role in regulating part of the immune response [13]. Glucocorticoids can suppress the production of cytokines and regulate the receptor levels. They are also involved in determining whether T-helper (Th) lymphocytes progress into either Th1 or Th2 phenotype. These two different types of Th cells secrete a different profile of cytokines, Th2 is predominant in a glucocorticoid environment. By inhibiting 11 β-HSD type 1, Th1 cytokine response would be favoured. It is also possible to inhibit 11 β-HSD type 2, thus by inhibiting the inactivation of cortisol, it may be possible to potentiate the anti-inflammatory effects of glucocorticoids.

Some embodiments of the present invention are defined in the appended claims.

SUMMARY EMBODIMENTS OF THE PRESENT INVENTION

In one embodiment the present invention provides a compound having Formula I

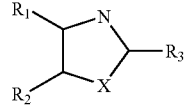

Formula I wherein one of $R_1$ and $R_2$ is a group of the formula

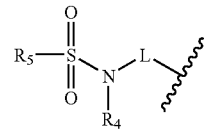

wherein $R_4$ is selected from H and hydrocarbyl, $R_5$ is a hydrocarbyl group and L is an optional linker group, or $R_1$ and $R_2$ together form a ring substituted with the group

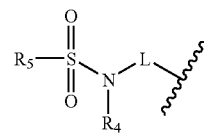

wherein $R_3$ is H or a substituent, and wherein X is selected from S, O, $NR_6$ and $C(R_7)(R_8)$, wherein $R_6$ is selected from H and hydrocarbyl groups, wherein each of $R_7$ and $R_8$ are independently selected from H and hydrocarbyl groups.

In one embodiment the present invention provides a pharmaceutical composition comprising (i) a compound having Formula I

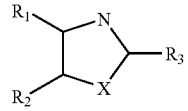

Formula I wherein one of $R_1$ and $R_2$ is a group of the formula

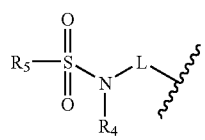

wherein $R_4$ is selected from H and hydrocarbyl, $R_5$ is a hydrocarbyl group and L is an optional linker group, or $R_1$ and $R_2$ together form a ring substituted with the group

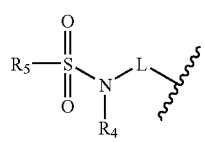

wherein $R_3$ is H or a substituent, and wherein X is selected from S, O, $NR_6$ and $C(R_7)(R_8)$, wherein $R_6$ is selected from H and hydrocarbyl groups, wherein each of $R_7$ and $R_8$ are independently selected from H and hydrocarbyl groups.

(ii) optionally admixed with a pharmaceutically acceptable carrier, diluent, excipient or adjuvant.

In one embodiment the present invention provides a compound having Formula I

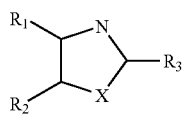

Formula I wherein one of $R_1$ and $R_2$ is a group of the formula

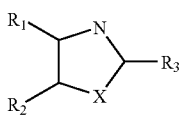

wherein $R_4$ is selected from H and hydrocarbyl, $R_5$ is a hydrocarbyl group and L is an optional linker group, or $R_1$ and $R_2$ together form a ring substituted with the group

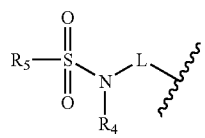

wherein $R_3$ is H or a substituent, and wherein X is selected from S, O, $NR_6$ and $C(R_7)(R_8)$, wherein $R_6$ is selected from H and hydrocarbyl groups, wherein each of $R_7$ and $R_8$ are independently selected from H and hydrocarbyl groups, for use in medicine.

In one embodiment the present invention provides a use of a compound in the manufacture of a medicament for use in the therapy of a condition or disease associated with 11β-HSD, wherein the compound has Formula I

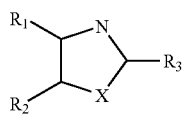

Formula I wherein one of $R_1$ and $R_2$ is a group of the formula

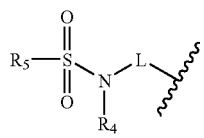

wherein $R_4$ is selected from H and hydrocarbyl, $R_5$ is a hydrocarbyl group and L is an optional linker group, or $R_1$ and $R_2$ together form a ring substituted with the group

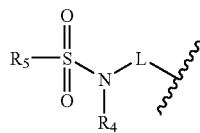

wherein $R_3$ is H or a substituent, and wherein X is selected from S, O, $NR_6$ and $C(R_7)(R_8)$, wherein $R_6$ is selected from H and hydrocarbyl groups, wherein each of $R_7$ and $R_8$ are independently selected from H and hydrocarbyl groups.

Some Advantages

One key advantage of the present invention is that the compounds of the present invention can act as 11β-HSD inhibitors. The compounds may inhibit the interconversion of inactive 11-keto steroids with their active hydroxy equivalents. Thus present invention provides methods by which the conversion of the inactive to the active form may be controlled, and to useful therapeutic effects which may be obtained as a result of such control. More specifically, but not exclusively, the invention is concerned with interconversion between cortisone and cortisol in humans.

Another advantage of the compounds of the present invention is that they may be potent 11β-HSD inhibitors in vivo.

Some of the compounds of the present invention are also advantageous in that they may be orally active.

The present invention may provide for a medicament for one or more of (i) regulation of carbohydrate metabolism, (ii) regulation of protein metabolism, (iii) regulation of lipid metabolism, (iv) regulation of normal growth and/or development, (v) influence on cognitive function, (vi) resistance to stress and mineralocorticoid activity.

Some of the compounds of the present invention may also be useful for inhibiting hepatic gluconeogenesis. The present invention may also provide a medicament to relieve the effects of endogenous glucocorticoids in diabetes mellitus, obesity (including centripetal obesity), neuronal loss and/or the cognitive impairment of old age. Thus, in a further embodiment, the invention provides the use of an inhibitor of 11β-HSD in the manufacture of a medicament for producing one or more therapeutic effects in a patient to whom the medicament is administered, said therapeutic effects selected from inhibition of hepatic gluconeogenesis, an increase in insulin sensitivity in adipose tissue and muscle, and the prevention of or reduction in neuronal loss/cognitive impairment due to glucocorticoid-potentiated neurotoxicity or neural dysfunction or damage.

From an alternative point of view, the invention provides a method of treatment of a human or animal patient suffering from a condition selected from the group consisting of: hepatic insulin resistance, adipose tissue insulin resistance, muscle insulin resistance, neuronal loss or dysfunction due to glucocorticoid potentiated neurotoxicity, and any combination of the aforementioned conditions, the method comprising the step of administering to said patient a composition comprising a pharmaceutically active amount of a compound in accordance with the present invention.

Some of the compounds of the present invention may be useful for the treatment of cancer, such as breast cancer, as well as (or in the alternative) non-malignant conditions, such as the prevention of auto-immune diseases, particularly when pharmaceuticals may need to be administered from an early age.

DETAILED EMBODIMENTS OF THE PRESENT INVENTION

In one embodiment the present invention provides a compound having Formula I

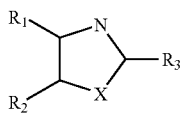

Formula I wherein one of $R_1$ and $R_2$ is a group of the formula

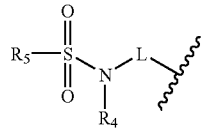

wherein $R_4$ is selected from H and hydrocarbyl, $R_5$ is a hydrocarbyl group and L is an optional linker group, or $R_1$ and $R_2$ together form a ring substituted with the group

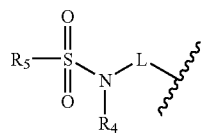

wherein $R_3$ is H or a substituent, and wherein X is selected from S, O, $NR_6$ and $C(R_7)(R_8)$, wherein $R_6$ is selected from H and hydrocarbyl groups, wherein each of $R_7$ and $R_8$ are independently selected from H and hydrocarbyl groups.

In one embodiment the present invention provides a pharmaceutical composition comprising
(i) a compound having Formula I defined above
(ii) optionally admixed with a pharmaceutically acceptable carrier, diluent, excipient or adjuvant.

In one embodiment the present invention provides a compound having Formula I defined above, for use in medicine.

In one embodiment the present invention provides a use of a compound having Formula I defined above in the manufacture of a medicament for use in the therapy of a condition or disease associated with 11β-HSD.

In one embodiment the present invention provides a use of a compound having Formula I defined above in the manufacture of a medicament for use in the therapy of a condition or disease associated with adverse 11β-HSD levels.

In one embodiment the present invention provides a use of a compound having Formula I defined above in the manufacture of a pharmaceutical for inhibiting 11β-HSD activity.

In one embodiment the present invention provides a use of a compound having Formula I defined above in the manufacture of a pharmaceutical for inhibiting 11β-HSD activity.

In one embodiment the present invention provides a method comprising (a) performing a 11β-HSD assay with one or more candidate compounds having Formula I defined above; (b) determining whether one or more of said candidate compounds is/are capable of modulating 11β-HSD activity; and (c) selecting one or more of said candidate compounds that is/are capable of modulating 11β-HSD activity.

In one embodiment the present invention provides a method comprising (a) performing a 11β-HSD assay with one or more candidate compounds having Formula I defined above; (b) determining whether one or more of said candidate compounds is/are capable of inhibiting 11β-HSD activity; and (c) selecting one or more of said candidate compounds that is/are capable of inhibiting 11 β-HSD activity.

In one embodiment the present invention provides
a compound identified by the above method,
the use of the said compound in medicine,
a pharmaceutical composition comprising the said compound, optionally admixed with a pharmaceutically acceptable carrier, diluent, excipient or adjuvant,
use of the said compound in the manufacture of a medicament for use in the therapy of a condition or disease associated with 11β-HSD, and
use of the said compound in the manufacture of a medicament for use in the therapy of a condition or disease associated with adverse 11β-HSD levels.

For ease of reference, these and further embodiments of the present invention are now discussed under appropriate section headings. However, the teachings under each section are not necessarily limited to each particular section.

EXEMPLARY EMBODIMENTS

In one embodiment of the present invention the compound has Formula II

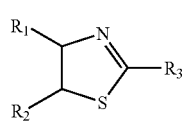

Formula II

In some embodiments of the present invention L is not present. In this embodiment the present invention provides a compound having Formula I Formula I

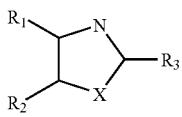

wherein one of $R_1$ and $R_2$ is a group of the formula

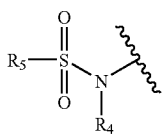

wherein $R_4$ is selected from H and hydrocarbyl, and $R_5$ is a hydrocarbyl group; or $R_1$ and $R_2$ together form a ring substituted with the group

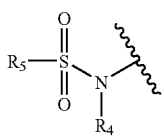

wherein $R_3$ is H or a substituent

In another embodiment of the present invention $R_1$ and $R_2$ together form a ring substituted with the group

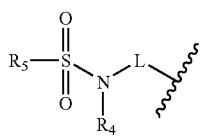

In one embodiment of the present invention $R_1$ and $R_2$ together form a carbocyclic ring.

In yet another embodiment of the present invention $R_1$ and $R_2$ together form a six membered ring.

In other embodiments of the present invention $R_1$ and $R_2$ together form a six membered carbocyclic ring.

In one embodiment of the present invention wherein $R_1$ and $R_2$ together form an aryl ring.

Exemplary compounds of the present invention are those having one of the following formulae.

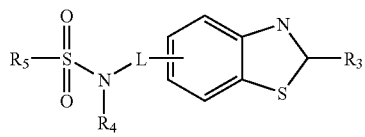
Formula III

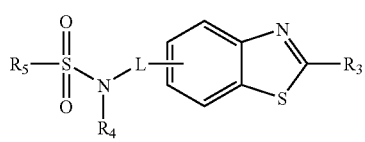
Formula IV

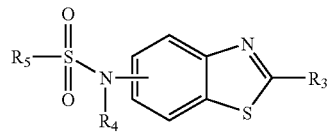
Formula V

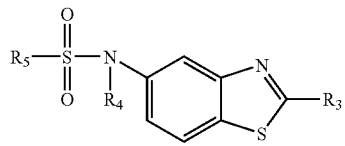
Formula VI

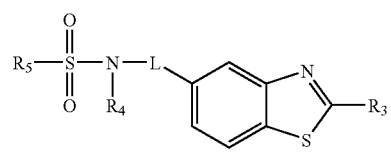
Formula VIa

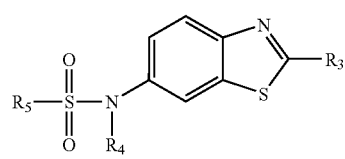
Formula VII

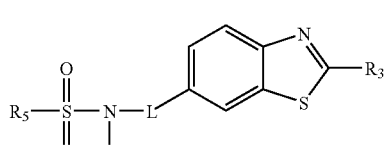
Formula VIIa

In some embodiments of the present invention $R_3$ is selected from H, hydrocarbyl, —S-hydrocarbyl, —S—H, halogen and $N(R_9)(R_{10})$, wherein each of $R_9$ and $R_{10}$ are independently selected from H and hydrocarbyl groups.

In other embodiments of the present invention $R_3$ is selected from H, hydroxy, alkyl especially $C_1$-$C_{10}$ alkyl groups, $C_1$-$C_6$ alkyl, e.g. $C_1$-$C_3$ alkyl group, methyl, ethyl, n-propyl, isopropyl, n-butyl, sec-butyl, tert-butyl, n-pentyl and other pentyl isomers, and n-hexyl and other hexyl isomers, alkoxy especially $C_1$-$C_{10}$ alkoxy groups, $C_1$-$C_6$ alkoxy, e.g. $C_1$-$C_3$ alkoxy group, methoxy, ethoxy, propoxy etc., alkinyl, e.g. ethinyl, or halogen, e.g. fluoro substituents.

When R3 is —S-hydrocarbyl, R3 may be, for example, selected from —S-alkyl, —S-carboxylic acid, —S-ether, and —S-amide, for example selected from —S—$C_{1-10}$alkyl, —S—$C_{1-10}$-carboxcylic acid, —S—$C_{1-10}$ether, and —S—$C_{1-10}$amide.

In one embodiment of the present invention $R_3$ is —$CH_3$.

Further embodiments of the present invention are those having one of the following formulae.

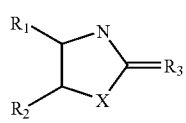
Formula Ia

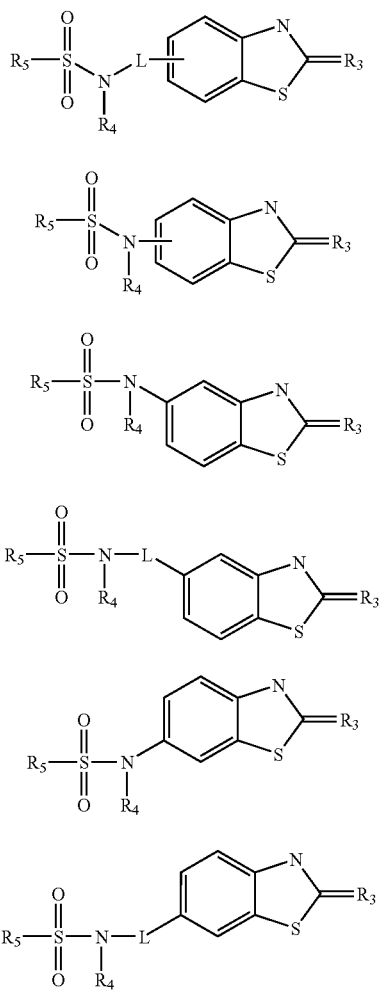

Formula VIII

Formula IX

Formula X

Formula Xa

Formula XI

Formula XIa

In further embodiments of the present invention, such as when the compound has Formula Ia, Formula VIII, Formula IX, Formula X, Formula Xa, Formula XI, or Formula XIa, $R_3$ is selected from O, hydrocarbyl, and $N(R_9)$ wherein $R_9$ is selected from H and hydrocarbyl groups. Optionally $R_3$ is selected from O, $C_1$-$C_{10}$ alkenyl groups, such as $C_1$-$C_6$ alkenyl group, and $C_1$-$C_3$ alkenyl group, NH and N—$C_1$-$C_{10}$ alkyl groups, such as N—$C_1$-$C_6$ alkyl group, and N—$C_1$-$C_3$ alkyl groups.

In further embodiments of the present invention $R_4$ is selected from H and $C_1$-$C_{10}$ alkyl groups, such as $C_1$-$C_6$ alkyl group, and $C_1$-$C_3$ alkyl group. In one embodiment, $R_4$ is H.

In yet further embodiments of the present invention $R_4$ is a group of the formula.

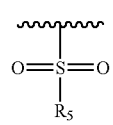

In these embodiments the group shown above as

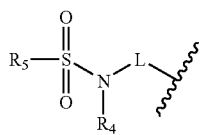

may be of the formula

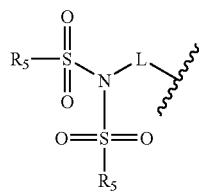

wherein each $R_5$ is independently selected from hydrocarbyl groups. Each $R_5$ may be the same of different to the other $R_5$. In one embodiment the two $R_5$ groups are the same.

In some embodiments of the invention $R_5$ is a cyclic hydrocarbyl group. For example, $R_5$ may be a cyclic hydrocarbyl group comprising a hydrocarbon ring.

$R_5$ may be a substituted ring or an unsubstituted ring. In some embodiments of the invention $R_5$ is substituted ring.

$R_5$ may be a carbocyclic ring.

$R_5$ may be a six membered ring.

$R_5$ may be a six membered carbocyclic ring. For example, $R_5$ may be a substituted six membered carbocyclic ring.

In some embodiments of the invention $R_5$ is an aryl ring. For example, $R_5$ is a substituted aryl ring.

In one embodiment $R_5$ is a group having the formula

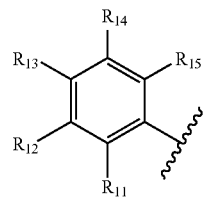

wherein each of $R_{11}$, $R_{12}$, $R_{13}$, $R_{14}$ and $R_{15}$ are independently selected from H, halogen, and hydrocarbyl groups.

For example, each of $R_{11}$, $R_{12}$, $R_{13}$, $R_{14}$ and $R_{15}$ may be independently selected from H, halogen, alkyl, such as $C_{1-6}$ alkyl, phenyl, O-alkyl, O-phenyl, nitrile, haloalkyl, such as $CF_3$, $CCl_3$ and $CBr_3$, carboxyalkyl, —$CO_2H$, $CO_2$alkyl, and NH-acetyl groups.

Two or more of $R_{11}$, $R_{12}$, $R_{13}$, $R_{14}$ and $R_{15}$ may join to form a ring. The two or more of $R_{11}$, $R_{12}$, $R_{13}$, $R_{14}$ and $R_{15}$ may or may not be adjacent. The ring may be carbocyclic or heterocyclic ring. The ring may be optionally substituted by any of the $R_{11}$, $R_{12}$, $R_{13}$, $R_{14}$ and $R_{15}$ substituents listed above. When two or more of $R_{11}$, $R_{12}$, $R_{13}$, $R_{14}$ and $R_{15}$ may join to form a ring the group

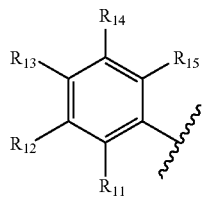

may provide a naphthyl, quinolyl, tetrahydroquinolyl, or benzotetrahydropyranyl, each of which may be substituted or unsubstituted.

Substituents

The compound of the present invention may have substituents other than those of the ring systems show herein. Furthermore the ring systems herein are given as general formulae and should be interpreted as such. The absence of any specifically shown substituents on a given ring member indicates that the ring member may substituted with any moiety of which H is only one example. The ring system may contain one or more degrees of unsaturation, for example is some embodiments one or more rings of the ring system are aromatic. The ring system may be carbocyclic or may contain one or more hetero atoms.

The compound of the invention, in particular the ring system compound of the invention of the present invention may contain substituents other than those show herein. By way of example, these other substituents may be one or more of: one or more halo groups, one or more 0 groups, one or more hydroxy groups, one or more amino groups, one or more sulphur containing group(s), one or more hydrocarbyl group(s)—such as an oxyhydrocarbyl group.

In general terms the ring system of the present compounds may contain a variety of non-interfering substituents. In particular, the ring system may contain one or more hydroxy, alkyl especially lower ($C_1$-$C_6$) alkyl, e.g. methyl, ethyl, n-propyl, isopropyl, n-butyl, sec-butyl, tert-butyl, n-pentyl and other pentyl isomers, and n-hexyl and other hexyl isomers, alkoxy especially lower ($C_1$-$C_6$) alkoxy, e.g. methoxy, ethoxy, propoxy etc., alkinyl, e.g. ethinyl, or halogen, e.g. fluoro substituents.

For some compounds of the present invention, the compound may be substituted with a hydrocarbylsulphanyl group. The term "hydrocarbylsulphanyl" means a group that comprises at least hydrocarbyl group (as herein defined) and sulphur, such as —S-hydrocarbyl, or —S-hydrocarbon. That sulphur group may be optionally oxidised.

In some embodiments of the present invention the hydrocarbylsulphanyl group is —S—$C_{1-10}$ alkyl, such as —S—$C_{1-5}$ alkyl, for example —S—$C_{13}$ alkyl, and also for example —S—$CH_2CH_2CH_3$, —S—$CH_2CH_3$ or —$SCH_3$

FURTHER EMBODIMENTS

For some applications, the compounds have a reversible action.

For some applications, the compounds have an irreversible action.

In one embodiment, the compounds of the present invention are useful for the treatment of breast cancer.

The compounds of the present invention may be in the form of a salt.

The present invention also covers novel intermediates that are useful to prepare the compounds of the present invention.

For example, the present invention covers novel alcohol precursors for the compounds. By way of further example, the present invention covers bis protected precursors for the compounds. Examples of each of these precursors are presented herein. The present invention also encompasses a process comprising each or both of those precursors for the synthesis of the compounds of the present invention.

Steroid Dehydrogenase

11β Steroid dehydrogenase may be referred to as "11β-HSD" or "HD" for short

In some embodiments of the invention 11β-HSD is 11β-HSD Type 1.

In some embodiments of the invention 11β-HSD is 11β-HSD Type 2.

Steroid Dehydrogenase Inhibition

It is believed that some disease conditions associated with HD activity are due to conversion of a inactive, cortisone to an active, cortisol. In disease conditions associated with HD activity, it would be desirable to inhibit HD activity.

Here, the term "inhibit" includes reduce and/or eliminate and/or mask and/or prevent the detrimental action of HD.

HD Inhibitor

In accordance with the present invention, the compound of the present invention is capable of acting as an HD inhibitor.

Here, the term "inhibitor" as used herein with respect to the compound of the present invention means a compound that can inhibit HD activity—such as reduce and/or eliminate and/or mask and/or prevent the detrimental action of HD. The HD inhibitor may act as an antagonist.

The ability of compounds to inhibit steroid dehydrogenase activity can be assessed using the suitable Assay Protocol presented in the Examples section.

It is to be noted that the compound of the present invention may have other beneficial properties in addition to or in the alternative to its ability to inhibit HD activity.

Hydrocarbyl

The term "hydrocarbyl group" as used herein means a group comprising at least C and H and may optionally comprise one or more other suitable substituents. Examples of such substituents may include halo, alkoxy, nitro, an alkyl group, a cyclic group etc. In addition to the possibility of the substituents being a cyclic group, a combination of substituents may form a cyclic group. If the hydrocarbyl group comprises more than one C then those carbons need not necessarily be linked to each other. For example, at least two of the carbons may be linked via a suitable element or group. Thus, the hydrocarbyl group may contain hetero atoms. Suitable hetero atoms will be apparent to those skilled in the art and include, for instance, sulphur, nitrogen and oxygen. A non-limiting example of a hydrocarbyl group is an acyl group.

A typical hydrocarbyl group is a hydrocarbon group. Here the term "hydrocarbon" means any one of an alkyl group, an alkenyl group, an alkynyl group, which groups may be linear, branched or cyclic, or an aryl group. The term hydrocarbon also includes those groups but wherein they have been optionally substituted. If the hydrocarbon is a branched structure having substituent(s) thereon, then the substitution may be on either the hydrocarbon backbone or on the branch; alternatively the substitutions may be on the hydrocarbon backbone and on the branch.

In some embodiments of the present invention, one or more hydrocarbyl groups is independently selected from optionally substituted alkyl group, optionally substituted haloalkyl group, aryl group, alkylaryl group, alkylarylakyl group, and an alkene group.

In some embodiments of the present invention, one or more hydrocarbyl groups is independently selected from $C_1$-$C_{10}$ alkyl group, such as $C_1$-$C_6$ alkyl group, and $C_1$-$C_3$ alkyl group. Typical alkyl groups include $C_1$ alkyl, $C_2$ alkyl, $C_3$ alkyl, $C_4$ alkyl, $C_5$ alkyl, $C_7$ alkyl, and $C_8$ alkyl.

In some embodiments of the present invention, one or more hydrocarbyl groups is independently selected from $C_1$-$C_{10}$ haloalkyl group, $C_1$-$C_6$ haloalkyl group, $C_1$-$C_3$ haloalkyl group, $C_1$-$C_{10}$ bromoalkyl group, $C_1$-$C_6$ bromoalkyl group, and $C_1$-$C_3$ bromoalkyl group. Typical haloalkyl groups include $C_1$ haloalkyl, $C_2$ haloalkyl, $C_3$ haloalkyl, $C_4$ haloalkyl, $C_5$ haloalkyl, $C_7$ haloalkyl, $C_8$ haloalkyl, $C_8$ bromoalkyl, $C_2$ bromoalkyl, $C_3$ bromoalkyl, $C_4$ bromoalkyl, $C_5$ bromoalkyl, $C_7$ bromoalkyl, and $C_8$ bromoalkyl.

In some embodiments of the present invention, one or more hydrocarbyl groups is independently selected from aryl groups, alkylaryl groups, alkylarylakyl groups, —$(CH_2)_{1-10}$-aryl, —$(CH_2)_{1-10}$-Ph, $(CH_2)_{1-10}$-Ph-$C_{1-10}$ alkyl, —$(CH_2)_{1-5}$-Ph, $(CH_2)_{1-5}$-Ph-$C_{1-5}$ alkyl, —$(CH_2)_{1-3}$-Ph, $(CH_2)_{1-3}$-Ph-$C_{1-3}$ alkyl, —$CH_2$-Ph, and —$CH_2$-Ph-$C(CH_3)_3$. The aryl groups may contain a hetero atom. Thus the aryl group or one or more of the aryl groups may be carbocyclic or more may heterocyclic. Typical hetero atoms include O, N and S, in particular N.

In some embodiments of the present invention, one or more hydrocarbyl groups is independently selected from —$(CH_2)_{1-10}$-cycloalkyl, —$(CH_2)_{1-10}$—$C_{3-10}$cycloalkyl, —$(CH_2)_{1-7}$—$C_{3-7}$cycloalkyl, —$(CH_2)_{1-5}$—$C_{3-5}$cycloalkyl, —$(CH_2)_{1-3}$—$C_{3-5}$cycloalkyl, and —$CH_2$—$C_3$cycloalkyl.

In some embodiments of the present invention, one or more hydrocarbyl groups is independently selected from alkene groups. Typical alkene groups include $C_1$-$C_{10}$ alkene group, $C_1$-$C_6$ alkene group, $C_1$-$C_3$ alkene group, such as $C_1$, $C_2$, $C_3$, $C_4$, $C_5$, $C_6$, or $C_7$ alkene group. In an exemplary embodiment the alkene group contains 1, 2 or 3 C═C bonds. In an exemplary embodiment the alkene group contains 1 C═C bond. In some embodiments at least one C═C bond or the only C═C bond is to the terminal C of the alkene chain, that is the bond is at the distal end of the chain to the ring system.

In some embodiments of the present invention, one or more hydrocarbyl groups is independently selected from oxyhydrocarbyl groups.

Oxyhydrocarbyl

The term "oxyhydrocarbyl" group as used herein means a group comprising at least C, H and O and may optionally comprise one or more other suitable substituents. Examples of such substituents may include halo-, alkoxy-, nitro-, an alkyl group, a cyclic group etc. In addition to the possibility of the substituents being a cyclic group, a combination of substituents may form a cyclic group. If the oxyhydrocarbyl group comprises more than one C then those carbons need not necessarily be linked to each other. For example, at least two of the carbons may be linked via a suitable element or group. Thus, the oxyhydrocarbyl group may contain hetero atoms. Suitable hetero atoms will be apparent to those skilled in the art and include, for instance, sulphur and nitrogen.

In one embodiment of the present invention, the oxyhydrocarbyl group is a oxyhydrocarbon group.

Here the term "oxyhydrocarbon" means any one of an alkoxy group, an oxyalkenyl group, an oxyalkynyl group, which groups may be linear, branched or cyclic, or an oxyaryl group. The term oxyhydrocarbon also includes those groups but wherein they have been optionally substituted. If the oxyhydrocarbon is a branched structure having substituent(s) thereon, then the substitution may be on either the hydrocarbon backbone or on the branch; alternatively the substitutions may be on the hydrocarbon backbone and on the branch.

Typically, the oxyhydrocarbyl group is of the formula $C_{1-6}O$ (such as a $C_{1-3}O$).

Animal Assay Model for Determining Oestrogenic Activity (Protocol 1)

Lack of in vivo Oestrogenicity

The compounds of the present invention may be studied using an animal model, in particular in ovariectomised rats. In this model, compounds which are oestrogenic stimulate uterine growth.

The compound (10 mg/Kg/day for five days) was administered orally to rats with another group of animals receiving vehicle only (propylene glycol). A further group received the estrogenic compound EMATE subcutaneously in an amount of 10 μg/day for five days. At the end of the study uteri were obtained and weighed with the results being expressed as uterine weight/whole body weight ×100.

Compounds having no significant effect on uterine growth are not oestrogenic.

Reporters

A wide variety of reporters may be used in the assay methods (as well as screens) of the present invention with selected reporters providing conveniently detectable signals (e.g. by spectroscopy). By way of example, a reporter gene may encode an enzyme which catalyses a reaction which alters light absorption properties.

Other protocols include enzyme-linked immunosorbent assay (ELISA), radioimmunoassay (RIA) and fluorescent activated cell sorting (FACS). A two-site, monoclonal-based immunoassay utilising monoclonal antibodies reactive to two non-interfering epitopes may even be used. These and other assays are described, among other places, in Hampton R et al (1990, Serological Methods, A Laboratory Manual, APS Press, St Paul Minn.) and Maddox D E et al (1983, J Exp Med 15 8:121 1).

Examples of reporter molecules include but are not limited to (β-galactosidase, invertase, green fluorescent protein, luciferase, chloramphenicol, acetyltransferase, (-glucuronidase, exo-glucanase and glucoamylase. Alternatively, radiolabelled or fluorescent tag-labelled nucleotides can be incorporated into nascent transcripts which are then identified when bound to oligonucleotide probes.

By way of further examples, a number of companies such as Pharmacia Biotech (Piscataway, N.J.), Promega (Madison, Wis.), and US Biochemical Corp (Cleveland, Ohio) supply commercial kits and protocols for assay procedures. Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. No. 3,817,837; 3,850,752; 3,939,350; 3,996,345; 4,277,437; 4,275,149 and 4,366,241.

Host Cells

The term "host cell"—in relation to the present invention includes any cell that could comprise the target for the agent of the present invention.

Thus, a further embodiment of the present invention provides host cells transformed or transfected with a polynucleotide that is or expresses the target of the present invention. In one embodiment of the present invention said polynucleotide is carried in a vector for the replication and expression of polynucleotides that are to be the target or are to express the target. The cells will be chosen to be compatible with the said vector and may for example be prokaryotic (for example bacterial), fungal, yeast or plant cells.

The gram negative bacterium *E. coli* is widely used as a host for heterologous gene expression. However, large amounts of heterologous protein tend to accumulate inside the cell. Subsequent purification of the desired protein from the bulk of *E. coli* intracellular proteins can sometimes be difficult.

In contrast to *E. coli*, bacteria from the genus *Bacillus* are very suitable as heterologous hosts because of their capability to secrete proteins into the culture medium. Other bacteria suitable as hosts are those from the genera *Streptomyces* and *Pseudomonas*.

Depending on the nature of the polynucleotide encoding the polypeptide of the present invention, and/or the desirability for further processing of the expressed protein, eukaryotic hosts such as yeasts or other fungi may be used. In general, yeast cells are preferred over fungal cells because they are easier to manipulate. However, some proteins are either poorly secreted from the yeast cell, or in some cases are not processed properly (e.g. hyperglycosylation in yeast). In these instances, a different fungal host organism should be selected.

Examples of suitable expression hosts within the scope of the present invention are fungi such as *Aspergillus* species (such as those described in EP-A-0184438 and EP-A-0284603) and *Trichoderma* species; bacteria such as *Bacillus* species (such as those described in EP-A-0134048 and EP-A-0253455), *Streptomyces* species and *Pseudomonas* species; and yeasts such as *Kluyveromyces* species (such as those described in EP-A-0096430 and EP-A-0301670) and *Saccharomyces* species. By way of example, typical expression hosts may be selected from *Aspergillus niger, Aspergillus niger* var. *tubigenis, Aspergillus niger* var. *awamori, Aspergillus aculeatus, Aspergillus nidulans, Aspergillus oryzae, Trichoderma reesei, Bacillus subtilis, Bacillus licheniformis, Bacillus amyloliquefaciens, Kluyveromyces lactis* and *Saccharomyces cerevisiae*.

The use of suitable host cells—such as yeast, fungal and plant host cells—may provide for post-translational modifications (e.g. myristoylation, glycosylation, truncation, lapidation and tyrosine, serine or threonine phosphorylation) as may be needed to confer optimal biological activity on recombinant expression products of the present invention.

Organism

The term "organism" in relation to the present invention includes any organism that could comprise the target according to the present invention and/or products obtained therefrom. Examples of organisms may include a fungus, yeast or a plant.

The term "transgenic organism" in relation to the present invention includes any organism that comprises the target according to the present invention and/or products obtained.

Transformation of Host Cells/Host Organisms

As indicated earlier, the host organism can be a prokaryotic or a eukaryotic organism. Examples of suitable prokaryotic hosts include *E. coli* and *Bacillus subtilis*. Teachings on the transformation of prokaryotic hosts is well documented in the art, for example see Sambrook et al (Molecular Cloning: A Laboratory Manual, 2nd edition, 1989, Cold Spring Harbor Laboratory Press) and Ausubel et al., Current Protocols in Molecular Biology (1995), John Wiley & Sons, Inc.

If a prokaryotic host is used then the nucleotide sequence may need to be suitably modified before transformation—such as by removal of introns.

In another embodiment the transgenic organism can be a yeast. In this regard, yeast have also been widely used as a vehicle for heterologous gene expression. The species *Saccharomyces cerevisiae* has a long history of industrial use, including its use for heterologous gene expression. Expression of heterologous genes in *Saccharomyces cerevisiae* has been reviewed by Goodey et al (1987, Yeast Biotechnology, D R Berry et al, eds, pp 401-429, Allen and Unwin, London) and by King et al (1989, Molecular and Cell Biology of Yeasts, E F Walton and G T Yarronton, eds, pp 107-133, Blackie, Glasgow).

For several reasons *Saccharomyces cerevisiae* is well suited for heterologous gene expression. First, it is non-pathogenic to humans and it is incapable of producing certain endotoxins. Second, it has a long history of safe use following centuries of commercial exploitation for various purposes. This has led to wide public acceptability. Third, the extensive commercial use and research devoted to the organism has resulted in a wealth of knowledge about the genetics and physiology as well as large-scale fermentation characteristics of *Saccharomyces cerevisiae*.

A review of the principles of heterologous gene expression in *Saccharomyces cerevisiae* and secretion of gene products is given by E Hinchcliffe E Kenny (1993, "Yeast as a vehicle for the expression of heterologous genes", Yeasts, Vol 5, Anthony H Rose and J Stuart Harrison, eds, 2nd edition, Academic Press Ltd.).

Several types of yeast vectors are available, including integrative vectors, which require recombination with the host genome for their maintenance, and autonomously replicating plasmid vectors.

In order to prepare the transgenic *Saccharomyces*, expression constructs are prepared by inserting the nucleotide sequence into a construct designed for expression in yeast. Several types of constructs used for heterologous expression have been developed. The constructs contain a promoter active in yeast fused to the nucleotide sequence, usually a promoter of yeast origin, such as the GAL1 promoter, is used. Usually a signal sequence of yeast origin, such as the sequence encoding the SUC2 signal peptide, is used. A terminator active in yeast ends the expression system.

For the transformation of yeast several transformation protocols have been developed. For example, a transgenic *Saccharomyces* according to the present invention can be prepared by following the teachings of Hinnen et al (1978, Proceedings of the National Academy of Sciences of the USA 75, 1929); Beggs, J D (1978, Nature, London, 275, 104); and Ito, H et al (1983, J Bacteriology 153, 163-168).

The transformed yeast cells are selected using various selective markers. Among the markers used for transformation are a number of auxotrophic markers such as LEU2, HIS4 and TRP1, and dominant antibiotic resistance markers such as aminoglycoside antibiotic markers, e.g. G418.

Another host organism is a plant. The basic principle in the construction of genetically modified plants is to insert genetic information in the plant genome so as to obtain a stable maintenance of the inserted genetic material. Several techniques exist for inserting the genetic information, the two main principles being direct introduction of the genetic information and introduction of the genetic information by use of a vector system. A review of the general techniques may be found in articles by Potrykus (Annu Rev Plant Physiol Plant Mol Biol [1991] 42:205-225) and Christou (Agro-Food-Industry Hi-Tech March/April 1994 17-27). Further teachings on plant transformation may be found in EP-A-0449375.

Thus, the present invention also provides a method of transforming a host cell with a nucleotide sequence that is to be the target or is to express the target. Host cells transformed with the nucleotide sequence may be cultured under conditions suitable for the expression of the encoded protein. The protein produced by a recombinant cell may be displayed on the surface of the cell. If desired, and as will be understood by those of skill in the art, expression vectors containing coding sequences can be designed with signal sequences which direct secretion of the coding sequences through a particular prokaryotic or eukaryotic cell membrane. Other recombinant constructions may join the coding sequence to nucleotide sequence encoding a polypeptide domain which will facilitate purification of soluble proteins (Kroll D J et al (1993) DNA Cell Biol 12:441-53).

Variants/Homologues/Derivatives

In addition to the specific amino acid sequences and nucleotide sequences mentioned herein, the present invention also encompasses the use of variants, homologue and derivatives thereof. Here, the term "homology" can be equated with "identity".

In the present context, an homologous sequence is taken to include an amino acid sequence which may be at least 75, 85 or 90% identical, for example at least 95 or 98% identical. Although homology can also be considered in terms of similarity (i.e. amino acid residues having similar chemical properties/functions), in the context of the present invention it is preferred to express homology in terms of sequence identity.

Homology comparisons can be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package (see below) the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al., 1984, Nucleic Acids Research 12:387). Examples of other software than can perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However it is preferred to use the GCG Bestfit program.

A further useful reference is that found in FEMS Microbiol Lett 1999 May 15; 174(2):247-50 (and a published erratum appears in FEMS Microbiol Lett 1999 Aug. 1; 177(1):187-8).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). It is preferred to use the public default values for the GCG package, or in the case of other software, the default matrix, such as BLOSUM62.

Once the software has produced an optimal alignment, it is possible to calculate % homology, for example % sequence identity. The software typically does this as part of the sequence comparison and generates a numerical result.

The sequences may also have deletions, insertions or substitutions of amino acid residues which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below. Amino acids in the same block in the second column and for example in the same line in the third column may be substituted for each other:

TABLE 1

| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

Expression Vectors

The nucleotide sequence for use as the target or for expressing the target can be incorporated into a recombinant replicable vector. The vector may be used to replicate and express the nucleotide sequence in and/or from a compatible host cell. Expression may be controlled using control sequences which include promoters/enhancers and other expression regulation signals. Prokaryotic promoters and promoters functional in eukaryotic cells may be used. Tissue specific or stimuli specific promoters may be used. Chimeric promoters may also be used comprising sequence elements from two or more different promoters described above.

The protein produced by a host recombinant cell by expression of the nucleotide sequence may be secreted or may be contained intracellularly depending on the sequence and/or the vector used. The coding sequences can be designed with signal sequences which direct secretion of the substance coding sequences through a particular prokaryotic or eukaryotic cell membrane.

Fusion Proteins

The target amino acid sequence may be produced as a fusion protein, for example to aid in extraction and purification. Examples of fusion protein partners include glutathione-S-transferase (GST), 6×His, GAL4 (DNA binding and/or transcriptional activation domains) and (-galactosidase. It may also be convenient to include a proteolytic cleavage site between the fusion protein partner and the protein sequence of interest to allow removal of fusion protein sequences. In one embodiment of the present invention the fusion protein will not hinder the activity of the target.

The fusion protein may comprise an antigen or an antigenic determinant fused to the substance of the present invention. In this embodiment, the fusion protein may be a non-naturally occurring fusion protein comprising a substance which may act as an adjuvant in the sense of providing a generalised stimulation of the immune system. The antigen or antigenic determinant may be attached to either the amino or carboxy terminus of the substance.

In another embodiment of the invention, the amino acid sequence may be ligated to a heterologous sequence to encode a fusion protein. For example, for screening of peptide libraries for agents capable of affecting the substance activity, it may be useful to encode a chimeric substance expressing a heterologous epitope that is recognised by a commercially available antibody.

Therapy

The compounds of the present invention may be used as therapeutic agents—i.e. in therapy applications.

The term "therapy" includes curative effects, alleviation effects, and prophylactic effects.

The therapy may be on humans or animals, for example female animals.

Pharmaceutical Compositions

In one embodiment, the present invention provides a pharmaceutical composition, which comprises a compound according to the present invention and optionally a pharmaceutically acceptable carrier, diluent or excipient (including combinations thereof).

The pharmaceutical compositions may be for human or animal usage in human and veterinary medicine and will typically comprise any one or more of a pharmaceutically acceptable diluent, carrier, or excipient. Acceptable carriers or diluents for therapeutic use are well known in the pharmaceutical art, and are described, for example, in Remington's Pharmaceutical Sciences, Mack Publishing Co. (A. R. Gennaro edit. 1985). The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s).

Preservatives, stabilisers, dyes and even flavouring agents may be provided in the pharmaceutical composition. Examples of preservatives include sodium benzoate, sorbic acid and esters of p-hydroxybenzoic acid. Antioxidants and suspending agents may be also used.

There may be different composition/formulation requirements dependent on the different delivery systems. By way of example, the pharmaceutical composition of the present invention may be formulated to be delivered using a minipump or by a mucosal route, for example, as a nasal spray or aerosol for inhalation or ingestable solution, or parenterally in which the composition is formulated by an injectable form, for delivery, by, for example, an intravenous, intramuscular or subcutaneous route. Alternatively, the formulation may be designed to be delivered by both routes.

Where the agent is to be delivered mucosally through the gastrointestinal mucosa, it should be able to remain stable during transit though the gastrointestinal tract; for example, it should be resistant to proteolytic degradation, stable at acid pH and resistant to the detergent effects of bile.

Where appropriate, the pharmaceutical compositions can be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

Combination Pharmaceutical

The compound of the present invention may be used in combination with one or more other active agents, such as one or more other pharmaceutically active agents. By way of example, the compounds of the present invention may be used in combination with other 11β-HSD inhibitors and/or other inhibitors such as an aromatase inhibitor (such as for example, 4hydroxyandrostenedione (4-OHA)), and/or a steroid sulphatase inhibitors such as EMATE and/or steroids— such as the naturally occurring sterneurosteroids dehydroepiandrosterone sulfate (DHEAS) and pregnenolone sulfate (PS) and/or other structurally similar organic compounds.

In addition, or in the alternative, the compound of the present invention may be used in combination with a biological response modifier.

The term biological response modifier ("BRM") includes cytokines, immune modulators, growth factors, haematopoiesis regulating factors, colony stimulating factors, chemotactic, haemolytic and thrombolytic factors, cell surface receptors, ligands, leukocyte adhesion molecules, monoclonal antibodies, preventative and therapeutic vaccines, hormones, extracellular matrix components, fibronectin, etc. For some applications, for example, the biological response modifier is a cytokine. Examples of cytokines include: interleukins (IL)—such as IL-1, IL-2, IL-3, IL-4, IL-5, IL-6, IL-7, IL-8, IL-9, IL-10, IL-11, IL-12, IL-19; Tumour Necrosis Factor (TNF)— such as TNF-α; Interferon alpha, beta and gamma; TGF-β. For some applications, for example the cytokine is tumour necrosis factor (TNF). For some applications, the TNF may be any type of TNF—such as TNF-α, TNF-β, including derivatives or mixtures thereof. In one embodiment of the present invention the cytokine is TNF-α. Teachings on TNF may be found in the art—such as WO-A-98/08870 and WO-A-98/13348.

Administration

Typically, a physician will determine the actual dosage which will be most suitable for an individual subject and it will vary with the age, weight and response of the particular patient. The dosages below are exemplary of the average case. There can, of course, be individual instances where higher or lower dosage ranges are merited.

The compositions of the present invention may be administered by direct injection. The composition may be formulated for parenteral, mucosal, intramuscular, intravenous, subcutaneous, intraocular or transdermal administration. Depending upon the need, the agent may be administered at a dose of from 0.01 to 30 mg/kg body weight, such as from 0.1 to 10 mg/kg, for example from 0.1 to 1 mg/kg body weight.

By way of further example, the agents of the present invention may be administered in accordance with a regimen of 1 to 4 times per day, for example once or twice per day. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Aside from the typical modes of delivery—indicated above—the term "administered" also includes delivery by techniques such as lipid mediated transfection, liposomes, immunoliposomes, lipofectin, cationic facial amphiphiles (CFAs) and combinations thereof. The routes for such delivery mechanisms include but are not limited to mucosal, nasal, oral, parenteral, gastrointestinal, topical, or sublingual routes.

The term "administered" includes but is not limited to delivery by a mucosal route, for example, as a nasal spray or aerosol for inhalation or as an ingestable solution; a parenteral route where delivery is by an injectable form, such as, for example, an intravenous, intramuscular or subcutaneous route.

Thus, for pharmaceutical administration, the compounds of the present invention can be formulated in any suitable manner utilising conventional pharmaceutical formulating techniques and pharmaceutical carriers, adjuvants, excipients, diluents etc. and usually for parenteral administration. Approximate effective dose rates may be in the range from 1 to 1000 mg/day, such as from 10 to 900 mg/day or even from 100 to 800 mg/day depending on the individual activities of the compounds in question and for a patient of average (70 Kg) bodyweight. More usual dosage rates for the more active compounds will be in the range 200 to 800 mg/day, for example, 200 to 500 mg/day, also for example from 200 to 250 mg/day. They may be given in single dose regimes, split dose regimes and/or in multiple dose regimes lasting over several days. For oral administration they may be formulated in tablets, capsules, solution or suspension containing from 100 to 500 mg of compound per unit dose. Alternatively and in some embodiments of the present invention the compounds will be formulated for parenteral administration in a suitable parenterally administrable carrier and providing single daily dosage rates in the range 200 to 800 mg, for example 200 to 500, for example 200 to 250 mg. Such effective daily doses will, however, vary depending on inherent activity of the active ingredient and on the bodyweight of the patient, such variations being within the skill and judgement of the physician.

Cell Cycling

The compounds of the present invention may be useful in the method of treatment of a cell cycling disorder.

As discussed in "Molecular Cell Biology" 3rd Ed. Lodish et al. pages 177-181 different eukaryotic cells can grow and divide at quite different rates. Yeast cells, for example, can divide every 120 min., and the first divisions of fertilised eggs in the embryonic cells of sea urchins and insects take only 1530 min. because one large pre-existing cell is subdivided. However, most growing plant and animal cells take 10-20 hours to double in number, and some duplicate at a much slower rate. Many cells in adults, such as nerve cells and striated muscle cells, do not divide at all; others, like the fibroblasts that assist in healing wounds, grow on demand but are otherwise quiescent.

Still, every eukaryotic cell that divides must be ready to donate equal genetic material to two daughter cells. DNA synthesis in eukaryotes does not occur throughout the cell division cycle but is restricted to a part of it before cell division.

The relationship between eukaryotic DNA synthesis and cell division has been analysed in cultures of mammalian cells that were all capable of growth and division. In contrast to bacteria, it was found, eukaryotic cells spend only a part of their time in DNA synthesis, and it is completed hours before cell division (mitosis). Thus a gap of time occurs after DNA synthesis and before cell division; another gap was found to occur after division and before the next round of DNA synthesis. This analysis led to the conclusion that the eukaryotic cell cycle consists of an M (mitotic) phase, a $G_1$ phase (the first gap), the S (DNA synthesis) phase, a $G_2$ phase (the second gap), and back to M. The phases between mitoses ($G_1$, S, and $G_2$) are known collectively as the interphase.

Many nondividing cells in tissues (for example, all quiescent fibroblasts) suspend the cycle after mitosis and just prior to DNA synthesis; such "resting" cells are said to have exited from the cell cycle and to be in the $G_0$ state.

It is possible to identify cells when they are in one of the three interphase stages of the cell cycle, by using a fluorescence-activated cell sorter (FACS) to measure their relative DNA content: a cell that is in $G_1$ (before DNA synthesis) has a defined amount x of DNA; during S (DNA replication), it has between x and 2x; and when in $G_2$ (or M), it has 2x of DNA.

The stages of mitosis and cytokinesis in an animal cell are as follows (a) Interphase. The $G_2$ stage of interphase immediately precedes the beginning of mitosis. Chromosomal DNA has been replicated and bound to protein during the S phase, but chromosomes are not yet seen as distinct structures. The nucleolus is the only nuclear substructure that is visible under light microscope. In a diploid cell before DNA replication there are two morphologic chromosomes of each type, and the cell is said to be 2n. In $G_2$, after DNA replication, the cell is 4n. There are four copies of each chromosomal DNA. Since the sister chromosomes have not yet separated from each other, they are called sister chromatids.

b) Early prophase. Centrioles, each with a newly formed daughter centriole, begin moving toward opposite poles of the cell; the chromosomes can be seen as long threads. The nuclear membrane begins to disaggregate into small vesicles.

(c) Middle and late prophase. Chromosome condensation is completed; each visible chromosome structure is composed of two chromatids held together at their centromeres. Each chromatid contains one of the two newly replicated daughter DNA molecules. The microtubular spindle begins to radiate from the regions just adjacent to the centrioles, which are moving closer to their poles. Some spindle fibres reach from pole to pole; most go to chromatids and attach at kinetochores.

(d) Metaphase. The chromosomes move toward the equator of the cell, where they become aligned in the equatorial plane. The sister chromatids have not yet separated.

(e) Anaphase. The two sister chromatids separate into independent chromosomes. Each contains a centromere that is linked by a spindle fibre to one pole, to which it moves. Thus one copy of each chromosome is donated to each daughter cell. Simultaneously, the cell elongates, as do the pole-to-pole spindles. Cytokinesis begins as the cleavage furrow starts to form.

(f) Telophase. New membranes form around the daughter nuclei; the chromosomes uncoil and become less distinct, the nucleolus becomes visible again, and the nuclear membrane forms around each daughter nucleus. Cytokinesis is nearly complete, and the spindle disappears as the microtubules and other fibres depolymerise. Throughout mitosis the "daughter" centriole at each pole grows until it is full-length. At telophase the duplication of each of the original centrioles is completed, and new daughter centrioles will be generated during the next interphase.

(g) Interphase. Upon the completion of cytokinesis, the cell enters the $G_1$ phase of the cell cycle and proceeds again around the cycle.

It will be appreciated that cell cycling is an important cell process. Deviations from normal cell cycling can result in a number of medical disorders. Increased and/or unrestricted cell cycling may result in cancer. Reduced cell cycling may result in degenerative conditions. Use of the compound of the present invention may provide a means to treat such disorders and conditions.

Thus, the compound of the present invention may be suitable for use in the treatment of cell cycling disorders such as cancers, including hormone dependent and hormone independent cancers.

In addition, the compound of the present invention may be suitable for the treatment of cancers such as breast cancer, ovarian cancer, endometrial cancer, sarcomas, melanomas, prostate cancer, pancreatic cancer etc. and other solid tumours.

For some applications, cell cycling is inhibited and/or prevented and/or arrested, for example wherein cell cycling is prevented and/or arrested. In one embodiment cell cycling may be inhibited and/or prevented and/or arrested in the $G_2$/M phase. In one embodiment cell cycling may be irreversibly prevented and/or inhibited and/or arrested, such as wherein cell cycling is irreversibly prevented and/or arrested.

By the term "irreversibly prevented and/or inhibited and/or arrested" it is meant after application of a compound of the present invention, on removal of the compound the effects of the compound, namely prevention and/or inhibition and/or arrest of cell cycling, are still observable. More particularly by the term "irreversibly prevented and/or inhibited and/or arrested" it is meant that when assayed in accordance with the cell cycling assay protocol presented herein, cells treated with a compound of interest show less growth after Stage 2 of the protocol I than control cells. Details on this protocol are presented below.

Thus, the present invention provides compounds which: cause inhibition of growth of oestrogen receptor positive (ER+) and ER negative (ER−) breast cancer cells in vitro by preventing and/or inhibiting and/or arresting cell cycling; and/or cause regression of nitroso-methyl urea (NMU)-induced mammary tumours in intact animals (i.e. not ovariectomised), and/or prevent and/or inhibit and/or arrest cell cycling in cancer cells; and/or act in vivo by preventing and/or inhibiting and/or arresting cell cycling and/or act as a cell cycling agonist.

Cell Cycling Assay (Protocol 2)

Procedure

Stage 1

MCF-7 breast cancer cells are seeded into multi-well culture plates at a density of 105 cells/well. Cells were allowed to attach and grown until about 30% confluent when they are treated as follows:

Control—no treatment

Compound of Interest (COI) 20 µM

Cells are grown for 6 days in growth medium containing the COI with changes of medium/COI every 3 days. At the end of this period cell numbers were counted using a Coulter cell counter.

Stage 2

After treatment of cells for a 6-day period with the COI cells are re-seeded at a density of $10^4$ cells/well. No further treatments are added. Cells are allowed to continue to grow for a further 6 days in the presence of growth medium. At the end of this period cell numbers are again counted.

Cancer

As indicated, the compounds of the present invention may be useful in the treatment of a cell cycling disorder. A particular cell cycling disorder is cancer.

Cancer remains a major cause of mortality in most Western countries. Cancer therapies developed so far have included blocking the action or synthesis of hormones to inhibit the growth of hormone-dependent tumours. However, more aggressive chemotherapy is currently employed for the treatment of hormone-independent tumours.

Hence, the development of a pharmaceutical for anti-cancer treatment of hormone dependent and/or hormone independent tumours, yet lacking some or all of the side-effects associated with chemotherapy, would represent a major therapeutic advance.

We believe that the compound of the present invention provides a means for the treatment of cancers and, especially, breast cancer.

In addition or in the alternative the compound of the present invention may be useful in the blocking the growth of cancers including leukaemias and solid tumours such as breast, endometrium, prostate, ovary and pancreatic tumours.

Other Therapies

It is also to be understood that the compound/composition of the present invention may have other important medical implications.

For example, the compound or composition of the present invention may be useful in the treatment of the disorders listed in WO-A-99/52890-viz:

In addition, or in the alternative, the compound or composition of the present invention may be useful in the treatment of the disorders listed in WO-A-98/05635. For ease of reference, part of that list is now provided: diabetes including Type II diabetes, obesity, cancer, inflammation or inflammatory disease, dermatological disorders, fever, cardiovascular effects, haemorrhage, coagulation and acute phase response, cachexia, anorexia, acute infection, HIV infection, shock states, graft-versus-host reactions, autoimmune disease, reperfusion injury, meningitis, migraine and aspirin-dependent anti-thrombosis; tumour growth, invasion and spread, angiogenesis, metastases, malignant, ascites and malignant pleural effusion; cerebral ischaemia, ischaemic heart disease, osteoarthritis, rheumatoid arthritis, osteoporosis, asthma, multiple sclerosis, neurodegeneration, Alzheimer's disease, atherosclerosis, stroke, vasculitis, Crohn's disease and ulcerative colitis; periodontitis, gingivitis; psoriasis, atopic dermatitis, chronic ulcers, epidermolysis bullosa; corneal ulceration, retinopathy and surgical wound healing; rhinitis, allergic conjunctivitis, eczema, anaphylaxis; restenosis, congestive heart failure, endometriosis, atherosclerosis or endosclerosis.

In addition, or in the alternative, the compound or composition of the present invention may be useful in the treatment of disorders listed in WO-A-98/07859. For ease of reference, part of that list is now provided: cytokine and cell proliferation/differentiation activity; immunosuppressant or immunostimulant activity (e.g. for treating immune deficiency, including infection with human immune deficiency virus; regulation of lymphocyte growth; treating cancer and many autoimmune diseases, and to prevent transplant rejection or induce tumour immunity); regulation of haematopoiesis, e.g. treatment of myeloid or lymphoid diseases; promoting growth of bone, cartilage, tendon, ligament and nerve tissue, e.g. for healing wounds, treatment of burns, ulcers and periodontal disease and neurodegeneration; inhibition or activation of follicle-stimulating hormone (modulation of fertility); chemotactic/chemokinetic activity (e.g. for mobilising specific cell types to sites of injury or infection); haemostatic and thrombolytic activity (e.g. for treating haemophilia and stroke); antiinflammatory activity (for treating e.g. septic shock or Crohn's disease); as antimicrobials; modulators of e.g. metabolism or behaviour; as analgesics; treating specific deficiency disorders; in treatment of e.g. psoriasis, in human or veterinary medicine.

In addition, or in the alternative, the composition of the present invention may be useful in the treatment of disorders listed in WO-A-98/09985. For ease of reference, part of that list is now provided: macrophage inhibitory and/or T cell inhibitory activity and thus, anti-inflammatory activity; anti-immune activity, i.e. inhibitory effects against a cellular and/or humoral immune response, including a response not associated with inflammation; inhibit the ability of macrophages and T cells to adhere to extracellular matrix components and fibronectin, as well as up-regulated fas receptor expression in T cells; inhibit unwanted immune reaction and inflammation including arthritis, including rheumatoid arthritis, inflammation associated with hypersensitivity, allergic reactions, asthma, systemic lupus erythematosus, collagen diseases and other autoimmune diseases, inflammation associated with atherosclerosis, arteriosclerosis, atherosclerotic heart disease, reperfusion injury, cardiac arrest, myocardial infarction, vascular inflammatory disorders, respiratory distress syndrome or other cardiopulmonary diseases, inflammation associated with peptic ulcer, ulcerative colitis and other diseases of the gastrointestinal tract, hepatic fibrosis, liver cirrhosis or other hepatic diseases, thyroiditis or other glandular diseases, glomerulonephritis or other renal and urologic diseases, otitis or other oto-rhino-laryngological diseases, dermatitis or other dermal diseases, periodontal diseases or other dental diseases, orchitis or epididimo-orchitis, infertility, orchidal trauma or other immune-related testicular diseases, placental dysfunction, placental insufficiency, habitual abortion, eclampsia, pre-eclampsia and other immune and/or inflammatory-related gynaecological diseases, posterior uveitis, intermediate uveitis, anterior uveitis, conjunctivitis, chorioretinitis, uveoretinitis, optic neuritis, intraocular inflammation, e.g. retinitis or cystoid macular oedema, sympathetic ophthalmia, scleritis, retinitis pigmentosa, immune and inflammatory components of degenerative fondus disease, inflammatory components of ocular trauma, ocular inflammation caused by infection, proliferative vitreo-retinopathies, acute ischaemic optic neuropathy, excessive scarring, e.g. following glaucoma filtration operation, immune and/or inflammation reaction against ocular implants and other immune and inflammatory-related ophthalmic diseases, inflammation associated with autoimmune diseases or conditions or disorders where, both in the central nervous system (CNS) or in any other organ, immune and/or inflammation suppression would be beneficial, Parkinson's disease, complication and/or side effects from treatment of Parkinson's disease, AIDS-related dementia complex HIV-related encephalopathy, Devic's disease, Sydenham chorea, Alzheimer's disease and other degenerative diseases, conditions or disorders of the CNS, inflammatory components of stokes, post-polio syndrome, immune and inflammatory components of psychiatric disorders, myelitis, encephalitis, subacute sclerosing pan-encephalitis, encephalomyelitis, acute neuropathy, subacute neuropathy, chronic neuropathy, Guillaim-Barre syndrome, Sydenham chora, myasthenia gravis, pseudo-tumour cerebri, Down's Syndrome, Huntington's disease, amyotrophic lateral sclerosis, inflammatory components of CNS compression or CNS trauma or infections of the CNS, inflammatory components of muscular atrophies and dystrophies, and immune and inflammatory related diseases, conditions or disorders of the central and peripheral nervous systems, post-traumatic inflammation, septic shock, infectious diseases, inflammatory complications or side effects of surgery, bone marrow transplantation or other transplantation complications and/or side effects, inflammatory and/or immune complications and side effects of gene therapy, e.g. due to infection with a viral carrier, or inflammation associated with AIDS, to suppress or inhibit a humoral and/or cellular immune response, to treat or ameliorate monocyte or leukocyte proliferative diseases, e.g. leukaemia, by reducing the amount of monocytes or lymphocytes, for the prevention and/or treatment of graft rejection in cases of transplantation of natural or artificial cells, tissue and organs such as cornea, bone marrow, organs, lenses, pacemakers, natural or artificial skin tissue.

As previously mentioned, in one embodiment the present invention provides use of a compound as described herein in the manufacture of a composition for use in the therapy of a condition or disease associated with 11β-HSD. Conditions and diseases associated with 11β-HSD have been reviewed in Walker, E. A,; Stewart, P. M.; Trends in Endocrinology and Metabolism, 2003, 14 (7), 334-339.

In an exemplary embodiment, the condition or disease is selected from the list consisting of:
   metabolic disorders, such as diabetes and obesity
   cardiovascular disorders, such as hypertension
   glaucoma
   inflammatory disorders, such as arthritis or asthma
   immune disorders
   bone disorders, such as osteoporosis
   cancer
   intra-uterine growth retardation apparent mineralocorticoid excess syndrome (AME)
polycystic ovary syndrome (PCOS)
hirsutism
acne
oligo- or amenorrhea
adrenal cortical adenoma and carcinoma
Cushing's syndrome
pituitary tumours
invasive carcinomas
breast cancer; and
endometrial cancer.

SUMMARY

In summation, the present invention provides compounds for use as steroid dehydrogenase inhibitors, and pharmaceutical compositions for the same.

BRIEF DESCRIPTION OF THE FIGURES

The present invention will be described in further detail by way of example only with reference to the accompanying figures in which:—

FIG. 12(A) shows the effect of protein; FIG. 12(B) shows the effect of cortisone; and FIG. 12(C) shows the effect of Tween-80.

EXAMPLES

Figure 1:
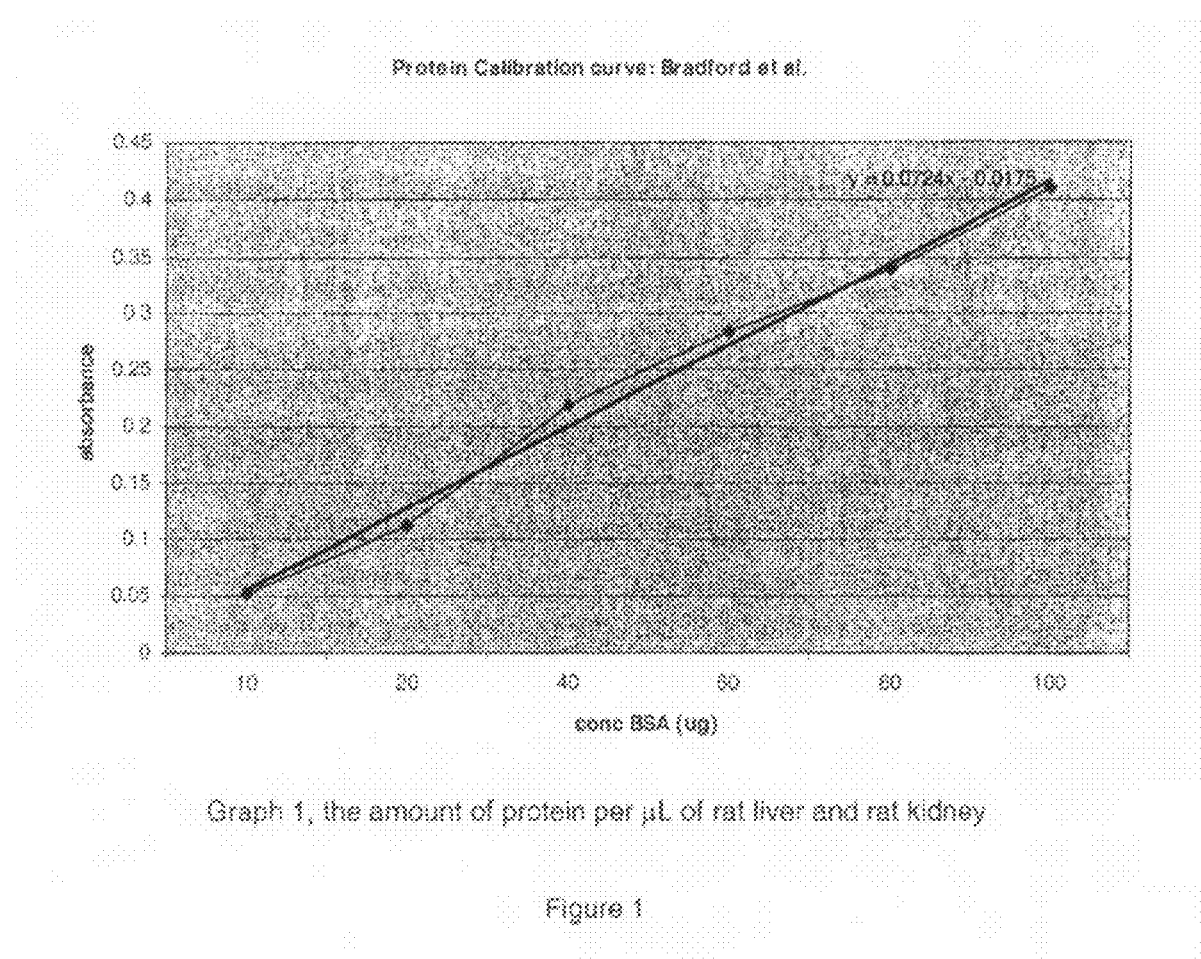
FIG. 1 is of graph 1 which shows the amount of protein per µL of rat liver and rat kidney.

The present invention will now be described only by way of example.

Materials and Methods

Materials

Enzymes—Rat livers and rat kidneys were obtained from normal Wistar rats (Harlan Olac, Bicester, Oxon, UK). Both the kidneys and livers were homogenised on ice in PBS-sucrose buffer (1 g/10 ml) using an Ultra-Turrax. After the livers and kidneys were homogenised the homogenate was centrifuged for five minutes at 4000 rpm. The supernatant obtained was removed and stored in glass vials at −20° C. The amount of protein per µl of rat liver and kidney cytosol was determined using the Bradford method [14].

Apparatus

Incubator: mechanically shaken water bath, SW 20, Germany.

Evaporator, Techne Driblock DB 3A, UK

TLC aluminium sheets 20×20 cm silica gel 60 $F_{254}$, Merck, Germany.

Scintillation vials: 20 ml polypropylene vials with caps, SARSTEDT, Germany.

Scintillation counter: Beckman LS 6000 SC, Beckman Instruments Inc., USA.

Solutions

Assay medium: PBS-sucrose buffer, Dulbecco's Phosphate Buffered Saline, 1 tablet/100 ml with 0.25 M sucrose, pH 7.4 BDH Laboratory supplies, UK.

Scintillation fluid: Ecoscint A (National Diagnostics, USA).

Radioactive compound solutions: [1,2,6,7-$^3$H]-cortisol (Sp. Ac. 84 Ci/mmol) NEN Germany, [4-$^{14}$C]-cortisol (Sp. Ac. 53 mCi/mmol) NEN Germany.

$CrO_3$ and Acetic acid (Sigma Chemical Co., UK).

Extraction fluid: Di-ethylether, Fischer Chemicals, UK.

Bradford Reagent solution: Coomassie Brilliant Blue G-250, 100 mg in 95% ethanol with 100 ml of phosphoric acid (85% w/v) diluted to 1 litre.

Compounds
  Inhibitors: compounds were synthesised in accordance with the synthetic routes below.
  Cofactor: NADPH and NADP, Sigma Chemical Co., UK.

Methods

Synthesis of Radio Labelled Cortisone

Labelled cortisol (F) ($^3$H—F and $^{14}$C—F) was oxidised at the C-11 position with $CrO_3$ in order to synthesize to the corresponding labelled cortisone ($^3$H-E and $^{14}$C-E).

For this reaction F was oxidised in a 0.25% $CrO_3$ (w/v) dissolved in a 50% acetic-acid/distilled water (v/v) solution. The labelled F was then added to 1 ml of the $CrO_3$ solution, vortex mixed and put in an incubator for 20 minutes at 37° C. The aqueous reaction mixture was extracted twice with 4 ml of di-ethylether, the di-ethylether was then evaporated and the residue transferred to a TLC-plate, which was developed in the following system, chloroform:methanol 9:1 (v/v). Unlabelled cortisone (E) was also run on the TLC-plate to locate the position of the labelled steroids. After locating the spot of the labelled steroids this area is cut out from the TLC-plate and eluted with 0.5 ml of methanol.

The Amount of Protein Per μL of Rat Liver and Rat Kidney

The amount of protein in rat liver and rat kidney needed to be determined. The experiment was done according to the Bradford method [14]. The following method was used: first a BSA (protein) solution was prepared (1 mg/ml). Protein solutions containing 10 to 100 μg protein were pipetted into tubes and volumes adjusted with distilled water. Then 5 ml of protein reagent was added to the tubes and vortex mixed. The absorbance was measured at 595 nm after 15 minutes and before 1 hour in 3 ml cuvettes against a reagent blank. The weight of the protein was plotted against the corresponding absorbance resulting in a standard curve used to determine the protein concentration in rat liver and rat kidney cytosols.

Assay Validation—Enzyme Concentration and Time-Dependency of 11 β-HSD Activity

Before carrying out 11 β-HSD assays to examine the conversion E to F and F to E and the influence that different inhibitors have on these conversions the amount of rat liver homogenate and rat kidney homogenate and their incubation time need to be determined.

11 β-HSD type 1 is the enzyme responsible for the conversion E to F and this type of enzyme is present in rat liver. The substrate solution used in this assay contained 70,000 cpm/ml $^3$H-E in PBS-sucrose and 0.5 μM of unlabelled E and co-factor NADPH (9 mg/10 ml of substrate solution). 1 ml of the substrate solution and the different amounts of rat liver homogenate was added to all tubes.

The amount of rat liver homogenate needed for an assay was determined by incubating the substrate solution with 25, 50, 100 and 150 μl for 30, 60, 90 and 120 minutes at 37° C. in a water bath with the tubes being mechanically shaken. After the incubation 50 μL of recovery solution was added, containing about 8,000 cpm/50 μL of $^{14}$C—F and 50 μg/50 μL of unlabelled F for visualising the spot on the TLC-plate, to correct for the losses made in the next two steps. F was then extracted from the aqueous phase with 4 ml of ether (2×30 sec cycle, vortex mix). The aqueous phase was then frozen using dry-ice and the organic layer was decanted and poured into smaller tubes and evaporated. 6 drops of ether were then added to the small tubes to re-dissolve the residue which was transferred to an aluminium thin layer chromatography plate (TLC-plate). The TLC-plate was developed in a TLC tank under saturated conditions. The solvent system used was chloroform:methanol 9:1 (v/v). The F spots on the TLC-plate were visualised under UV-light and cut out from the TLC-plate ($R_f$=0.45). The spots from the TLC-plate were then put into scintillation vials and 0.5 ml of methanol was added to all vials to elute the radioactivity from the TLC-plate for 5 minutes. 10 ml of Ecoscint was added to the scintillation vials and they were put into the scintillation counter to count amount of product formed.

The same procedure was used for the 11 β-HSD type 2 assay, the conversion F to E, to determine the amount of rat kidney to be used and the incubation time. Except this time the substrate solution contained $^3$H—F and unlabelled F and the recovery contained $^{14}$C-E and unlabelled E and cortisone has a $R_f$ value of 0.65 on the TLC-plate.

Assay Procedure—The 11 β-HSD Inhibitors

In these assays the influence of different inhibitors on the 11 β-HSD activity both in reductive (type 1) and oxidative (type 2) directions were assessed. In the reductive direction E is the substrate and F the product and visa versa in the case of oxidation. The method described here is for the oxidative direction.

The substrate solution contained about 50,000 cpm/ml $^3$H—F in PBS-sucrose and 0.5 μM F. 1 ml of the substrate solution was added to each tube, the inhibitors were also added, at a 10 μM concentration, to each tube except to the "control" and "blank" tubes. 150 μL was added to all tubes except to the blanks, this was done to correct for the amount of $^3$H—F spontaneously formed. The tubes were incubated for 60 minutes in a mechanically shaken water bath at 37° C. The amount of kidney liver homogenate and incubation time used resulted from the enzyme- and time-dependency assay. After incubation 50 μL of recovery was added to correct for the losses made in the next steps, containing 5000 cpm/50 μL of $^{14}$C-E and 50 μg/50 μL of unlabelled E (to visualise the spot on the TLC-plate). The aqueous mixture was then extracted with 4 ml of ether (2×30 sec cycle, vortex mix). After freezing the aqueous phase, the ether (upper) layer was decanted into smaller tubes and evaporated at 45° C. until completely dry. The residue was then re-dissolved in 6 drops of ether and transferred to a TLC-plate. The TLC-plate was developed in chloroform:methanol (9:1 v/v) solvent system, the TLC-plate ran for about 90 minutes until the solvent front had moved about 18 cm. The position of the product E was visualised under UV-light and cut out from the TLC-plate and put into scintillation vials. Radioactivity was eluted over 5 minutes with 0.5 ml methanol. 0.5 ml of PBS-sucrose and 10 ml of Ecoscint were then added and vortex mixed before counting in the scintillation counter. Before counting the samples, two total activity vials were prepared. These contained 0.5 ml of the substrate solution, 50 μL of the recovery, 0.5 ml of methanol and 10 ml of Ecoscint. These two total activity vials were needed to determine the amount of $^{14}$C-E and $^3$H—F added in the beginning to make the calculations.

In case of the reductive direction, E to F, the same method was used. Only the substrate solution containing $^3$H-E and unlabelled E and the recovery containing $^{14}$C—F and unlabelled F are different to the method used in the oxidative direction.

After testing all the inhibitors at 10 μM a dose-response experiment was done for the most potent 11 β-HSD type 1 and type 2 inhibitors. To look at the percentage of inhibition four different concentrations, 1, 5, 10 and 20 μM, were used. The method for both the rat liver, type 1 the reductive, and rat kidney, type 2 the oxidative, stay the same throughout the entire experiment.

Results

The Amount of Prot in Per μL of Rat Liver and Rat Kidney

An initial experiment was carried out to determine the amount of protein in rat liver cytosol and rat kidney cytosol, to be added to each tube. Graph 1 in FIG. 1 shows the standard curve from which the amount of protein used in both experiments was calculated. The amount of protein added to each tube in the rat liver experiment was 75.5 μg (per 25 μL). In the rat kidney experiment the amount of protein added to each tube was 135.6 μg (per 150 μL).

Enzyme Concentration and Time-Dependency of 11 β-HSD Activity

Figure 2:
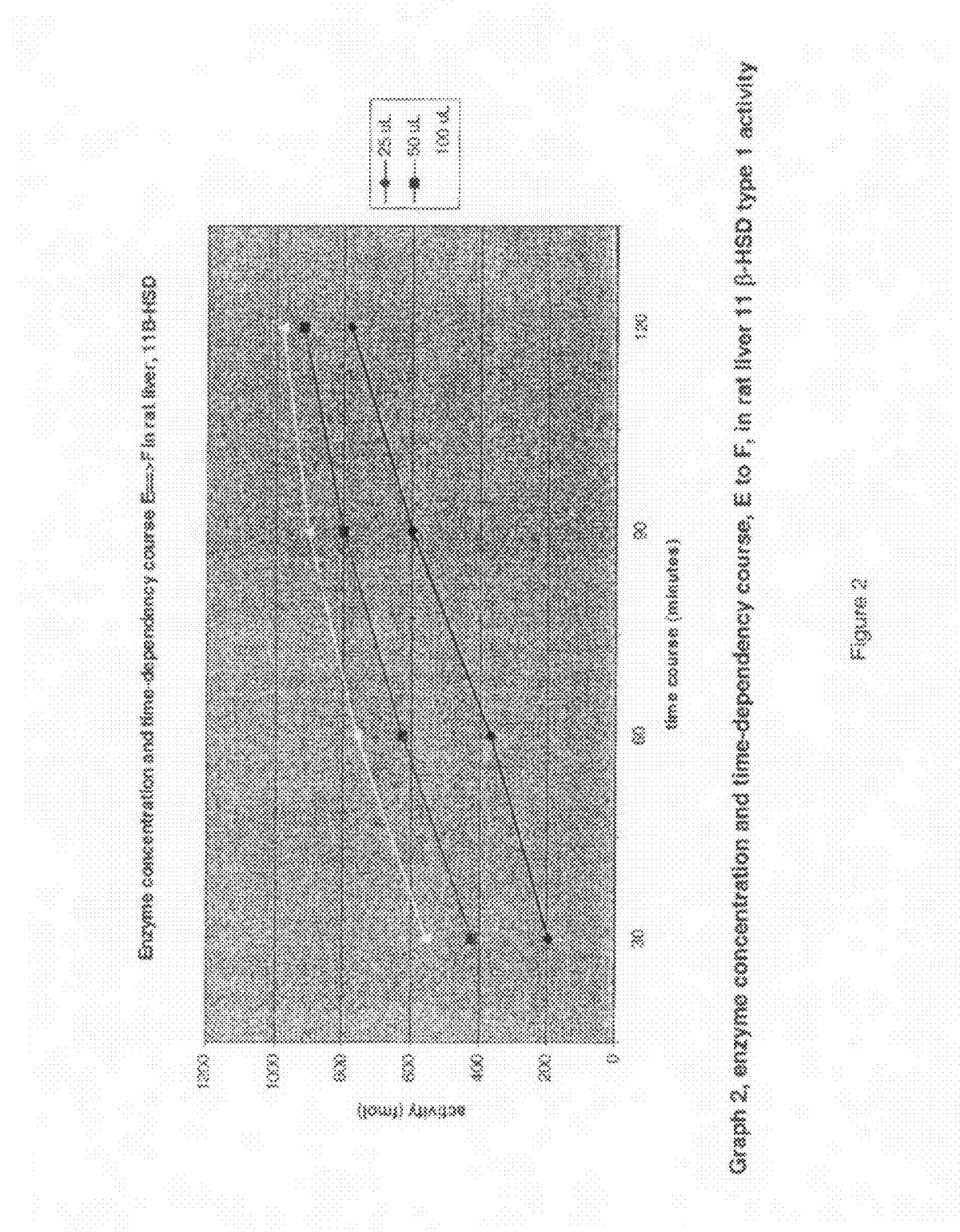
FIG. 2 is of graph 2 which shows the enzyme concentration and time-dependency course, E to F, in rat liver, 11 β-HSD type 1 activity.
Figure 3:
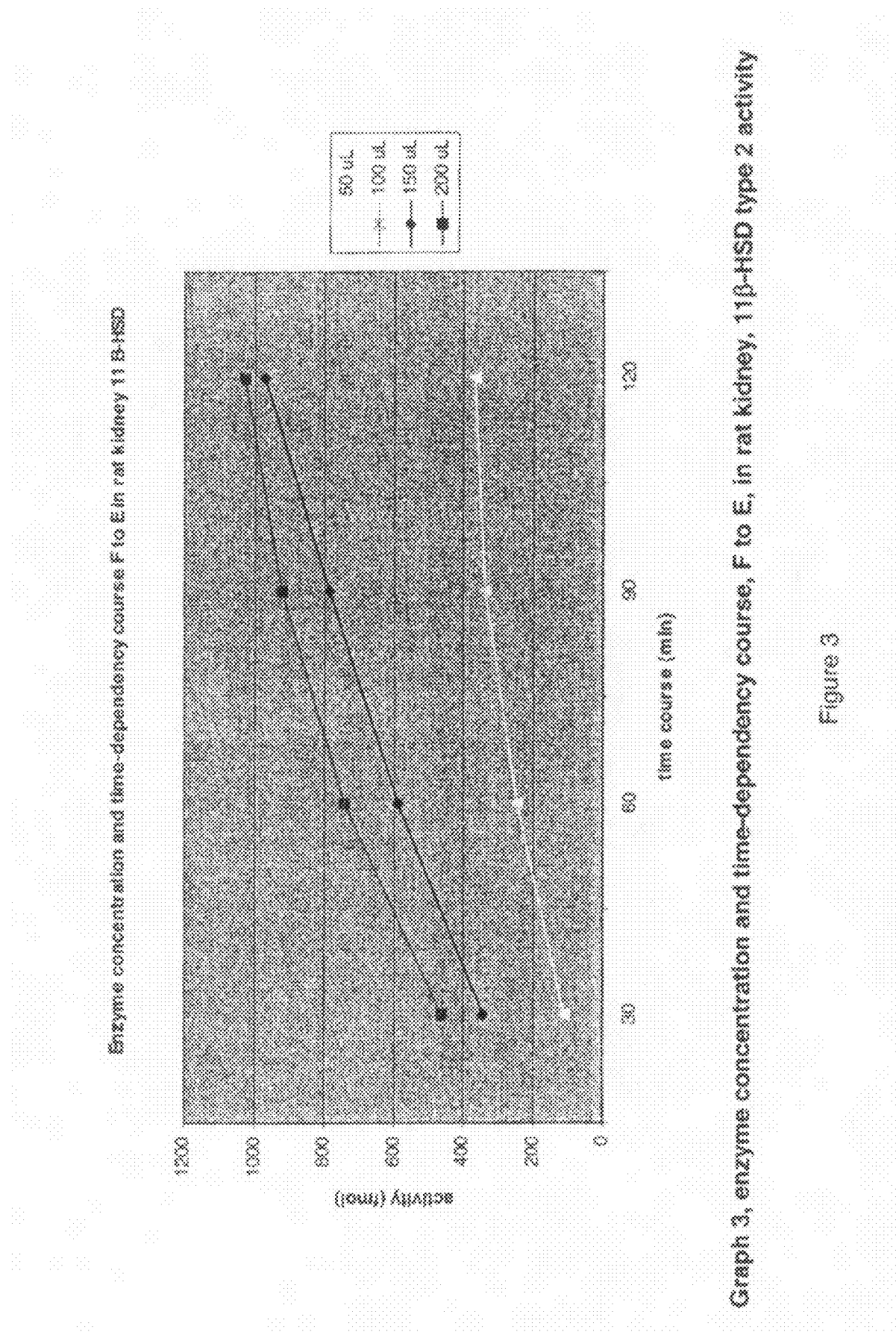
FIG. 3 is of graph 3 which shows the enzyme concentration and time-dependency course, F to E, in rat kidney, 11 β-HSD type 2 activity.

In this experiment the amount of rat liver homogenate and rat kidney homogenate added to each tube and the incubation time was determined. Graph 2 in FIG. 2 shows the enzyme concentration and time-dependency course of the rat liver experiment E to F, 11 β-HSD type 1 activity. Graph 3 in FIG. 3 shows the enzyme concentration and time-dependency course F to E, 11 β-HSD type 2 activity. After drawing the graphs the optimal amount of rat liver cytosol and rat kidney cytosol and both their incubation times were selected. One important rule when selecting both variables, to select an amount of rat liver and rat kidney and incubation time on a linear part of the graph. This is done to avoid fluctuations in enzyme activity. The amount of rat liver cytosol selected was 25 μL and 90 minutes of incubation time, the amount of rat kidney cytosol selected was 150 μL and 60 minutes of incubation time.

The 11 β-HSD Inhibitors

In this experiment the influence of different inhibitors on the conversion E to F and F to E was determined. The reason why inhibition in both directions was examined was to make a comparison between the inhibitors and which type of 11 β-HSD they inhibit more. Compounds were screened for their ability to inhibit 11 β-HSD type 1 (E to F) and type 2 (F to E). All the inhibitors were initially tested at a 10 μM concentration. The percent of inhibition was calculated as the percentage of decrease in radio labelled $^3$H-E and $^3$H—F of product formed, compared with the control activity (the tubes without an inhibitor in it). All the results calculated are means, n=2.

TABLE 2

| | | Inhibitory Effect | |
|---|---|---|---|
| STX No. | Structure | % inhibition of 11β HSD1 @ 10 μM typical sd ± 5% | % inhibition of 11β HSD2 @ 10 μM typical sd ± 5% |
| 412 | | 27 | 3 |
| 413 | | 53 n = 2 $IC_{50}$ = 6.6 μM | 0.2 |
| 421 | | 60 n = 2 $IC_{50}$ = 10 μM | 0.9 |
| 424 | | 24 | 0.7 |

TABLE 2-continued

Inhibitory Effect

| STX No. | Structure | % inhibition of 11β HSD1 @ 10 μM typical sd ± 5% | % inhibition of 11β HSD2 @ 10 μM typical sd ± 5% |
| --- | --- | --- | --- |
| 425 | 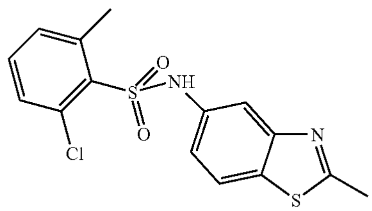 | 40 | 0.0 |
| 469 | 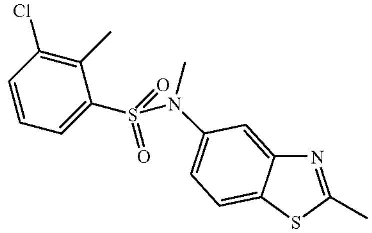 | 63 | 29 |
| 470 | 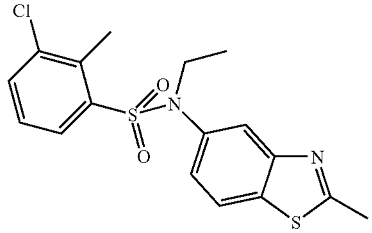 | 39 | 30 |
| 519 | 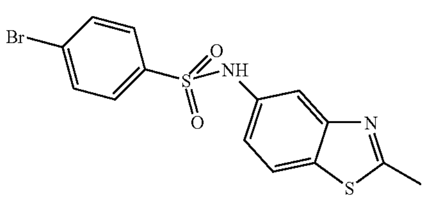 | 48 | 8 |
| 521 | 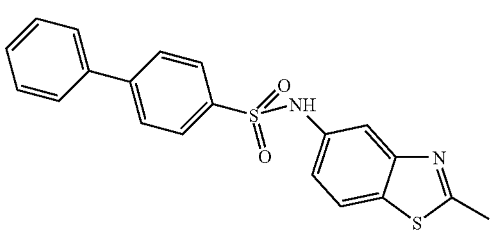 | 0.5 | 5 |
| 522 | 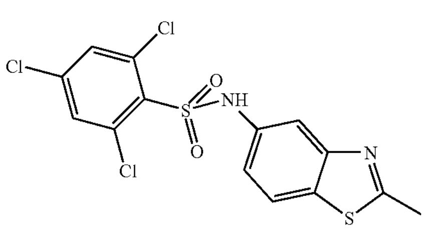 | 37 | 6 |

TABLE 2-continued

Inhibitory Effect

| STX No. | Structure | % inhibition of 11β HSD1 @ 10 μM typical sd ± 5% | % inhibition of 11β HSD2 @ 10 μM typical sd ± 5% |
| --- | --- | --- | --- |
| 523 | 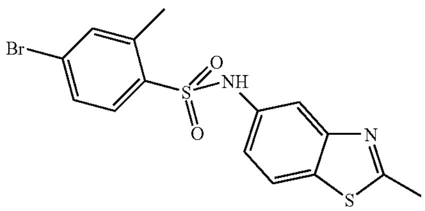 | 21 | 8 |
| 524 | 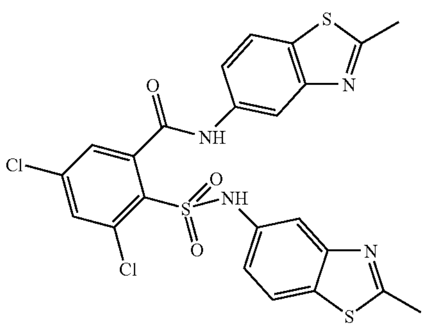 | 31 | 53 |
| 552 | 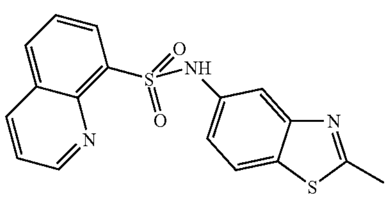 | 18 | 24 |
| 553 | 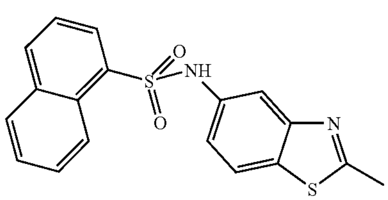 | 0.7 | 18 |
| 554 | 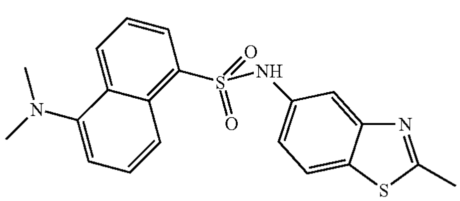 | 69 | 43 |
| 575 | 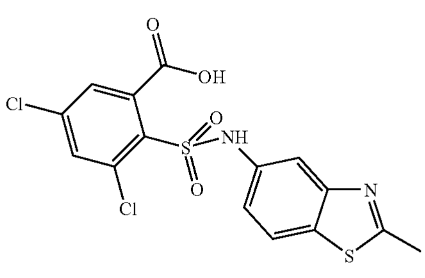 | 62 | 1.6 |

TABLE 2-continued

| | Inhibitory Effect | |
|---|---|---|
| STX No. Structure | % inhibition of 11β HSD1 @ 10 μM typical sd ± 5% | % inhibition of 11β HSD2 @ 10 μM typical sd ± 5% |
| 580 | 75 | 1.4 |
| 581 | 77 | 32 |
| 582 | 40 | 0.7 |
| 583 | 29 | 0.4 |
| 584 | 48 | 10 |
| 585 | 48 | 1.6 |

TABLE 2-continued
Inhibitory Effect
| STX No. | Structure | % inhibition of 11β HSD1 @ 10 μM typical sd ± 5% | % inhibition of 11β HSD2 @ 10 μM typical sd ± 5% |
|---|---|---|---|
| 701 | 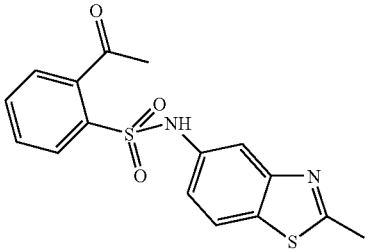 | 34 | 36 |
| 703 | 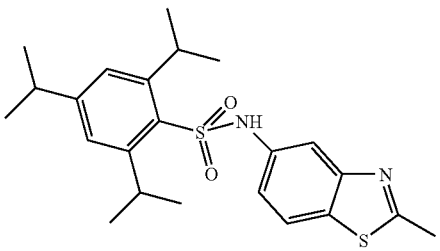 | 35 | 4 |
| 704 | 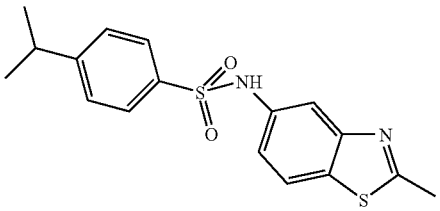 | 38 | 4 |
| 705 | 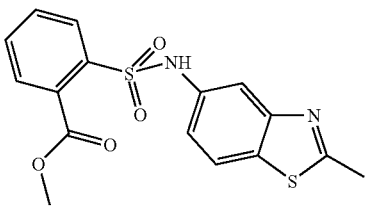 | 6 | 6 |
| 706 | 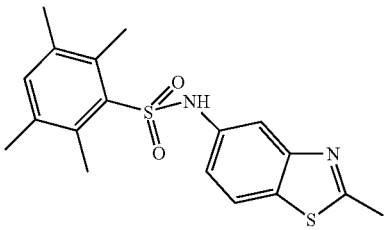 | 29 | 7 |
| 707 | 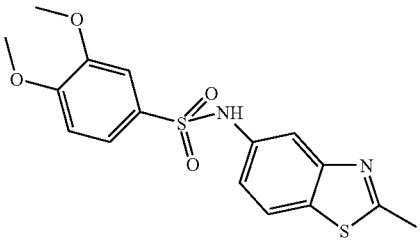 | 21 | 11 |

TABLE 2-continued

Inhibitory Effect

| STX No. | Structure | % inhibition of 11β HSD1 @ 10 μM typical sd ± 5% | % inhibition of 11β HSD2 @ 10 μM typical sd ± 5% |
|---|---|---|---|
| 708 | 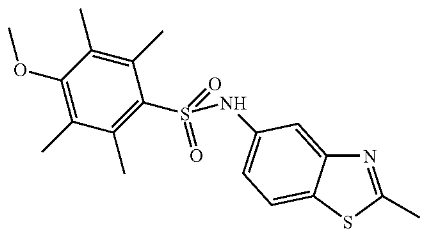 | 39 | 11 |
| 709 | 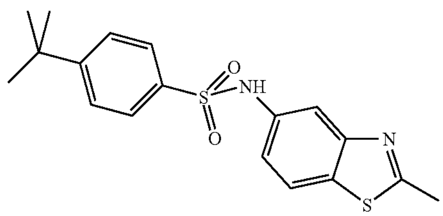 | 10 | 13 |
| 710 | 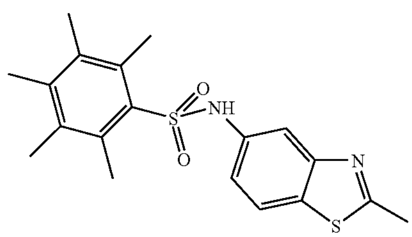 | 55 | 10 |
| 711 | 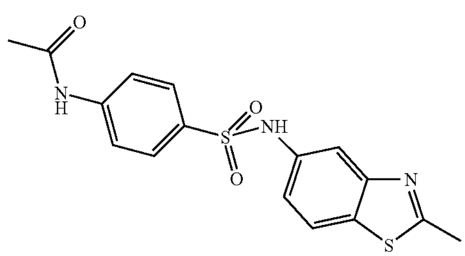 | 37 | 6 |
| 712 | 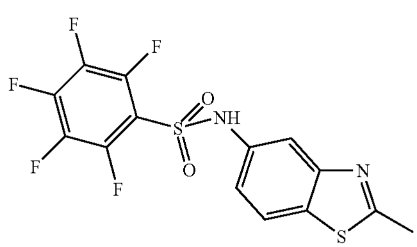 | 24 | 3 |
| 713 | 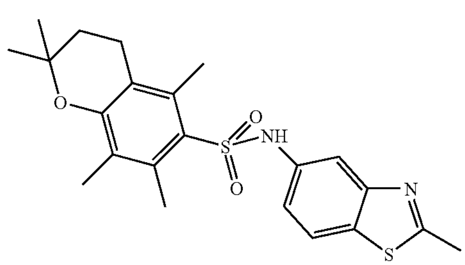 | 26 | 3 |

TABLE 2-continued

Inhibitory Effect

| STX No. | Structure | % inhibition of 11β HSD1 @ 10 μM typical sd ± 5% | % inhibition of 11β HSD2 @ 10 μM typical sd ± 5% |
|---|---|---|---|
| 730 | 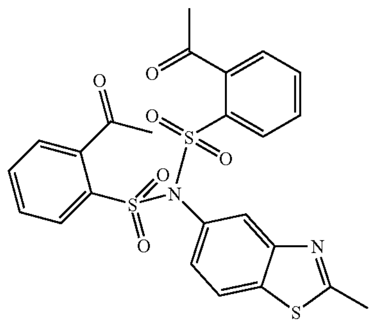 | 32 | 9 |
| 731 | 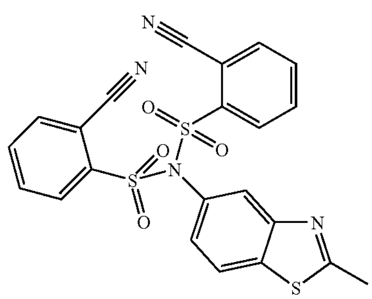 | 45 | 12 |
| 750 | 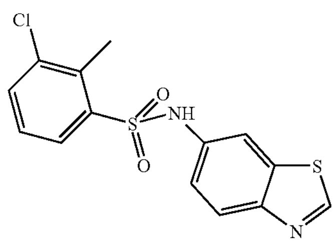 | 4 | 10 |
| 751 | 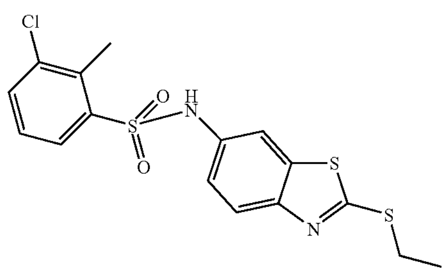 | 10 | 5 |
| 752 | 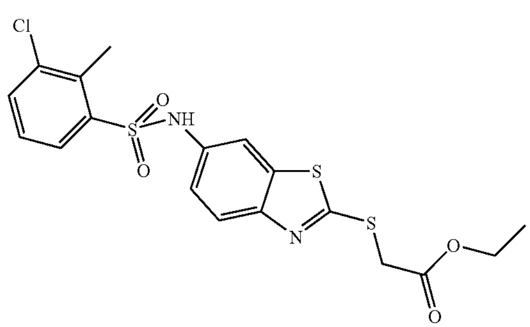 | 5 | 1 |

TABLE 2-continued

| | | Inhibitory Effect | |
|---|---|---|---|
| STX No. | Structure | % inhibition of 11β HSD1 @ 10 μM typical sd ± 5% | % inhibition of 11β HSD2 @ 10 μM typical sd ± 5% |
| 753 | [structure] | 8 | 2 |
| 754 | [structure] | 20 | 6 |
| 755 | [structure] | 21 | 8 |

Biological Assay Development Using Human 11β-Hydroxysteroid Dehydrogenase Type 1.

Standard Operating Procedure for the 11β-Hydroxysteroid Dehydrogenase Type 1 Cortisol Radioimmunoassay.

11β HSD1 Cortisol RIA

Reagents: Cortisone, Cortisol (Hydrocortisone), NADPH, Glucose-6-phosphate, Glycyrrhetinic acid (GA), Dextran coated charcoal (C6197) and DMSO were obtained from Sigma Aldrich, Carbenoxolone was obtained from ICN Biomedicals, Product 215493001, $^3$H-cortisone was obtained from American Radiolabelled Compounds Inc, Product ART-743, $^3$H-cortisol was obtained from NEN, Product NET 396, $^{14}$C-cortisol was obtained from NEN, Product NEC 163, human hepatic microsomes were obtained from XenoTech, product H0610/Lot 0210078, rat hepatic microsomes were obtained from XenoTech, SPA beads were obtained from Amersham, Product RPNQ0017, the Immunoassay kit was obtained from Assay Designs, Product 900-071, the Immunologicals Direct anti-cortisol antibody was Product OBT 0646, the Sigma anti-cortisol antibody was Product C8409 and the Immunotech antibody was supplied by Beckman, Product IMBULK3 6D6.

Buffer Solutions

Buffer 1, from Barf [15]: 30 mM Tris-HCL, pH 7.2, containing 1 mM EDTA

Buffer 2, from the Sterix protocol: PBS (pH 7.4) containing 0.25M sucrose

Buffer 3, from the Sigma RIA protocol: 50 mM Tris-HCL, pH 8, containing 0.1 M NaCL and 0.1% gelatin Stop solution, from Barf [15]: 1 mM glycyrrhetinic acid in 100% DMSO Enzyme assays were carried out in the presence of 181 μM NADPH, 1 mM Glucose-6-Phosphate and cortisone concentrations indicated for each experiment.

Enzyme assay buffer: 30 mM Tris-HCL, pH 7.2 containing 1 mM EDTA

Antibody binding buffer: 50 mM Tris-HCL, pH 8, containing 0.1 M NaCl and 0.1% gelatin Compound preparation: Prepare 10 mM stock solutions in 100% DMSO at 100 times the required assay concentration. Dilute into assay buffer 1 in 25. Also dilute neat DMSO 1 in 25 into assay buffer for controls.

Substrate preparation: Prepare a solution of cortisone in ethanol 600 times the required assay concentration (175 nM). Dilute this 1 in 50 into assay buffer.

Prepare NADPH as a 1.8 mg/ml solution in assay buffer.

Prepare G-6-P as a 3.65 mg/ml solution in assay buffer.

Mix these 3 solutions 1:1:1 to make a solution of sufficient volume for 25 µl additions to each sample. Add 0.5 µCi tritiated cortisone per 25 µl and mix the solution well.

Microsome preparation: Dilute stock 20 mg/ml solution 1 in 100 with assay buffer.

Antibody preparation: Dilute stock antibody solution to 17 µg/ml in antibody binding buffer.

Dextran coated charcoal preparation: Make a 20 mg/ml solution in antibody binding buffer and chill on ice.

Enzyme assay: To a u-bottom polypropylene 96 well plate add:

25 µl compound dilution or diluted DMSO to controls, NSB's and blanks

10 µl 1 mM GA in DMSO (enzyme stop solution) to blanks

25 µl substrate mixture to all samples

50 µl diluted microsomes to all samples

Incubate plate for 30 min at 37° C. shaking

Add 10 µl enzyme stop solution to all wells except the blanks

Add 100 µl antibody solution to all wells except the NSB's, add antibody binding buffer to these wells Incubate at 37° C. for 1 h Chill plate on ice for 15 min Add 50 µl/well charcoal solution and mix with an 8-channel pipette (4-5 aspirations)

Chill the plate on ice

Centrifuge at 4° C., 2000×g for 15 min

Transfer 100 µl supernatant into an Optiplate, also add 25 µl substrate mixture to 2 empty wells to indicate counting efficiency Add 200 µl Microscint-40 to all wells and count on a Topcount Radioimmunoassay The 11β HSD1 enzyme assay was carried out following the standard operating procedure described above in u-bottom polypropylene 96 well plates or 1.5 ml Eppendorf tubes as indicated for each experiment. Subsequent to stopping the enzyme reaction, 100 µl antibody prepared in buffer 3 unless otherwise indicated was added to test samples and 100 µl buffer 3 was added to the NSB samples. The samples were incubated for 1 hour at 37° C. and the chilled on ice for 15 mins. Dextran coated charcoal (50 µl/sample) prepared to the indicated concentration in buffer 3 was added and the samples were mixed (vortex for tubes and aspiration 5 times with an 8-channel pipette for 96 well plates) and chilled for a further 10 min. The samples were centrifuged at 2000×g for 15 min at 4° C. to pellet the charcoal. Aliquots of the supernatant (100 µl) were transferred to an Optiplate and counted on the Topcount in 150-200 µl Microscint 40. In some experiments, aliquots of supernatant were transferred to scintillation vials and counted on the Tricarb LSC in 5 ml Ultima Gold scintillant.

11β HSD1 Assay Development

11β HSD1 TLC format assay

S Paration of Cortison and Cortisol

Prior to performing an enzyme assay, solvent systems reported in the literature for separation of cortisone from cortisol were investigated [16, 17]. Solutions of cortisone and cortisol at 10 mg/ml were prepared in methanol, and aliquots spotted onto a silica gel TLC plate. The plate was run in $CH_2Cl_2$: IMS 92:8 v/v (2). The plate was then air dried and sprayed with 0.1% Rhodamine B in methanol to visualise the spots. The table below describes the separation obtained.

TABLE 3

| Separation of cortisone from cortisol by TLC | | |
|---|---|---|
| Steroid | Distance run from origin (cm) | Solvent front migration/ steroid migration (cm) |
| Cortisone | 7.5 | 2.3 |
| Cortisol | 4.5 | 3.8 |

This separation was considered adequate for use in an enzyme assay.

Figure 4:
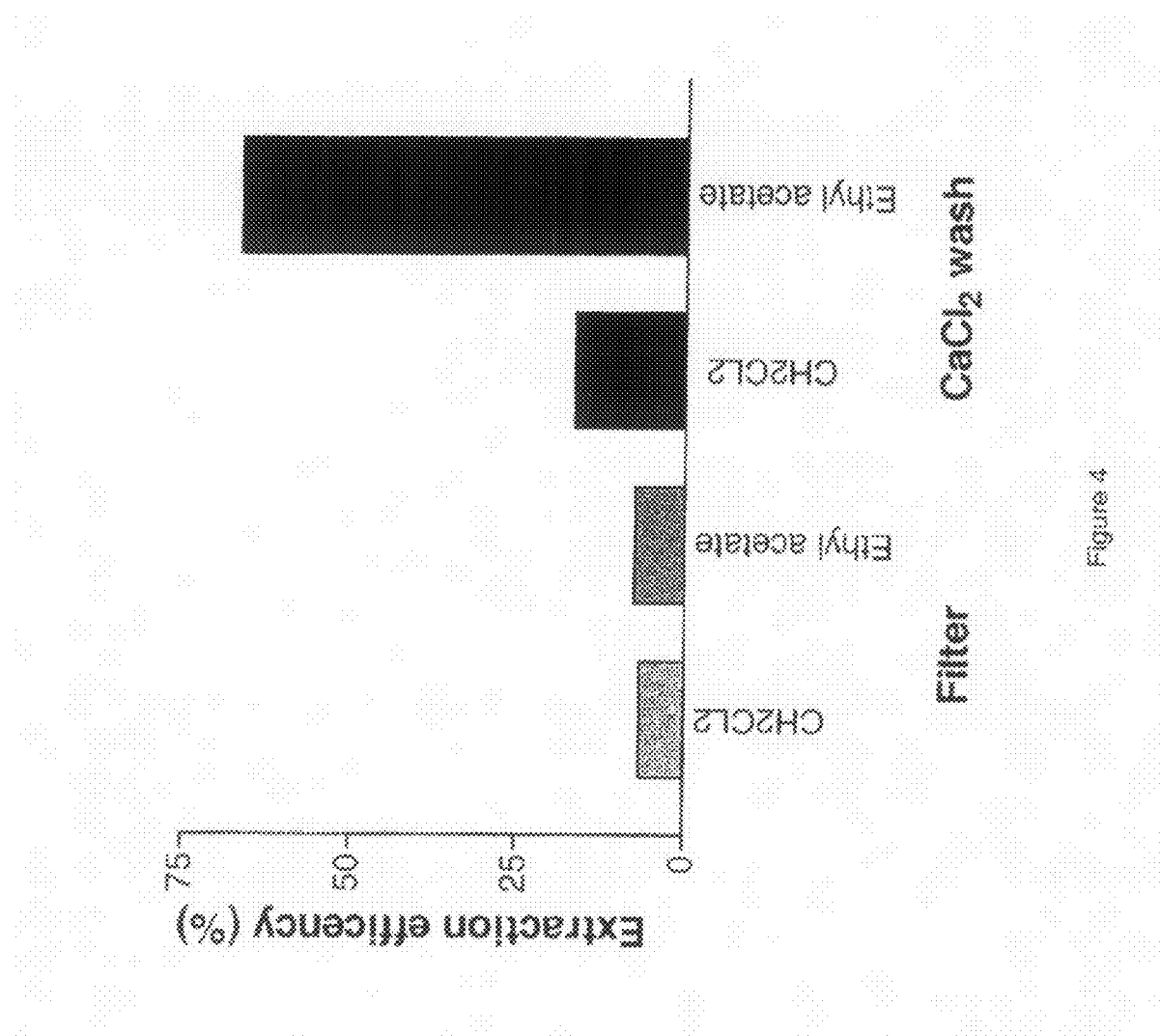
FIG. 4 is a graph showing extraction efficiencies obtained with four extraction methods.

The literature details several methods of extracting cortisol from aqueous solution [16, 17]. In order to select a method for use, [$^{14}$C]-labelled cortisol was obtained from NEN. A stock was prepared in phosphate buffered saline (PBS) containing 4000 DPM in 50 µl with cold cortisol (1 µg) added as a carrier. The final ethanol concentration was 0.4%. Aliquots of this solution were added to glass tubes (100 µl) and the following extractions were carried out: 1. 1 ml $CH_2Cl_2$, vortex and pass through phase separating filter paper (Whatman, IPS) 2. 1 ml ethyl acetate, vortex and pass through phase separating filter paper 3. 1 ml $CH_2Cl_2$ and 200 µl 0.05% $CaCl_2$, vortex, centrifuge (50 µg for 5 min) and remove upper aqueous phase 4. 1 ml ethyl acetate and 200 µl 0.05% $CaCl_2$, vortex, centrifuge (50 µg for 5 min) and collect upper organic phase. The organic phases were dried and the residues were taken up in 100 µl IMS. An aliquot of this was spotted onto a TLC plate and the plate run as before. Following visualisation with Rhodamine B, the spots were scraped into scintillation vials and counted on a liquid scintillation counter (Packard TriCarb) in 5 ml Ultima gold scintillant. Extraction efficiencies were calculated and are given in FIG. 4.

From these results it appears that 90% of the cortisol is lost by phase separating filtration. Ethyl acetate appears to extract cortisol more efficiently than $CH_2Cl_2$, possibly because the organic phase is easier to collect. Ethyl acetate appears to be a suitable method of extraction.

Human and Rat Hepatic Microsomal 11β-HSD1 Activity.

Figure 5:
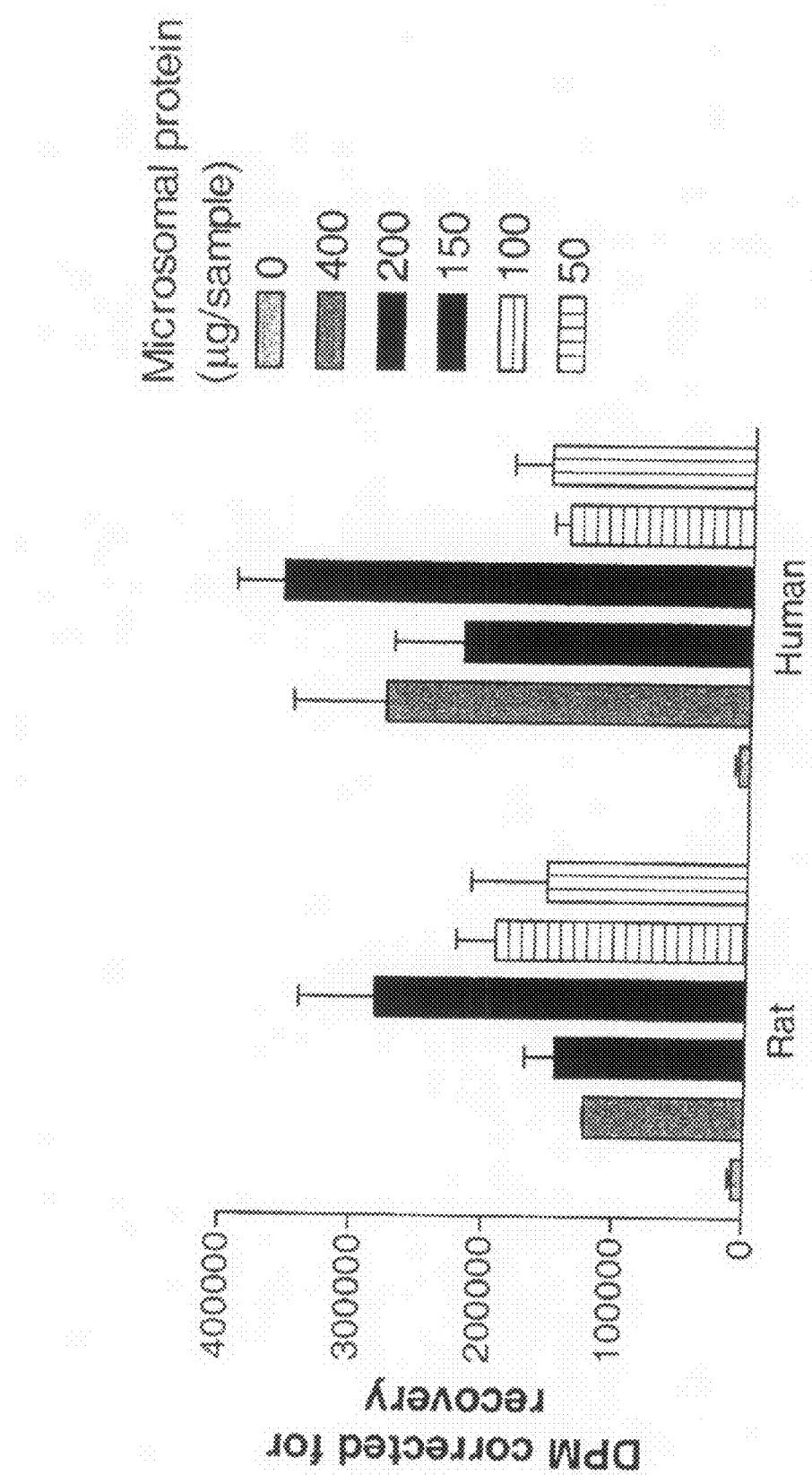
FIG. 5 is a graph showing a comparison of 11β-HSD1 activity in rat and human hepatic microsomes.

11β-HSD1 activity in rat and human hepatic microsomes was evaluated, to determine the minimum microsomal protein concentrations required for measurement of enzyme activity. The experiment was done according to the Bradford Method [14]. The assay was performed in Buffer 2 and the cortisone concentration used was 2 µM containing 0.5 µCi [$^3$H]-cortisone per incubation. Microsomes were tested at concentrations ranging from 50 µg to 400 µg protein per incubation in a final incubation volume of 100 µl in glass tubes. Samples were incubated for 1 h in a shaking water bath at 37° C. and the assay was stopped by addition of 1 ml ethyl acetate. To correct for recovery, 50 µl [$^{14}$C]-cortisol was added to the samples followed by 200 µl 0.05% $CaCl_2$. The samples were vortex mixed and centrifuged as described above. The upper organic phase was removed and dried down, and the residue dissolved in 100 µl methanol and 50 µl aliquots were spotted onto TLC plates, which were run as described above. Samples were counted on a TriCarb liquid scintillation counter using a dual label programme. Recovery efficiency was determined from the DPM obtained in 50 µl [$^{14}C$]-cortisol solution, which was counted with the samples. Results are shown in FIG. 5.

The 11β-HSD1 activities in rat and human microsomes were similar, 0.7 µmol/mg/min and 0.5 µmol/mg/min for rat and human microsomes respectively. The activity in human microsomes is apparently not related to microsomal protein concentration, which may suggest that that the protein concentration range examined is too high.

Figure 6:
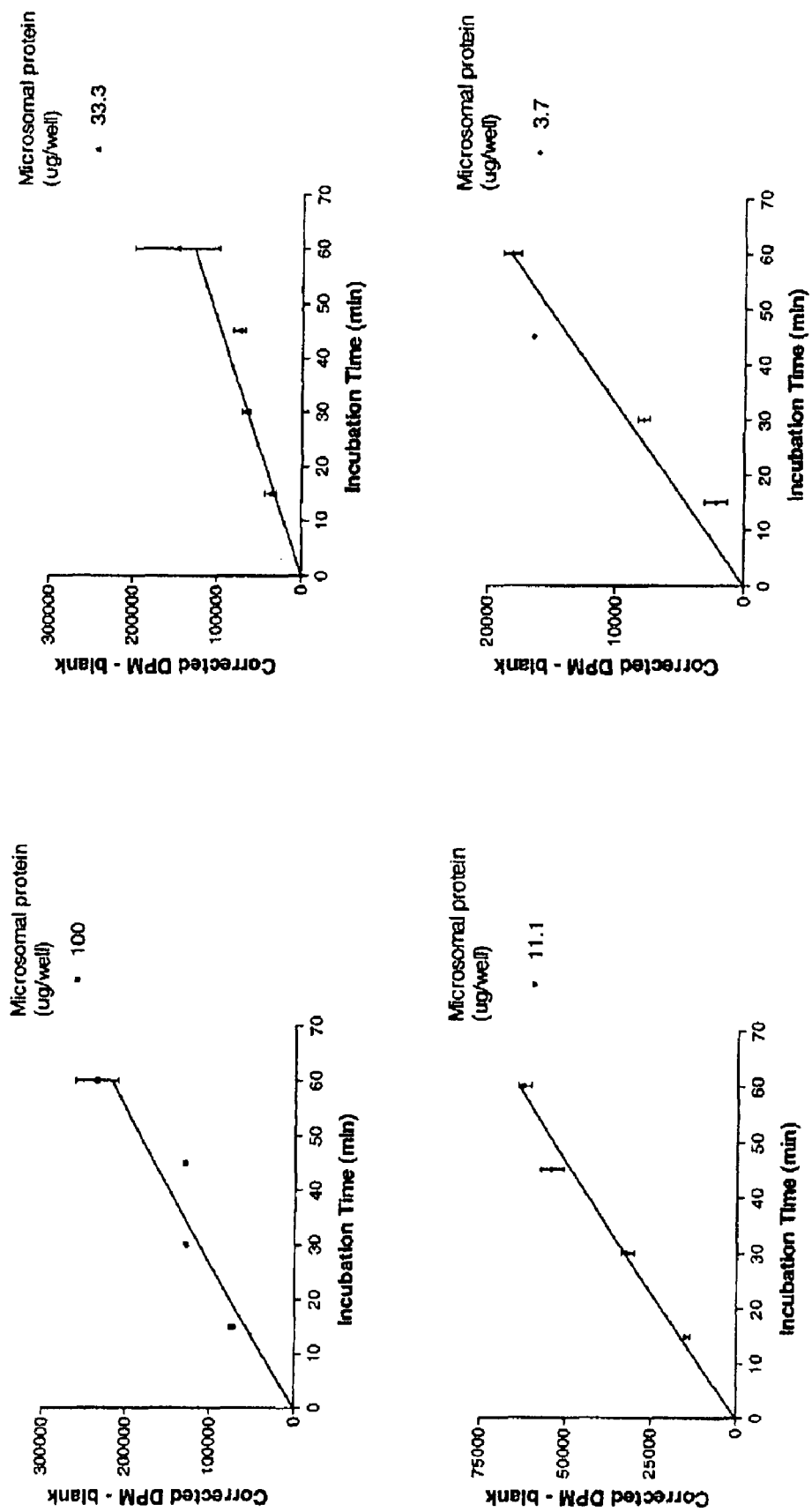
FIG. 6 is a series of graphs showing the effect of incubation time on human microsomal 11β-HSD1 activity.
Figure 7:
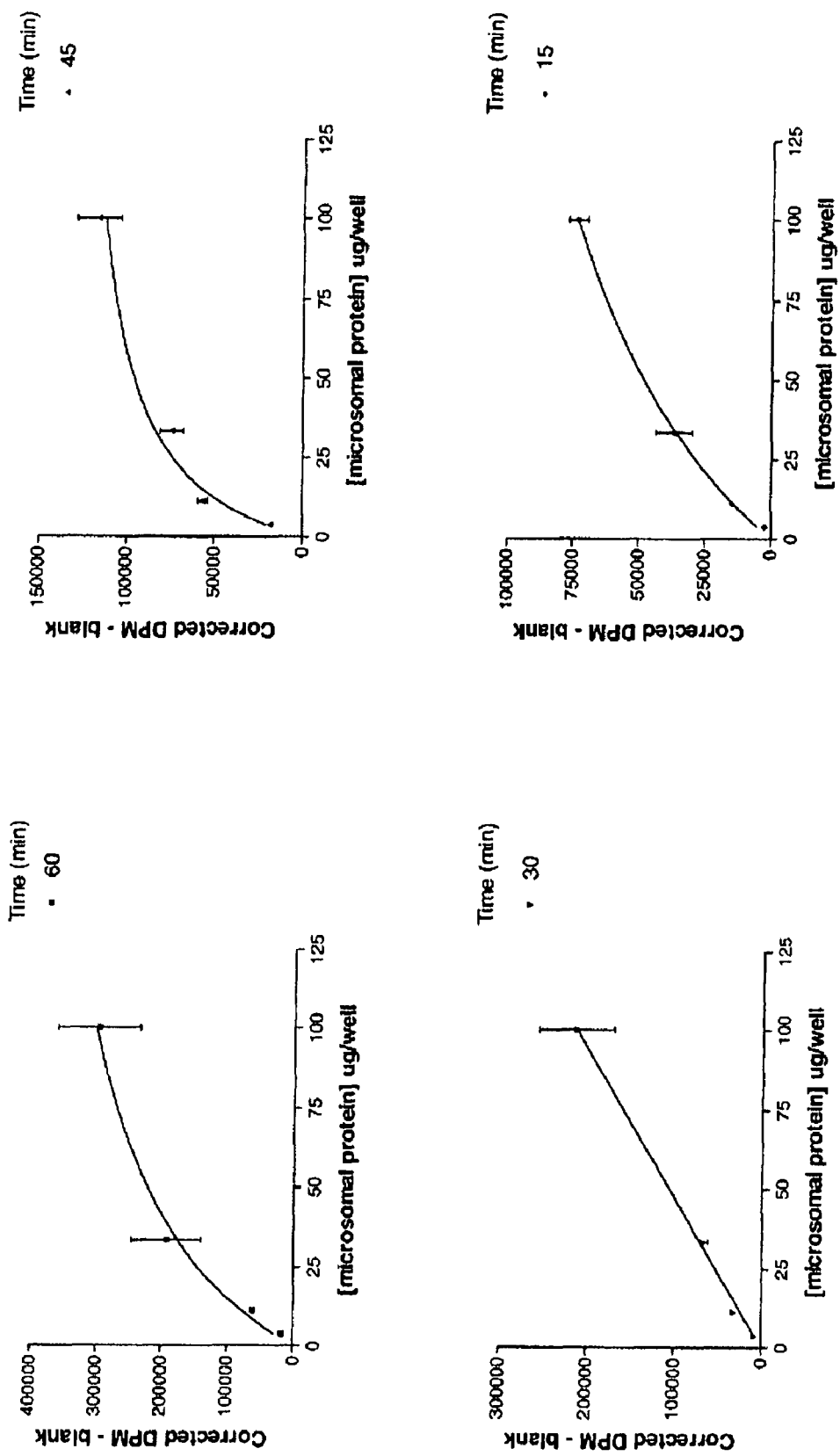
FIG. 7 is a series of graphs showing the effect of microsomal protein concentration on human microsomal 11β-HSD1 activity.

Lower human microsome protein concentrations were evaluated; 3.7 µg to 100 µg per sample. The time course of activity was also determined, from 0 to 60 minutes at 37° C. The extraction conditions were as described above. The results from these experiments are shown in FIGS. 6 and 7.

The results shown in FIGS. 6 and 7 demonstrate that enzyme activity is linear at incubation times up to 30 min at all the microsomal protein concentrations tested, and that enzyme activity is linear at microsomal protein concentrations below 30 µg per sample.

Figure 8:
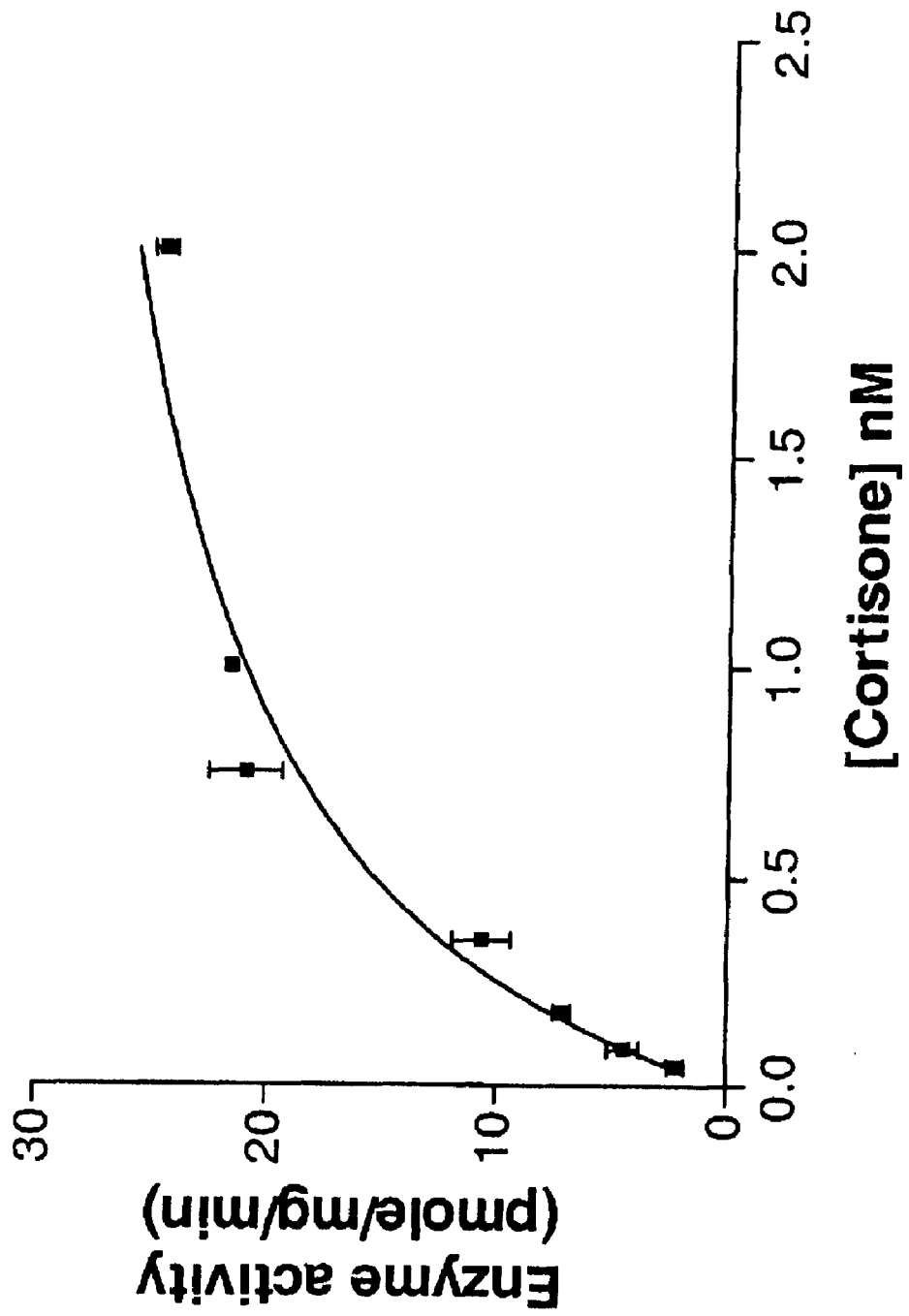
FIG. 8 is a graph showing the substrate (cortisone) saturation curve for human hepatic microsomal 11β HSD1.

The influence of substrate concentration on activity was examined. The [$^3H$]-cortisone concentration was kept constant at 0.5 µCi/sample, and unlabelled cortisone varied from 44 nM to 2 µM. The assay was carried out with 10 µg microsomal protein per sample with an incubation time of 30 minutes at 37° C. The results are shown in FIG. 8. A double reciprocal plot (Lineweaver-Burke) of these data gives an apparent Km for cortisone of 660 nM, FIG. 9.

Figure 10:
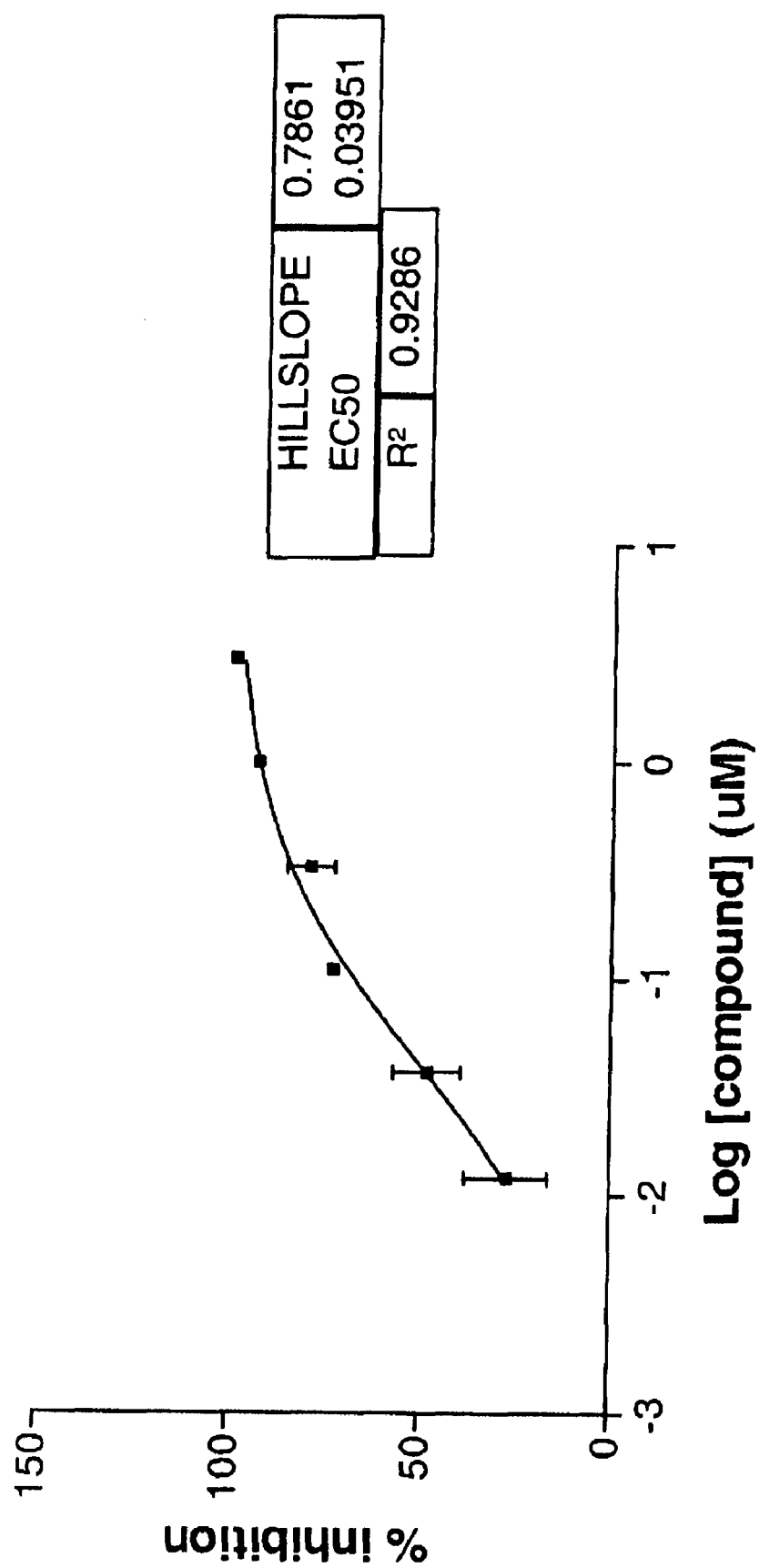
FIG. 10 is a graph showing the $IC_{50}$ determination for glycyrrhetinic acid.
Figure 11:
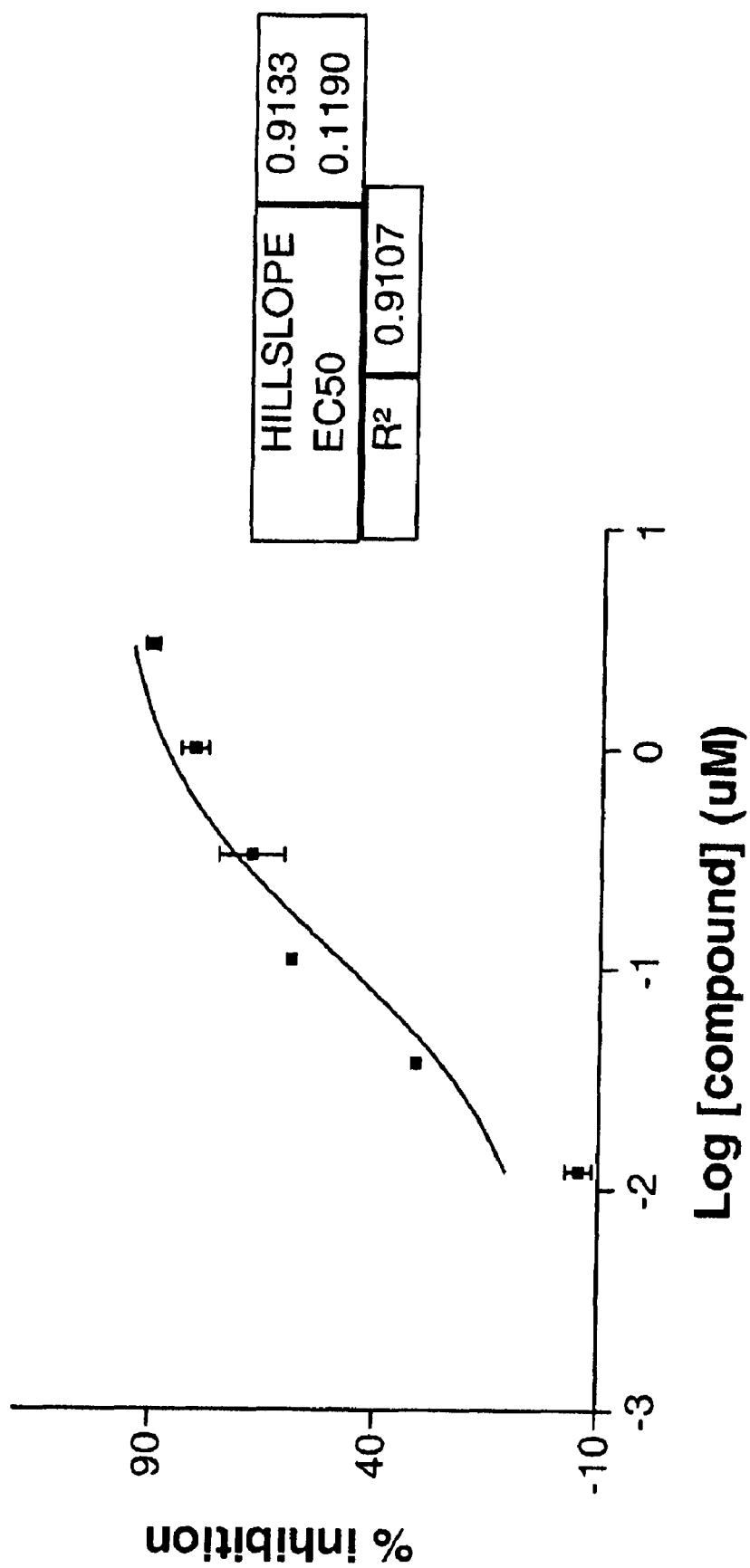
FIG. 11 is a graph showing the $IC_{50}$ determination for carbenoxolone.

The standard compounds glycyrrhetinic acid and carbenoxolone were examined in this assay system, as part of the validation process. The assay was performed using 175 nM cortisone substrate, with 10%1 g microsomal protein and a 30 minute incubation at 37° C., as described by Barf [15]. Although the data in FIGS. 8 and 9 above suggest that this substrate concentration is not saturating under these assay conditions. Glycyrrhetinic acid and carbenoxolone were tested at concentrations from 0.012 µM to 3 µM, the DMSO concentration was 1% in all samples. The results are shown in FIGS. 10 and 11.

Glycyrrhetinic acid and carbenoxolone give $IC_{50}$ values of 40 nM and 119 nM respectively. The $IC_{50}$ reported for carbenoxolone by Barf et al. using the SPA format and recombinant 11β-HSD is 330 nM [15], approximately three-fold less potent. The difference in potency in the two assay systems is probably due to the different assay conditions, SPA compared to the end point, and also the enzyme source, native hepatic enzyme compared to recombinant enzyme.

The assay conditions described above support good enzyme activity however, which should be transferable to a 96 well plate format.

Development of High Throughput 11β HSD1 Assays

Supply of the antibody used by Barf [15] in the Scintillation Proximity assay (SPA) proved problematic. A sample batch of the antibody (from Immunotech) was tested for suitability and a second order was placed for a larger quantity. A robust 96 well plate assay using Radioimmunoassay (RIA) format was developed using the Immunotech antibody available, this is described below.

Immunoassay Format

An Assay Designs enzyme immunoassay system was evaluated as a potential assay format. The basis of the assay is competition for antibody binding between sample cortisol, generated by 11β-HSD1, and labelled cortisol binding. The anti-cortisol detection antibody provided in the kit is a mouse monoclonal, reported to cross react less than 0.1% with cortisone. The kit is designed for the analysis of cortisol levels in saliva, urine, serum and plasma and also in tissue culture media, rather than for determining enzyme activity however.

Figure 12:
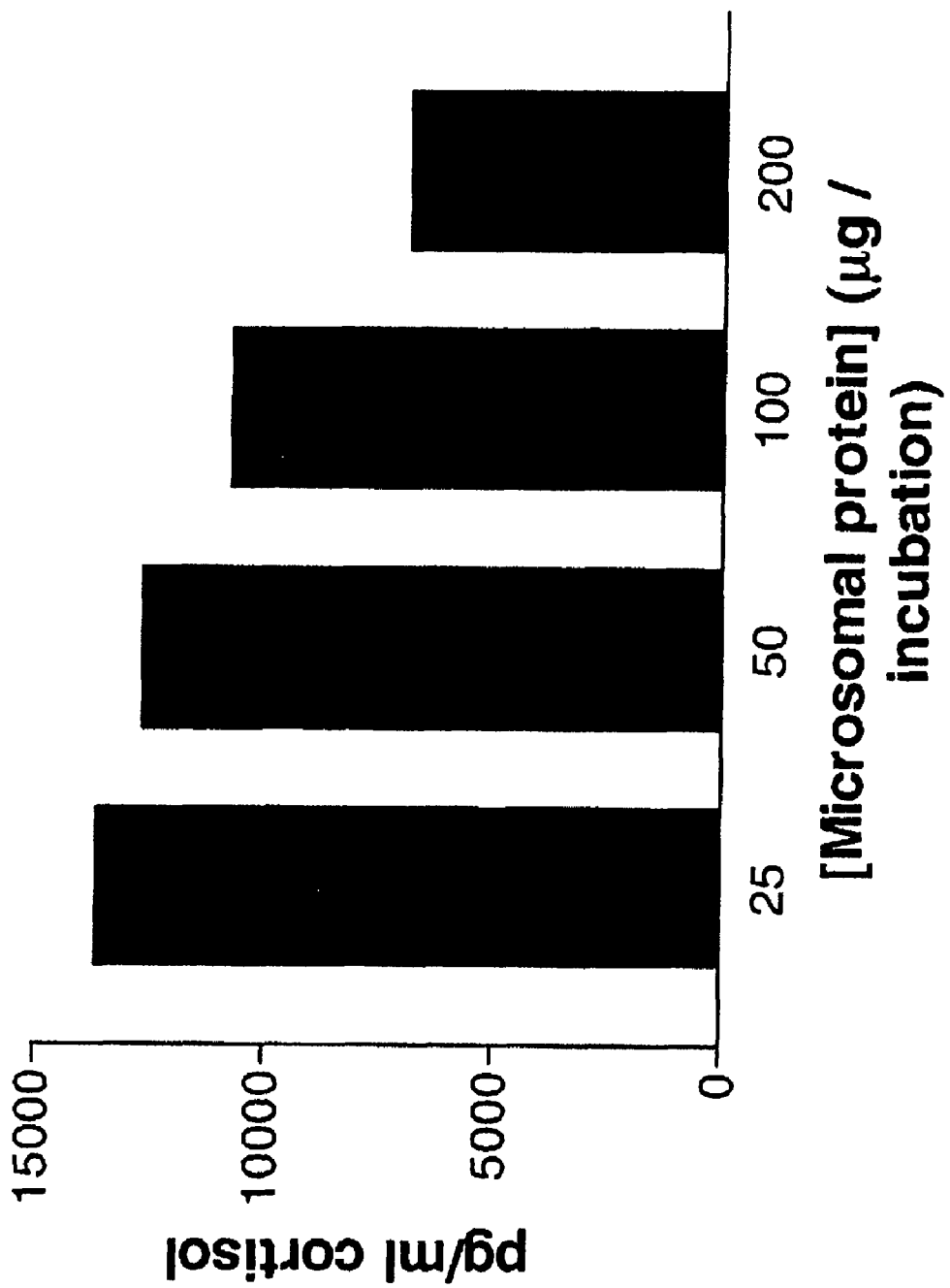
FIGS. 12(A), 12(B) and 12(C) are graphs showing the 11β-HSD1 activity measured by Immunoassay.
Figure 12:
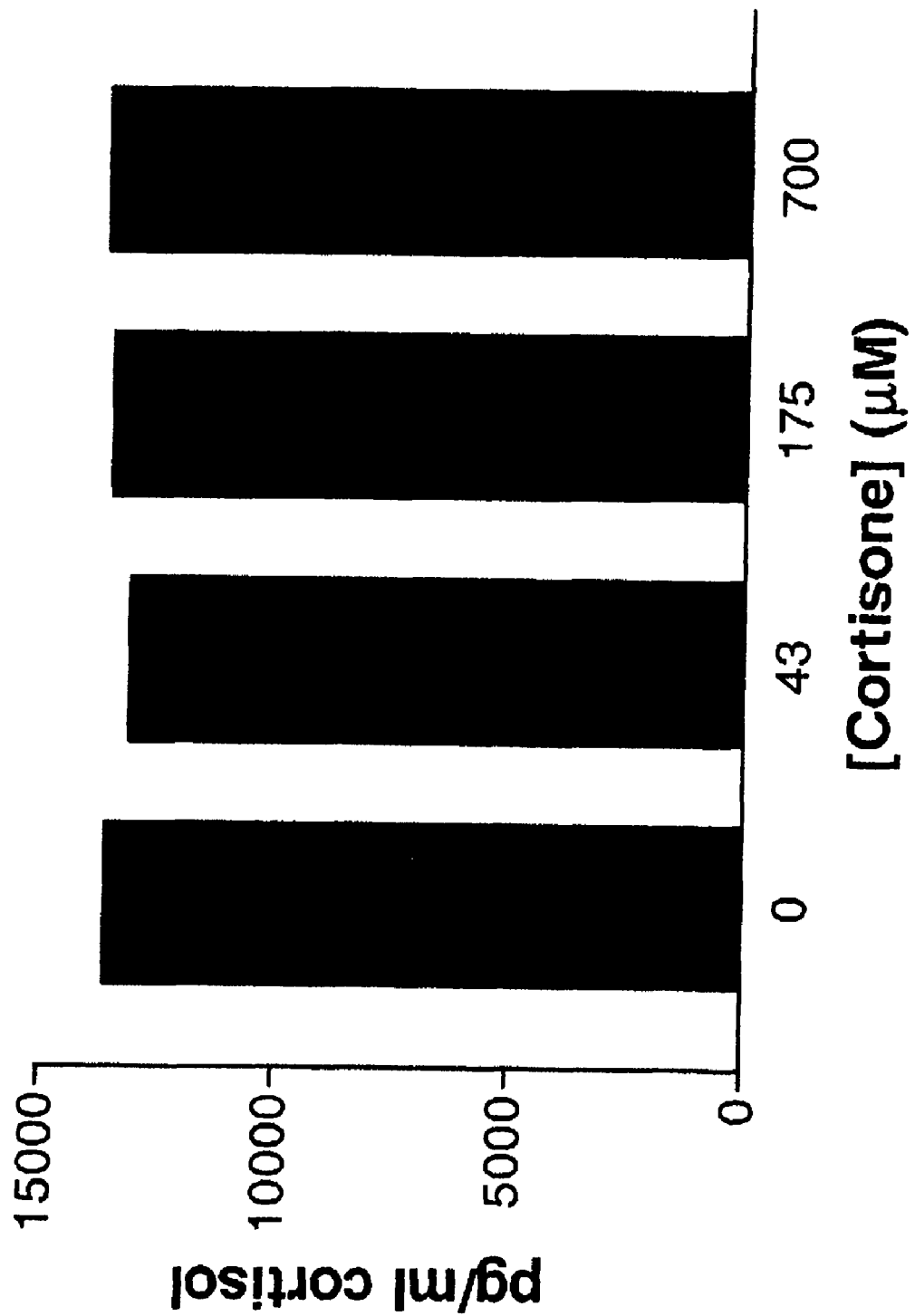
Figure 12:
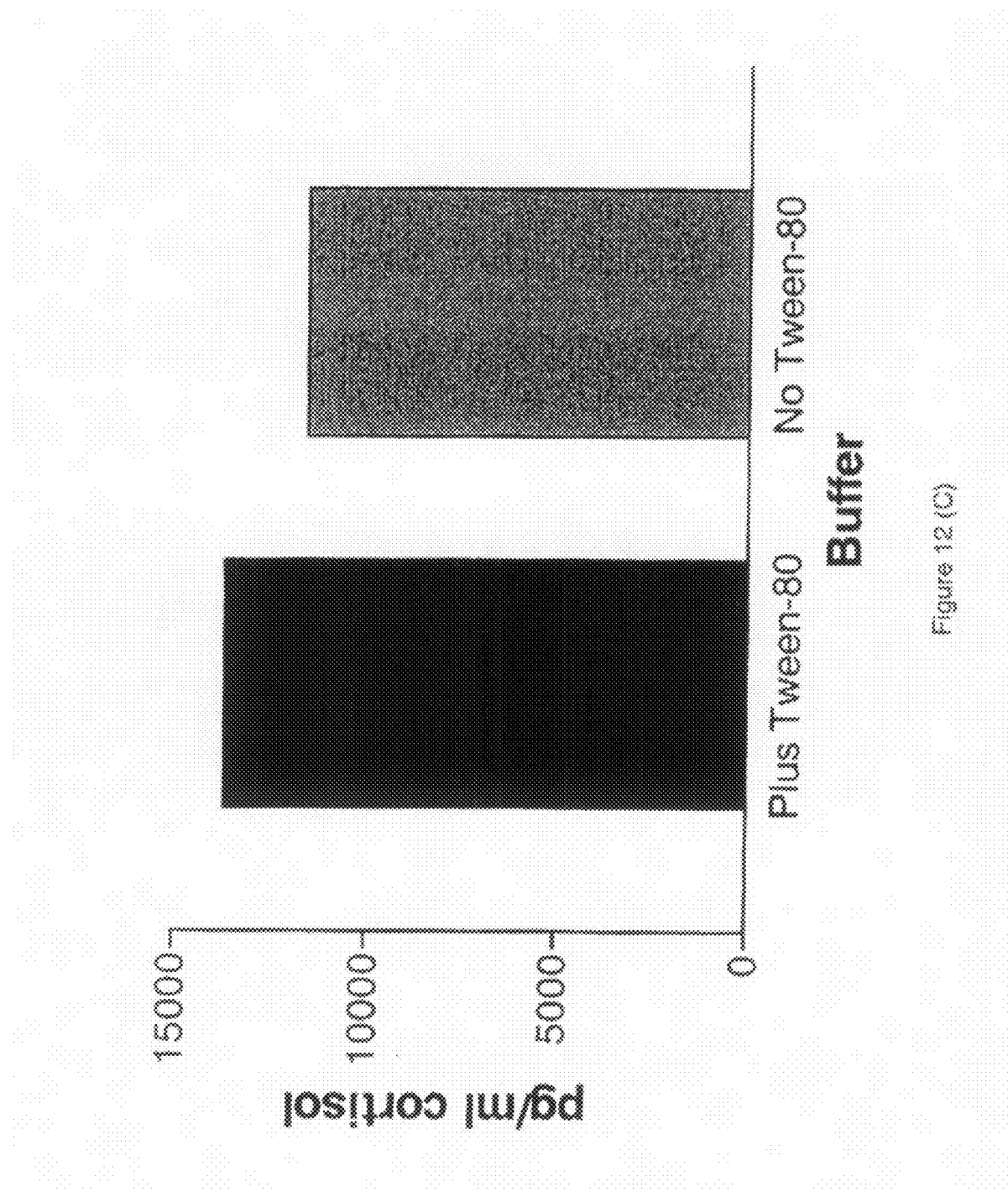

The 11β-HSD1 enzyme assay conditions described by Barf et al [15] were used; human hepatic microsomes in Buffer 1 at protein concentrations from 25 µg to 200 µg, cortisone at concentrations from 44 nM to 700 nM incubated for 60 minutes at 37° C. The effect of 0.9% Tween 80 was also investigated, as this detergent is reported to improve the activity of enzymes involved in steroid metabolism. Results are shown in FIG. 12.

FIG. 12(A) shows the effect of protein. Data taken from the 700 µM cortisone group tested in the presence of Tween-80.

FIG. 12(B) shows the effect of cortisone. Data taken from the 25 µg microsomal protein group tested in the presence of Tween-80.

FIG. 12(C) shows the effect of Tween-80. Data taken from the 25 µg microsomal protein group tested in the presence of 700 µM cortisone.

The assay detected cortisol in the standard curve (313 pg/ml to 10,000 pg/ml) as expected but the signal obtained from the enzyme assay samples decreased with increasing microsomal protein concentration, suggesting that the microsomal protein may interfere with the immunoassay, FIG. 12(A). Addition of exogenous cortisone had no effect on levels of cortisol detected in the enzyme assay samples, suggesting the antibody does not cross react with cortisone, FIG. 12(B). Inclusion of detergent in the enzyme assay buffer had little effect, FIG. 12(C).

Figure 13:
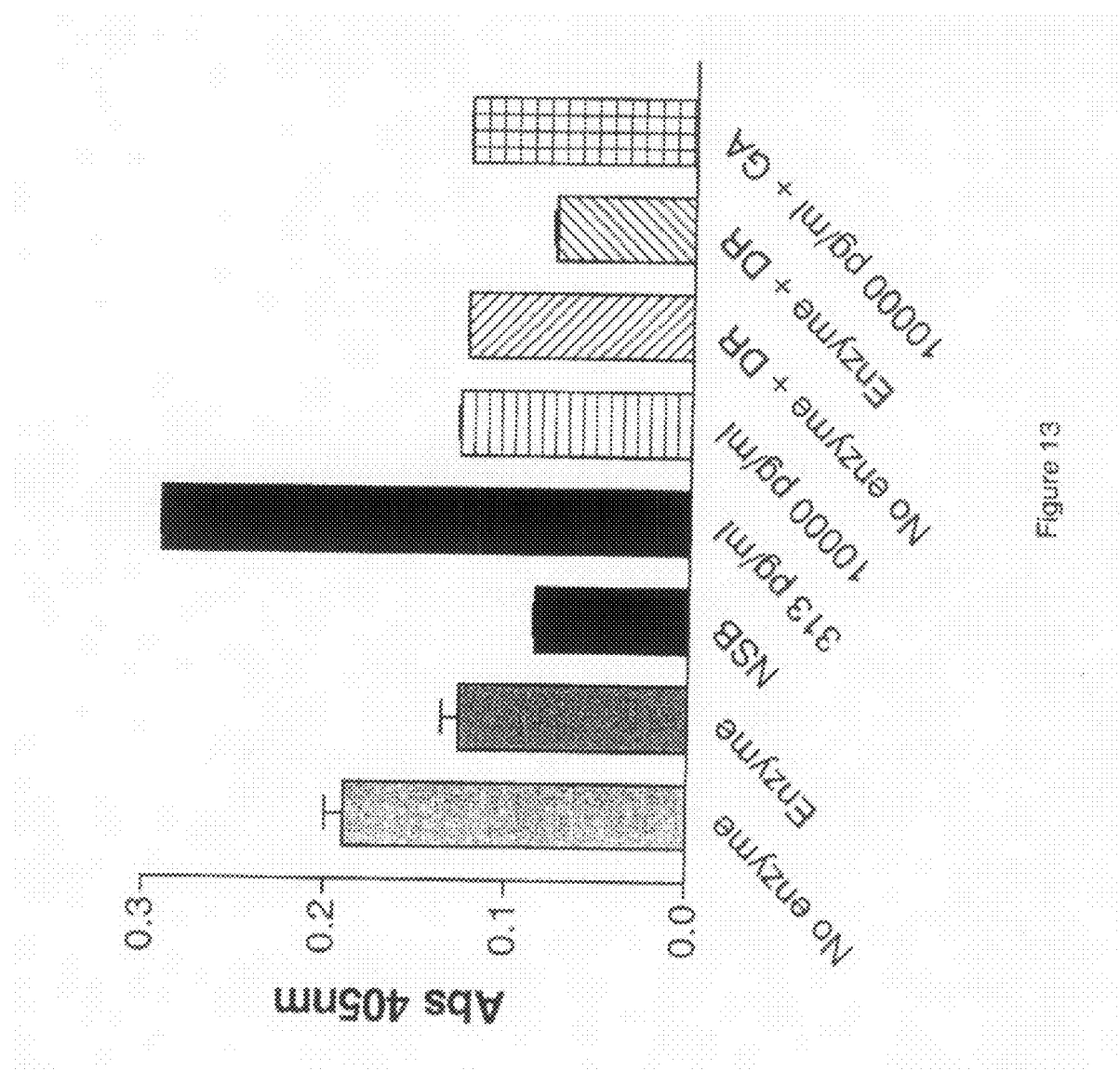
FIG. 13 is a graph showing the evaluation of the Assay Designs Cortisol Immunoassay.

The assay conditions were varied to determine if it was feasible to use the immunoassay system to detect 11β-HSD1 activity; 24 µg microsomal protein per sample and 2 µM cortisone substrate in Buffer 2. Enzyme activity was also measured in samples following the addition of steroid displacement reagent; a kit component which releases cortisol from cortisol binding protein, if present in the sample. The assay detected the cortisol in the standard curve (313 pg/ml to 10,000 pg/ml). FIG. 13 shows the absorbance at 405 m obtained for the different groups:

The lowest and highest concentrations of the cortisol standard have been included in FIG. 13 as 313 pg/ml and 1000 pg/ml together with the NSB absorbance to show the dynamic range obtained in the assay.

Absorbance obtained in the presence of reaction mixture taken from samples incubated with microsomal protein ("Enzyme") are lower than those in the presence of reaction mixture not containing microsomal protein ("No enzyme") indicating increases in levels of cortisol.

In the presence of the kit steroid displacement reagent ("DR") these two reaction mixtures show the same pattern but the signal is depressed.

Glycyrrhetinic acid (GA) in the presence of the top concentration of cortisol standard has no effect on the ability of the kit to measure cortisol concentrations.

Figure 14:
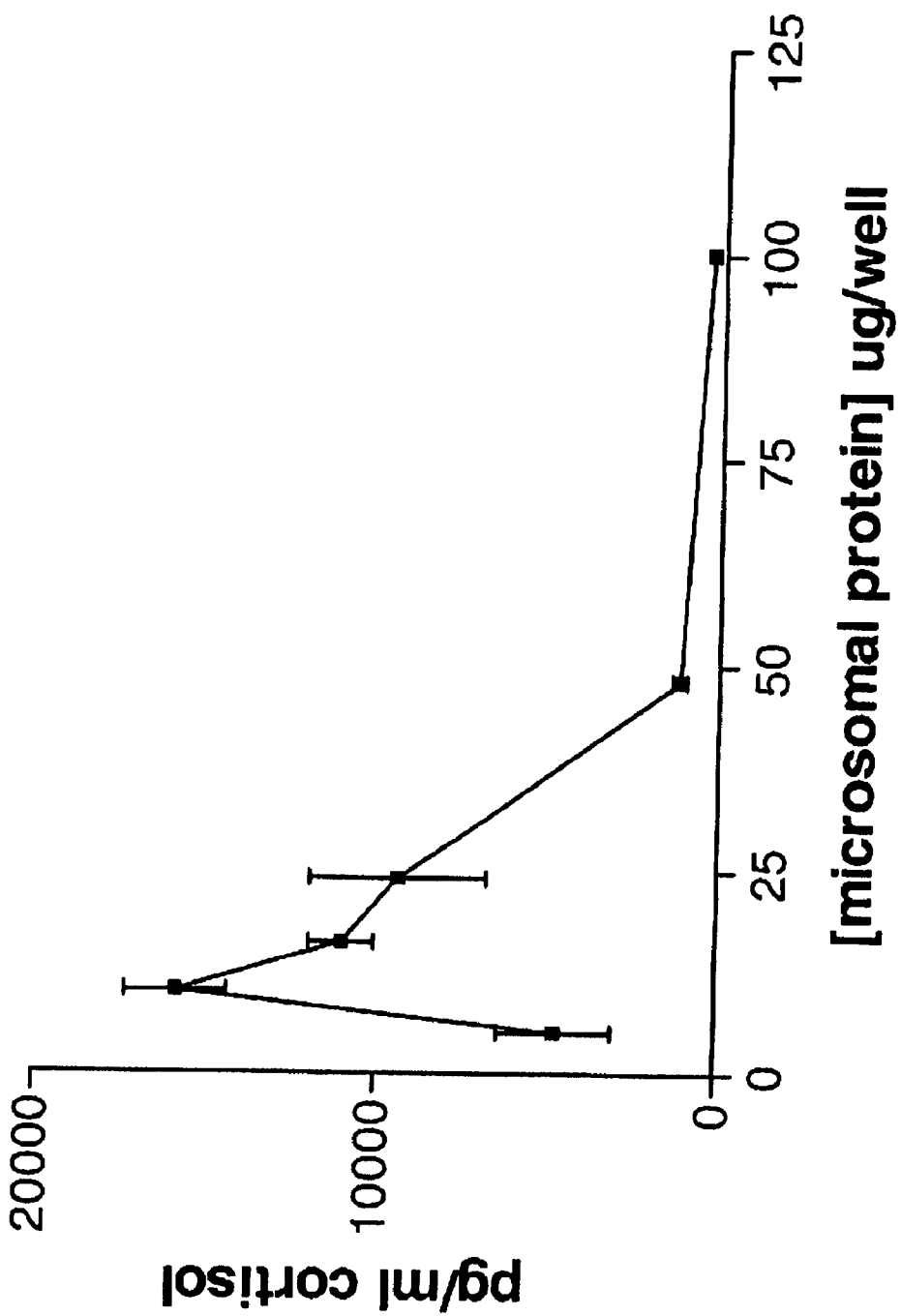
FIG. 14 is a graph showing the effect of increasing microsomal protein on measurement of 11β HSD1 activity detected by Assay Designs Immunoassay.

Although the signal to background ratio of 2.5 for the assay is rather poor, these data demonstrate that the antibody can bind the cortisol:AP conjugate and that this can be displaced by cortisol. An experiment was carried out to examine the effect of increasing microsomal protein concentration, in an attempt to improve the signal to noise obtained. Microsomal protein was tested from 100 μg/incubation down to 5 μg/incubation using 2 μM cortisone in Buffer 2. All other conditions were identical to those detailed above. The results are shown in FIG. 14.

Decreasing microsomal protein from 10 μg/incubation to 5 μg/incubation results in a corresponding decrease in enzyme activity. Increasing microsomal protein above 10 μg/incubation results in a quenching of signal which may be due to the colour of the microsomes. Therefore the dynamic range of this assay cannot be improved by increasing the microsomal protein concentration.

RIA development using Immunotech Antibody

Figure 15:
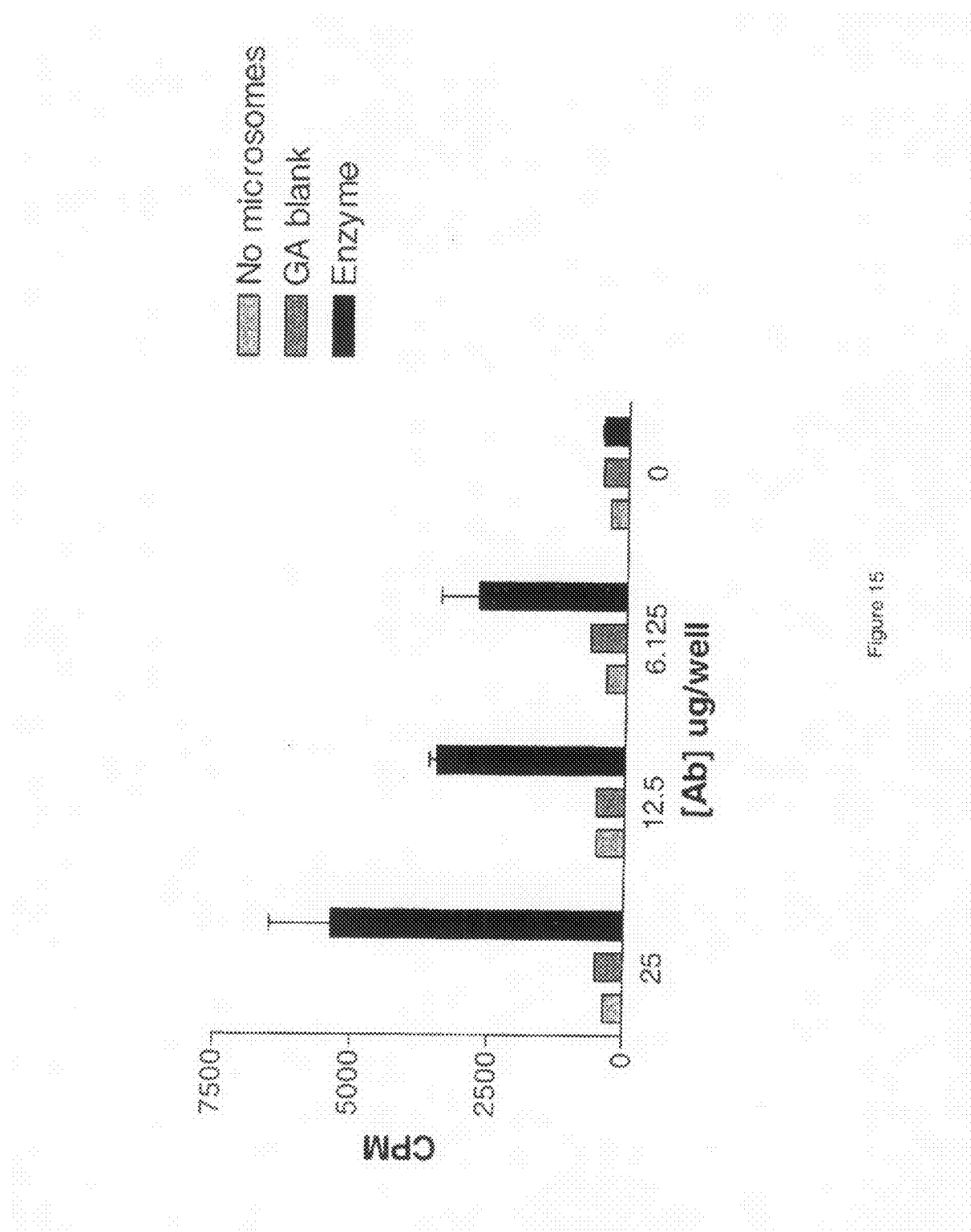
FIG. 15 is a graph showing the detection of 11β HSD1 activity by RIA using the Immunotech anti-cortisol antibody.

The 11β HSD1 assay was carried out using 10 μg/well human hepatic microsomal protein. The Immunotech antibody was used in the RIA at concentrations from 6.25 μg/well to 25 μg/well, the results are shown in FIG. 15.

The Immunotech antibody worked well in the assay and gave good signal to background at all the concentrations tested. The signal to noise with 12.5 and 6.1 μg antibody per well was similar suggesting it may be possible to reduce the antibody concentration.

Figure 16:
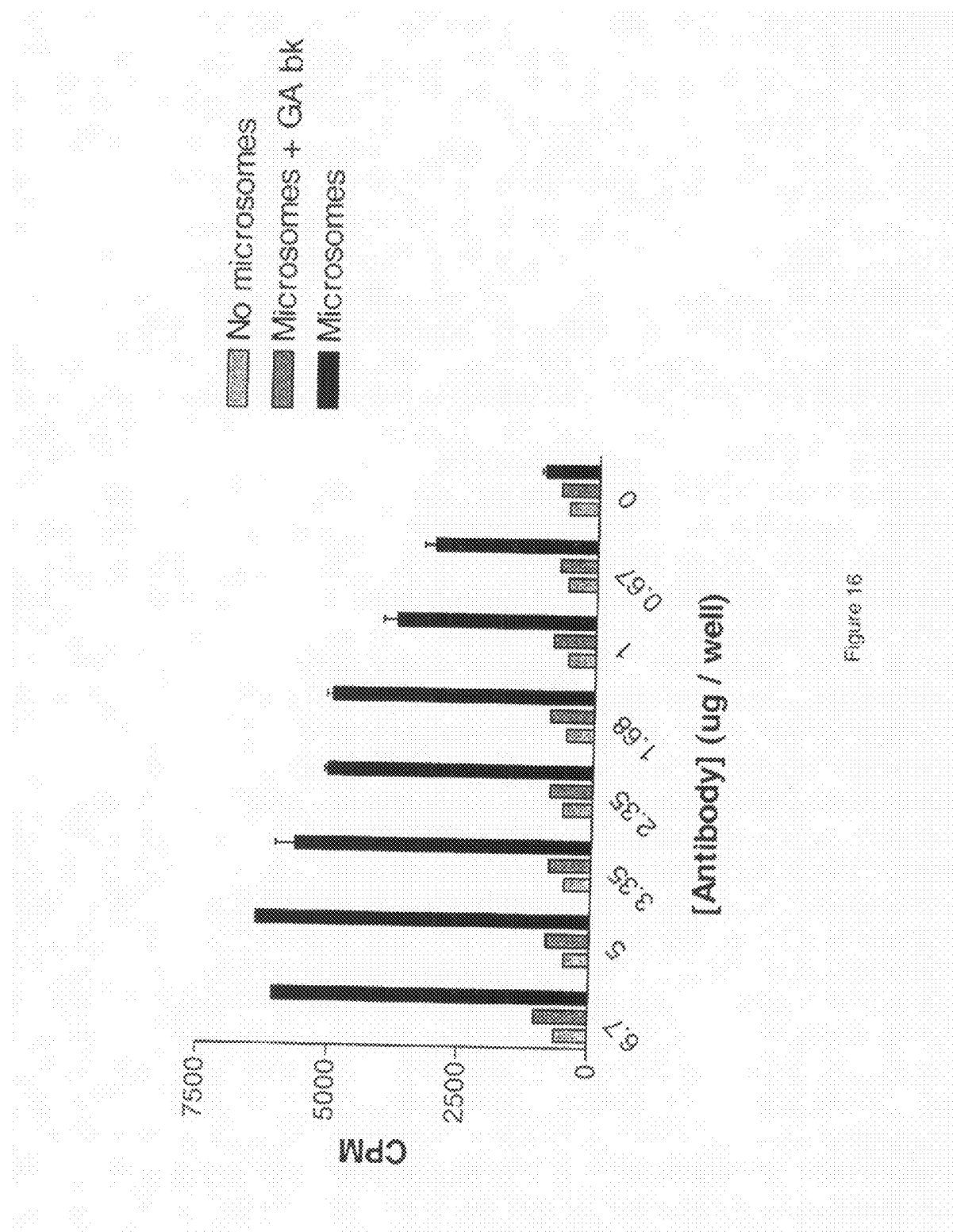
FIG. 16 is a graph showing the effect of lowering the Immunotech antibody concentration on the signal to noise (microsome group compared to GA blank group).
Figure 17:
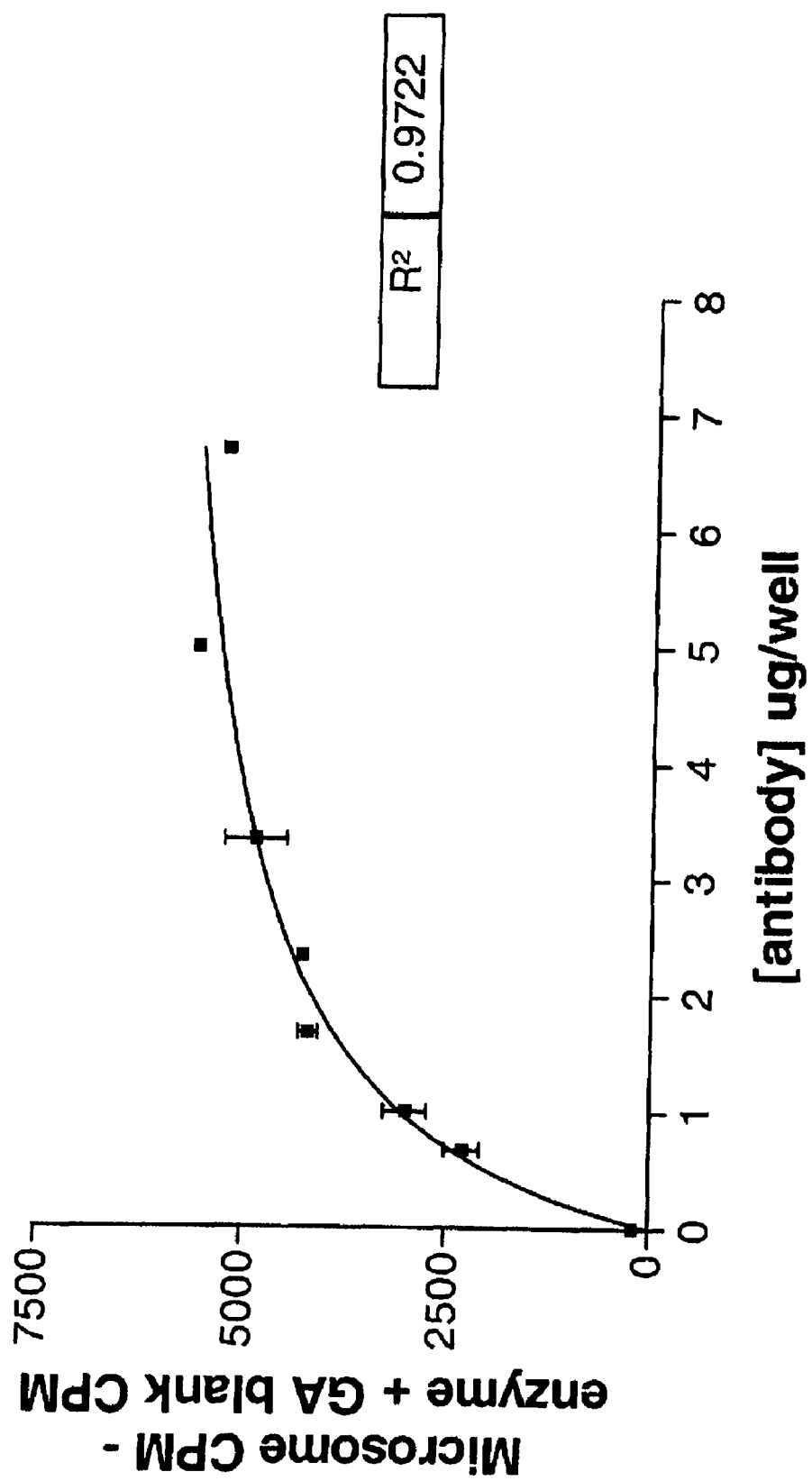
FIG. 17 is a graph showing the Immunotech antibody saturation curve for detection of 11β HSD1 activity by RIA.

The antibody titre, at concentrations from 0.67 μl g/well to 6.7 μg/well, was examined. The 11β HSD1 assay was carried out using human microsomal protein at 20 μg/well, to generate the optimum signal to background. Each antibody concentration was tested against a "no enzyme" blank (buffer substituted for microsomes), a "GA blank" (10 μl stop solution added prior to microsomes) and a control group. The results are shown in FIGS. 16 and 17.

The saturation curve indicates that there is no difference in the detection of enzyme activity above 1.68 μg/well. The signal to background ratio with this antibody concentration is good, (6 fold). Consequently the antibody will be used at 1.7 μg/well in future assays.

Figure 18:
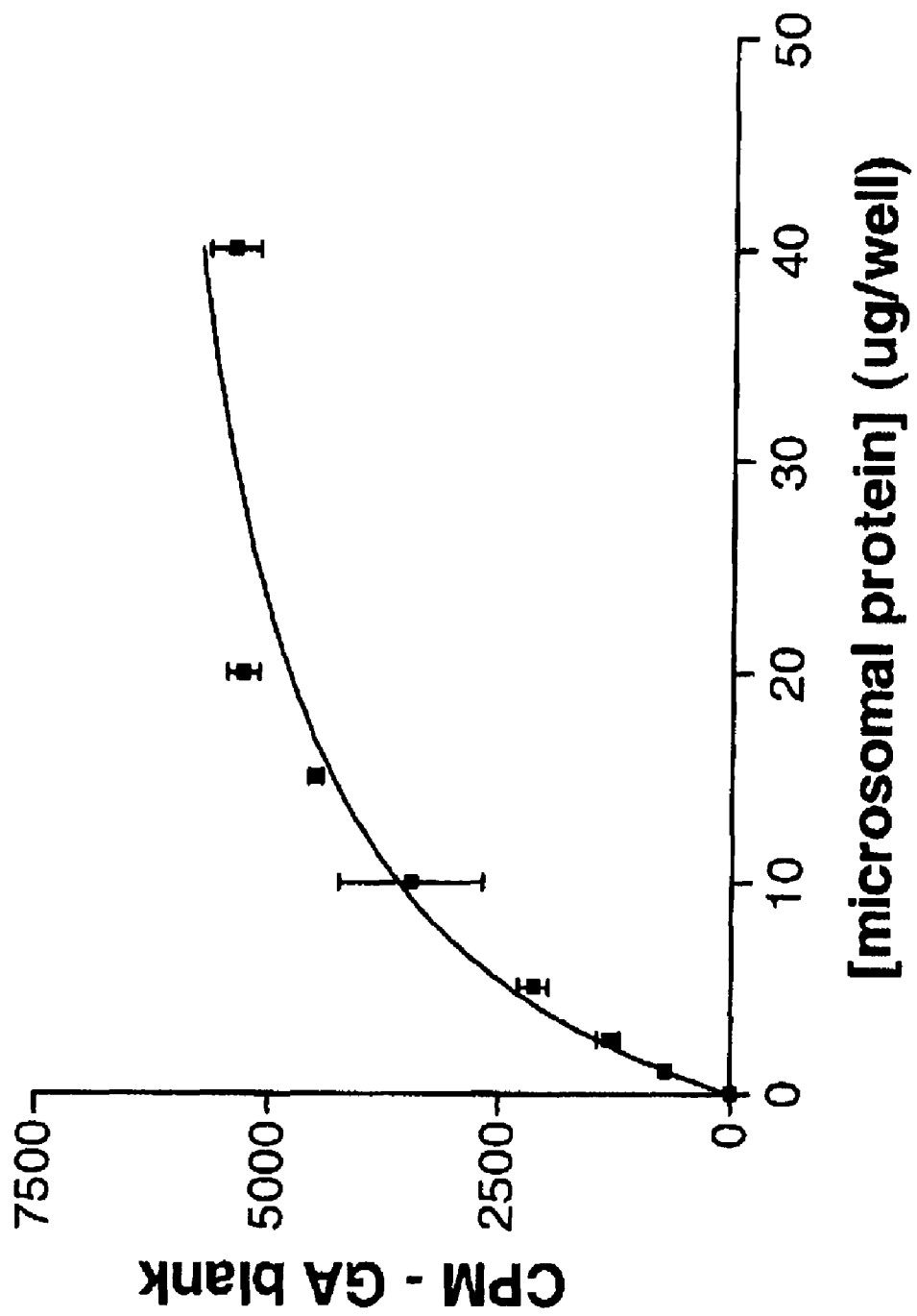
FIG. 18 is a graph showing the linearity of human hepatic microsomal 11β HSD1 activity detected by RIA.

Linearity of enzyme activity with human hepatic microsomal protein concentration using RIA detection was examined. The 11β HSD1 assay was carried with microsomal protein concentrations varying from 1 μg/well to 40 μg/well. 11β HSD1 activity was linear with protein up to concentrations of 20 μg/well, FIG. 18, confirming the results obtained with the classical enzyme assay (FIG. 7).

The optimal concentration of human microsomal protein to use in the assay appears to be 10 μg/well.

Figure 19:
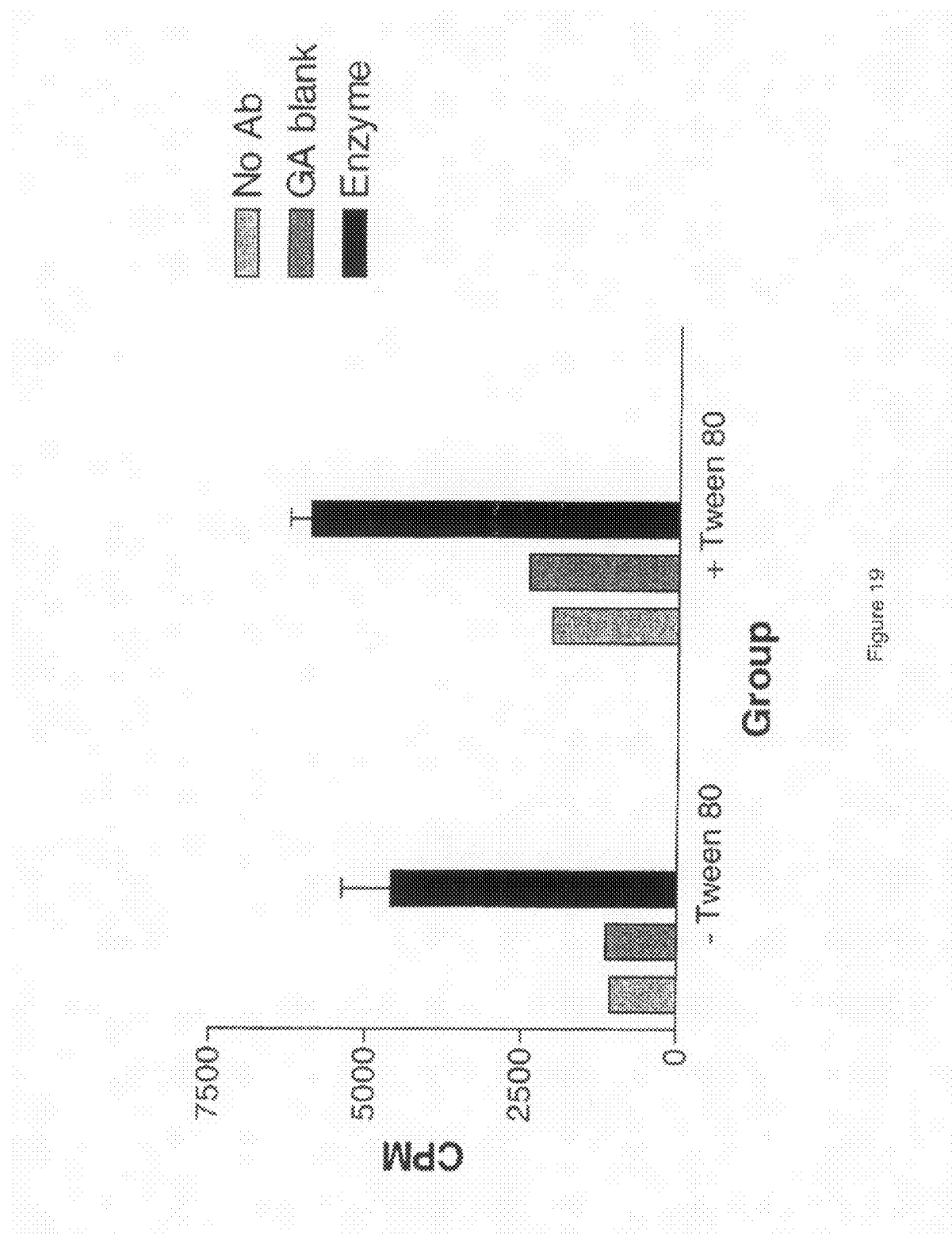
FIG. 19 is a graph showing the effect of Tween 80 on detection of human hepatic microsomal 11β HSD1 activity by RIA.

The effect of including Tween 80 in the enzyme assay buffer was also investigated. This assay was carried out in parallel with the assay above and under the same conditions except that the enzyme assay buffer (Buffer 2) contained 0.05% Tween 80. Microsomal protein was tested at four concentrations. Tween 80 was found to increase the blank CPM, reducing the signal to noise of the assay. Representative data, from the group tested 10 μg/well microsomal protein, are shown in FIG. 19. Similar results were obtained with all the microsome protein concentrations examined, consequently Tween will not be used in future studies.

Figure 20:
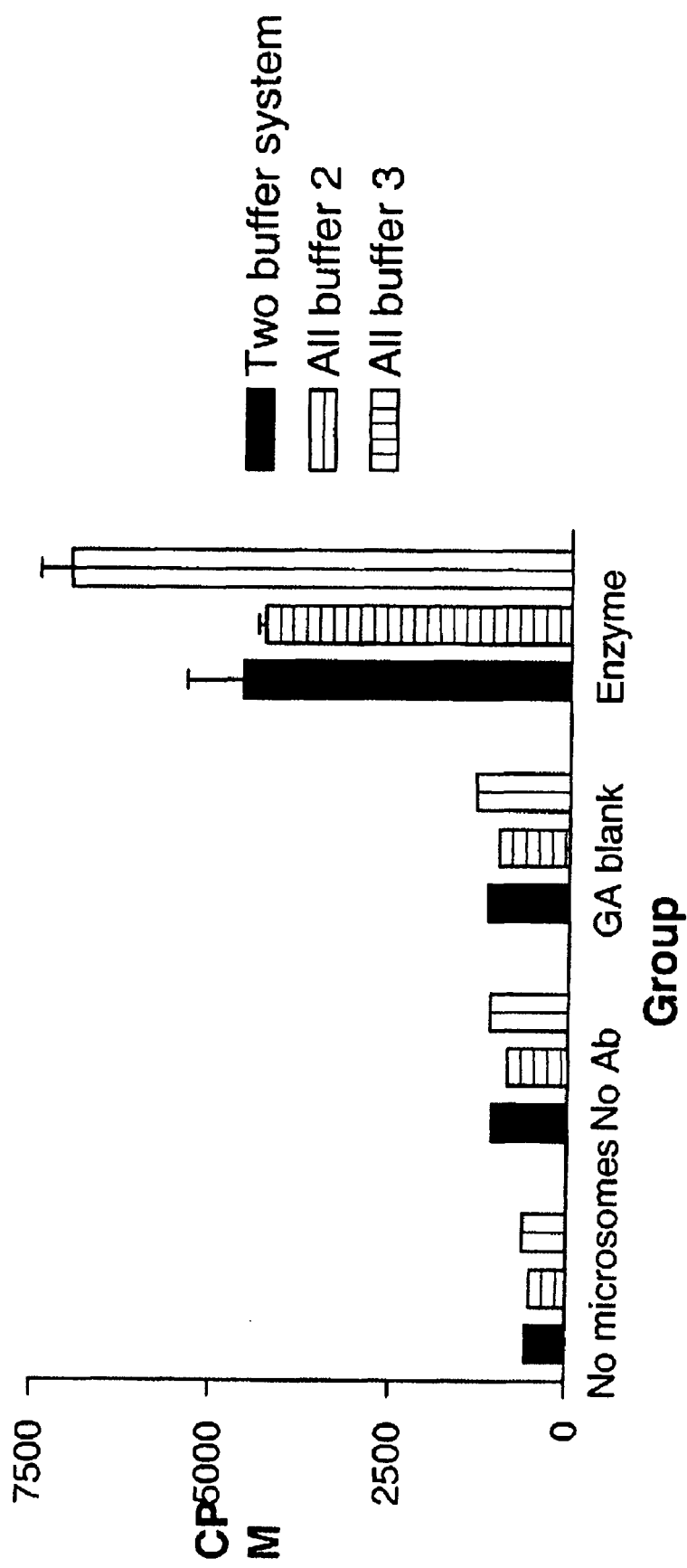
FIG. 20 is a graph showing the effect of buffer systems on detection of human hepatic microsomal 11β HDS1 activity by RIA.

To simplify the protocol such that both enzyme assay and RIA stages are carried out in the same buffer, both phases were carried out in either enzyme assay buffer (Buffer 2) or Buffer 3 (RIA buffer). The microsomal protein concentration used was 10 μg/well and the cortisone concentration was 175 nM. Performing both enzyme assay and RIA in Buffer 3 appears to improve the data slightly, FIG. 20.

Figure 21:
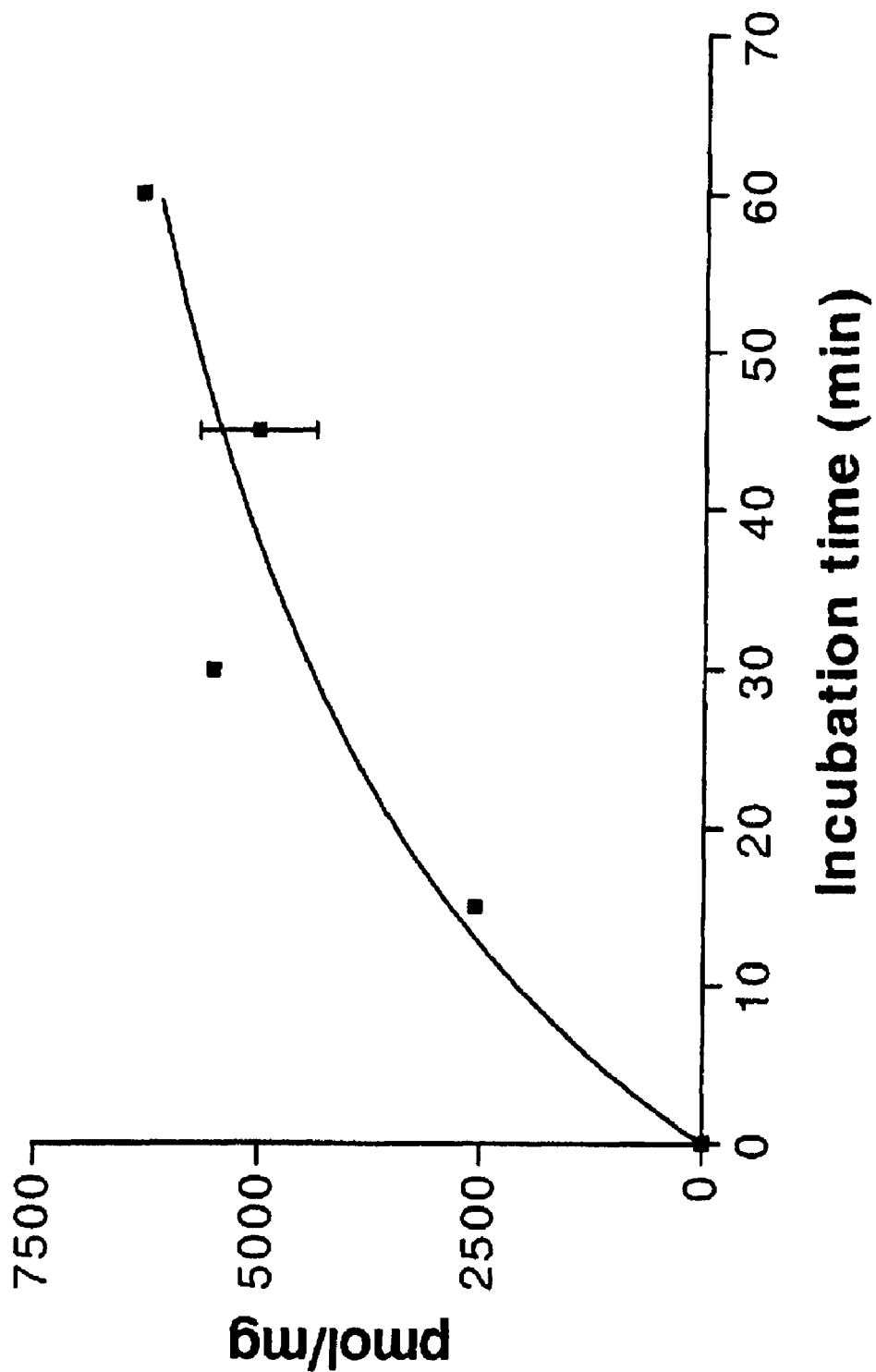
FIG. 21 is a graph showing the linearity of human hepatic microsomal 11β HSD1 activity with incubation time detected by RIA.

Linearity of enzyme activity with incubation time was investigated. The enzyme assay was carried out with 10%1 g/well microsomal protein and with 175 nM cortisone, and stopped at varying time points, the results are shown in FIG. 21.

With microsome protein concentrations of 10 μg/well and 175 nM substrate, the reaction is linear at time points up to 30 minutes. These results indicate that a substrate concentration of 175 nM is too low. The apparent Km observed in the classical 11β HSD1 assay was 660 nM (FIGS. 8 and 9), although these assays are end-point measurement, hence it is not certain that initial rates were measured in the low substrate groups with a 30 minute incubation time. However, published Km values for cortisone in human hepatic microsomal 11β HSD1 assays are in the micromolar range [18, 19]. Although 175 nM substrate is well below the apparent Km, it may not be possible to increase the concentration significantly for two reasons:

(i) If the compounds are competitive with cortisone, the measured inhibition will fall if the substrate is increased above the concentration used in Refer nc 1.

(ii) Increasing the substrate concentration will reduce the specific activity of the label, reducing the sensitivity of the assay. This could be overcome by adding higher concentrations of [$^3$H]-cortisone, but the protocol uses 0.5 μCi/well and there is a cost implication if higher levels of radioactivity are used.

Figure 22:
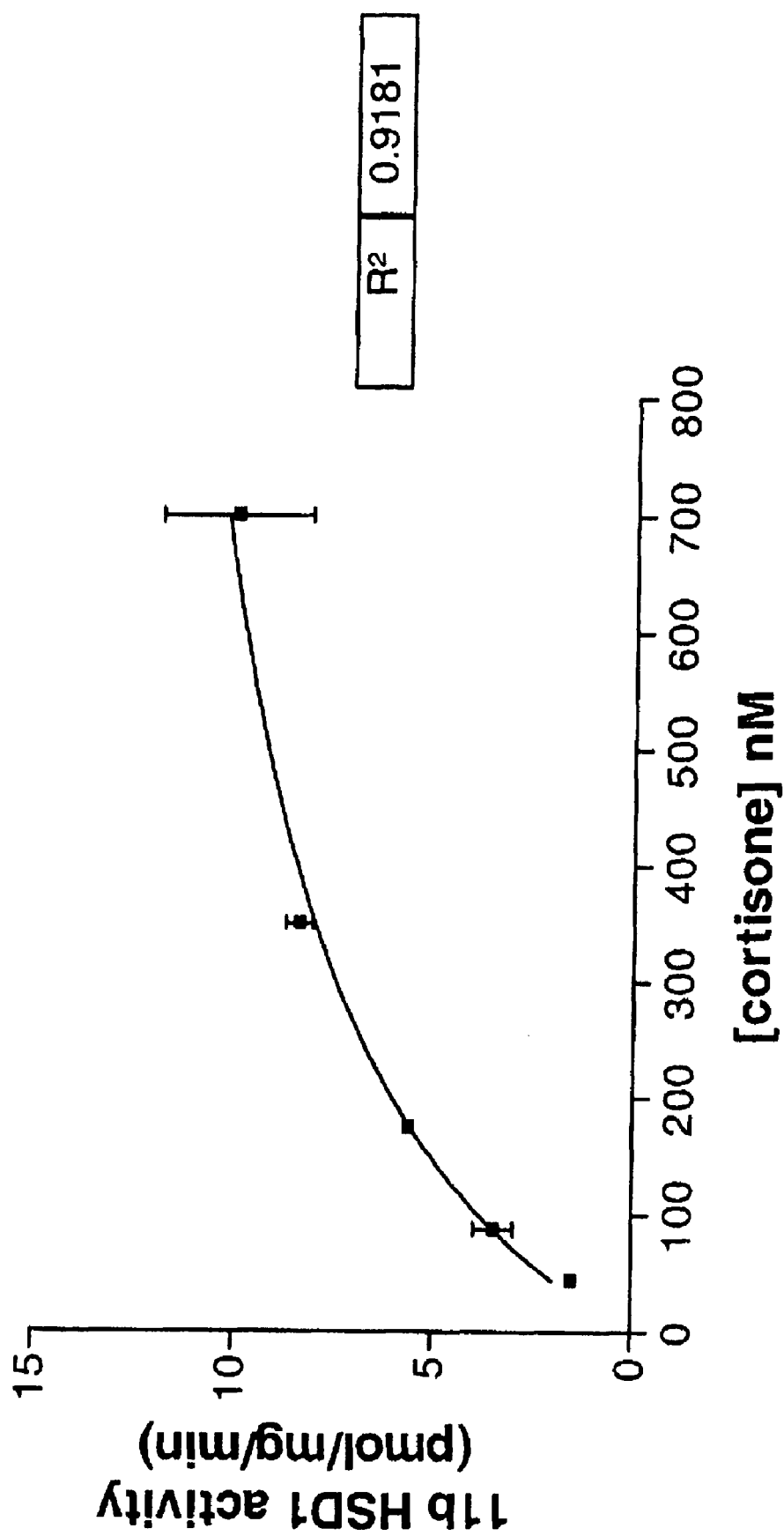
FIG. 22 is a graph showing the substrate saturation curve for human hepatic microsomal 11β HDS1 activity detected by RIA.

Substrate saturation was examined. The enzyme assay was carried out exactly described in the methods section, in Buffer 3 with 10 μg/well microsomal protein and with [cold cortisone] as indicated. [3H]-cortisone was 0.5 μCi/sample throughout. The reaction was stopped after 30 min by the addition of 10 μl stop solution. The RIA was carried out exactly as indicated in the methods section. The results are shown in FIGS. 22 and 23.

Figure 9:
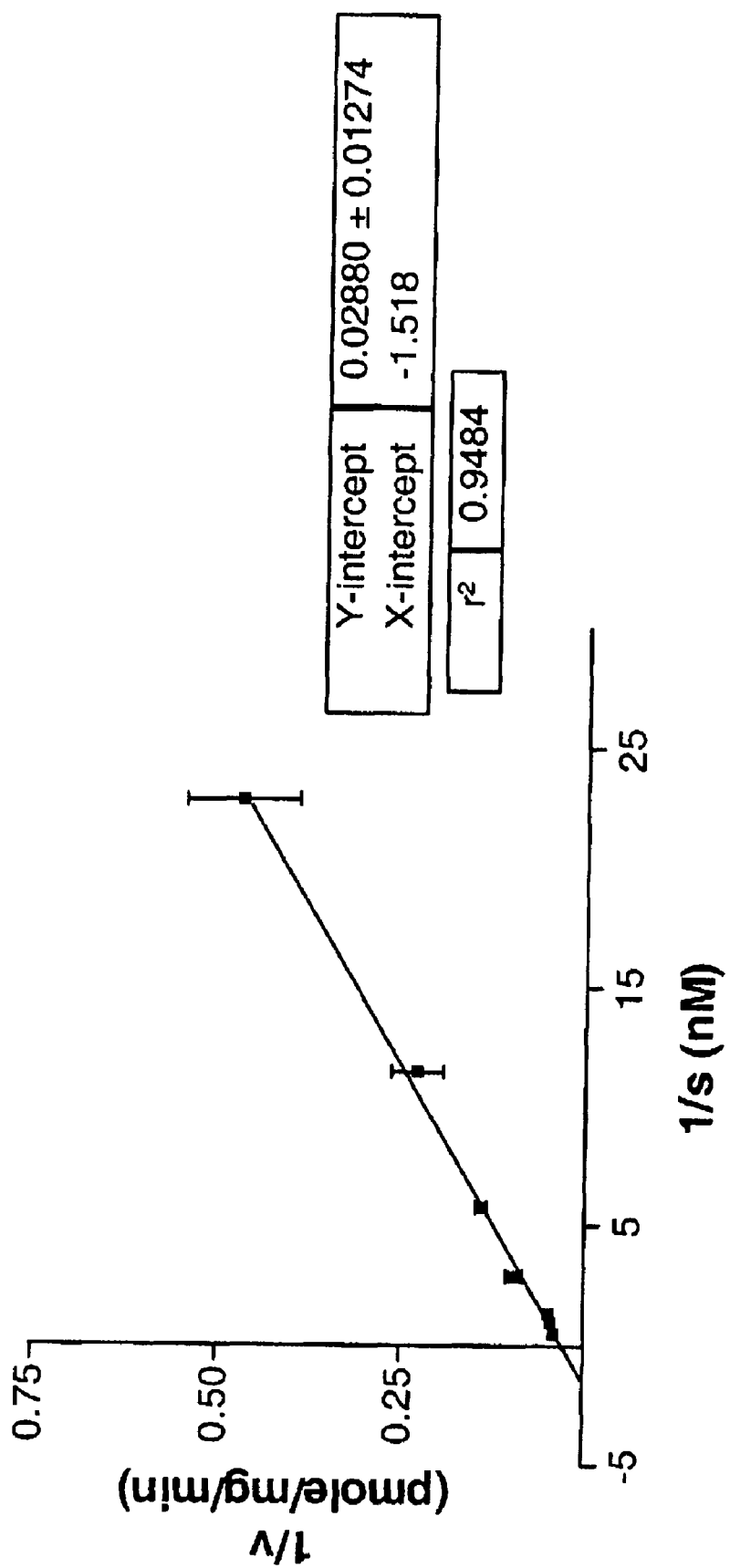
FIG. 9 is a Lineweaver-Burke plot of substrate saturation data for human hepatic microsomal 11β HSD1.
Figure 23:
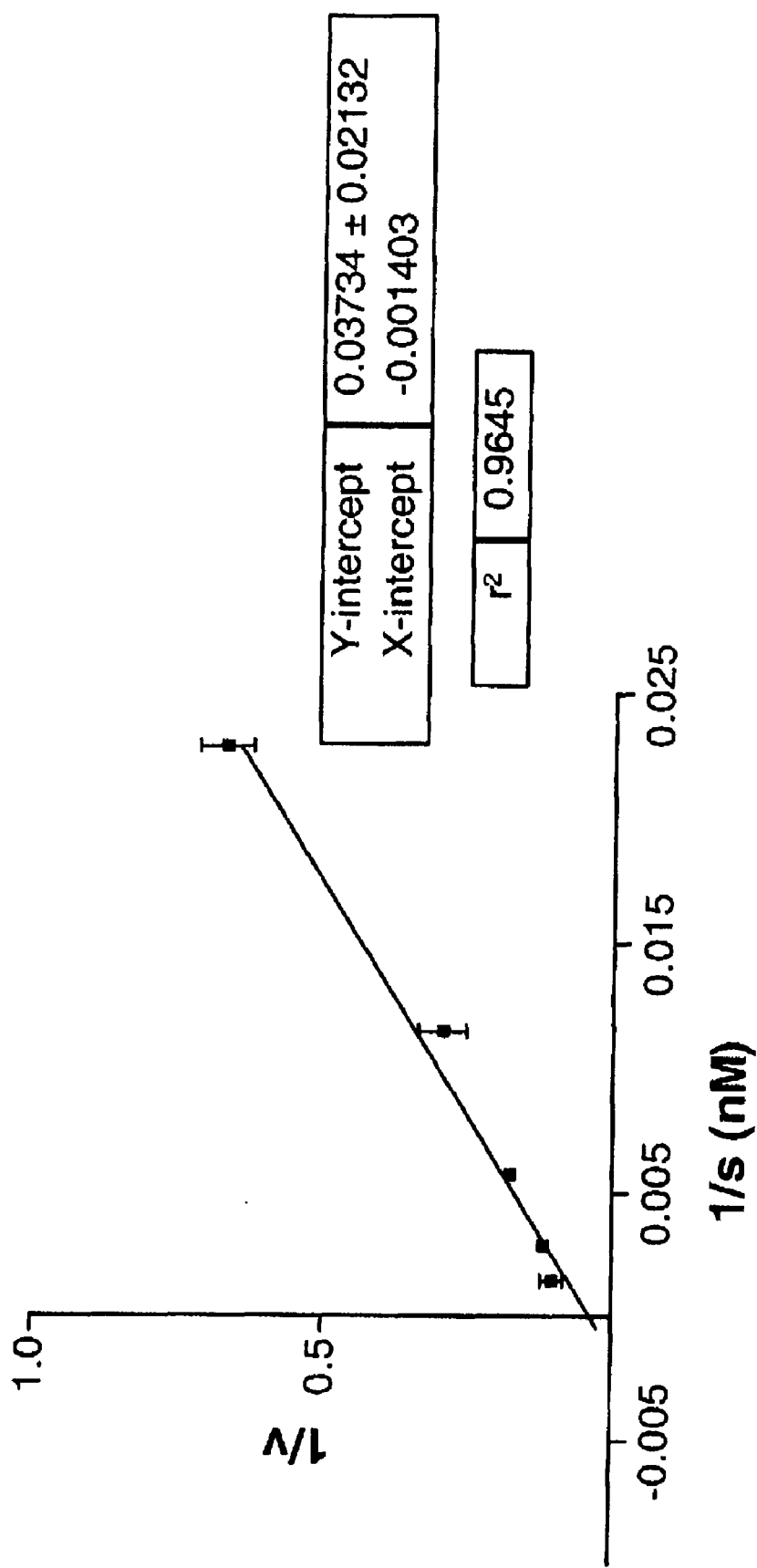
FIG. 23 is a Lineweaver-Burke plot of substrate saturation data for human hepatic microsomal 11β HDS1 activity detected by RIA.

The apparent Km (700 nM), determined from the Lineweaver-Burke plot of these data shown in FIG. 23 is very similar to that determined in the tic format 11β HSD1 assay (FIG. 9, apparent Km ~660 nM). The data suggests that at 10 μg microsomal protein, the enzyme is not saturated at 175 nM cortisone, over an incubation period of 30 minutes.

Lowering the microsomal protein concentration or the incubation time to bring the reaction within the linear range would partly overcome the problem. However either of these adjustment adjustments would decrease the assay sensitivity, and decrease the apparent potency of inhibitors. Consequently the initial experiments were performed with 175 nM cortisone.

11β-HSD1 Assay Validation

Figure 24:
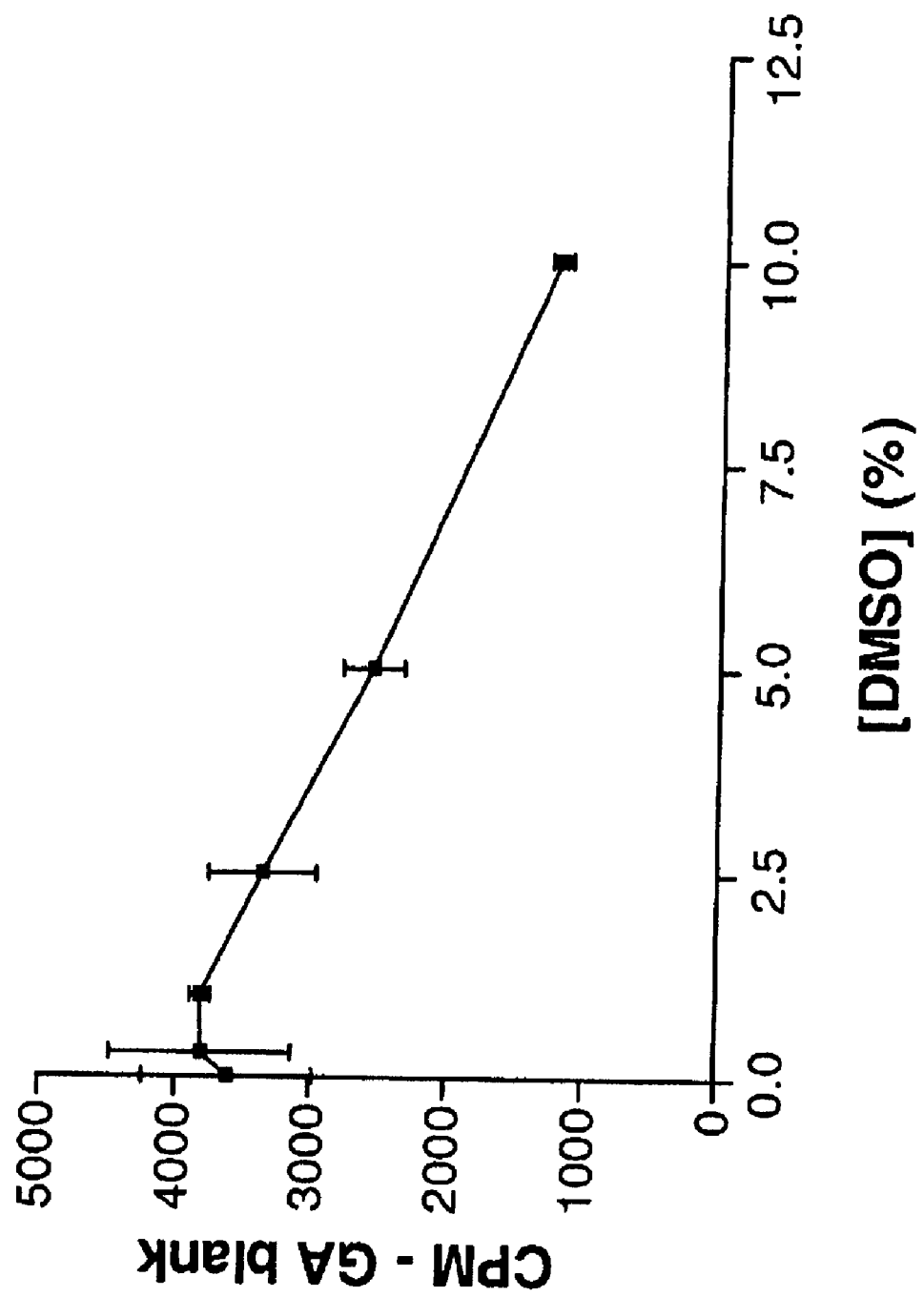
FIG. 24 is a graph showing the DMSO tolerance of human hepatic microsomal 11β HSD1 activity.

Prior to compound testing, the tolerance of the enzyme assay to DMSO was determined. Inclusion of DMSO at 1% in the enzyme assay does not affect total or blank values, but slightly increases enzyme activity and the signal to noise ratio (Table 4). The experiment was repeated over a range of DMSO concentrations from 0.3 to 10%, FIG. 24.

TABLE 4

Control and blank CPM obtain d in the Glycyrrh tinic acid IC$_{50}$ assay showing effect of 1% DMSO and signal to noise ratio obtained.

| Group | 1% DMSO | No DMSO |
|---|---|---|
| NSB | 670 | 661 |
| GA blank | 640 | 660 |
| Control | 3515 | 2583 |
| Signal to noise | 5 fold | 4 fold |

There is a slight increase in microsomal enzyme activity in the presence of 0.3% and 1% DMSO. At DMSO concentrations above 1%, there is a linear reduction in enzyme activity. It is reported that DMSO can both increase and reduce microsomal enzyme activity, depending on the concentration, presumably due to effects on the microsomal membranes. On the basis of these data, it is intended that compounds be screened in the presence of 1% DMSO.

Figure 25:
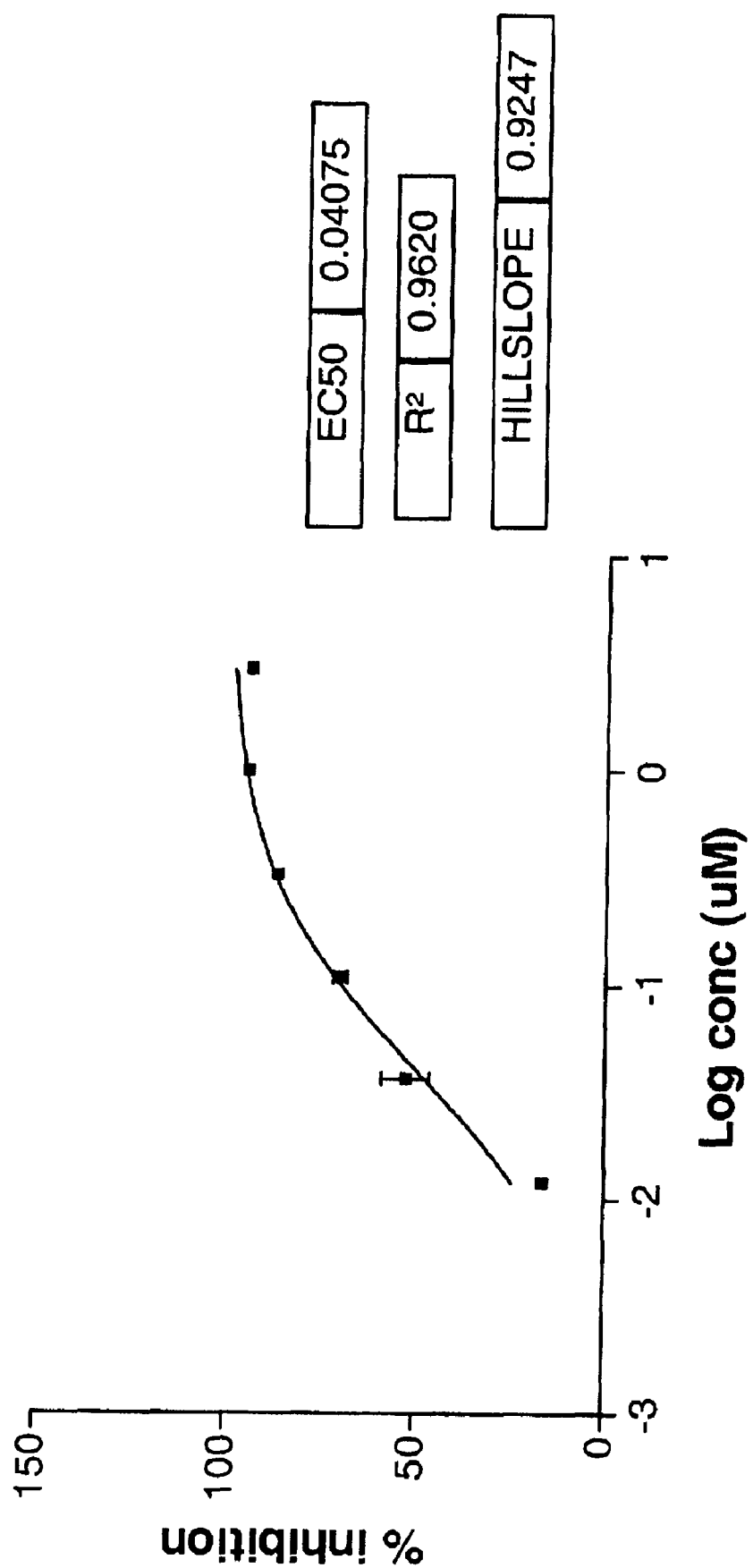
FIG. 25 is an $IC_{50}$ curve for inhibition of human hepatic microsomal 11β HSD1 activity by glycyrrhetinic acid.

An $IC_{50}$ value was generated for the standard inhibitor glycyrrhetinic acid, the compound was tested at concentrations between 0.012 μM and 3 μM, with a final DMSO concentration of 1%, FIG. 25.

Glycyrrhetinic acid gives a concentration-related inhibition of the enzyme with an $IC_{50}$ of 41 nM, with good curve fit values ($r^2$=0.962) and Hillslope. This is similar to the value of 40 nM generated using the tlc format assay, (see FIG. 10). An $IC_{50}$ value of 30 nM has been reported for glycyrrhetinic acid inhibition of 11β HSD1 in human hepatic microsomes, using dehydro-dexamethasone as the substrate [19]. However, these values are lower than the value reported by Barf et al. [15].

TABLE 5

Inhibition Data

| STX No. | Structure | % inhibition of Human 11βHSD1 @ 10 μM typical sd ± 5% N = 2 |
|---|---|---|
| 976 | 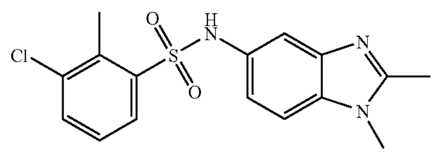 | 110 |
| 993 | 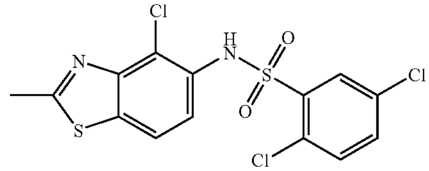 | 89 |
| 994 | 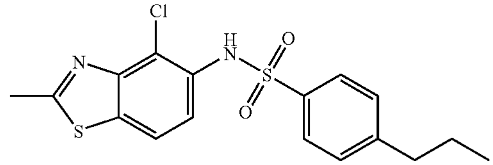 | 83 |
| 1029 | 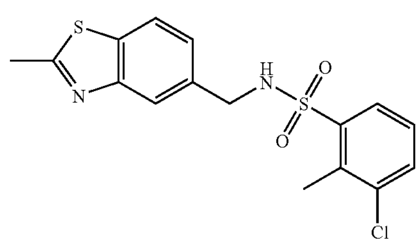 | 78 |
| 984 | 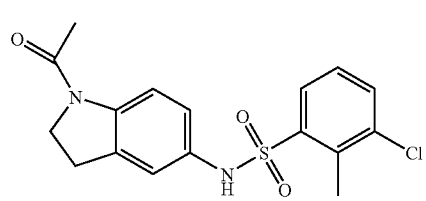 | 73 |

TABLE 5-continued

Inhibition Data

| STX No. | Structure | % inhibition of Human 11βHSD1 @ 10 μM typical sd ± 5% N = 2 |
|---|---|---|
| 995 | 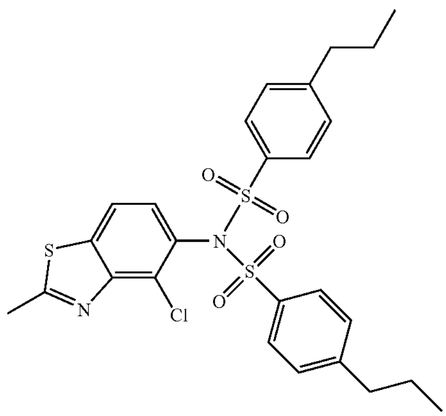 | 68 |
| 469 | 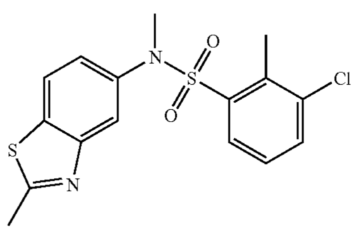 | 66 |
| 1018 | 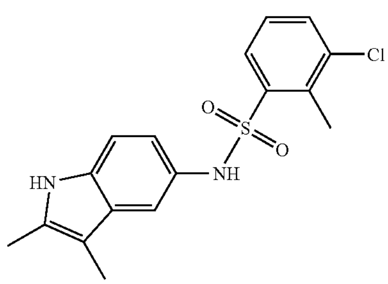 | 66 |
| 986 | 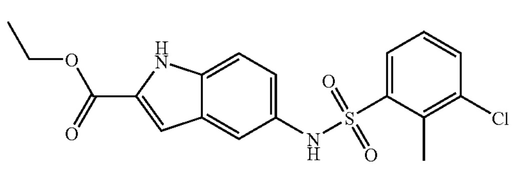 | 65 |
| 1020 | 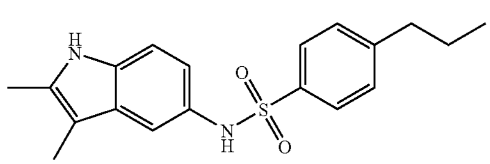 | 64 |

TABLE 5-continued

Inhibition Data

| STX No. | Structure | % inhibition of Human 11βHSD1 @ 10 μM typical sd ± 5% N = 2 |
|---|---|---|
| 996 | 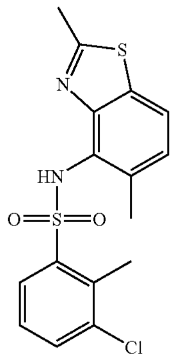 | 63 |
| 987 | 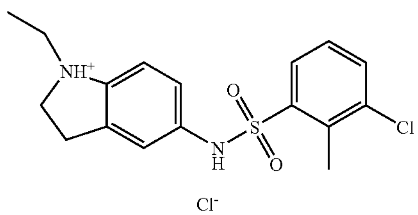 | 62 |
| 1030 | 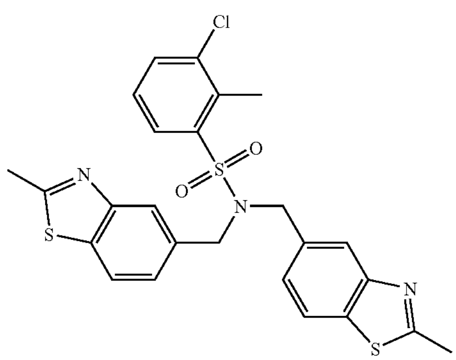 | 61 |
| 523 | 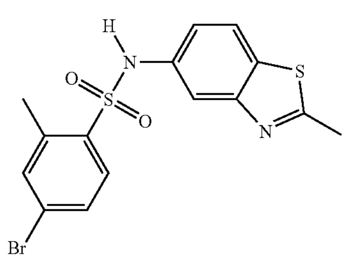 | 61 |
| 992 | 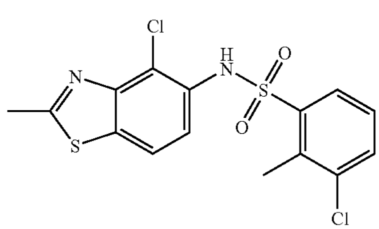 | 61 |

TABLE 5-continued

Inhibition Data

| STX No. | Structure | % inhibition of Human 11βHSD1 @ 10 μM typical sd ± 5% N = 2 |
|---------|-----------|-------------------------------------------------------------|
| 985 | 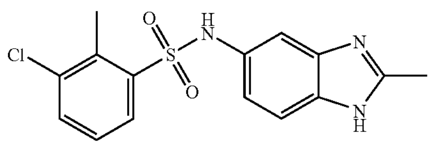 | 61 |
| 977 | 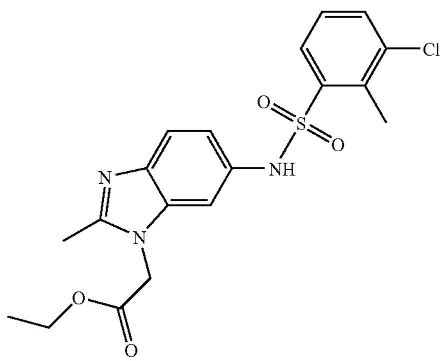 | 61 |
| 1019 | 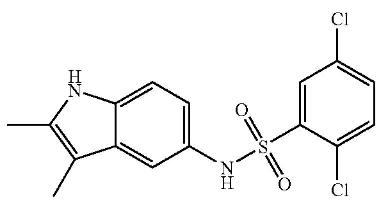 | 61 |
| 521 | 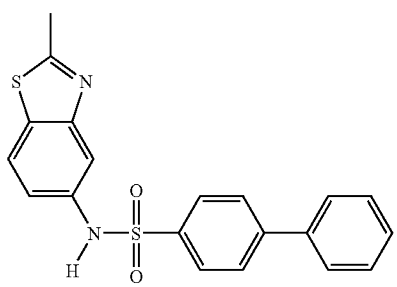 | 60 |
| 978 | 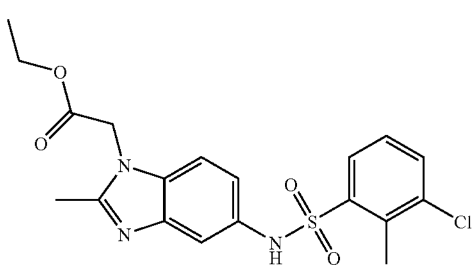 | 60 |

TABLE 5-continued

Inhibition Data

| STX No. | Structure | % inhibition of Human 11βHSD1 @ 10 μM typical sd ± 5% N = 2 |
|---|---|---|
| 1017 | 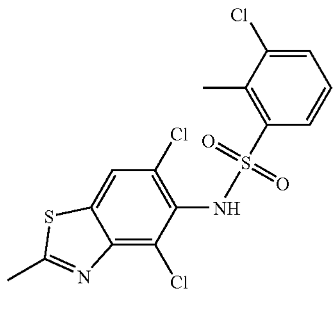 | 60 |
| 998 | 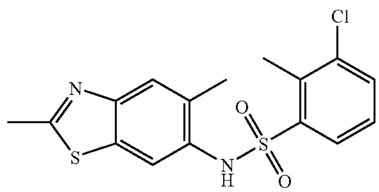 | 58 |
| 585 | 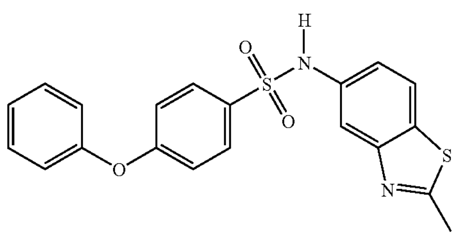 | 58 |
| 999 | 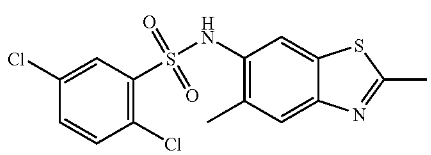 | 55 |
| 1021 | 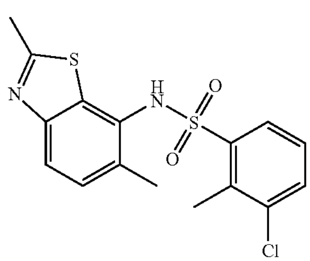 | 54 |
| 470 | 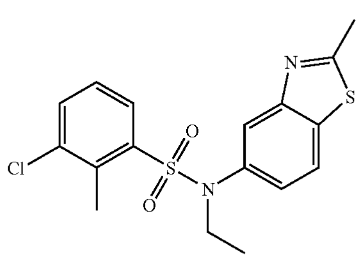 | 54 |

TABLE 5-continued

Inhibition Data

| STX No. | Structure | % inhibition of Human 11βHSD1 @ 10 μM typical sd ± 5% N = 2 |
|---|---|---|
| 554 | 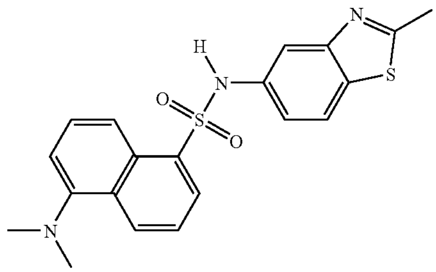 | 53 |
| 982 | 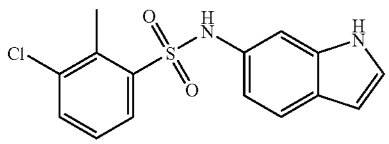 | 53 |
| 991 | 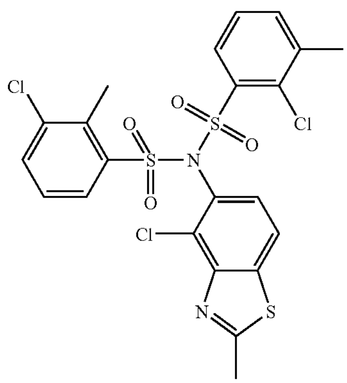 | 51 |
| 997 | 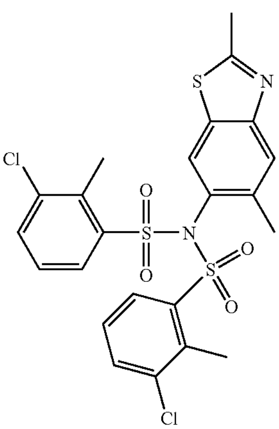 | 51 |
| 575 | 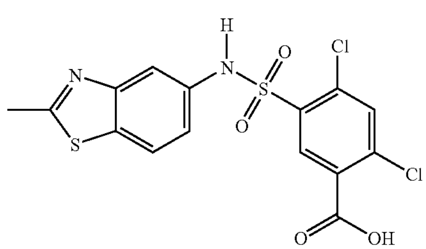 | 50 |

TABLE 5-continued

Inhibition Data

| STX No. | Structure | % inhibition of Human 11βHSD1 @ 10 μM typical sd ± 5% N = 2 |
|---|---|---|
| 709 | 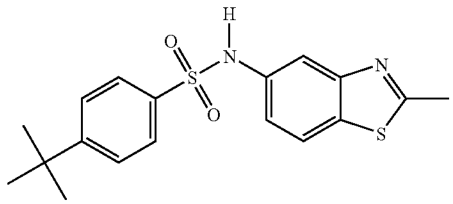 | 49 |
| 553 | 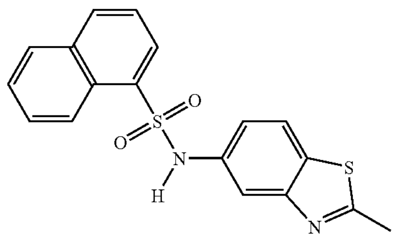 | 48 |
| 519 | 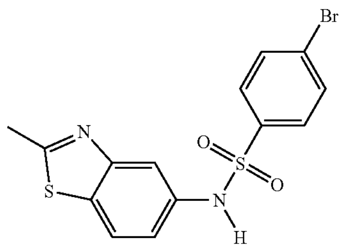 | 48 |
| 424 | 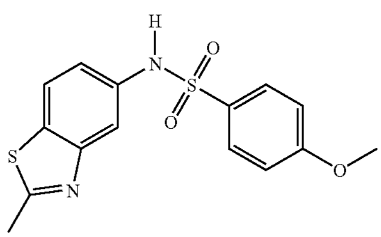 | 47 |
| 522 | 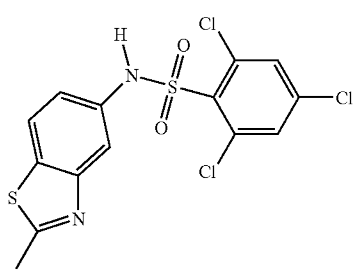 | 47 |
| 552 | 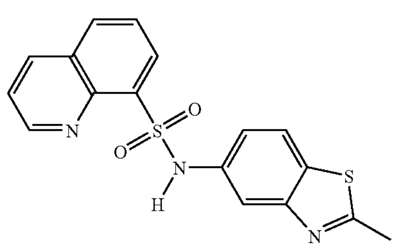 | 45 |

TABLE 5-continued

Inhibition Data

| STX No. | Structure | % inhibition of Human 11βHSD1 @ 10 μM typical sd ± 5% N = 2 |
|---|---|---|
| 975 | 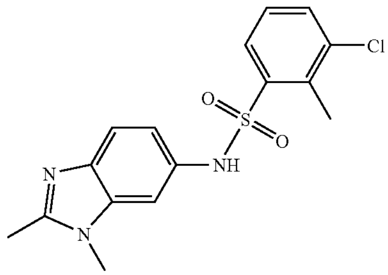 | 45 |
| 989 | 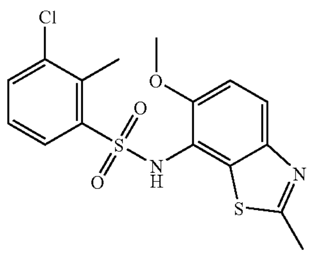 | 45 |
| 704 | 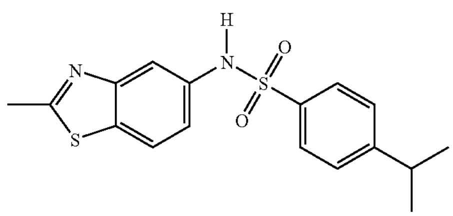 | 44 |
| 524 | 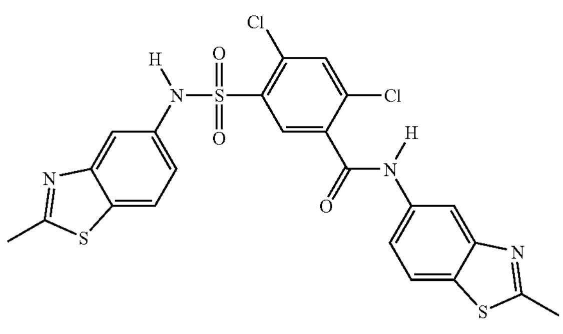 | 44 |
| 421 | 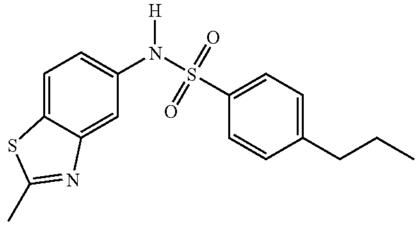 | 42 |

TABLE 5-continued

Inhibition Data

| STX No. | Structure | % inhibition of Human 11βHSD1 @ 10 μM typical sd ± 5% N = 2 |
|---|---|---|
| 425 | 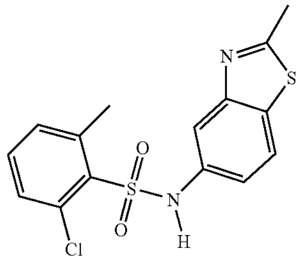 | 41 |
| 701 | 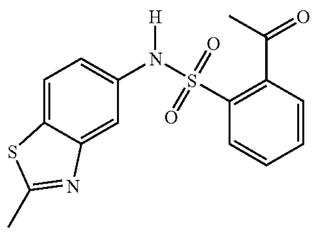 | 41 |
| 981 | 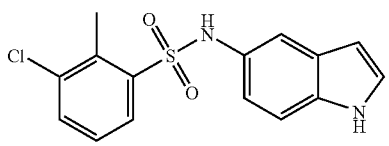 | 40 |
| 703 | 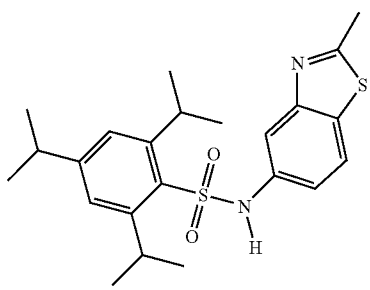 | 37 |
| 412 | 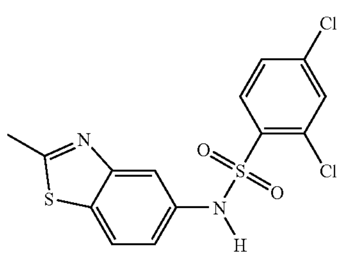 | 36 |
| 710 | 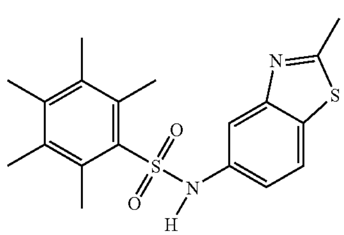 | 35 |

TABLE 5-continued

Inhibition Data

| STX No. | Structure | % inhibition of Human 11βHSD1 @ 10 μM typical sd ± 5% N = 2 |
|---|---|---|
| 582 | (structure) | 34 |
| 580 | (structure) | 30 |
| 413 | (structure) | 29 |
| 581 | (structure) | 29 |
| 583 | (structure) | 28 |
| 705 | (structure) | 28 |

TABLE 5-continued

Inhibition Data

| STX No. | Structure | % inhibition of Human 11βHSD1 @ 10 μM typical sd ± 5% N = 2 |
|---|---|---|
| 831 | *(structure)* | 28 |
| 751 | *(structure)* | 22 |
| 708 | *(structure)* | 21 |
| 584 | *(structure)* | 20 |

Sulphonamide Synthesis

Method A

To the amine (1 eq.) dissolved in pyridine (3 eq.) was added the corresponding sulphonyl chloride (1.2 eq.) and the reaction mixture was stirred at RT under $N_2$ overnight. The resulting mixture was poured into aq. HCl and the organic layer was extracted with ethyl acetate, dried ($MgSO_4$), filtered and concentrated under reduced pressure to give the desired sulphonamide as crystalline solid or as a thick syrup. The crude compound was then purified by flash chromatography using EtOAc/hexane (3:2) or $CH_2Cl_2$/EtOAc (4:1) as eluent to give crystalline solid.

Method B

To the amine (1 eq.) dissolved in $Et_3N$ (5 eq.) was added the corresponding sulphonyl chloride (1.2 eq.) and the reaction mixture was stirred at RT under $N_2$ overnight. The resulting mixture was poured into water and the organic layer was extracted with ethyl acetate, dried ($MgSO_4$), filtered and concentrated under reduced pressure to give the desired sulphonamide as crystalline solid or as a thick syrup. The crude compound was then purified by flash chromatography using EtOAc/hexane (3:2) or $CH_2Cl_2$/EtOAc (4:1) as eluent to give crystalline solid.

Note: Insoluble amines and sulphonyl chlorides were dissolved in minimum amount of $CH_2Cl_2$, THF or DMF.

Method C

To a solution Arylsulphonyl chloride (1.1 eq.) in DCM were added Pyridine (2.2 eq.) and catalytic amount of DMAP. The solution was stirred at room temperature under nitrogen for 10 minutes. Then the amine (1 eq.) was added and the reaction mixture was stirred at room temperature under nitrogen for 4~16 hrs. The resulting mixture was partitioned between DCM and 5% sodium bicarbonate. The organic layer was washed with brine, dried over $MgSO_4$, and concentrated to give a solid or a thick syrup. The crude compound was then purified by flash chromatography to give desired arylsulphonamide as crystalline solid.

DGS03020A (STX412)

Synthesised by method A. Off-white crystals of DGS03020A (186 mg; 55%). mp 189-190° C.; TLC $R_f$: 0.68 EtOAc/Hexane (3:2); $^1$H NMR (CDCl$_3$) δ 2.80 (s, 3H, CH$_3$), 7.13 (s, 1H, N—H, exchanged with D$_2$O), 7.212 (dd, 1H, Ar—H, J=2.34 Hz and 8.59 Hz), 7.27 (dd, 1H, Ar—H, J=1.95 Hz and 8.59 Hz), 7.51 (d, 1H, Ar—H, J=1.95 Hz), 7.65 (d, 1H, Ar—H, J=1.95 Hz), 7.69 (d, 1H, Ar—H, J=8.59 Hz), 7.91 (d, 1H, Ar—H, J=8.59 Hz); MS (FAB+) 372.9 [100, (M+H)$^+$]; HRMS m/z (FAB+) 372.9627, $C_{14}H_{10}{}^{35}Cl_2N_2O_2S_2$ requires 372.9639, 376.9574, $C_{14}H_{10}{}^{37}Cl_2N_2O_2S_2$ requires 376.9580; HPLC $t_r$ 3.65 min (92:08=MeOH:H$_2$O).

DGS03022A (STX413)

Synthesised by method A. Off-white crystals of DGS03022A (233 mg; 72%). mp 178° C.; TLC $R_f$: 0.71 EtOAc/Hexane (3:2); $^1$H NMR (CDCl$_3$) δ 2.75 (s, 3H, CH$_3$), 2.80 (s, 3H, CH$_3$), 6.75 (s, 1H, N—H, exchanged with D$_2$O), 7.11 (dd, 1H, Ar—H, J=1.95 Hz and 8.59 Hz), 7.17-7.21 (m, 1H, Ar—H), 7.53 (d, 1H, Ar—H, J=1.17 Hz), 7.55 (d, 1H, Ar—H, J=1.95 Hz), 7.68 (d, 1H, Ar—H, J=8.20 Hz), 7.92 (dd, 1H, Ar—H, J=1.17 Hz and 7.81 Hz); MS (FAB+) 164.1 [35, (5-Amino-2-methyl benzothiazole)$^+$], 353.0 [100, (M+H)$^+$]; HRMS m/z (FAB+) 353.0176, $C_{15}H_{14}{}^{35}ClN_2O_2S_2$ requires 353.0185, 355.0155, $C_{15}H_{14}{}^{37}ClN_2O_2S_2$ requires 355.0156; HPLC $t_r$ 3.78 min (92:08=MeOH:H$_2$O).

DGS03024A (STX421)

Synthesised by method A. White crystals of DGS03024A (240 mg; 76%). mp 133-134° C.; TLC $R_f$: 0.7 EtOAc/Hexane (3:2); $^1$H NMR (CDCl$_3$) δ 0.90 (t, 3H, CH$_3$CH$_2$CH$_2$, J=7.42 Hz), 1.56-1.66 (m, 2H, CH$_3$$\underline{CH_2}$CH$_2$), 2.59 (t, 2H, CH$_3$$\underline{CH_2}$CH$_2$, J=7.42 Hz), 2.80 (s, 3H, CH$_3$), 6.71 (s, 1H, N—H, exchanged with D$_2$O), 7.17 (d 1H, Ar—H, J=2.34 Hz and 8.59 Hz), 7.201-7.214 (m, 1H, Ar—H), 7.218-7.223 (m, 1H, Ar—H), 7.57 (d, 1H, Ar—H, J=2.34 Hz), 7.76-7.69 (m, 3H, Ar—H); MS (FAB+) 347.1 [100, (M+H)$^+$]; HRMS m/z (FAB+) 347.0881, $C_{17}H_{19}N_2O_2S_2$ requires 347.0887; HPLC $t_r$ 3.69 min (92:08=MeOH: H$_2$O).

DGS03034A (STX424)

Synthesised by method A. White crystals of DGS03034A (262 mg; 86%). mp 152° C.; TLC $R_f$: 0.48 EtOAc/Hexane (3:2); $^1$H NMR (CDCl$_3$) δ 10.31 (s, 1H, NH, Ex. With D$_2$O), 7.85 (d, 1H, Ar—H, J=8.59 Hz), 7.66-7.69 (m, 2H, Ar—H), 7.57 (d, 1H, Ar—H, J=1.95 Hz), 7.11 (dd, 1H, Ar—H, J=2.34 Hz and 8.59 Hz), 7.02-7.05 (m, 2H, Ar—H), 3.76 (s, 3H, OCH$_3$), 2.73 (s, 3H, CH$_3$); MS (FAB+) 164.0[25 (Amine SM$^+$)], 335.0 [100, (M+H)$^+$]; HRMS m/z (FAB+) 335.0519, $C_{15}H_{15}N_2O_3S_2$ requires 335.0524; HPLC $t_r$ 1.94 min (80:20=MeOH:H$_2$O).

DGS03036A (STX425)

Synthesised by method A. White crystals of DGS03036A (136 mg; 42%). mp 295-296° C.; TLC $R_f$: 0.56 EtOAc/Hexane (3:2); $^1$H NMR (DMSO-d$_6$) δ 10.66 (s, 1H, NH, Ex. With D$_2$O), 7.87 (d, 1H, Ar—H, J=8.59 Hz), 7.52 (d, 1H, Ar—H, J=1.95 Hz), 7.32-7.44 (m, 3H, Ar—H), 7.12 (dd, 1H, Ar—H, J=2.3 Hz and 8.59 Hz), 2.73 (s, 3H, CH$_3$), 2.64 (s, 3H, CH$_3$); MS (FAB+) 164.0 [40, (Starting amine)$^+$], 353.0 [100, (M+H)$^+$]; HRMS m/z (FAB+) 353.0187, $C_{15}H_{14}{}^{35}ClN_2O_2S_2$ requires 353.0185, 355.0165, $C_{15}H_{14}{}^{37}ClN_2O_2S_2$ requires 355.0155; HPLC $t_r$ 1.94 min (80:20=MeOH: H$_2$O).

DGS03058A (STX519)

Synthesised by method A. White crystals of DGS03058A (199 mg; 57%). mp 172° C.; TLC $R_f$: 0.56 EtOAc/Hexane (3:2); $^1$H NMR (DMSO-d$_6$) δ 10.53 (s, 1H, NH, Ex. With D$_2$O), 7.88 (d, 1H, Ar—H, J=8.59 Hz), 7.74-7.77 (m, 2H, Ar—H), 7.64-7.68 (m, 2H, Ar—H), 7.58 (d, 1H, Ar—H, J=1.95 Hz), 7.11 (dd, 1H, Ar—H, J=1.95 Hz and 8.59 Hz), 2.74 (s, 3H, CH$_3$); MS (FAB+) 384.9 [100, (M+H)$^+$]; HRMS m/z (FAB+) 384.9494, $C_{14}H_{12}{}^{79}BrN_2O_2S_2$ requires 384.9503, 382.9501, $C_{14}H_{12}{}^{79}BrN_2O_2S_2$ requires 382.9523; HPLC $t_r$ 2.64 min (90:10=MeOH: H$_2$O).

DGS03062B (STX469)

To a stirred solution of DGS03022A (50 mg, 0.14 mmol, 1 eq.) in anhy. DMF (5 ml) and NaH (7 mg, 0.16 mmol, 1.1 eq.) was added MeI (3 ml, 0.21 mmol, 1.5 eq.) and the mixture was stirred for 1 h. The resulting mixture was poured into water and the organic layer was extracted with ethyl acetate, dried (MgSO$_4$), filtered and concentrated under reduced pressure to give a yellow suspension. The crude compound (70 mg) was purified by flash chromatography using EtOAc/hexane (3:2) as eluent to give white crystals of DGS03062A (36 mg; 69%). mp 97-98° C.; TLC $R_f$: 0.61 EtOAc/Hexane (3:2); $^1$H NMR (CDCl$_3$) δ 7.73 (dd, 1H, Ar—H, J=1.17 Hz and 7.81 Hz), 7.37 (d, 1H, Ar—H, J=8.59 Hz), 7.59 (d, 1H, Ar—H, J=1.95 Hz), 7.49 (dd, 1H, Ar—H, J=1.17 Hz and 8.2 Hz), 7.24 (dd, 1H, Ar—H, J=2.34 Hz and 8.59 Hz), 7.11-7.15 (m, 1H, Ar—H), 3.24 (s, 3H, CH$_3$), 2.76 (s, 3H, CH$_3$), 2.35 (s, 3H, CH$_3$); MS (FAB+) 366.9 [100, (M+H)$^+$]; HRMS m/z (FAB+) 366.0262, $C_{16}H_{15}{}^{35}ClN_2O_2S_2$ requires 366.0262, 368.0300, $C_{16}H_{15}{}^{37}ClN_2O_2S_2$ requires 368.0234; HPLC $t_r$ 1.93 min (96:04=MeOH: H$_2$O).

DGS03072A (STX470)

To a stirred solution of DGS03022A (50 mg, 0.14 mmol, 1 eq.) in anhy. DMF (5 ml) and NaH (10 mg, 0.16 mmol, 1.1 eq.) was added EtI (23 mg, 0.21 mmol, 1.5 eq.) and the mixture was stirred for 1 h. The resulting mixture was poured into water and the organic layer was extracted with ethyl acetate, dried (MgSO$_4$), filtered and concentrated under reduced pressure to give a yellow suspension. The crude compound (75 mg) was purified by flash chromatography using EtOAc/hexane (3:2) as eluent to give a pale yellow thick syrup of DGS03072A (16 mg; 30%). TLC $R_f$: 0.71 EtOAc/Hexane (3:2); $^1$H NMR (CDCl$_3$) δ 7.76-7.78 (m, 2H, Ar—H), 7.66 (m, 1H, Ar—H), 7.53-7.55 (m, 1H, Ar—H), 7.27-7.28 (m, 1H, Ar—H), 7.14-7.18 (m, 1H, Ar—H), 7.11-7.18 (m, 1H, Ar—H), 5.30 (s, 1H, NH, Ex. with D$_2$O), 3.74 (q, 2H, Ar—H, J=7.42 Hz and 7.03 Hz), 2.83 (s, 3H, CH$_3$), 2.53 (s, 3H, CH$_3$), 1.12 (t, 3H, CH$_3$, J=7.03 Hz), MS (FAB+) 381.1 [100, (M+H)$^+$]; HRMS m/z (FAB+) 381.1062, $C_{17}H_{17}{}^{35}ClN_2O_2S_2$ requires 381.1058, 385.0952, $C_{17}H_{17}{}^{37}ClN_2O_2S_2$ requires 385.0949.

DGS03082A (STX521)

Synthesised by method A. White crystals of DGS03082A (230 mg; 67%). mp 85-86° C.; TLC $R_f$: 0.64 EtOAc/Hexane (3:2); $^1$H NMR (CDCl$_3$) δ 10.54 (s, 1H, NH, Ex. With D$_2$O), 7.87 (d, 1H, Ar—H, J=8.59 Hz), 7.84 (broad s, 4H, Ar—H), 7.67-7.69 (m, 2H, Ar—H), 7.62 (d, 1H, Ar—H, J=1.95 Hz), 7.39-7.49 (m, 3H, Ar—H), 7.17 (dd, 1H, Ar—H, J=1.95 Hz and 8.59 Hz), 2.73 (s, 3H, CH$_3$); MS (FAB+) 381.2 [100, (M+H)$^+$]; HRMS m/z (FAB+) 381.0730, $C_{20}H_{17}N_2O_2S_2$ requires 381.0731; HPLC $t_r$ 1.36 min (96:04=MeOH: H$_2$O).

DGS03084A (STX522)

Synthesised by method A. Yellow crystals of DGS03084A (46 mg; 10%). mp 253-254° C.; TLC $R_f$: 0.74 EtOAc/Hexane (3:2); $^1$H NMR (DMSO-d$_6$) δ 11.09 (s, 1H, NH, Ex. with D$_2$O), 7.91 (d, 1H, Ar—H, J=8.59 Hz), 7.86 (m, 2H, Ar—H), 7.59 (d, 1H, Ar—H, J=2.34 Hz), 7.15 (dd, 1H, Ar—H, J=1.95 Hz and 8.59 Hz), 2.74 (s, 3H, CH$_3$); MS (FAB+) 409.1 [100, (M+H)$^+$]; MS (FAB−) 407.0 [100, (M−H)$^+$]; HRMS m/z (FAB+) 406.9176, $C_{14}H_9{}^{35}Cl_3N_2O_2S_2$ requires 406.9167, 408.9136, $C_{14}H_9{}^{37}Cl_3N_2O_2S_2$ requires 408.9140.

DGS03086A (STX523)

Synthesised by method A. Pale yellow crystals of DGS03086A (101 mg; 57%). mp 219° C.; TLC $R_f$: 0.71 EtOAc/Hexane (3:2); $^1$H NMR (DMSO-$d_6$) δ 10.68 (s, 1H, NH, Ex. With $D_2O$), 7.87 (d, 1H, Ar—H, J=8.59 Hz), 7.79 (d, 1H, Ar—H, J=8.59 Hz), 7.64 (d, 1H, Ar—H, J=1.95 Hz), 7.54-7.57 (m, 2H, Ar—H), 7.11 (dd, 1H, Ar—H, J=2.34 Hz and 8.59 Hz), 2.73 (s, 3H, $CH_3$), 2.59 (s, 3H, $CH_3$); MS (FAB+) 399.0 [100, (M+H)$^+$], 164.1 [50, (Starting amine)+]; HRMS m/z (FAB+) 398.9663, $C_{15}H_{13}{}^{81}BrN_2O_2S_2$ requires 398.9569, 396.9684, $C_{15}H_{13}{}^{79}BrN_2O_2S_2$ requires 396.9689; HPLC $t_r$ 1.39 min (96:04=MeOH: $H_2O$).

DGS03064

2,4-Dichloro benzoic acid (10 g, 0.0523 mol, 1 eq.) was heated to 115° C. with excess chlorosulphuric acid (10.5 mL, 0.1571 mol, 3 eq.) under $N_2$ for 18 h. The resulting mixture was cooled and consciously poured into ice-water. The resulted white precipitate was filtered out, washed with plenty of water and dried under vacuum over night. The crude DGS03064 (11.5 g, 76%) was used for the subsequent reaction without further purification. mp 173-174° C.; TLC $R_f$: 0.48 (4:1, $CH_2Cl_2$/EtOAc); $^1$H NMR ($CDCl_3$) δ 8.28 (1H, s, Ar—H), 7.65 (1H, s, Ar—H); MS m/z (FAB+) 286.9 [100, (M+H)$^+$]; HRMS m/z (FAB+) 287.8798, $C_7H_3{}^{35}C_3O_4S$ requires 287.8818, 291.8755, $C_7H_3{}^{31}Cl_3O_4S$ requires 291.8759.

DGS03088A (STX524)

Synthesised by method B. Two compounds were isolated—DGS03088A and DGS03A. White crystals of DGS03088A (48 mg; 13%). mp 153-155° C.; TLC $R_f$: 0.79 EtOAc/Hexane (3:2); $^1$H NMR ($CDCl_3$) δ 8.31 (s, 1H, NH, Ex. With $D_2O$), 8.07 (s, 1H, NH, Ex. With $D_2O$), 8.07 (s, 1H, Ar—H), 7.71-7.79 (m, 4H, Ar—H), 7.67 (d, 1H, Ar—H, J=1.95 Hz), 7.58 (s, 1H, Ar—H), 7.27 (dd, 1H, Ar—H, J=2.72 Hz and 8.59 Hz), 2.83 (s, 3H, $CH_3$), 2.79 (s, 3H, $CH_3$); MS (FAB+) 562.9 [100, (M+H)$^+$]; HRMS m/z (FAB+) 562.9825, $C_{23}H_{17}{}^{35}Cl_2N_4O_3S_3$ requires 562.9839, 566.9778, $C_{23}H_{17}{}^{37}Cl_2N_4O_3S_3$ requires 566.9781; HPLC $t_r$ 1.33 min (96:04=MeOH: $H_2O$).

DGS03088-1 (STX575)

White crystals of DGS03088-1 (31 mg; 12%). mp 147-148° C.; TLC $R_f$: 0.45 EtOAc/Hexane (3:2); $^1$H NMR ($CDCl_3$) δ 8.45 (s, 1H, NH, Ex. With $D_2O$), 8.17 (d, 1H, Ar—H, J=8.09 Hz), 8.04 (s, 1H, Ar—H), 7.77 (s, 1H, Ar—H), 7.50 (d, 1H, Ar—H, J=1.83 Hz), 7.35 (dd, 1H, Ar—H, J=1.83 Hz and 8.05 Hz), 2.85 (s, 3H, $CH_3$); LC-MS 418.1 [100, (M$^+$)]; HPLC $t_r$ 1.97 min (96:04=MeOH:$H_2O$).

DGS03100A (STX552)

Synthesised by method B. White crystals of DGS03100A (224 mg; 69%). mp 222-223° C.; TLC $R_f$: 0.56 $CH_2Cl_2$/EtOAc (4:1); $^1$H NMR (DMSO-$d_6$) δ 10.27 (s, 1H, NH, Ex. With $D_2O$), 9.16-9.17 (m, 1H, Ar—H), 8.48-8.51 (m, 2H, Ar—H), 8.36-8.38 (m, 2H, Ar—H), 8.23-8.25 (m, 1H, Ar—H), 7.67-7.34 (m, 3H, Ar—H), 7.51-7.12 (m, 1H, Ar—H), 7.09-7.12 (m, 1H, Ar—H), 2.67 (s, 3H, $CH_3$); LC-MS 355.7 [(M)$^+$]; MS (FAB+) 356.0 [100, (M+H)$^+$]; HRMS m/z (FAB+) 356.0531, $C_{17}H_{14}N_3O_2S_2$ requires 356.0527; HPLC $t_r$ 1.86 min (96:04=MeOH: $H_2O$).

DGS03102A (STX553)

Synthesised by method B. Pale yellow crystals of DGS03102A (170 mg; 52%). mp 89-90° C.; TLC $R_f$: 0.55 $CH_2Cl_2$/EtOAc (4:1); $^1$H NMR (DMSO-$d_6$) δ 10.87 (s, 1H, NH, Ex. With $D_2O$), 8.28-8.24 (m, 1H, Ar—H), 8.06-8.22 (m, 2H, Ar—H), 8.05 (d, 1H, Ar—H, J=8.20 Hz), 7.60-7.77 (m, 2H, Ar—H), 7.47 (d, 1H, Ar—H, J=1.95 Hz), 7.04 (dd, 1H, Ar—H, J=1.95 Hz and 8.59 Hz), 2.69 (s, 3H, $CH_3$); MS (FAB+) 355.0 [100, (M+H)$^+$]; HRMS m/z (FAB+) 355.0576, $C_{18}H_{15}N_2O_2S_2$ requires 355.0575; HPLC $t_r$ 1.93 min (96:04=MeOH: $H_2O$).

DGS03104A (STX554)

Synthesised by method B. Yellow crystals of DGS03104A (230 mg; 63%). mp 85-86° C.; TLC $R_f$: 0.65 $CH_2Cl_2$/EtOAc (4:1); $^1$H NMR (DMSO-$d_6$) δ 10.84 (s, 1H, NH, Ex. With $D_2O$), 8.40-8.42 (m, 2H, Ar—H), 8.22-8.23 (m, 1H, Ar—H), 7.76-7.78 (m, 1H, Ar—H), 7.58-7.65 (m, 2H, Ar—H), 7.51-7.56 (m, 1H, Ar—H), 7.23-7.25 (m, 1H, Ar—H), 7.05-7.07 (m, 1H, Ar—H), 2.79 (s, 6H, 2×$CH_3$), 2.69 (s, 3H, $CH_3$); MS (FAB+) 398.1 [100, (M+H)$^+$]; HRMS m/z (FAB+) 398.0978, $C_{20}H_{20}N_3O_2S_2$ requires 398.0997; HPLC $t_r$ 2.01 min (96:04=MeOH $H_2O$).

DGS03116A (STX580)

Synthesised by method B. Pale yellow crystals of DGS03116A (151 mg; 44%). mp 153° C.; TLC $R_f$: 0.55 $CH_2Cl_2$/EtOAc (4:1); $^1$H NMR (DMSO-$d_6$) δ 10.96 (s, 1H, NH, Ex. With $D_2O$), 8.00 (d, 1H, Ar—H, J=2.34 Hz), 7.90 (d, 1H, Ar—H, J=8.59 Hz), 7.66-7.73 (m, 2H, Ar—H), 7.58 (d, 1H, Ar—H, J=2.34 Hz), 7.17 (dd, 1H, Ar—H, J=2.34 Hz and 8.59 Hz), 2.74 (s, 3H, $CH_3$); MS (FAB+) 372.8 [100, (M+H)$^+$]; HRMS m/z (FAB+) 375.9599, $C_{14}H_{11}{}^{37}Cl_2N_2O_2S_2$ requires 375.9502, 372.9606, $C_{14}H_{11}{}^{35}Cl_2N_2O_2S_2$ requires 372.9639; HPLC $t_r$ 2.98 min (90:10=MeOH: $H_2O$).

DGS03118A (STX581)

Synthesised by method B. White crystals of DGS03118A (416 mg; 42%). mp 88-89° C.; TLC $R_f$: 0.49 $CH_2Cl_2$/EtOAc (4:1); $^1$H NMR (DMSO-$d_6$) δ 10.47 (s, 1H, NH, Ex. With $D_2O$), 7.74 (d, 1H, Ar—H, J=8.59 Hz), 7.58-7.61 (m, 2H, Ar—H), 7.35-7.38 (m, 1H, Ar—H), 7.13-7.17 (m, 1H, Ar—H), 4.76-4.78 (m, 2H, $CH_2$), 3.75-3.79 (m, 2H, $CH_2$), 2.90-2.93 (m, 2H, $CH_2$), 2.73 (s, 3H, $CH_3$); MS (FAB+) 456.0 [100, (M+H)$^+$]; HRMS m/z (FAB+) 456.0663, $C_{19}H_{17}F_3N_3O_3S_2$ requires 456.0663; HPLC $t_r$ 1.63 min (96:04=MeOH:$H_2O$).

DGS03120A (STX582)

Synthesised by method B. Pale yellow crystals of DGS03120A (185 mg; 55%). mp 91-92° C.; TLC $R_f$: 0.51 $CH_2Cl_2$/EtOAc (4:1); $^1$H NMR (DMSO-$d_6$) δ 10.35 (s, 1H, NH, Ex. With $D_2O$), 7.85 (d, 1H, Ar—H, J=8.98 Hz), 7.69 (d, 1H, Ar—H, J=2.34 Hz), 7.61 (dd, 1H, Ar—H, J=2.73 Hz and 8.98 Hz), 7.55 (d, 1H, Ar—H, J=2.73 Hz), 7.20 (d, 1H, Ar—H, J=8.98 Hz), 7.15 (dd, 1H, Ar—H, J=2.3 Hz and 8.59 Hz), 3.89 (s, 3H, $OCH_3$), 2.73 (s, 3H, $CH_3$); MS (FAB+) 369.0 [100, (M+H)$^+$]; HRMS m/z (FAB+) 371.0114, $C_{15}H_{14}{}^{35}ClN_2O_3S_2$ requires 371.0105, 369.0135, $C_{15}H_{14}{}^{35}ClN_2O_3S_2$ requires 369.0134; HPLC $t_r$ 1.68 min (96:04=MeOH: $H_2O$).

DGS03122A (STX731)

Synthesised by method B. Two compounds were isolated—DGS03122A and DGS03122B. Yellow crystals of DGS03122A (67 mg; 22%). mp 272-273° C.; TLC $R_{f:0.59}$ $CH_2Cl_2$/EtOAc (4:1); $^1$H NMR (DMSO-$d_6$) δ 8.15 (m, 5H, Ar—H), 8.02-8.09 (m, 4H, Ar—H), 7.74 (d, 1H, Ar—H, J=2.3 Hz), 7.14 (dd, 1H, Ar—H, J=1.95 Hz and 8.59 Hz), 2.84 (s, 3H, $CH_3$); MS (FAB+) 495.0 [100, (M+H)$^+$]; HPLC $t_r$ 1.79 min (90:10=MeOH:$H_2O$).

DGS03122B (STX583)

Yellow crystals of DGS03122B (47 mg; 16%). mp 204-206° C.; TLC $R_f$: 0.48 $CH_2Cl_2$/EtOAc (4:1); $^1$H NMR (DMSO-$d_6$) δ 10.95 (s, 1H, NH, Ex. With $D_2O$), 8.03-8.07 (m, 2H, Ar—H), 7.86-7.91 (m, 2H, Ar—H), 7.77-7.81 (m, 1H, Ar—H), 7.55 (d, 1H, Ar—H, J=1.95 Hz), 7.12 (dd, 1H, Ar—H, J=2.34 Hz and 8.59 Hz), 2.74 (s, 3H, $CH_3$); MS (FAB+) 330.0 [100, (M+H)$^+$]; HRMS m/z (FAB+) 330.0370, $C_{15}H_{12}N_3O_2S_2$ requires 330.0371; HPLC $t_r$ 1.84 min (90:10=MeOH: $H_2O$).

DGS03124A (STX584)

Synthesised by method B. Pale yellow crystals of DGS03124A (125 mg; 55%). mp 188-189° C.; TLC $R_f$: 0.37 $CH_2Cl_2$/EtOAc (4:1); $^1$H NMR (DMSO-$d_6$) δ 10.09 (s, 1H, NH, Ex. With $D_2O$), 7.81 (d, 1H, Ar—H, J=8.59 Hz), 7.63 (d, 1H, Ar—H, J=8.20 Hz), 7.56 (d, 1H, Ar—H, J=1.95 Hz), 7.14 (dd, 1H, Ar—H, J=1.95 Hz and 8.59 Hz), 6.96 (s, 1H, Ar—H), 6.81 (d, 1H, Ar—H, J=8.59 Hz), 3.87 (s, 3H, $OCH_3$), 2.72 (s, 3H, $CH_3$), 2.28 (s, 3H, $CH_3$); MS (FAB+) 219.1 [20, (sulphonyl chloride-H)$^+$], 349.0 [100, (M+H)$^+$]; HRMS m/z (FAB+) 349.0678, $C_{16}H_{17}N_2O_3S_2$ requires 349.0681; HPLC $t_r$ 1.80 min (96:04=MeOH:$H_2O$).

DGS03126A (STX585)

Synthesised by method B. Pale yellow crystals of DGS03126A (145 mg; 40%). mp 84-86° C.; TLC $R_f$: 0.71 $CH_2Cl_2$/EtOAc (4:1); $^1$H NMR (DMSO-$d_6$) δ 10.42 (s, 1H, NH, Ex. With $D_2O$), 7.88 (d, 1H, Ar—H, J=8.59 Hz), 7.73-7.77 (m, 2H, Ar—H), 7.59 (d, 1H, Ar—H, J=1.95 Hz), 7.41-7.46 (m, 2H, Ar—H), 7.22-7.26 (m, 2H, Ar—H), 7.13 (dd, 1H, Ar—H, J=8.59 Hz and 2.34 Hz), 7.02-7.10 (m, 4H, Ar—H), 2.75 (s, 3H, $CH_3$); MS (FAB+) 397.0 [100, (M+H)$^+$]; HRMS m/z (FAB+) 397.0671, $C_{20}H_{17}N_2O_3S_2$ requires 397.0681; HPLC $t_r$ 1.93 min (96:04=MeOH: $H_2O$).

DGS03130A (STX730)

Synthesised by method B. Two compounds were isolated—DGS03130A and DGS03130B. Synthesised by method B. Pale yellow crystals of DGS03130A (105 mg; 33%). mp 125-126° C.; TLC $R_f$: 0.55 $CH_2Cl_2$/EtOAc (4:1); $^1$H NMR (DMSO-$d_6$) δ 8.21-8.24 (m, 4H, Ar—H), 8.13 (d, 1H, Ar—H, J=8.59 Hz), 7.99-8.03 (m, 4H, Ar—H), 7.57 (d, 1H, Ar—H, J=1.95 Hz), 7.03 (dd, 1H, Ar—H, J=8.59 Hz and 1.95 Hz), 2.82 (s, 3H, $CH_3$); 2.69 (s, 6H, 2×$CH_3$); MS (FAB+) 529.0 [100, (M+H)$^+$]; MS (FAB−) 527.1 [70, (M−H)$^+$], 345.0 [100, (M-2-Acetyl sulphonyl chloride)$^+$]; HPLC $t_r$ 1.81 min (96:04=MeOH: $H_2O$).

DGS03130B (STX701)

Pale yellow crystals of DGS03130A (45 mg; 14%). mp 169° C.; TLC $R_f$: 0.42 $CH_2Cl_2$/EtOAc (4:1); $^1$H NMR (DMSO-$d_6$) δ 10.63 (s, 1H, NH, Ex. With $D_2O$), 8.04-8.07 (m, 2H, Ar—H), 7.86-7.89 (m, 3H, Ar—H), 7.59 (d, 1H, Ar—H, J=1.95 Hz), 7.13 (dd, 1H, Ar—H, J=8.9 Hz and 2.3 Hz), 3.73 (s, 3H, $CH_3$); 2.56 (s, 3H, $CH_3$); MS (FAB+) 347.0 [100, (M+H)$^+$], 219.1 [10, (sulphonyl chloride+H)$^+$]; HRMS m/z (FAB+) 347.0522, $C_{16}H_{15}N_2O_3S_2$ requires 347.0524; HPLC $t_r$ 1.77 min (96:04=MeOH: $H_2O$).

DGS03134A (STX703)

Synthesised by method B. Pale yellow crystals of DGS03134A (91 mg; 23%). mp 206-207° C.; TLC $R_f$: 0.81 $CH_2Cl_2$/EtOAc (4:1); $^1$H NMR (DMSO-$d_6$) δ 10.37 (s, 1H, NH, Ex. With $D_2O$), 7.87 (d, 1H, Ar—H, J=8.59 Hz), 7.46 (d, 1H, Ar—H, J=1.95 Hz), 7.19 (s, 2H, Ar—H), 7.07 (dd, 1H, Ar—H, J=8.59 Hz and 1.95 Hz), 4.13-4.20 (m, 2H, 2×($CH_3$)$_2$$\underline{H}$), 2.83-2.89 (m, 1H, ($CH_3$)$_2$$\underline{H}$), 2.72 (s, 3H, $CH_3$), 1.15 (d, 12H, 4×($CH_3$)$_2$, J=7.03 Hz), 1.11 (d, 9H, 2×($CH_3$)$_2$, J=6.64 Hz); LC-MS 429.72 (M)$^+$; HPLC $t_r$ 2.84 min (90:10=MeOH:$H_2O$).

DGS03136A (STX704)

Synthesised by method B. Pale yellow crystals of DGS03136A (225 mg; 71%). mp 54-55° C.; TLC $R_f$: 0.50 $CH_2Cl_2$/EtOAc (4:1); $^1$H NMR (CDCl$_3$) δ 7.65 (m, 3H, Ar—H), 7.58 (d, 1H, Ar—H, J=2.34 Hz), 7.18 (dd, 1H, Ar—H, J=8.6 Hz and 1.95 Hz), 6.84-6.85 (m, 2H, Ar—H), 6.82 (s, 1H, NH, Ex. With $D_2O$), 4.51-4.60 (m, 1H, ($CH_3$)$_2$$\underline{H}$), 2.80 (s, 3H, $CH_3$), 1.31 (s, 6H, ($CH_3$)$_2$); LC-MS 347.6 (M)$^+$; HRMS m/z (FAB+) 347.0847, $C_{17}H_{19}N_2O_2S_2$ requires 347.0837; HPLC $t_r$ 2.39 min (90:10=MeOH:$H_2O$).

DGS03138B (STX705)

Synthesised by method B. Pale yellow crystals of DGS03138B (24 mg; 7%). mp 248° C.; TLC $R_f$: 0.52 $CH_2Cl_2$/EtOAc (4:1); $^1$H NMR (CDCl$_3$) δ 8.18 (d, 1H, Ar—H, J=8.59 Hz), 8.15 (d, 1H, Ar—H, J=1.95 Hz), 7.89-8.04 (m, 4H, Ar—H), 7.51 (dd, 1H, Ar—H, J=8.20 Hz and 1.95 Hz), 7.27 (s, 1H, NH, Ex. With $D_2O$), 2.89 (s, 3H, $CH_3$), 1.59 (s, 3H, $CH_3$); LC-MS 372.90 (M+$CH_3$CN)$^+$; HRMS m/z (FAB+) 371.2281, $C_{16}H_{15}N_2O_4S_2$ requires 371.2278; HPLC $t_r$ 2.22 min (90:10=MeOH:$H_2O$).

DGS03140A (STX711)

Synthesised by method B. Brown crystals of DGS03140A (85 mg; 26%). mp 73-75° C.; TLC $R_f$: 0.59 $CH_2Cl_2$/EtOAc (4:1); $^1$H NMR (CDCl$_3$) δ 7.85 (d, 1H, Ar—H, J=8.59 Hz), 7.80 (d, 1H, Ar—H, J=8.59 Hz), 7.68 (s, 1H, NH, Ex. With $D_2O$), 7.57 (d, 1H, Ar—H, J=1.95 Hz), 7.54 (s, 1H, NH, Ex. With $D_2O$), 7.24 (d, 1H, Ar—H, J=2.34 Hz), 7.18 (dd, 1H, Ar—H, J=8.20 Hz and 1.95 Hz), 7.03 (dd, 1H, Ar—H, J=8.59 Hz and 2.34 Hz), 6.77 (dd, 1H, Ar—H, J=8.59 Hz and 2.34 Hz), 2.78 (s, 3H, $CH_3$), 2.24 (s, 3H, $CH_3$); LC-MS 362.32 (M)$^+$; HRMS m/z (FAB+) 361.0587, $C_{16}H_{16}N_3O_3S_2$ requires 361.0636; HPLC $t_r$ 2.09 min (90:10=MeOH $H_2O$).

DGS03142A (STX706)

Synthesised by method B. Pale yellow crystals of DGS03142A (79 mg; 24%). mp 89-91° C.; TLC $R_f$: 0.65 $CH_2Cl_2$/EtOAc (4:1); $^1$H NMR (CDCl$_3$) δ 7.78 (d, 1H, Ar—H, J=8.20 Hz), 7.61 (d, 1H, Ar—H, J=1.56 Hz), 6.98 (dd, 1H, Ar—H, J=1.95 Hz and 8.20 Hz), 6.93 (s, 1H, Ar—H), 6.92 (s, 1H, NH, Ex. With $D_2O$), 3.99 (s, 6H, 2×$CH_3$), 3.93 (s, 6H, 2×$CH_3$), 2.85 (s, 3H, $CH_3$); LC-MS 361.48 (M)$^+$; HRMS m/z (FAB+) 361.1605, $C_{18}H_{21}N_2O_2S_2$ requires 361.1606; HPLC $t_r$ 2.26 min (90:10=MeOH:$H_2O$).

DGS03144A (STX707)

Synthesised by method B. Pale yellow crystals of DGS03144A (79 mg; 24%). mp 89-91° C.; TLC $R_f$: 0.69 $CH_2Cl_2$/EtOAc (4:1); $^1$H NMR (CDCl$_3$) δ 7.70 (d, 1H, Ar—H, J=8.59 Hz), 7.58 (d, 1H, Ar—H, J=2.34 Hz), 7.39 (dd, 1H, Ar—H, J=2.34 Hz and 8.59 Hz), 7.19 (d, 1H, Ar—H, J=1.95 Hz), 7.17 (t, 1H, Ar—H, J=1.95 Hz), 6.83 (d, 1H, Ar—H, J=8.59 Hz), 6.59 (s, 1H, NH, Ex. With $D_2O$), 3.89 (s, 3H, $OCH_3$), 3.76 (s, 3H, $OCH_3$), 2.81 (s, 3H, $CH_3$); LC-MS 363.02 (M)$^+$; HRMS m/z (FAB+) 365.0642, $C_{16}H_{17}N_2O_4S_2$ requires 365.0585; HPLC $t_r$ 2.15 min (90:10=MeOH: $H_2O$).

DGS03146A (STX708)

Synthesised by method B. Pale yellow crystals of DGS03146A (181 mg; 51%). mp 175° C.; TLC $R_f$: 0.57 $CH_2Cl_2$/EtOAc (4:1); $^1$H NMR (CDCl$_3$) δ 7.71 (dd, 1H, Ar—H, J=2.3 Hz and 8.98 Hz), 7.59 (d, 1H, Ar—H, J=1.95 Hz), 7.43 (d, 1H, Ar—H, J=8.98 Hz), 7.21 (dd, 1H, Ar—H, J=1.95 Hz and 8.59 Hz), 6.67 (s, 1H, NH, Ex. With $D_2O$), 2.81 (s, 3H, $OCH_3$), 1.59 (s, 6H, 2×$CH_3$), 1.29 (s, 6H, 2×$CH_3$);

LC-MS 377.01 (M)$^+$; HRMS m/z (FAB+) 377.0988, $C_{18}H_{21}N_2O_3S_2$ requires 377.0994; HPLC $t_r$ 2.53 min (90:10=MeOH:H$_2$O).

DGS03148A (STX709)

Synthesised by method B. Off-white crystals of DGS03148A (102 mg; 31%). mp 214-215° C.; TLC R$_f$: 0.62 CH$_2$Cl$_2$/EtOAc (4:1); $^1$H NMR (CDCl$_3$) δ 7.71-7.73 (m, 2H, Ar—H), 7.60-7.61 (m, 1H, Ar—H), 7.44-7.46 (m, 2H, Ar—H), 7.21-7.24 (m, 2H, Ar—H), 6.61 (s, 1H, NH, Ex. With D$_2$O), 2.83 (s, 3H, CH$_3$), 1.31 (s, 9H, (CH$_3$)$_3$); LC-MS 360.12 (M)$_r$; HRMS m/z (FAB+) 361.1057, $C_{19}H_{21}N_2O_3S_2$ requires 361.1044; HPLC $t_r$ 2.67 min (90:10=MeOH H$_2$O).

DGS03150A (STX710)

Synthesised by method B. Pale yellow crystals of DGS03150A (101 mg; 30%). mp 200-201° C.; TLC R$_f$: 0.50 CH$_2$Cl$_2$/EtOAc (4:1); $^1$H NMR (CDCl$_3$) δ 7.65 (d, 1H, Ar—H, J=8.59 Hz), 7.44 (d, 1H, Ar—H, J=1.95 Hz), 7.09 (dd, 1H, Ar—H, J=1.95 Hz and 8.59 Hz), 6.75 (s, 1H, NH, Ex. With D$_2$O), 2.79 (s, 3H, CH$_3$), 2.57 (s, 6H, 2×CH$_3$), 2.24 (s, 3H, CH$_3$), 2.19 (s, 6H, 2×CH$_3$); LC-MS 374.10 (M)$^+$; HRMS m/z (FAB+) 375.1195, $C_{19}H_{23}N_2O_2S_2$ requires 375.1201; HPLC $t_r$ 3.15 min (80:20=MeOH:H$_2$O).

DGS03152A (STX712)

Synthesised by method B. Pale yellow crystals of DGS03152A (120 mg; 33%). mp 181-182° C.; TLC R$_f$: 0.65 CH$_2$Cl$_2$/EtOAc (4:1); $^1$H NMR (CDCl$_3$) δ 7.63 (d, 1H, Ar—H, J=8.59 Hz), 7.59 (d, 1H, Ar—H, J=2.3 Hz), 7.22 (dd, 1H, Ar—H, J=2.3 Hz and 8.59 Hz), 4.91 (s, 1H, NH, Ex. With D$_2$O), 3.82 (s, 3H, CH$_3$); LC-MS 392.96 (M)$^+$; HRMS m/z (FAB+) 394.9941, $C_{14}H_8F_5N_2O_2S_2$ requires 394.9947; HPLC $t_r$ 2.49 min (90:10=MeOH:H$_2$O).

DGS03158A (STX713)

Synthesised by method B. Yellow crystals of DGS03158A (158 mg; 40%). mp 334-335° C.; TLC R$_f$: 0.47 CH$_2$Cl$_2$/EtOAc (4:1); $^1$H NMR (CDCl$_3$) δ 7.65 (d, 1H, Ar—H, J=8.59 Hz), 7.47 (d, 1H, Ar—H, J=2.3 Hz), 7.10 (dd, 1H, Ar—H, J=2.3 Hz and 8.59 Hz), 6.69 (s, 1H, NH, Ex. With D$_2$O), 2.79 (s, 3H, CH$_3$), 2.61 (t, 2H, CH$_2$, J=6.64 Hz), 2.55 (s, 3H, CH$_3$), 2.51 (s, 3H, CH$_3$), 2.08 (s, 3H, CH$_3$), 1.79 (t, 2H, CH$_2$, J=7.03 Hz), 1.29 (s, 6H, 2×CH$_3$); LC-MS 431.11 (M)$^+$; HPLC $t_r$ 3.24 min (90:10=MeOH:H$_2$O).

Synthesis of Benzothiazole Arylsulphonamide Derivatives

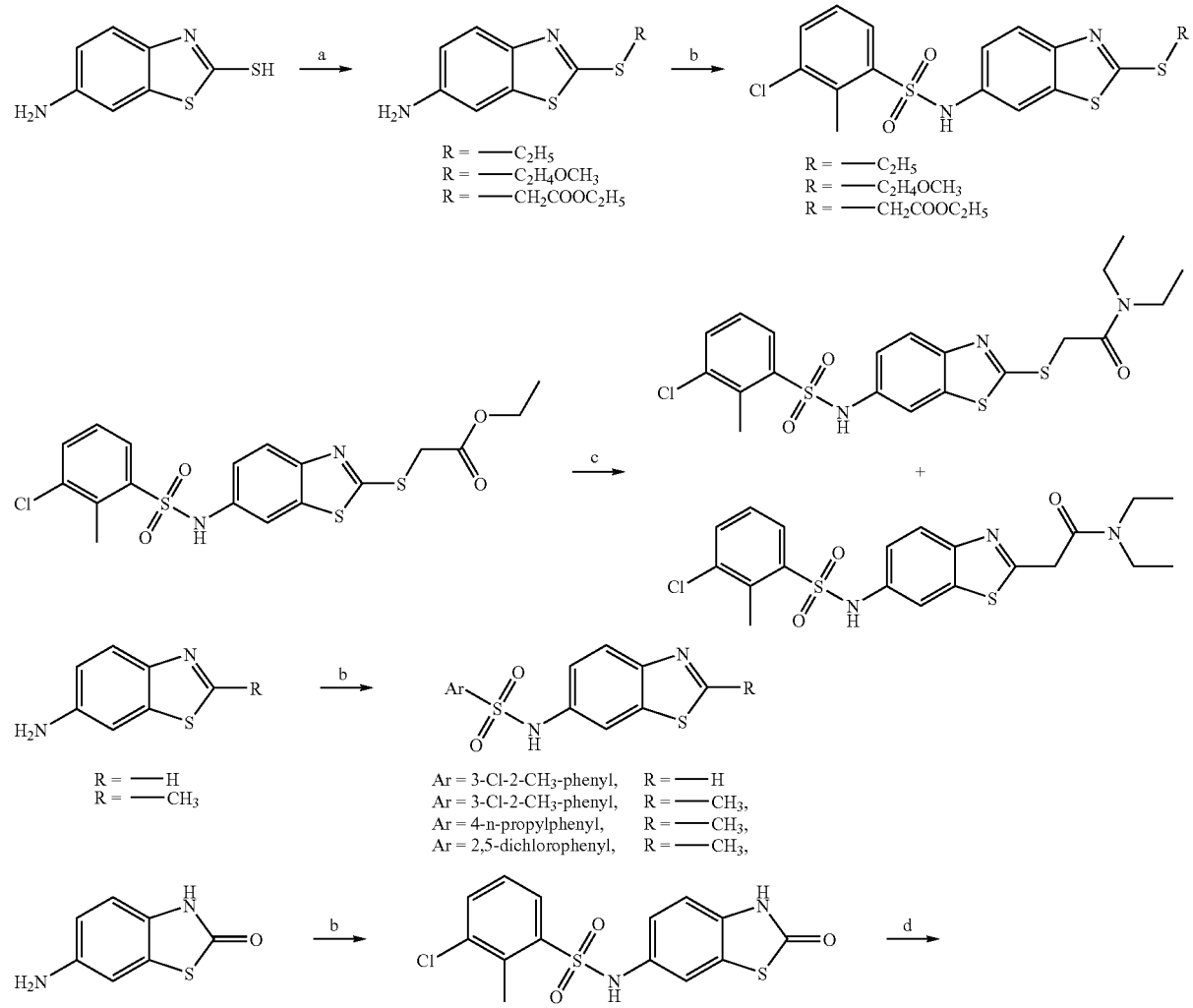

-continued
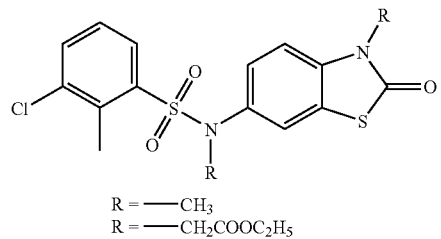
R = —CH$_3$
R = —CH$_2$COOC$_2$H$_5$
a) RX, NaH, THF r.t.
b) ArSO$_3$Cl, DCM, Pyridine or ArSO$_3$Cl, DCM, Pyridine/DMAP
c) Diethylamine, DCM, AlCl$_3$
d) RX, K$_2$CO$_3$, Acetone, reflux
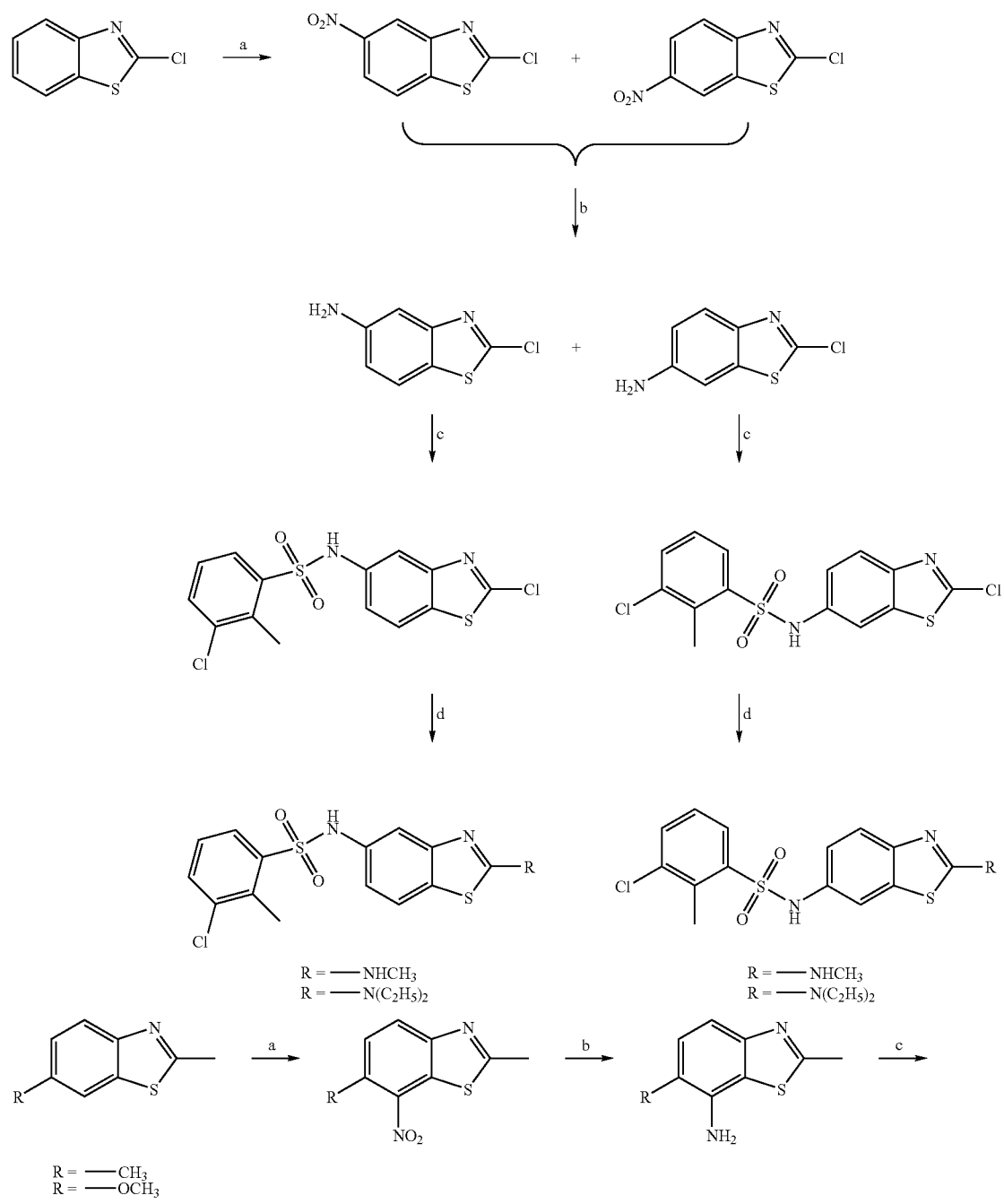

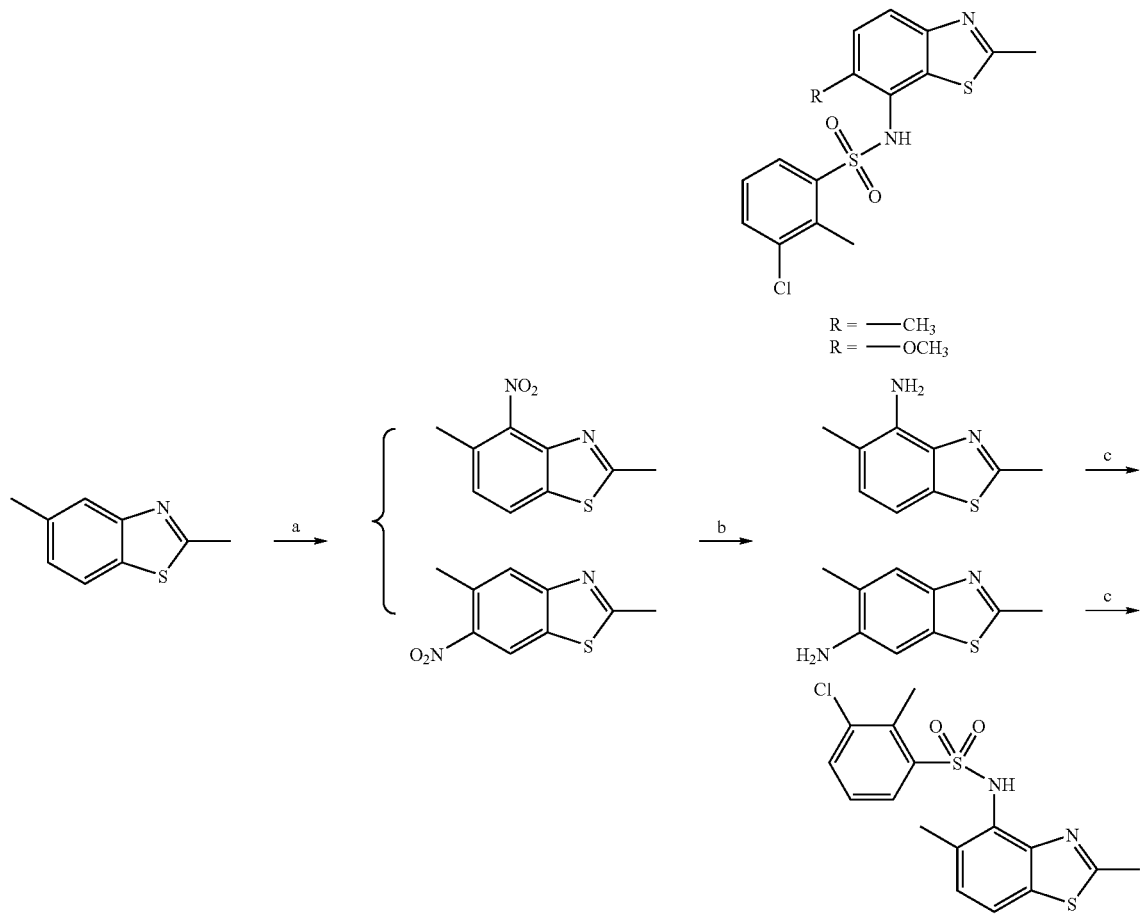
a) HNO₃, H₂SO₄ -5 -0° C.
b) H₂, 5% Pd/C, C₂H₅OH,
c) ArSO₃Cl, DCM, Pyridine or ArSO₃Cl, DCM, Pyridine/DMAP
d) amine, THF, reflux
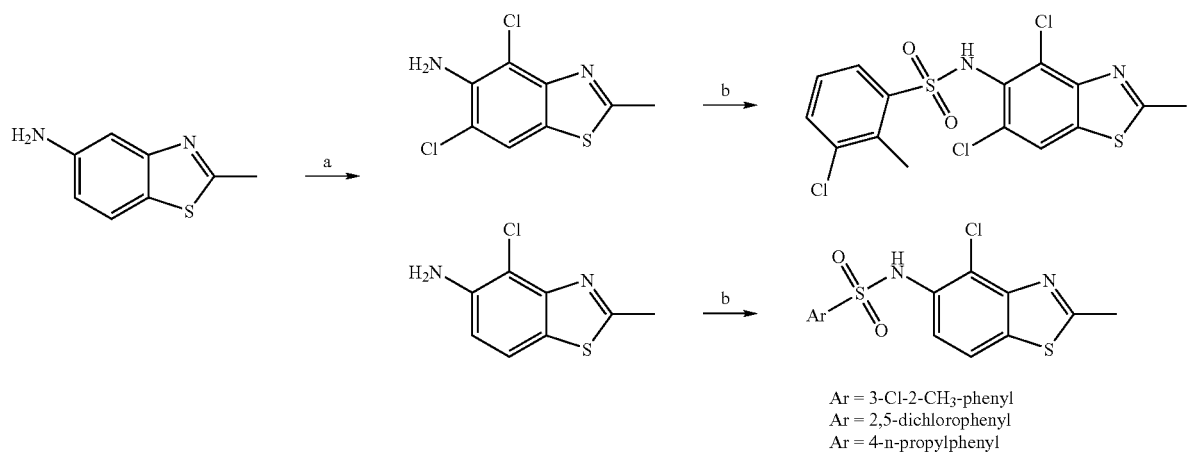

-continued
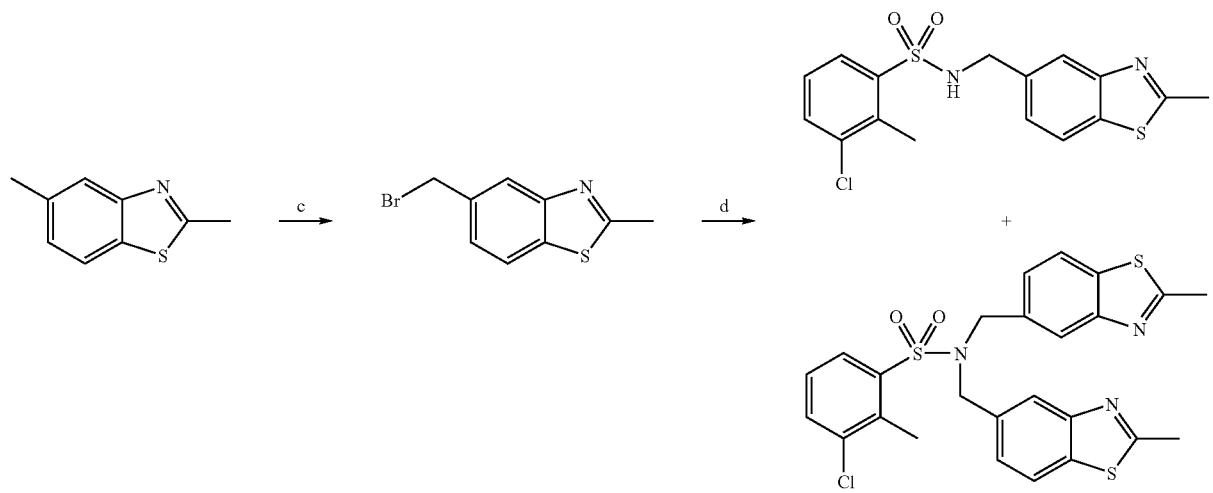
a) N-chlorosuccinimide, IPA
b) ArSO₃Cl, DCM, Pyridine or ArSO₃Cl, DCM, Pyridine/DMAP
c) N-bromosuccinimide, CCl4, benzoyl peroxide
d) 3-chloro-2methylbenzenesulphonamide, K₂CO₃, CH₃CN
STX751, XDS01141
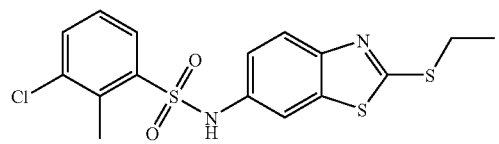
STX752, XDS01142
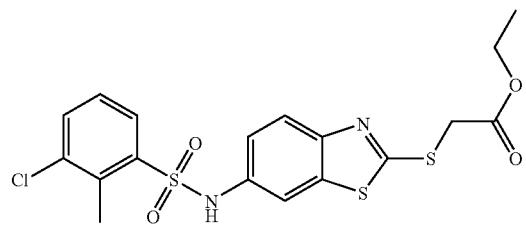
STX754, XDS01144
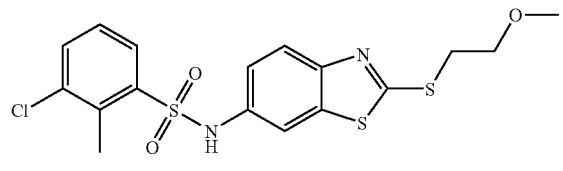
STX755, XDS01145A
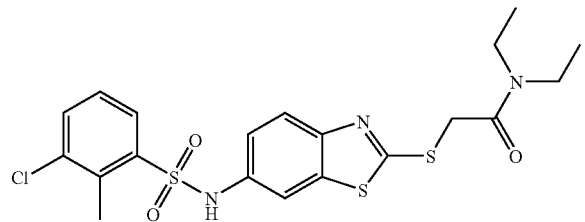
STX763, XDS01145B
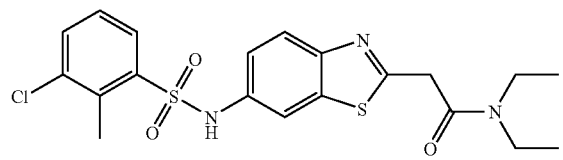
STX750, XDS01139
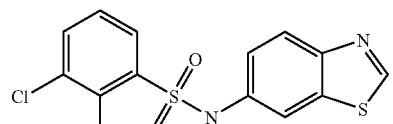
STX886, XDS01187B
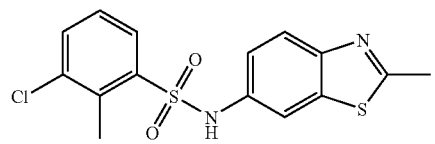
STX887, XDS01187A
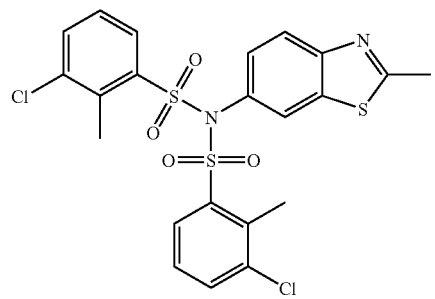

-continued
STX888, XDS01188B
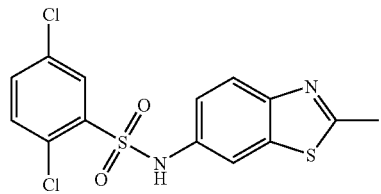
STX889, XDS01188A
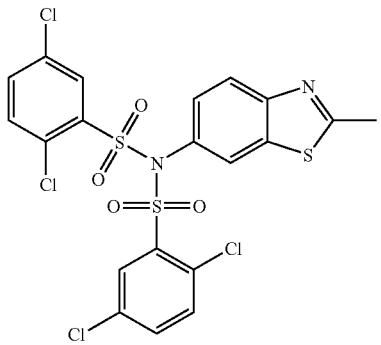
STX890, XDS01189
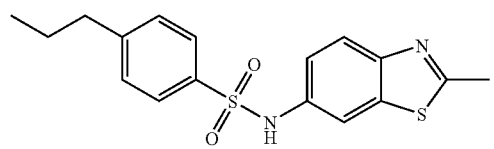
STX753, XDS01143
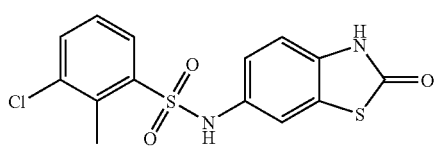
STX831, XDS01163
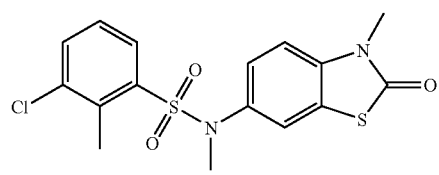
STX764, XDS01149
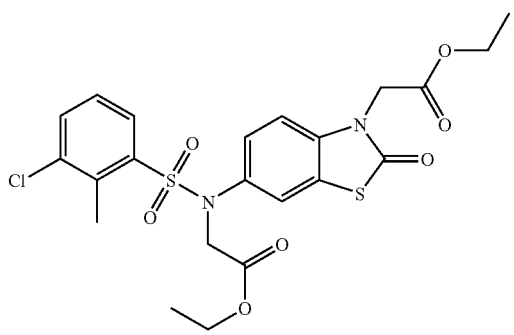
STX767, XDS01151A
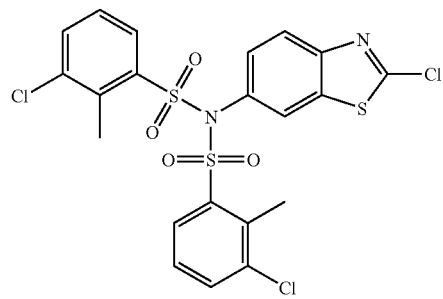
STX768, XDS01151B
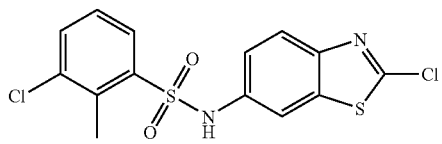
STX834, XDS01168
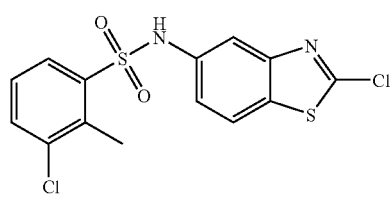
STX833, XDS01167
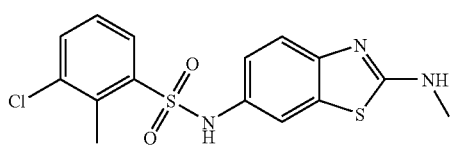
STX835, XDS01176
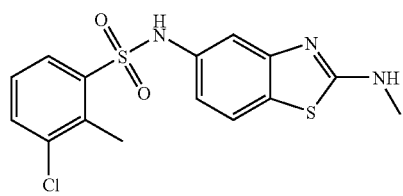
STX836, XDS01177
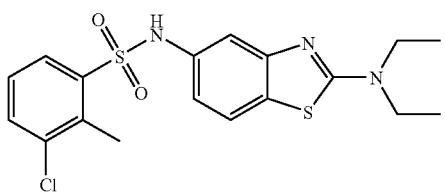

-continued
STX878, XDS01164
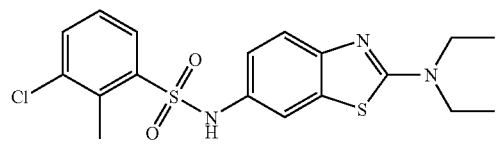
STX989, XDS02038
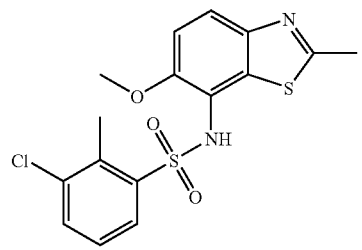
STX1021, XDS02069
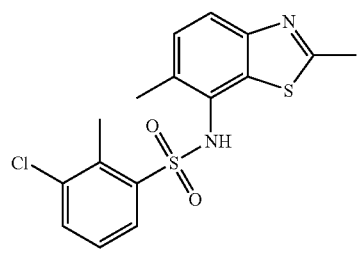
STX996, XDS02047
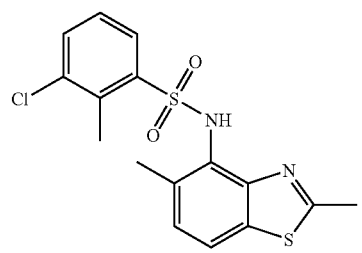
STX997, XDS02048A
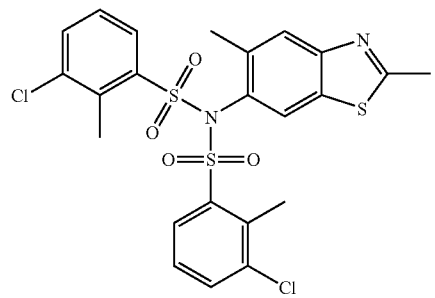
STX998, XDS02048B
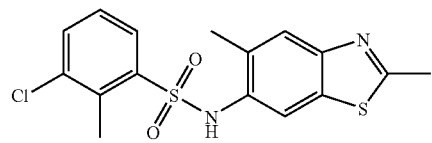
STX999, XDS02049
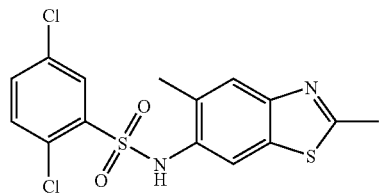
STX992, XDS02042B
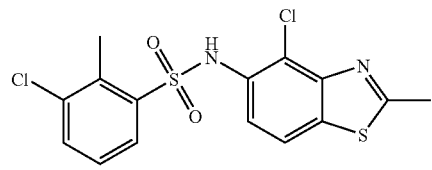
STX991, XDS02042A
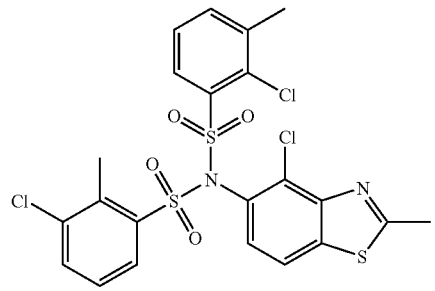
STX993, XDS02043B
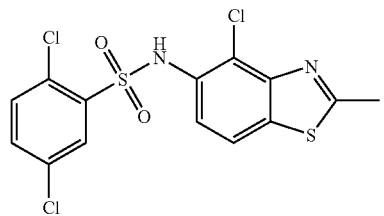

-continued
STX991, XDS02042A
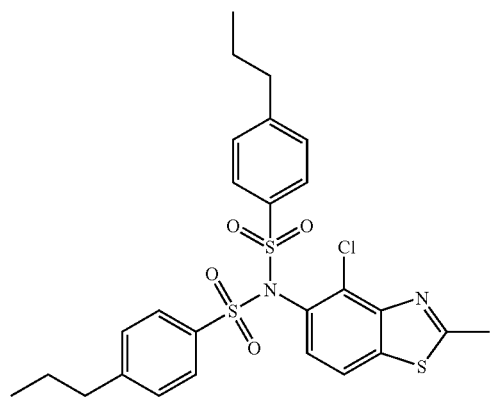
STX994, XDS02044B
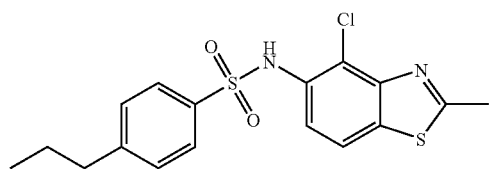
STX1017, XDS02055B
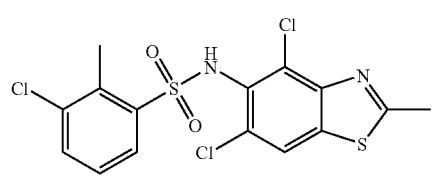
STX1029, XDS02070A
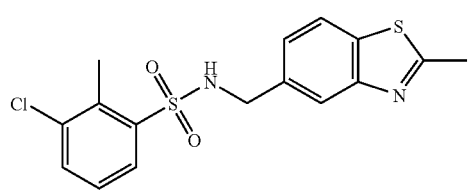
STX1030, XDS02070B
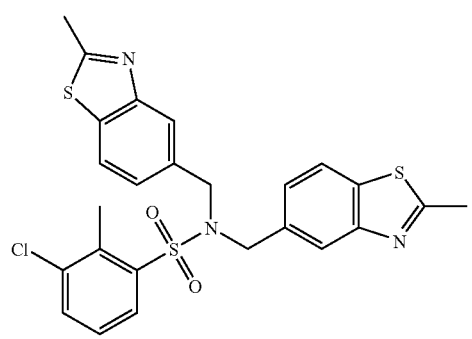
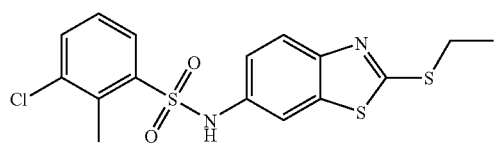
STX751, XDS01141
-continued
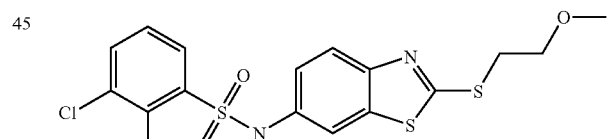
STX754, XDS01144
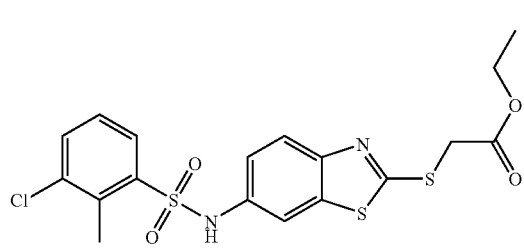
STX752, XDS01142
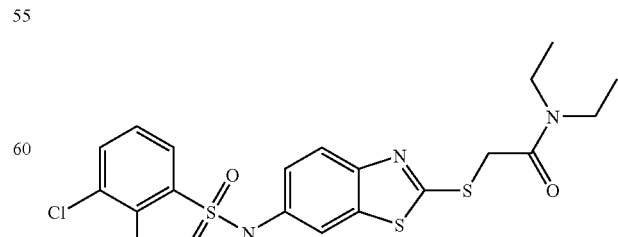
STX755, XDS01145A -continued
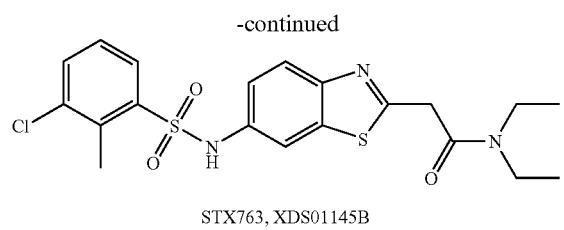
STX763, XDS01145B
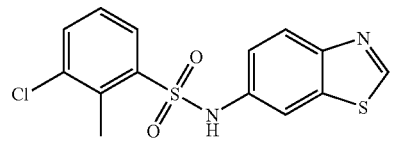
STX750, XDS01139
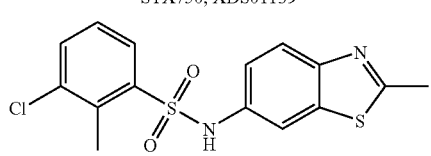
STX886, XDS01187B
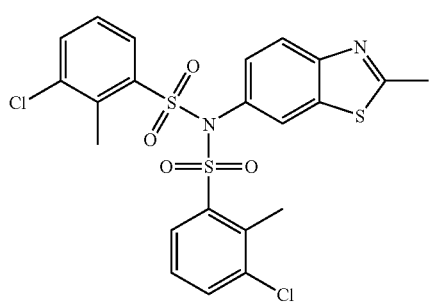
STX887, XDS01187A
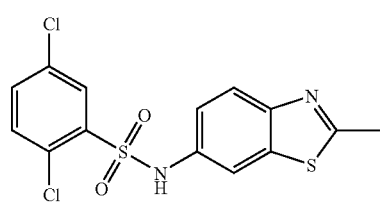
STX888, XDS01188B
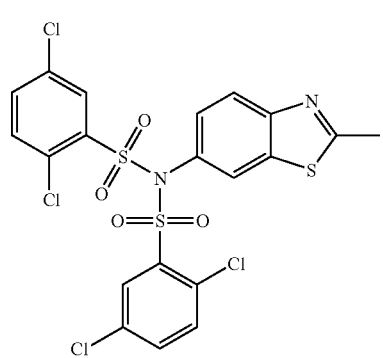
STX889, XDS01188A
-continued
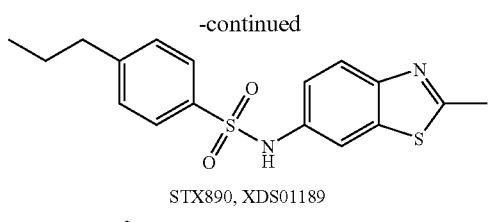
STX890, XDS01189
STX753, XDS01143
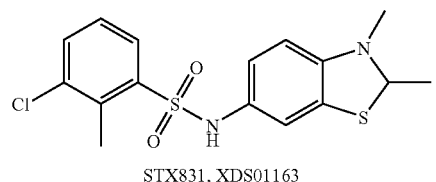
STX831, XDS01163
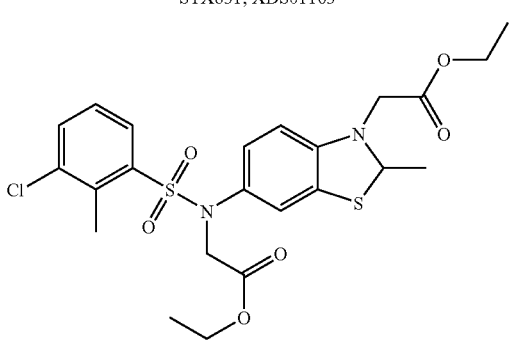
STX764, XDS01149
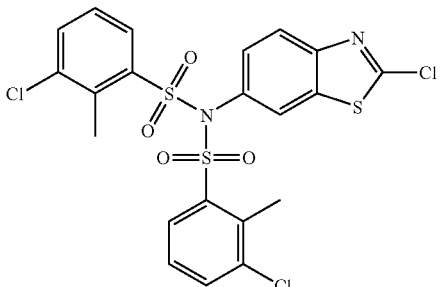
STX767, XDS01151A
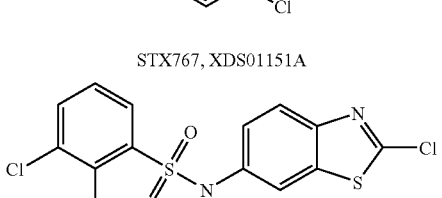
STX768, XDS01151B
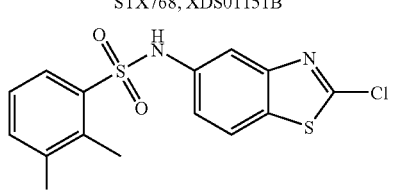
STX834, XDS01168

-continued
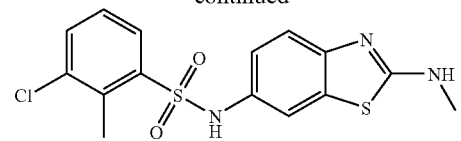
STX833, XDS01167
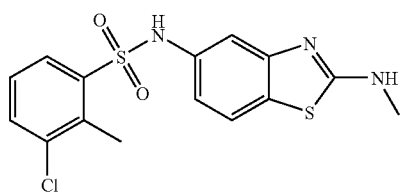
STX835, XDS01176
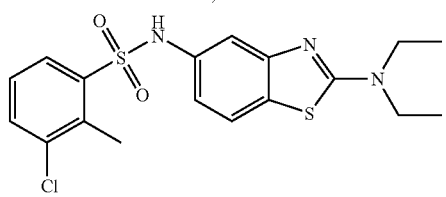
STX836, XDS01177
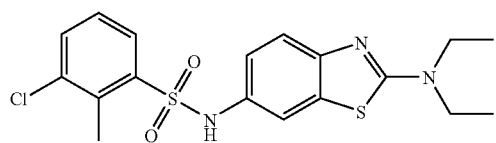
STX878, XDS01164
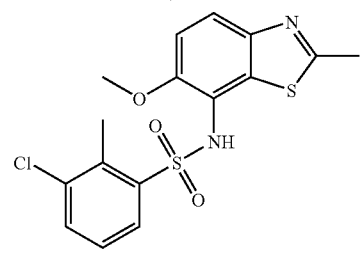
STX989, XDS02038
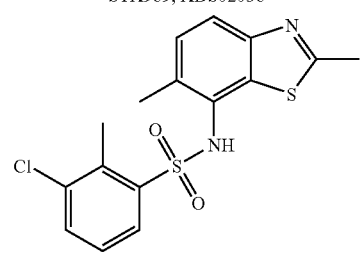
STX1021, XDS02069
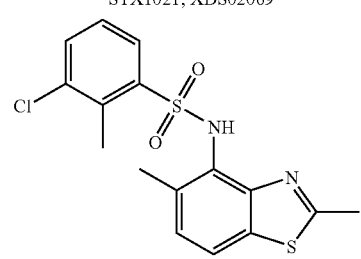
STX996, XDS02047
-continued
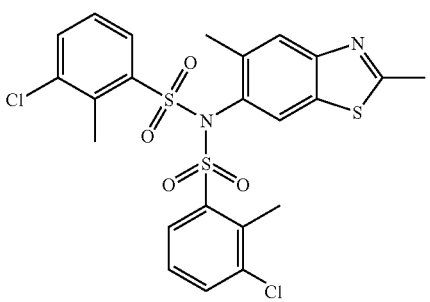
STX997, XDS02048A
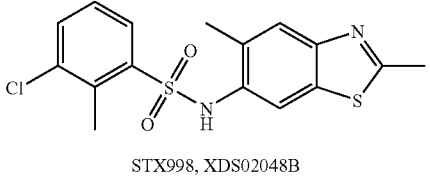
STX998, XDS02048B
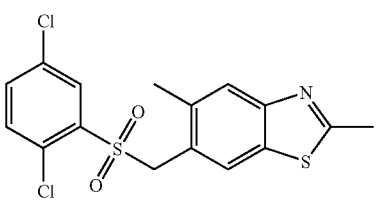
STX999, XDS02049
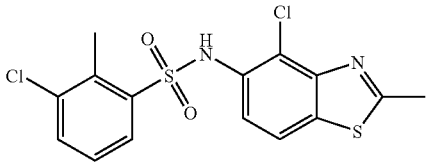
STX992, XDS02042B
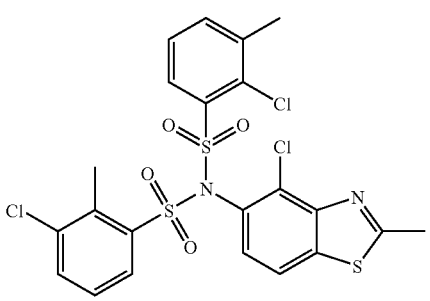
STX991, XDS02042A
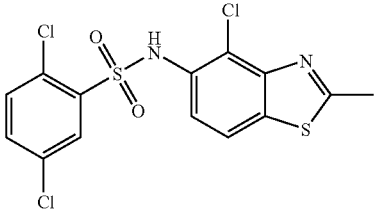
STX993, XDS02043B

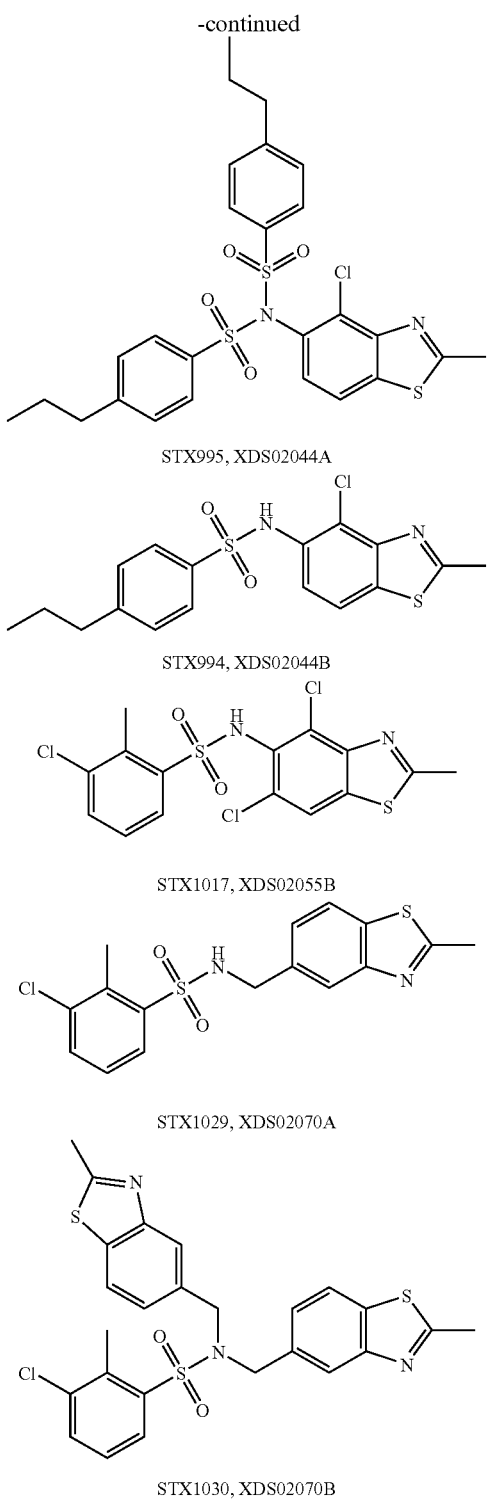

General Method for the Preparation of N-Benzothiazol Benzenesulphonamid Derivatives:

To a solution arylsulphonyl chloride (1.1 eq.) in DCM (5-10 mL) were added pyridine (2.2 eq.) and catalytic amount of DMAP. The solution was stirred at room temperature under nitrogen for 10 minutes. Then the amine (1 eq.) was added and the reaction mixture was stirred at room temperature under nitrogen for 4-16 hrs. The resulting mixture was partitioned between DCM and 5% sodium bicarbonate. The organic layer was washed with brine, dried over $MgSO_4$, and concentrated to give a yellow residue. The crude compound was then purified by flash chromatography to give desired benzenesulphonamide as crystalline solid. (Yield 40-90%).

Synthesis of
2-Alkylsulfanyl-benzothiazol-6-yl-amine

To a solution of 6-amino-2-merceptobenzothiazole (273 mg, 1.5 mmol) in anhydrous THF (10 mL) was added NaH (60% dispersion, 1.5 mmol), followed by alkyl halide (1.5 mmol). The mixture was stirred at rt for 24 h, partitioned between ethyl acetate and 5% sodium bicarbonate. The organic phase was washed with brine, dried over sodium sulphate and concentrated in vacuo to a yellow solid, which was purified with recrystallization or flash chromatography. (Yield 60-90%).

The following amines were synthesized with the method described above:

2-Ethylsulfanylbenzothiazol-6-ylamine

Yellow crystalline solid. mp 77-78° C. (lit. 77° C.). TLC single spot at $R_f$ 0.78 (8% methanol/DCM); $^1$H NMR (270 MHz, DMSO): δ 7.50 (1H, d, J=8.5 Hz, 4-H), 6.98 (1H, d, J=2.2 Hz, 7-H), 6.69 (1H, dd, J=8.5, 2.2 Hz, 5-H), 5.33 (2H, broad, $NH_2$), 3.23 (2H, q, J=7.3 Hz, $SCH_2$), 1.35 (3H, t, J=7.3 Hz, $CH_3$). (Francolor, S. A.; U.S. Pat. No. 2,500,093; 1945)

2-(2-Methoxyethylsulfanyl)-benzothiazol-6-ylamine

Yellow thick syrup. TLC single spot at $R_f$ 0.65 (30% ethyl acetate/DCM); $^1$H NMR (270 MHz, DMSO): δ 7.49 (1H, d, J=8.8 Hz, 4-H), 6.97 (1H, d, J=2.2 Hz, 7-H), 6.69 (1H, dd, J=8.8, 2.2 Hz, 5-H), 5.34 (2H, broad, $NH_2$), 3.63 (2H, t, J=6.3 Hz, $CH_2$), 3.43 (2H, t, J=6.3 Hz, $CH_2$), 3.26 (3H, s, $CH_3$).

(6-aminobenzothiazol-2-ylm rcapto)-acetic acid ethylester

Off white solid. mp 87-89° C. (lit. 92° C., [20]); TLC single spot at $R_f$ 10.72 (8% methanol/DCM); $^1$H NMR (270 MHz, DMSO): δ 7.48 (1H, d, J=8.7 Hz, 4-H), 7.01 (1H, d, J=1.8 Hz, 7-H), 6.71 (1H, dd, J=8.7, 1.8 Hz, 5-H), 5.58 (2H, broad, $NH_2$), 4.17 (2H, s, $SCH_2$), 4.12 (2H, t, J=7.3 Hz, $CH_2$), 1.19 (3H, t, J=7.3 Hz, $CH_3$).

The following compounds were synthesized with the general method for N-benzothiazole benzenesulphonamide:

3-Chloro-N-(2-ethylsulfanylbenzothiazol-6-yl)-2-methylbenzenesulphonamide (STX751, XDS01141)

Off-white solid (220 mg; 55%). TLC single spot at $R_1$: 0.83 (17% EtOAc/DCM); HPLC purity 96% ($t_R$ 1.9 nm in methanol); $^1$HNMR (400 MHz, DMSO-$d_6$) δ 10.8 (1H, s, NH), 7.89 (1H, dd, J=8.0, 1.0 Hz, 6'-H of benzene), 7.71 (1H, d, J=8 Hz, 4-H of benzothiazole), 7.70 (1H, d, J=2 Hz, 7-H of benzothiazole), 7.70 (1H, dd, J=8.0, 1.0 Hz, 4'-H of benzene), 7.36 (1H, t, J=8 Hz, 5'-H of benzene), 7.15 (1H, dd, J=8.0, 2.0 Hz, 5-H of benzothiazole), 3.30 (2H, q, J=7.0 Hz, $SCH_2$), 2.66 (3H, s, $CH_3$), 1.38 (3H, t, J=7.0 Hz, $CH_3$); APCI-MS 397.99 (M)$^+$; FAB-HRMS calcd for $C_{16}H_{16}ClN_2O_2S_3$ (MH$^+$) 399.0062, found 399.0048.

[6-(3-Chloro-2-methylbenzenesulphonylamino)-benzothiazol-2-ylsulfanyl]-acetic acid ethyl ester (STX752, XDS01142)

White crystalline solid (210 mg; 46%). TLC single spot at $R_1$: 0.69 (17% EtOAc/DCM); HPLC purity 99% ($t_R$ 2.9 min in 10% water-methanol); $^1$HNMR (400 MHz, DMSO-$d_6$) δ 10.8 (1H, s, SO$_2$NH), 7.88 (1H, dd, J=8.0, 1.0 Hz, 6'-H of benzene), 7.72 (1H, d, J=2.0 Hz, 7-H of benzothiazole), 7.69 (1H, dd, J=8.0, 1.0 Hz, 4'-H of benzene), 7.68 (1H, d, J=8.0 Hz, 4-H of benzothiazole), 7.36 (1H, t, J=8.0 Hz, 5'-H of benzene), 7.15 (1H, dd, J=8.0, 2.0 Hz, 5-H of benzothiazole), 4.25 (2H, s, 2-SCH$_2$—), 4.13 (2H, q, J=7.1 Hz, COOCH$_2$), 2.64 (3H, s, CH$_3$), 1.17 (3H, t, J=7.1 Hz, 2-COOCH$_2$CH$_3$); APCI-MS 456.0 (M)$^+$; FAB-HRMS calcd for C$_{18}$H$_{18}$ClN$_2$O$_4$S$_3$ (MH$^+$) 457.0117, found 457.0109.

3-Chloro-N-[2-(2-methoxyethylsulfanyl)-benzothiazol-6-yl]-2-methylbenz nesulphonamid (STX754, XDS01144)

Off-White solid (150 mg; 77%). TLC single spot at $R_f$ 0.60 (17% EtOAc/DCM); HPLC purity 94% ($t_R$ 3.1 min in 10% water-methanol); $^1$HNMR (400 MHz, DMSO-$d_6$) δ 10.8 (1H, s, SO$_2$NH), 7.88 (1H, dd, J=8, 1 Hz, 6'-H of benzene), 7.71 (1H, d, J=8 Hz, 4-H of benzothiazole), 7.70 (1H, dd, J=8, 1 Hz, 4'-H of benzene), 7.69 (1H, d, J=2 Hz, 7-H of benzothiazole), 7.36 (1H, t, J=8 Hz, 5'-H of benzene), 7.15 (1H, dd, J=8, 2 Hz, 5-H of benzothiazole), 3.64 (2H, t, J=6 Hz, CH$_2$), 3.50 (2H, t, J=6 Hz, SCH$_2$), 3.27 (3H, s, CH$_3$), 2.65 (3H, s, CH$_3$); APCI-MS 428.0 (M)$^+$; FAB-HRMS calcd for C$_{17}$H$_{18}$ClN$_2$O$_3$S$_3$ (MH$^+$) 429.0168, found 429.0159.

2-[6-(3-Chloro-2-methylbenzenesulphonylamino)-benzothiazol-2-ylsulfanyl]-N,N-diethylacetamide (STX755, XDS01145) and 2-[6-(3-chloro-2-methyl-benzenesulphonylamino)-benzothiazol-2-yl]-N,N-diethylacetamide (STX763, XDS01145B)

To a suspension of AlCl$_3$ (50 mg) in DCM (5 ml) was added diethylamine (0.4 ml). The solution was stirred under nitrogen at room temperature for 10 minutes. [6-(3-Chloro-2-methyl-benzenesulphonylamino)-benzothiazol-2-ylsulfanyl]-acetic acid ethyl ester (STX752, 100 mg) was added and the mixture was kept stirring at room temperature for 30 minutes. The reaction was quenched with water, partitioned between DCM and 5% NaHCO$_3$. The organic phase was washed with water, dried over MgSO$_4$ and evaporated in vacuo to give a yellow residue, which was purified with flash column chromatography using 20-30% ethyl acetate-DCM as eluting solvent. STX755 (50 mg, 47%) was obtained as white solid. TLC single spot at $R_f$ 10.60 (25% EtOAc/DCM); HPLC purity 89% ($t_R$ 2.7 min in 10% water-methanol); $^1$HNMR (270 MHz, DMSO-$d_6$) δ 10.7 (1H, s, SO$_2$NH), 7.86 (1H, d, J=8 Hz, 6'-H of benzene), 7.64-7.68 (3H, m, 4'-H of benzene and 4,7-H of benzothiazole), 7.34 (1H, t, J=8 Hz, 5'-H of benzene), 7.12 (1H, dd, J=8, 2 Hz, 5-H of benzothiazole), 4.42 (2H, s, 2-SCH$_2$—), 3.26-3.38 (4H, m, —N(CH$_2$)$_2$—), 2.50 (3H, s, 1'-CH$_3$), 1.17 (3H, t, J=7 Hz, —NCH$_2$CH$_3$), 1.00 (3H, t, J=7 Hz, —NCH$_2$CH$_3$); APCI-MS 484.0 (M)$^+$; FAB-HRMS calcd for C$_{20}$H$_{23}$ClN$_3$O$_3$S$_3$ (MH$^+$) 484.0590, found 484.0584.

STX763 (25 mg, 25%) was obtained as white solid. TLC single spot at $R_f$ 10.39 (25% EtOAc/DCM); LCMS purity 98% ($t_R$ 6.9 min in 10% water-CH$_3$CN); $^1$HNMR (400 MHz, DMSO-$d_6$) δ 10.8 (1H, s, SO$_2$NH), 7.88 (1H, dd, J=8.1, 1.2 Hz, 6'-H of benzene), 7.79 (1H, d, J=8.6 Hz, 4-H), 7.72 (1H, d, J=2.0 Hz, 7-H), 7.68 (1H, dd, J=8.1, 1.2 Hz, 4'-H of benzene), 7.35 (1H, t, J=8.1 Hz, 5'-H of benzene), 7.17 (1H, dd, J=8.6, 2 Hz, 5-H of benzothiazole), 4.2 (2H, s, 2-SCH$_2$—), 3.26-3.38 (4H, m, —N(CH$_2$)$_2$—), 2.65 (3H, s, CH$_3$), 1.10 (3H, t, J=7 Hz, —NCH$_2$CH$_3$), 1.02 (3H, t, J=7 Hz, —NCH$_2$CH$_3$); APCI-MS 451.0 (M)$^+$; FAB-HRMS calcd for C$_{20}$H$_{23}$ClN$_3$O$_3$S$_2$ (MH$^+$) 452.0869, found 452.0870.

3-Chloro-N-benzothiazol-6-yl-2-methylbenzene-sulphonamide (STX750, XDS01139)

Light pink needles (260 mg; 77%). TLC single spot at $R_f$ 0.46 (17% EtOAC/DCM); HPLC purity 99% ($t_R$ 2.5 min in 10% water-methanol); $^1$HNMR (400 MHz, DMSO-$d_6$) δ 10.9 (1H, S, SO$_2$NH), 9.25 (1H, s, 2-H of benzothiazole), 7.95 (1H, d, J=9 Hz, 4-H of benzothiazole), 7.92 (1H, dd, J=8.0, 1.0 Hz, 6'-H of benzene), 7.84 (1H, d, J=2 Hz, 7-H of benzothiazole), 7.70 (1H, dd, J=8.0, 1.0 Hz, 4'-H of benzene), 7.37 (1H, t, J=8 Hz, 5'-H of benzene), 7.25 (1H, dd, J=9.0, 2.0 Hz, 5-H of benzothiazole), 2.66 (3H, s, CH$_3$); APCI-MS 337.9 (M)$^+$; FAB-HRMS calcd for C$_{20}$H$_{23}$ClN$_3$O$_3$S$_2$ (MH$^+$) 452.0869, found 452.0870.

3-Chloro-N-(2-methylbenzothiazol-6-yl)-2-methyl-benzenesulphonamide (STX886, XDS01187B)

Off-white solid. TLC single spot at $R_f$ 0.65 (10% methano/DCM); HPLC purity >99% ($t_R$ 2.4 min in 10% water-methanol); $^1$HNMR (270 MHz, DMSO-$d_6$) δ 10.7 (1H, s, NH), 7.87 (1H, dd, J=7.8, 1.9 Hz, ArH), 7.75 (1H, d, J=8.8 Hz, ArH), 7.69 (1H, d, J=2.2 Hz, ArH), 7.68 (1H, dd, J=7.8, 1.9 Hz, ArH), 7.34 (1H, t, J=7.8 Hz, ArH), 7.15 (1H, dd, J=8.8, 2.2 Hz, ArH), 2.71 (3H, s, CH$_3$), 2.63 (3H, s, CH$_3$); APCI-MS 351 (M–H)$^+$; FAB-HRMS calcd for C$_{15}$H$_{14}$ClN$_2$O$_2$S$_2$ (MH$^+$) 353.0185, found 353.0197.

N-(2-methylbenzothiazol-6-yl)-N-(3-chloro-2-methylphenylsulphonyl)-3-chloro-2-methylbenzene-sulphonamide (STX887, XDS01187A)

Off-white powder. TLC single spot at $R_f$ 0.89 (10% methanol/DCM); HPLC purity 91% ($t_R$ 3.1 min in 10% water-methanol); $^1$HNMR (270 MHz, DMSO-$d_6$) δ 8.09 (1H, d, J=2.2 Hz, ArH), 7.92 (1H, d, J=8.6 Hz, ArH), 7.85-7.90 (4H, m, ArH), 7.46 (2H, t, J=8.0 Hz, ArH), 7.35 (1H, dd, J=8.8, 2.2 Hz, ArH), 2.81 (3H, s, CH$_3$), 2.33 (6H, s, 2×CH$_3$); APCI-MS 539 (M–H)$^+$; FAB-HRMS calcd for C$_{22}$H$_{19}$C$_{12}$N$_2$O$_4$S$_3$ (MH$^+$) 540.9884, found 540.9897.

2,5-Dichloro-N-(2-methylbenzothiazol-6-yl)-benzenesulphonamide (STX888, XDS01188B)

White crystalline solid. TLC single spot at $R_f$ 0.68 (10% methano/DCM); HPLC purity >99% ($t_R$ 2.3 min in 10% water-methanol); $^1$HNMR (270 MHz, DMSO-$d_6$) δ 10.9 (1H, s, NH), 7.98 (1H, d, J=2.3 Hz, ArH), 7.76 (1H, d, J=8.9 Hz, ArH), 7.74 (1H, d, J=2.3 Hz, ArH), 7.69 (1H, dd, J=8.6, 2.3 Hz, ArH), 7.66 (1H, d, J=8.6 Hz, ArH), 7.18 (1H, dd, J=8.9, 2.3 Hz, ArH), 2.71 (3H, s, CH$_3$); APCI-MS 371 (M–H)$^+$; FAB-HRMS calcd for C$_{14}$H$_{11}$Cl$_2$N$_2$O$_2$S$_2$ (MH$^+$) 372.9639, found 372.9651.

N-(2-Methylbenzothiazol-6-yl)-N-(2,5-dichlorophenylsulphonyl)-2,5-dichloro-benzenesulphonamide (STX889, XDS01188A)

Yellow solid. TLC single spot at $R_f$ 0.72 (10% methanol/DCM); HPLC purity 94% ($t_R$ 2.9 min in 10% water-methanol); $^1$HNMR (270 MHz, DMSO-$d_6$) δ 8.13 (1H, d, J=2.2 Hz, ArH), 7.99 (2H, d, J=2.4 Hz, ArH), 7.90-7.94 (3H, m, ArH), 7.77 (2H, d, J=8.4 Hz, ArH), 7.29 (1H, dd, J=8.6, 2.2 Hz, ArH), 2.86 (3H, s, CH$_3$); APCI-MS 581 (M)$^+$; FAB-HRMS calcd for C$_{20}$H$_{13}$Cl$_4$N$_2$O$_4$S$_3$ (MH$^+$) 580.8792, found 580.8777.

N-(2-Methylbenzothiazol-6-yl)-4-propylbenzenesulphonamide (STX890, XDS01189)

Off-white solid. TLC single spot at $R_f$ 0.72 (10% methanol/DCM); HPLC purity 99% ($t_R$ 2.3 min 10% water-methanol); $^1$HNMR (270 MHz, DMSO-$d_6$) δ 10.3 (1H, s, NH), 7.67 (1H, d, J=8.7 Hz, ArH) 7.64 (1H, d, J=1.5 Hz, ArH), 7.59 (2H, d, J=7.7 Hz, ArH), 7.27 (2H, d, J=7.7 Hz, ArH), 7.09 (1H, dd, J=8.7, 1.5 Hz, ArH), 2.65 (3H, s, CH$_3$), 2.49 (2H, t, J=7.9 Hz, CH$_2$), 1.47 (2H, sextet, J=7.9 Hz, CH$_2$), 0.58 (3H, t, J=7.9 Hz, CH$_3$); APCI-MS 345 (M–H)$^+$; FAB-HRMS calcd for C$_{17}$H$_{19}$N$_2$O$_2$S$_2$ (MH$^+$) 347.0888, found 347.0904.

3-Chloro-2-methyl-N-(2-oxo-2,3-dihydro-benzothiazol-6-yl)-benzenesulphonamide (STX753, XDS01143)

White crystalline solid (160 mg; 45%). TLC single spot at $R_f$ 0.42 (17% EtOAc/DCM); —HPLC purity 98% ($t_R$ 2.3 min in 10% water-methanol); $^1$HNMR (400 MHz, DMSO-$d_6$) δ 11.8 (1H, s, 3-NH), 10.5 (1H, s, SO$_2$NH), 7.81 (1H, dd, J=8, 1 Hz, 6'-H of benzene), 7.71 (1H, dd, J=8, 1 Hz, 4'-H of benzene), 7.36 (1H, t, J=8 Hz, 5'-H of benzene), 7.28 (1H, d, J=2 Hz, 7-H of benzothiazole), 6.93-6.98 (2H, m, 4,5-H of benzothiazole), 2.63 (3H, s, CH$_3$); APCI-MS 353.7 (M)$^+$; FAB-HRMS calcd for C$_{14}$H$_{12}$ClN$_2$O$_3$S$_2$ (MH$^+$) 354.9978, found 354.9980.

3-Chloro-N-methyl-N-(3-methyl-2-oxo-2,3-dihydro-benzothiazol-6-yl)-2-methylbenzenesulphonamide (STX831, XDS01163)

To a solution of STX753 (66 mg, 0.19 mmol) in acetone (3 mL) was added potassium carbonate (66 mg), followed by methyl iodide (66 mg). The mixture was stirred at rt for 2 h, extracted into DCM and washed with brine. After drying over sodium sulphate, the solvent was removed in vacuo to give an oily residue that was purified with flash chromatography. Off white solid (59 mg, 80%) was obtained. TLC single spot at $R_f$ 0.37 (100% DCM); HPLC purity 99% ($t_R$ 2.0 min in 10% water-methanol); $^1$HNMR (400 MHz, DMSO-$d_6$) δ 7.73-7.80 (2H, m, ArH), 7.61 (1H, d, J=2.1 Hz, ArH), 7.42 (1H, t, J=8.0 Hz, ArH), 7.29 (1H, d, J=8.8 Hz, ArH), 7.21 (1H, dd, J=8.1, 2.1 Hz, ArH), 3.38 (3H, s, CH$_3$), 3.32 (3H, s, CH$_3$), 2.33 (3H, s, CH$_3$); APCI-MS 383 (MH$^+$)$^+$; FAB-HRMS calcd for C$_{16}$H$_{16}$ClN$_2$O$_3$S$_2$ (MH$^+$) 383.0291, found 383.0273.

[(3-Chloro-2-methylbenzenesulphonyl)-(3-ethoxycarbonylmethyl-2-oxo-2,3-dihydro-benzothiazol-6-yl)-amino]-acetic acid ethyl ester (STX764, XDS01149)

To a solution of STX753 (20 mg, 0.056 mmol) in acetone (3 mL) was added potassium carbonate (20 mg), followed by methyl 2-bromoethyl acetate (50 μl). The mixture was stirred at rt for 4 h, extracted into EtOAc and washed with brine. After drying over sodium sulphate, the solvent was removed in vacuo to give an oily residue that was purified with flash chromatography. White crystalline solid (20 mg, 68%) was obtained. TLC single spot at $R_f$ 0.51 (30% ethyl acetate/hexane); HPLC purity 98% ($t_R$ 2.6 min in 10% water-methanol); $^1$HNMR (400 MHz, DMSO-$d_6$) δ 7.75-7.78 (2H, m, ArH), 7.70 (1H, d, J=2.3 Hz, ArH), 7.37 (1H, t, J=8.2 Hz, ArH), 7.30 (1H, d, J=8.6 Hz, ArH), 7.24 (1H, dd, J=8.6, 2.3 Hz, ArH), 4.81 (2H, s, CH$_2$), 4.56 (2H, s, CH$_2$), 4.14 (2H, q, J=7.0 Hz, CH$_2$), 4.06 (2H, q, J=7.0 Hz, CH$_2$), 2.44 (3H, s, CH$_3$), 1.19 (3H, t, J=7.0 Hz, CH$_3$), 1.13 (3H, t, J=7.0 Hz, CH$_3$); FAB-MS 527 (MH)$^+$; FAB-HRMS calcd for C$_{22}$H$_{24}$ClN$_2$O$_7$S$_2$ (MH$^+$) 527.0713, found 527.0694.

Synthesis of 2-chlorobenzothiazol-6-yl-amine and 2-chloro-benzothiazol-5-yl-amine To a solution of 2-chlorobenzothiazole (12.0 g, 70.7 mmol) in concentrated H$_2$SO$_4$ (60 mL) was added HNO$_3$ (69% solution, 6 mL) dropwise at 0° C. for 20 min. The mixture was stirred at 5° C. for 3 h, poured into ice-water (150 mL). The precipitate was collected and washed with 5% sodium bicarbonate and water, dried in vacuo. $^1$H NMR analysis showed the mixture contained 78% 6-nitro-2-chlorobenzothiazole and 8% 5-nitro-2-chlorobenzothiazole. Recrystallization from ethanol gave 6-nitro-2-chlorobenzothiazole as white crystalline solid (11 g, 72%). 3.5 g of the solid was dissolved in refluxing ethanol-acetic acid (150: 15 mL), Iron powder was added in one portion. The mixture was refluxed for 1.5 h, filtered. The filtrate was concentrated in vacuo to half volume and neutralized with 10% NaOH to pH 7.5, extracted with ethyl acetate. The organic phase was washed with brine, dried over magnesium sulphate and evaporated to give a residue, which was recrystallized from ethanol. Light purple crystals (2.5 g, 83%) were obtained. Mp 160-164° C.; TLC single spot at $R_f$ 0.27 (30% EtOAc/hexane); $^1$HNMR (270 MHz, DMSO-$d_6$) δ 7.58 (1H, d, J=9.0 Hz, 4-H), 7.03 (1H, d, J=2.0 Hz, 7-H), 6.77 (1H, dd, J=9.0, 2.0 Hz, 5-H), 5.55 (2H, s, NH$_2$). The mother liquor from the recrystallization of nitration product was evaporated and subjected to iron powder reduction as described above. The crude product was purified with flash chromatography (ethyl acetate-DCM gradient elution) to give 2-chloro-benzothiazol-5-yl-amine as yellow solid. Mp 146-149° C.; TLC single spot at $R_f$ 0.52 (10% EtOAc/DCM); $^1$HNMR (270 MHz, DMSO-$d_6$) δ 7.63 (1H, d, J=8.6 Hz, 7-H), 7.05 (1H, d, J=2.3 Hz, 4-H), 6.78 (1H, dd, J=8.6, 2.3 Hz, 6-H), 5.40 (2H, s, NH$_2$).

The following compounds were synthesized with the general method for N-benzothiazole benzenesulphonamide:

N-(2-chlorobenzothiazol-6-yl)-N-(3-chloro-2-methylphenylsulphonyl)-3-chloro-2-methylbenzenesulphonamide (STX767, XDS01151A)

White crystalline solid. TLC single spot at $R_f$ 0.78 (33% EtOAc/DCM); HPLC purity 95% ($t_R$ 6.4 min in 10% water-methanol); $^1$HNMR (270 MHz, DMSO-$d_6$) δ 8.21 (1H, d, J=1.3 Hz, ArH), 8.00 (1H, d, J=8.8 Hz, ArH), 7.83-7.90 (4H, m, ArH), 7.46 (2H, t, J=8.0 Hz, ArH), 7.37 (1H, dd, J=8.8, 1.8 Hz, ArH), 2.33 (6H, s, 2×CH$_3$); APCI-MS 560 (M)$^+$; FAB-HRMS calcd for C$_{21}$H$_{16}$Cl$_3$N$_2$O$_4$S$_3$ (MH$^+$) 560.9338, found 560.9344.

3-Chloro-N-(2-chlorobenzothiazol-6-yl)-2-methyl-benzenesulphonamide (STX768, XDS01151B)

Off-white crystalline solid. TLC single spot at $R_f$ 0.68 (33% EtOAC/DCM); HPLC purity 99% ($t_R$ 1.7 min in methanol); $^1$HNMR (270 MHz, DMSO-$d_6$) δ 10.9 (1H, s, NH), 7.91 (1H, d, J=8.1 Hz, ArH), 7.82 (1H, d, J=8.8 Hz, ArH), 7.80 (1H, d, J=3.1 Hz, ArH), 7.70 (1H, d, J=8.1 Hz, ArH), 7.36 (1H, t, J=8.1 Hz, ArH), 7.23 (1H, dd, J=8.8, 3.0 Hz, ArH), 2.63 (3H, s, $CH_3$); APCI-MS 372 (M)$^+$; FAB-HRMS calcd for $C_{14}H_{11}Cl_2N_2O_2S_2$ (MH$^+$) 372.9639, found 372.9651.

3-Chloro-N-(2-chlorobenzothiazol-5-yl)-2-methyl-benzene sulphonamide (STX834, XDS01168)

White crystalline solid. TLC single spot at $R_f$ 0.52 (30% EtOAc/hexane); HPLC purity 99% ($t_R$ 1.7 nm in methanol); $^1$HNMR (270 MHz, DMSO-$d_6$) δ 10.9 (1H, s, NH), 7.91-7.96 (2H, m, ArH), 7.71 (1H, d, J=8.1 Hz, ArH), 7.58 (1H, d, J=2.2 Hz, ArH), 7.39 (1H, d, J=8.1 Hz, ArH), 7.22 (1H, dd, J=8.1, 2.2 Hz, ArH), 2.64 (3H, s, $CH_3$); APCI-MS 371 (M–H)$^+$; FAB-HRMS calcd for $C_{14}H_{11}Cl_2N_2O_2S_2$ (MH$^+$) 372.9639, found 372.9656.

3-Chloro-2-methyl-N-(2-methylaminobenzothiazol-6-yl)-benzenesulphonamide (STX833, XDS01167)

The solution of 3-chloro-N-(2-chlorobenzothiazol-6-yl)-2-methylbenzenesulphonamide (STX768, 150 mg, 0.40 mmol) in $CH_3NH$-THF (2M, 3 mL) was stirred at 82° C. in a sealed tube for 24 h, extracted with ethyl acetate. The organic phase was washed brine, dried over sodium sulphate and concentrated in vacuo to give a residue that was purified with flash chromatography (ethyl acetate/DCM gradient elution). White crystals (100 mg, 68%) were obtained. TLC single spot at $R_f$ 0.27 (30% EtOAc/DCM); HPLC purity 99% ($t_R$ 1.8 min in 4% water-methanol); $^1$HNMR (270 MHz, DMSO-$d_6$) δ 10.2 (1H, s, NH), 7.82 (1H, q, J=4.8 Hz, NH), 7.72 (1H, d, J=7.7 Hz, ArH), 7.61 (1H, d, J=7.7 Hz, ArH), 7.29 (1H, d, J=2.2 Hz, ArH), 7.26 (1H, t, J=8.0 Hz, ArH), 7.15 (1H, d, J=8.7 Hz, ArH), 6.79 (1H, dd, J=8.7, 2.2 Hz, ArH), 2.80 (3H, d, J=4.8 Hz, $NCH_3$), 2.54 (3H, s, $CH_3$); APCI-MS 366 (M–H)$^+$; FAB-HRMS calcd for $C_{15}H_{15}ClN_3O_2S_2$ (MH$^+$) 368.0294, found 368.0292.

3-Chloro-2-methyl-N-(2-methylaminobenzothiazol-5-yl)-benzenesulphonamide (STX835, XDS01176)

The compound was prepared as described for STX833 using 3-chloro-N-(2-chlorobenzothiazol-5-yl)-2-methylbenzenesulphonamide (STX834, 80 mg, 0.21 mmol) as starting material. White crystals (60 mg, 78%) were obtained. TLC single spot at $R_f$ 0.25 (30% EtOAc/DCM); HPLC purity 99% ($t_R$ 2.3 min in 10% water-methanol); $^1$HNMR (270 MHz, DMSO-$d_6$) δ 10.5 (1H, s, NH), 7.96 (1H, q, J=4.7 Hz, NH), 7.86 (1H, d, J=8.1 Hz, ArH), 7.69 (1H, d, J=8.1 Hz, ArH), 7.47 (1H, d, J=8.0 Hz, ArH), 7.37 (1H, t, J=8.1 Hz, ArH), 7.05 (1H, d, J=1.9 Hz, ArH), 6.73 (1H, dd, J=8.0, 1.9 Hz, ArH), 2.88 (3H, d, J=4.7 Hz, $NCH_3$), 2.64 (3H, s, $CH_3$); APCI-MS 368 (MH$^+$)$^+$; FAB-HRMS calcd for $C_{15}H_{15}ClN_3O_2S_2$ (MH$^+$) 368.0294, found 368.0292.

3-Chloro-N-(2-diethylaminobenzothiazol-5-yl)-2-methylbenzenesulphonamid (STX836, XDS01177)

The compound was prepared as described for STX833 using 3-chloro-N-(2-chlorobenzothiazol-5-yl)-2-methylbenzenesulphonamide (STX834, 70 mg, 0.18 mmol) and diethylamine-THF (3 mL) as starting material. White crystals (50 mg, 68%) were obtained. TLC single spot at $R_f$ 0.60 (30% EtOAc/DCM); HPLC purity 97% ($t_R$ 3.0 min in 10% water-methanol), $^1$HNMR (270 MHz, DMSO-$d_6$) δ 10.5 (1H, s, NH), 7.85 (1H, d, J=7.9 Hz, ArH), 7.68 (1H, d, J=8.0 Hz, ArH), 7.52 (1H, d, J=8.4 Hz, ArH), 7.36 (1H, t, J=8.0 Hz, ArH), 7.06 (1H, d, J=2.2 Hz, ArH), 6.75 (1H, dd, J=8.3, 2.2 Hz, ArH), 3.45 (4H, q, J=7.0 Hz, $N(CH_2)_2$), 2.63 (3H, s, $CH_3$), 1.15 (6H, t, J=7.0 Hz, 2×$CH_3$); APCI-MS 410 (MH$^+$)$^+$; FAB-HRMS calcd for $C_{18}H_{21}ClN_3O_2S_2$ (MH$^+$) 410.0764, found 410.0753.

3-Chloro-N-(2-diethylaminobenzothiazol-6-yl)-2-methylbenzenesulphonamide (STX878, XDS01164)

The compound was prepared as described for STX833 using 3-chloro-N-(2-chlorobenzothiazol-6-yl)-2-methylbenzenesulphonamide (STX768, 240 mg, 0.64 mmol) and diethylamine-IPA (3 mL) as starting material. Off-white crystalline solid (128 mg, 49%) were obtained. TLC single spot at $R_f$ 0.33 (30% EtOAc/hexane); HPLC purity 96% ($t_R$ 2.2 min in 4% water-methanol); $^1$HNMR (270 MHz, DMSO-$d_6$) δ 7.56-7.62 (3H, m, ArH), 7.18-7.27 (2H, m, ArH), 7.00 (1H, dd, J=8.5, 1.7 Hz, ArH), 5.52 (1H, s, NH), 3.54 (4H, q, J=7.0 Hz, $N(CH_2)_2$), 2.25 (3H, s, $CH_3$), 1.22 (6H, t, J=7.0 Hz, 2×$CH_3$); APCI-MS 409 (M)$^+$; FAB-HRMS calcd for $C_{18}H_{21}ClN_3O_2S_2$ (MH$^+$) 410.0764, found 410.0698.

Synthesis of 2,6-Dimethylbenzothiazol-7-ylamine

To a solution of 2,6-dimethylbenzothiazol (350 mg, 2.15 mmol) in Conc. $H_2SO_4$ (4 mL) was added $HNO_3$ (69%, 0.3 mmol) at 0° C. After stirred at 0° C. for 0.5 h, the mixture was poured over ice-water. The precipitate was collected and washed with 5% sodium bicarbonate and water, recrystallized from ethanol to give 7-nitro-2,6-dimethylbenzothiazol as yellow solid (160 mg). The product (150 mg) was hydrogenated over 5% Pd/C in ethanol-THF (10:2 mL) at atmosphere pressure to give 2,6-dimethyl-benzothiazol-7-ylamine as yellow solid (120 mg). TLC single spot at $R_f$ 0.55 (10% EtOAc/DCM); $^1$H NMR (270 MHz, DMSO): δ 7.07 (2H, s, ArH), 5.23 (2H, s, $NH_2$), 2.73 (3H, s, $CH_3$), 2.20 (3H, s, $CH_3$).

Synthesis of 6-Methoxy-2-methylbenzothiazol-7-ylamine

The compound was prepared as described above starting from 6-methoxy-2-methylbenzothiazol. Yellow solid was obtained. mp 117-119° C. (lit. 121-122° C.); TLC single spot at $R_f$ 0.55 (40% EtOAc/DCM); $^1$H NMR (270 MHz, DMSO): δ 7.14 (1H, d, J=8.7 Hz, ArH), 7.05 (1H, d, J=8.7 Hz, ArH), 5.10 (2H, broad, $NH_2$), 3.83 (3H, s, $OCH_3$), 2.71 (3H, s, $CH_3$).

(Friedman, S. G. J Gen Chem USSR 31, 1961, 3162-3167)

Synthesis of 2,5-Dimethylbenzothiazol-4-ylamine and 2,5-Dimethylbenzothiazol-6-ylamine To a solution of 2,5-dimethylbenzothiazol (1.63 g, 10 mmol) in Conc. $H_2SO_4$ (12 mL) was added $HNO_3$ (69%, 1 mmol) at −5° C. After stirred at −5-0° C. for 2 h, the mixture was poured over ice-water (150 mL). The precipitate was collected and washed with 5% sodium bicarbonate, water and 70% ethanol. The product (1.98 g) was a mixture of 4-nitro-2,5-dimethylbenzothiazol and 6-nitro-2,5-dimethylbenzothiazol in 1:1 ratio judged by NMR. The product (998 mg) was hydrogenated over 5% Pd/C (600 mg) in ethanol-THF (50:20 mL) at atmosphere pressure to give a yellow solid (880 mg). Separation with flash chromatography (EtOAc/DCM gradient elution) yielded 2,5-dimethylbenzothiazol-4-ylamine as yellow crystals (400 mg). TLC single spot at $R_f$ 0.60 (15% EtOAc/DCM); $^1$H NMR (270 MHz, DMSO): δ 7.05 (1H, d, J=8.0 Hz, ArH), 6.99 (1H, d, J=8.0 Hz, ArH), 5.26 (2H, s, NH$_2$), 2.74 (3H, s, CH$_3$), 2.18 (3H, s, CH$_3$); APCI-MS 177 (M–H)$^+$.

2,5-Dimethylbenzothiazol-6-ylamine was obtained as yellow solid (320 mg). TLC single spot at $R_f$ 0.55 (15% EtOAc/DCM); $^1$H NMR (270 MHz, DMSO): δ 7.47 (1H, s, ArH), 7.05 (1H, s, ArH), 5.05 (2H, s, NH$_2$), 2.65 (3H, s, CH$_3$), 2.16 (3H, s, CH$_3$); APCI-MS 177 (M–H)$^+$.

Synthesis of 4-chloro-2-methylbenzothiazol-5-ylamine and 4,6-dichloro-2-methylbenzothiazol-5-ylamine To a solution of 5-amino-2-methylbenzothiazole (818 mg, 4.99 mmol) in isopropanol (12 mL) was added N-chlorosuccinimide (732 mg, 5.48 mmol). The mixture was stirred at 60° C. for 15 min., partitioned between DCM and 5% sodium bicarbonate. The organic phase was washed with brine, dried over sodium sulphate and concentrated in vacuo to give a residue that was purified with flash chromatography (EtOAc/DCM gradient elution). 4-Chloro-2-methylbenzothiazol-5-ylamine was obtained as off-white crystalline solid (510 mg, 51%). mp 121-122° C. (lit. 124° C.); TLC single spot at $R_f$ 0.51 (20% EtOAc/DCM); $^1$H NMR (270 MHz, DMSO): δ 7.61 (1H, d, J=8.6 Hz, ArH), 6.91 (1H, d, J=8.6 Hz, ArH), 5.49 (2H, s, NH$_2$), 2.75 (3H, s, CH$_3$); APCI-MS 199 (MH)$^+$.

4,6-Dichloro-2-methylbenzothiazol-5-ylamine was obtained as yellow solid (60 mg, 5%). TLC single spot at $R_f$ 0.57 (20% EtOAc/DCM); $^1$H NMR (270 MHz, DMSO): δ 7.89 (1H, s, ArH), 5.26 (2H, s, NH$_2$), 2.77 (3H, s, CH$_3$); APCI-MS 233 (MH)$^+$.

The following compounds were synthesized with the general method for N-benzothiazole benzenesulphonamide.

3-Chloro-N-(6-methoxy-2-methylbenzothiazol-7-yl)-2-methylbenzenesulphonamide (STX989, XDS02038)

White crystalline solid. TLC single spot at $R_f$ 0.71 (30% EtOAc/DCM); HPLC purity 99% ($t_R$ 2.3 min in 10% water-methanol); $^1$HNMR (270 MHz, DMSO-d$_6$) δ 10.1 (1H, s, NH), 7.76 (1H, d, J=8.9 Hz, ArH), 7.72 (1H, d, J=8.2 Hz, ArH), 7.53 (1H, d, J=8.2 Hz, ArH), 7.23 (1H, t, J=8.2 Hz, ArH), 7.05 (1H, d, J=8.9 Hz, ArH), 3.29 (3H, s, OCH$_3$), 2.74 (3H, s, CH$_3$), 2.70 (3H, s, CH$_3$); APCI-MS 381 (M–H)$^+$; FAB-HRMS calcd for C$_{16}$H$_{16}$ClN$_2$O$_3$S$_2$ (MH$^+$) 383.0291, found 383.0284.

3-Chloro-N-(2,6-dimethyl-benzothiazol-7-yl)-2-methyl-benzenesulphonamide (STX1021, XDS02069)

Off-white crystalline solid. TLC single spot at $R_f$ 0.49 (10% EtOAc/DCM); HPLC purity 98% ($t_R$ 2.0 min 20% water-methanol); $^1$HNMR (270 MHz, DMSO-d$_6$) δ 10.3 (1H, s, NH), 7.78 (1H, d, J=7.9 Hz, ArH), 7.74 (1H, d, J=8.4 Hz, ArH), 7.64 (1H, d, J=7.9 Hz, ArH), 7.34 (1H, t, J=7.9 Hz, ArH), 7.30 (1H, d, J=7.9 Hz, ArH), 2.68 (3H, s, CH$_3$), 2.61 (3H, s, CH$_3$), 2.03 (3H, s, CH$_3$); FAB-MS 367 (MH)$^+$; FAB-HRMS calcd for C$_{16}$H$_{16}$ClN$_2$O$_2$S$_2$ (MH$^+$) 367.0342, found 367.0347.

3-Chloro-N-(2,5-dimethyl-benzothiazol-4-yl)-2-methyl-benzenesulphonamide (STX996, XDS02047)

White crystalline solid. TLC single spot at $R_f$ 0.76 (10% EtOAc/DCM); HPLC purity >99% ($t_R$ 2.9 min 10% water-methanol); $^1$HNMR (270 MHz, DMSO-d$_6$) δ 9.98 (1H, s, NH), 7.81 (1H, d, J=8.3 Hz, ArH), 7.64 (1H, d, J=7.9 Hz, ArH), 7.45 (1H, d, J=7.9 Hz, ArH), 7.31 (1H, d, J=8.3 Hz, ArH), 7.12 (1H, t, J=7.9 Hz, ArH), 2.73 (3H, s, CH$_3$), 2.47 (3H, s, CH$_3$), 2.44 (3H, s, CH$_3$); APCI-MS 367 (MH)$^+$; FAB-HRMS calcd for C$_{16}$H$_{16}$ClN$_2$O$_2$S$_2$ (MH$^+$) 367.0342, found 367.0342.

N-(2,5-dimethylbenzothiazol-6-yl)-N-(3-chloro-2-methylphenylsulphonyl)-3-chloro-2-methylbenzenesulphonamide (STX997, XDS02048A)

Off-white syrup. TLC single spot at $R_f$ 0.78 (10% EtOAc/DCM); HPLC purity 85% ($t_R$ 4.2 min in 10% water-methanol); $^1$H NMR (270 MHz, DMSO-d$_6$) δ 8.06 (1H, s, ArH), 7.86-7.95 (5H, m, ArH), 7.68 (1H, s, ArH), 7.52 (2H, t, J=8.2 Hz, ArH), 2.83 (3H, s, CH$_3$), 2.29 (6H, s, 2×CH$_3$), 2.05 (3H, s, CH$_3$); APCI-MS 555 (MH)$^+$; FAB-HRMS calcd for C$_{23}$H$_{21}$Cl$_2$N$_2$O$_4$S$_3$ (MH$^+$) 555.0040, found 555.0041.

3-Chloro-N-(2,5-dimethylbenzothiazol-6-yl)-2-methylbenzenesulphonamide (STX998, XDS02048B)

White crystalline solid. TLC single spot at $R_f$ 0.39 (10% EtOAc/DCM); HPLC purity 96% ($t_R$ 2.1 min in 10% water-methanol); $^1$HNMR (270 MHz, DMSO-d$_6$) δ 10.0 (1H, s, NH), 7.74 (1H, d, J=7.9 Hz, ArH), 7.70 (1H, s, ArH), 7.67 (1H, d, J=7.9 Hz, ArH), 7.63 (1H, s, ArH), 7.33 (1H, t, J=7.9 Hz, ArH), 2.75 (3H, s, CH$_3$), 2.60 (3H, s, CH$_3$), 2.13 (3H, s, CH$_3$); APCI-MS 367 (MH)$^+$; FAB-HRMS calcd for C$_{16}$H$_{16}$ClN$_2$O$_2$S$_2$ (MH$^+$) 367.0342, found 367.0350.

2,5-Dichloro-N-(2,5-dimethylbenzothiazol-6-yl)-benzenesulphonamide (STX999, XDS02049)

White crystalline solid. TLC single spot at $R_f$ 0.43 (10% EtOAc/DCM); HPLC purity 98% ($t_R$ 2.0 min 10% water-methanol); $^1$HNMR (270 MHz, DMSO-d$_6$) δ 10.3 (1H, s, NH), 7.76 (3H, s, ArH), 7.72 (1H, s, ArH), 7.67 (1H, s, ArH), 2.75 (3H, s, CH$_3$), 2.23 (3H, s, CH$_3$); APCI-MS 387 (MH)$^+$; FAB-HRMS calcd for C$_{15}$H$_{13}$Cl$_2$N$_2$O$_2$S$_2$ (MH$^+$) 386.9795, found 386.9806.

N-(4-Chloro-2-methyl-benzothiazol-5-yl)-N-(3-chloro-2-methylphenylsulphonyl)-3-chloro-2-methyl-benzenesulphonamide (STX991, XDS02042A)

White powder. TLC single spot at $R_f$ 0.75 (8% EtOAc/DCM); HPLC purity >99% ($t_R$ 4.4 min in 10% water-methanol); $^1$HNMR (270 MHz, DMSO-d$_6$) δ 8.19 (1H, d, J=8.7 Hz, ArH), 7.93 (4H, d, J=8.2 Hz, ArH), 7.59 (1H, d, J=8.7 Hz, ArH), 7.50 (2H, d, J=8.2 Hz, ArH), 2.85 (3H, s, CH$_3$), 2.41 (6H, s, 2×CH$_3$); APCI-MS 575 (MH)$^+$; FAB-HRMS calcd for C$_{22}$H$_{18}$Cl$_3$N$_2$O$_4$S$_3$ (MH$^+$) 574.9494, found 574.9492.

3-Chloro-N-(4-chloro-2-methylbenzothiazol-5-yl)-2-methylbenzenesulphonamide (STX992, XDS02042B)

White crystalline solid. TLC single spot at $R_f$ 0.69 (8% EtOAc/DCM); HPLC purity 99% ($t_R$ 2.5 min 10% water-methanol); $^1$HNMR (270 MHz, DMSO-d$_6$) δ 10.5 (1H, s, NH), 7.96 (1H, d, J=8.7 Hz, ArH), 7.73 (1H, d, J=7.9 Hz, ArH), 7.64 (1H, d, J=7.9 Hz, ArH), 7.30 (1H, d, J=8.7 Hz, ArH), 7.29 (1H, t, J=7.9 Hz, ArH), 2.79 (3H, s, CH$_3$), 2.70 (3H, s, CH$_3$); APCI-MS 385 (M−H)$^+$; FAB-HRMS calcd for C$_{15}$H$_{13}$Cl$_2$N$_2$O$_2$S$_2$ (MH$^+$) 386.9795, found 386.9790.

2,5-Dichloro-N-(4-chloro-2-methylbenzothiazol-5-yl)-benzenesulphonamide (STX993, XDS02043B)

White crystalline solid. TLC single spot at R$_f$ 10.71 (8% EtOAc/DCM); HPLC purity 99% (t$_R$ 5.0 min in 10% water-methanol); $^1$HNMR (270 MHz, DMSO-d$_6$) δ 10.7 (1H, s, NH), 7.97 (1H, d, J=8.6 Hz, ArH), 7.71-7.78 (3H, m, ArH), 7.28 (1H, d, J=8.6 Hz, ArH), 2.81 (3H, s, CH$_3$); APCI-MS 407 (MH$^+$); FAB-HRMS calcd for C$_{14}$H$_{10}$Cl$_3$N$_2$O$_2$S$_2$ (MH$^+$) 406.9249, found 406.9234.

N-(4-Chloro-2-methylbenzothiazol-5-yl)-4-propyl-benzenesulphonamide (STX994, XDS02044B)

White crystalline solid. TLC single spot at R$_f$ 0.70 (8% EtOAc/DCM); HPLC purity 99% (t$_R$ 2.7 min in 10% water-methanol); $^1$HNMR (270 MHz, DMSO-d$_6$) δ 10.1 (1H, s, NH), 7.93 (1H, d, J=8.6 Hz, ArH), 7.60 (2H, d, J=8.2 Hz, ArH), 7.35 (2H, d, J=8.2 Hz, ArH), 7.28 (1H, d, J=8.4 Hz, ArH), 2.79 (3H, s, CH$_3$), 2.69 (2H, t, J=7.2 Hz, CH$_2$), 1.59 (2H, m, CH$_2$), 0.86 (3H, t, J=7.2 Hz, CH$_3$); APCI-MS 381 (MH$^+$)$^+$; FAB-HRMS calcd for C$_{17}$H$_{18}$ClN$_2$O$_2$S$_2$ (MH$^+$) 381.0498, found 381.0484.

N-(4-Chloro-2-methylbenzothiazol-5-yl)-N-(4-propylphenylsulphonyl)-4-propylbenzenesulphonamide (STX995, XDS02044A)

White powder. TLC single spot at R$_f$ 0.70 (8% EtOAc/DCM); HPLC purity 99% (t$_R$ 3.8 min in 10% water-methanol); $^1$H NMR (270 MHz, DMSO-d$_6$) δ 8.10 (1H, d, J=8.4 Hz, ArH), 7.74 (4H, d, J=8.1 Hz, ArH), 7.50 (4H, d, J=8.1 Hz, ArH), 7.08 (1H, d, J=8.4 Hz, ArH), 2.91 (3H, s, CH$_3$), 2.71 (4H, t, J=7.1 Hz, 2×CH$_2$), 1.59 (4H, m, CH$_2$), 0.86 (6H, t, J=7.1 Hz, 2×CH$_3$); APCI-MS 561 (M−H)$^+$; FAB-HRMS calcd for C$_{26}$H$_{28}$ClN$_2$O$_4$S$_3$ (MH$^+$) 563.0900, found 563.0886.

Synthesis of 3-Chloro-2-methyl-N-(2-methyl-benzothiazol-5-ylmethyl)-benzenesulphonamide (STX1029, XDS02070A) and 3-Chloro-2-methyl-N,N-bis-(2-methyl-benzothiazol-5-ylmethyl)-benzenesulphonamide (STX1030, XDS02070B)

To a solution of 3-chloro-2-methylbenzenesulphonamide (103 mg, 0.5 mmol) in CH$_3$CN was added potassium carbonate (100 mg), followed 5-bromomethyl-2-methylbenzothiazole (121 mg, 0.5 mmol). The mixture was refluxed under N$_2$ for 6 h, partitioned between ethyl acetate and water. The organic phase was washed brine, dried over sodium sulphate and concentrated in vacuo to give a yellow residue, which was separated with flash chromatography (ethyl acetate/DCM, gradient elution). STX1029 was obtained as white solid. TLC single spot at R$_f$ 0.55 (10% EtOAc/DCM); HPLC purity >99% (t$_R$ 2.0 min in 10% water-methanol); $^1$HNMR (270 MHz, CDCl$_3$) δ7.89 (1H, d, J=7.9 Hz, ArH), 7.66 (1H, d, J=7.9 Hz, ArH), 7.65 (1H, d, J=1.3 Hz, ArH), 7.49 (1H, d, J=7.9 Hz, ArH), 7.17 (1H, d, J=7.9 Hz, ArH), 7.13 (1H, dd, J=7.9, 1.5 Hz, ArH), 5.35 (1H, t, J=5.9 Hz, NH), 4.24 (2H, d, J=5.9 Hz, CH$_2$), 2.79 (3H, s, CH$_3$), 2.62 (3H, s, CH$_3$); APCI-MS 367 (MH)$^+$; FAB-HRMS calcd for C$_{16}$H$_{16}$ClN$_2$O$_2$S$_2$ (MH$^+$) 367.0342, found 367.0330.

STX1030 was obtained as white solid. TLC single spot at R$_f$ 0.50 (10% EtOAc/DCM); HPLC purity 99% (t$_R$ 6.1 min in 20% water-methanol); $^1$HNMR (270 MHz, DMSO-d$_6$) δ 7.87 (3H, d, J=8.1 Hz, ArH), 7.75 (1H, d, J=8.0 Hz, ArH), 7.59 (2H, broad w$_{1/2}$=1.1 Hz, ArH), 7.38 (1H, t, J=8.0 Hz, ArH), 7.11 (2H, dd, J=8.1, 1.1 Hz, ArH), 4.56 (4H, s, 2×NCH$_2$), 2.78 (6H, s, 2×CH$_3$), 2.58 (3H, s, CH$_3$); APCI-MS 528 (MH)$^+$; FAB-HRMS calcd for C$_{25}$H$_{23}$ClN$_3$O$_2$S$_3$ (MH$^+$) 528.0641, found 528.0630.

Synthesis of N-Indole or N-Indolin Arysulfonamid Derivatives

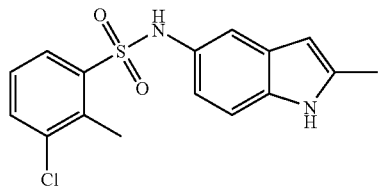

STX832, XDS01165

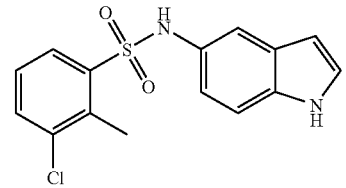

STX981, XDS02019

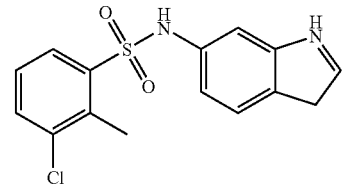

STX982, XDS02020

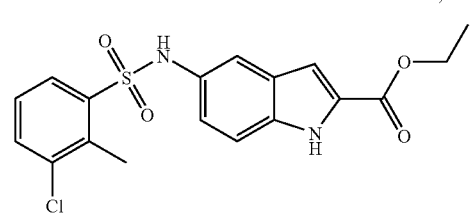

STX986, XDS02030

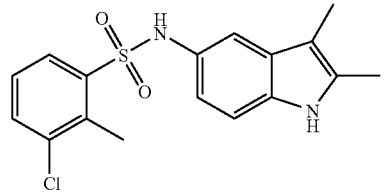

STX1018, XDS02061

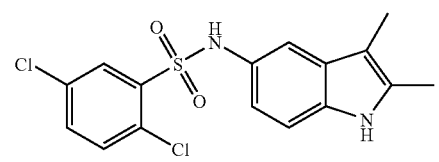

STX1019, XDS02062

-continued

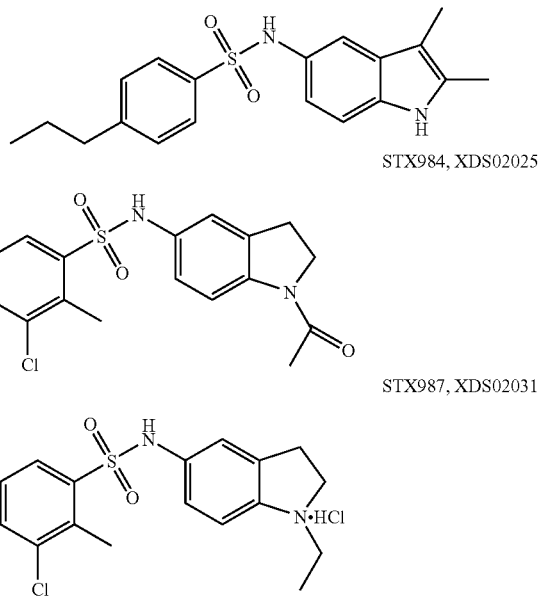

General Method for Synthesis N-Indole or N-Indoline Arylsulphonamide Derivatives (STX832, STX981-982, STX984, STX986-987, STX1018-1020)

To a solution arylsulphonyl chloride (1.1 eq.) in DCM were added pyridine (2.2 eq.) and catalytic amount of DMAP, followed by the corresponding amine (1 eq.). The reaction mixture was stirred at rt under nitrogen for 4-6 h, then partitioned between ethyl acetate and 5% sodium bicarbonate after TLC showed completion of the reaction. The organic layer was washed with brine, dried over sodium sulphate, and concentrated in vacuo to give crude product as solid or thick syrup. The compound was then purified by flash chromatography (methanol-DCM gradient elution) to give desired arylsulphonamide as crystalline solid. Yield ranges from 50-85%.

3-Chloro-2-methyl-N-(2-methyl-1H-indol-5-yl)-benzenesulphonamide (STX832, XDS01165)

White crystalline solid. TLC single spot at $R_f$ 0.68 (30% ethyl acetate/hexane); HPLC purity >99% ($t_R$ 1.8 min in 4% water-methanol); $^1$H NMR (270 MHz, DMSO): δ 10.9 (1H, s, NH), 9.98 (1H, s, NH), 7.72 (1H, d, J=8 Hz, ArH), 7.63 (1H, d, J=8 Hz, ArH), 7.27 (1H, t, J=8 Hz, ArH), 7.07 (1H, d, J=8 Hz, ArH), 7.05 (1H, d, J=2 Hz, ArH), 6.67 (1H, dd, J=8, 2 Hz, ArH), 5.99 (1H, s, 3-H), 2.60 (3H, s, CH$_3$), 2.29 (3H, s, CH$_3$); APCI-MS 334 (M$^+$); FAB-HRMS calcd for C$_{16}$H$_{16}$ClN$_2$O$_2$S (MH$^+$) 335.0621, found 335.0609

3-Chloro-2-methyl-N-(1H-indol-5-yl)-benzenesulphonamide (STX981, XDS02019)

White crystalline solid. TLC single spot at $R_f$ 10.72 (6% methanol/DCM); HPLC purity 98% ($t_R$ 2.1 min in 10% water-methanol); $^1$H NMR (270 MHz, DMSO): δ 11.1 (1H, s, NH), 10.1 (1H, s, NH), 7.76 (1H, d, J=7.9 Hz, ArH), 7.66 (1H, d, J=7.9 Hz, ArH), 7.22-7.32 (4H, m, ArH), 6.81 (1H, dd, J=7.9, 1.2 Hz, ArH), 6.33 (1H, broad, 3-H), 2.64 (3H, s, CH$_3$); APCI-MS 319 (M–H$^+$); FAB-HRMS calcd for C$_{15}$H$_{14}$ClN$_2$O$_2$S (MH$^+$) 321.0465, found 321.0453.

3-Chloro-2-methyl-N-(1H-indol-6-yl)-benzenesulphonamide (STX982, XDS02020)

White crystalline solid. TLC single spot at $R_f$ 0.88 (10% methanol/DCM); HPLC purity 98% ($t_R$ 2.5 min in 20% water-methanol); $^1$H NMR (270 MHz, DMSO): δ 11.0 (1H, s, NH), 10.3 (1H, s, NH), 7.80 (1H, d, J=7.9 Hz, ArH), 7.67 (1H, d, J=7.9 Hz, ArH), 7.31-7.38 (2H, m, ArH), 7.26 (1H, m, ArH), 7.80 (1H, d, J=1.2 Hz, ArH), 6.75 (1H, dd, J=7.9, 1.2 Hz, ArH), 6.31 (1H, broad, 3-H), 2.65 (3H, s, CH$_3$); APCI-MS 319 (M–H$^+$); FAB-HRMS calcd for C$_{15}$H$_{14}$ClN$_2$O$_2$S (MH$^+$) 321.0465, found 321.0446.

5-(3-Chloro-2-methylbenzenesulfonylamino)-1H-indole-2-carboxylic acid ethyl ester (STX986, XDS02030)

White crystalline solid. TLC single spot at $R_f$ 0.82 (8% methanol/DCM); HPLC purity >99% ($t_R$ 2.3 min in 10% water-methanol); $^1$H NMR (270 MHz, DMSO): δ 11.9 (1H, s, NH), 10.3 (1H, s, NH), 7.78 (1H, d, J=7.9 Hz, ArH), 7.67 (1H, d, J=7.9 Hz, ArH), 7.28-7.33 (3H, m, ArH), 7.06 (1H, d, J=2.2 Hz, ArH), 7.00 (1H, dd, J=8.2, 2.2 Hz, ArH), 4.32 (2H, q, J=6.9 Hz, OCH$_2$), 2.63 (3H, s, CH$_3$), 1.31 (3H, t, J=6.9 Hz, CH$_3$); APCI-MS 391 (M–H$^+$); FAB-HRMS calcd for C$_{18}$H$_{18}$ClN$_2$O$_4$S (MH$^+$) 393.0676, found 393.0659

3-Chloro-2-methyl-N-(2,3-dimethyl-1H-indol-5-yl)-benzenesulphonamide (STX1018, XDS02061)

White crystalline solid. TLC single spot at $R_f$ 0.83 (30% ethyl acetate/hexane); HPLC purity 97% ($t_R$ 2.9 min in 20% water-methanol); $^1$H NMR (270 MHz, DMSO): δ 10.6 (1H, s, NH), 10.0 (1H, s, NH), 7.74 (1H, d, J=7.5 Hz, ArH), 7.65 (1H, d, J=7.5 Hz, ArH), 7.29 (1H, t, J=8.0 Hz, ArH), 7.05 (1H, d, J=8.6 Hz, ArH), 6.99 (1H, d, J=1.7 Hz, ArH), 6.66 (1H, dd, J=8.6, 1.7 Hz, ArH), 2.62 (3H, s, CH$_3$), 2.25 (3H, s, CH$_3$), 2.03 (3H, s, CH$_3$); APCI-MS 349 (MH$^+$); FAB-HRMS calcd for C$_{17}$H$_{18}$ClN$_2$O$_2$S (MH$^+$) 349.0778, found 349.0737.

2,5-Dichloro-N-(2,3-dimethyl-1H-indol-5-yl)-benzenesulphonamide (STX1019, XDS02062)

White amorphous powder. TLC single spot at $R_f$ 0.82 (10% ethyl acetate/hexane); HPLC purity 98% ($t_R$ 3.0 min in 20% water-methanol); $^1$H NMR (270 MHz, DMSO): δ 10.7 (1H, s, NH), 10.2 (1H, s, NH), 7.80 (1H, m, ArH), 7.67-7.70 (2H, m, ArH), 7.07 (1H, d, J=8.5 Hz, ArH), 7.05 (1H, d, J=1.7 Hz, ArH), 6.73 (1H, dd, J=8.5, 1.7 Hz, ArH), 2.25 (3H, s, CH$_3$), 2.04 (3H, s, CH$_3$); APCI-MS 367 (M–H$^+$); FAB-HRMS calcd for C$_{16}$H$_{14}$Cl$_2$N$_2$O$_2$S (M$^+$) 368.0153, found 368.0146

4-n-Propyl-N-(2,3-dimethyl-1H-indol-5-yl)-benzenesulphonamide (STX1020, XDS02063)

Off-white crystalline solid. TLC single spot at $R_f$ 0.82 (10% ethyl acetate/hexane); HPLC purity 97% ($t_R$ 2.9 min in 20% water-methanol); $^1$H NMR (270 MHz, DMSO): δ 10.6 (1H, s, NH), 9.6 (1H, s, NH), 7.56 (2H, d, J=8.3 Hz, ArH), 7.30 (2H, d, J=8.3 Hz, ArH), 7.03 (1H, d, J=8.3 Hz, ArH), 6.95 (1H, d, J=1.7 Hz, ArH), 6.68 (1H, dd, J=8.3, 1.7 Hz, ArH), 2.56 (2H, t, J=7.3 Hz, CH$_2$), 2.24 (3H, s, CH$_3$), 2.01 (3H, s, CH$_3$), 1.55 (2H, sextet, J=7.3 Hz, CH$_2$), 0.85 (3H, t, J=7.3 Hz, CH$_3$); APCI-MS 343 (MH$^+$); FAB-HRMS calcd for C$_{19}$H$_{22}$N$_2$O$_2$S (M$^+$) 342.1402, found 342.1403

3-Chloro-2-methyl-N-(1-acetyl-2,3-dihydro-1H-indol-5-yl)-benzenesulphonamide (STX984, XDS02025)

White crystalline solid. TLC single spot at R$_f$ 10.58 (5% methanol/DCM); HPLC purity 95% (t$_R$ 2.2 min in 20% water-methanol); $^1$H NMR (270 MHz, DMSO): δ 10.4 (1H, s, NH), 7.80-7.86 (2H, m, ArH), 7.71 (1H, d, J=7.8 Hz, ArH), 7.36 (1H, t, J=8.0 Hz, ArH), 6.93 (1H, d, J=1.8 Hz, ArH), 6.83 (1H, dd, J=8.2, 1.8 Hz, ArH), 4.01 (2H, t, J=8.3 Hz, CH$_2$), 3.03 (2H, t, J=8.4 Hz, CH$_2$), 2.62 (3H, s, CH$_3$), 2.09 (3H, s, CH$_3$); APCI-MS 363 (M–H$^+$); FAB-HRMS calcd for C$_{17}$H$_{18}$ClN$_2$O$_3$S (MH$^+$) 365.0727, found 365.0796.

5-(3-Chloro-2-methyl-benzenesulfonylamino)-1-ethyl-2,3-dihydro-1H-indolium chloride (STX987, XDS02031)

The free base of STX987 was synthesized as above. A purple amorphous powder was obtained; TLC single spot at R$_f$ 0.79 (8% methanol/DCM); $^1$H NMR (270 MHz, CDCl$_3$): δ 7.79 (1H, d, J=7.9 Hz, ArH), 7.53 (1H, d, J=7.9 Hz, ArH), 7.15 (1H, t, J=8.0 Hz, ArH), 6.75 (1H, d, J=1.8 Hz, ArH), 6.58 (1H, dd, J=8.1, 1.8 Hz, ArH), 6.35 (1H, s, NH), 6.22 (1H, d, J=8.1 Hz, ArH), 3.30 (2H, t, J=8.4 Hz, CH$_2$), 3.05 (2H, q, J=7.2 Hz, CH$_2$), 2.84 (2H, t, J=8.3 Hz, CH$_2$), 2.67 (3H, s, CH$_3$), 1.11 (3H, t, J=7.2 Hz, CH$_3$). The free base was treated with HCl-ether solution to give STX987 as light pink crystalline solid. HPLC purity 93% (t$_R$ 3.6 min in 20% water-methanol); $^1$H NMR (270 MHz, DMSO): δ 10.3 (1H, s, NH), 7.82 (1H, d, J=8.1 Hz, ArH), 7.72 (1H, d, J=8.1 Hz, ArH), 7.38 (1H, t, J=8.1 Hz, ArH), 6.79-6.89 (3H, m, broad, ArH), 3.42 (2H, t, J=8.4 Hz, CH$_2$), 3.16 (2H, q, J=7.0 Hz, CH$_2$), 2.91 (2H, t, J=8.4 Hz, CH$_2$), 2.62 (3H, s, CH$_3$), 1.10 (3H, t, J=7.0 Hz, CH$_3$); APCI-MS 349 (M–HCl—H$^+$); FAB-HRMS calcd for C$_{17}$H$_{20}$ClN$_2$O$_2$S (M–HCl+H$^+$) 351.0934, found 351.0941.

1-Acetyl-5-aminoindoline

The solution of 1-acetyl-5-nitroindoline (1.0 g, 4.85 mmol) in ethanol-THF (100 mL: 30 mL) was hydrogenated over 5% Pd/C (600 mg) at atmosphere pressure for 2 h, filtered through Celite and concentrated in vacuo to give a white solid which was recrystallized from ethanol. White crystalline solid (580 mg, 68%) was obtained. Mp 185-186.5° C. (lit 184-185° C., [21]); $^1$H NMR (270 MHz, DMSO): δ 7.73 (1H, d, J=8.6 Hz, ArH), 6.45 (1H, s broad, w1/2=1.8 Hz, ArH), 6.33 (1H, dd, J=8.6, 1.8 Hz, ArH), 4.82 (2H, s, NH$_2$), 3.97 (2H, t, J=8.4 Hz, CH$_2$), 2.99 (2H, t, J=8.4 Hz, CH$_2$), 2.07 (3H, s, CH$_3$); APCI-MS 175 (M–H$^+$).

1-Ethyl-5-aminoindoline

To a suspension of 1-acetyl-5-aminoindoline (130 mg, 0.74 mmol) in anhydrous THF (10 mL) was added LiAlH$_4$ (42 mg, 1.11 mmol). The mixture was stirred at rt for 6 h, quenched with saturated NH$_4$Cl and extracted with ethyl acetate. The organic phase was washed with brine, dried over sodium sulphate and concentrated in vacuo to give a purple residue (80 mg, 67%) that was used without further purification. $^1$H NMR (270 MHz, DMSO): δ 6.56 (1H, s, ArH), 6.47 (1H, d broad, J=8.1 Hz, ArH), 6.37 (1H, d, J=8.0 Hz, ArH), 3.29 (2H, s, NH$_2$), 3.20 (2H, t, J=7.6 Hz, CH$_2$), 3.02 (2H, q, J=6.9 Hz, CH$_2$), 2.86 (2H, t, J=7.6 Hz, CH$_2$), 1.17 (3H, t, J=6.9 Hz, CH$_3$).

Synthesis of 5-(3-chloro-2-methyl-benzene sulfonamino)-1H-indole-3-carboxylic acid methyl stir, STX1050 (KRB01132)

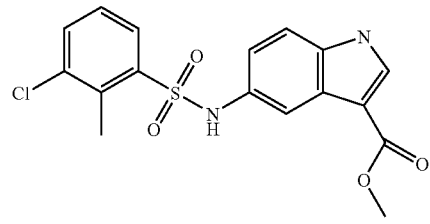

5-amino-1H-indole-3-carboxylic acid methyl ester (KRB01131): To a solution of 5-nitro-1H-indole-3-carboxylic acid methyl ester (206 mg, 0.940 mmol) in methanol (40 mL) was added 5% palladium on carbon (40 mg) and the mixture was stirred under 1 atm H$_2$ for 5 h. The mixture was filtered through celite and the filtrate evaporated to yield a brown solid that was used without further purification (173 mg, 97%), single spot at R$_f$ 0.64 (ethyl acetate). $^1$H NMR (d$_6$-DMSO): δ 11.50 (1H, s, N—H), 7.83 (1H, d, J=3.2 Hz), 7.17 (1H, d, J=2.0 Hz), 7.14 (1H, d, J=8.4 Hz), 6.56 (1H, dd, J=8.6, 2.2 Hz), 4.77 (2H, s, N—H$_2$), 3.76 (3H, s).

To a solution of 3-chloro-2-methylbenzenesulphonyl chloride (124 mg, 0.552 mmol) in dichloromethane (4 mL) was added pyridine (100 μL, 1.3 mmol) and the mixture was stirred under N$_2$ for 5 min, after which time 5-amino-1H-indole-carboxylic acid methyl ester (100 mg, 0.526 mmol) was added. The resulting mixture was stirred for 1.5 h at room temperature, then saturated NaHCO$_3$ solution (15 mL) was added and the mixture was extracted into ethyl acetate (20 mL). The organic phase was washed with brine, dried (Na$_2$SO$_4$), filtered and evaporated to give a residue that was purified using flash chromatography to afford a white solid (129 mg, 65%), single spot at R$_f$ 0.84 (ethyl acetate). mp 216.8-219.3° C., [22], HPLC purity 99+% (t$_R$ 2.07 min in 10% water-acetonitrile). $^1$H NMR (d$_6$-DMSO): δ 11.91 (1H, s), 10.32 (1H, s), 8.03 (1H, d, J=3.0 Hz), 7.82 (1H, d, J=7.9 Hz), 7.70-7.67 (2H, m), 7.37-7.31 (2H, m), 6.95 (1H, dd, J=8.6, 2.0 Hz), 3.77 (3H, s), 2.65 (3H, s). LCMS: 377.09. FAB-MS (MH$^+$, C$_{17}$H$_{15}$ClN$_2$O$_4$S): calcd 378.0441, found 378.0439.

Synthesis of Benzimidazol Arylsulphonamide Derivatives
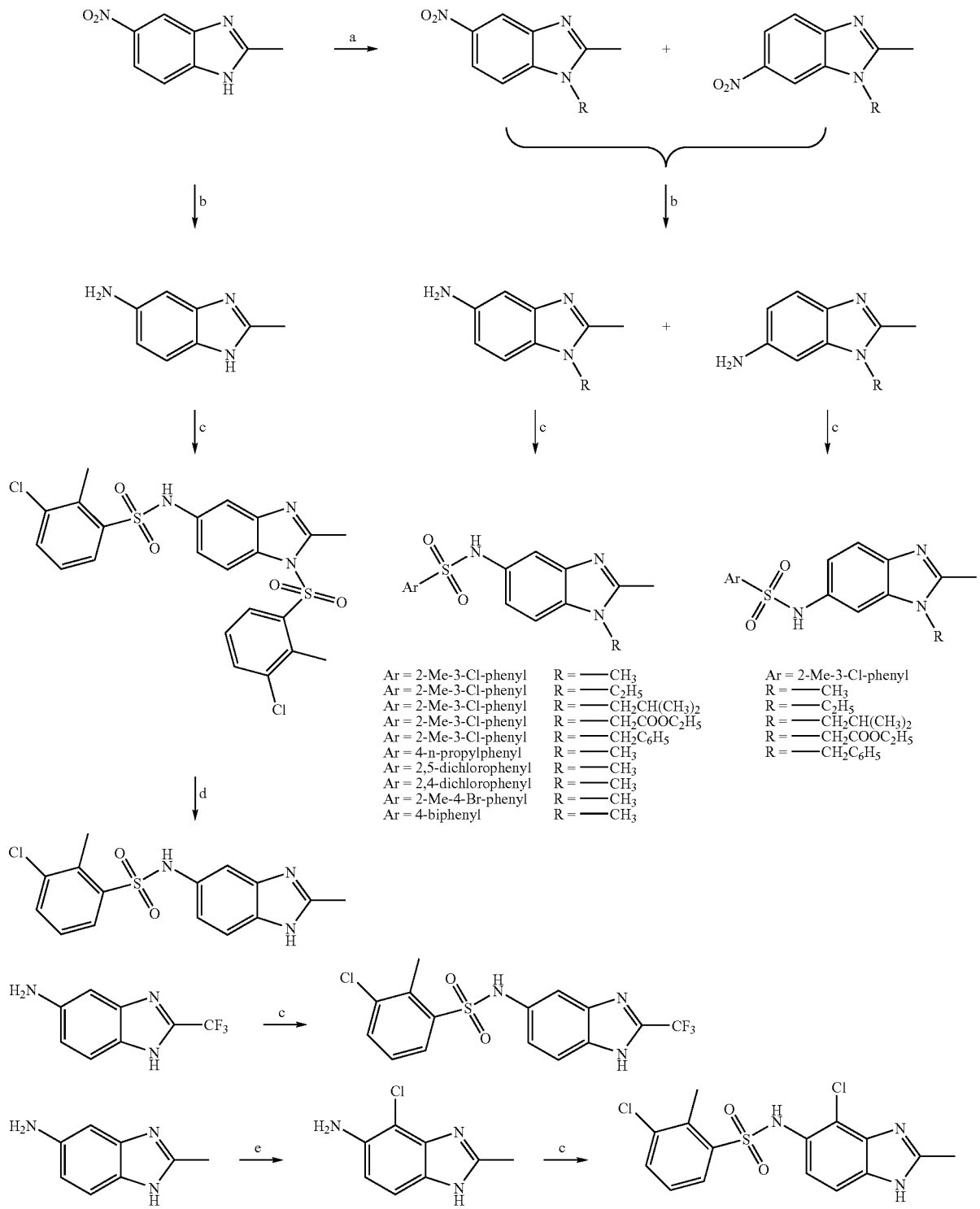
a) RX, K$_2$CO$_3$, Acetone, rt or reflux
b) H$_2$/5% Pd—C, Ethanol-THF r.t. or Fe AcOH-ethanol
c) ArSO$_3$Cl, DCM Pyridine or ArSO$_3$Cl, DCM, Pyridine/DMAP
d) HOBt, THF, r.t.
e) N-chlorosuccimide, IPA STX975, XDS02001
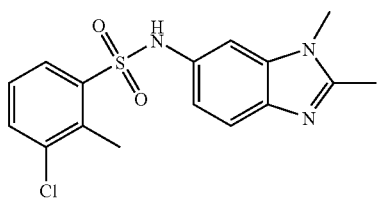
STX976, XDS02003
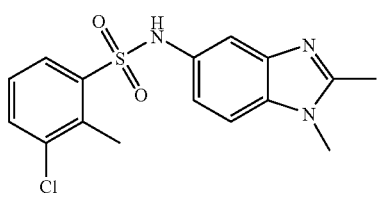
STX1121, XDS02102
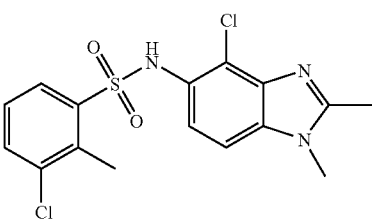
STX1112, XDS02088
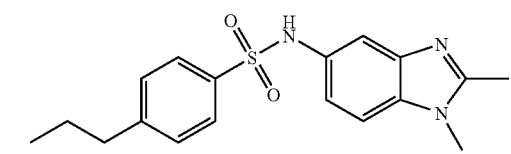
STX1113, XDS02089
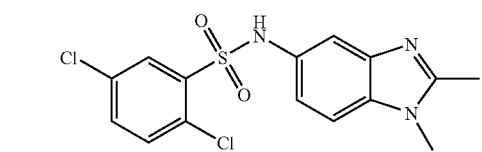
STX1114, XDS02090
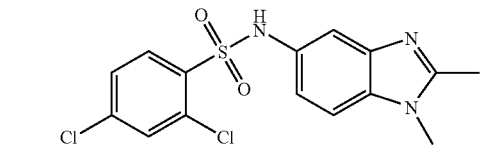
STX1115, XDS02091
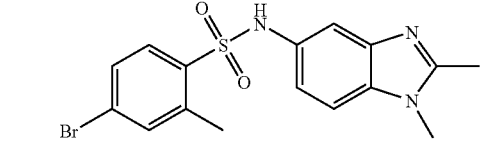
STX1116, XDS02092
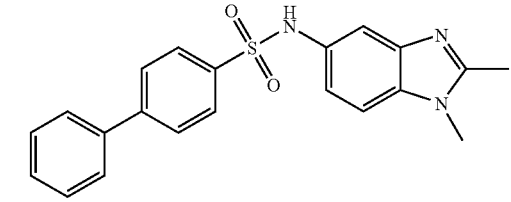
-continued
STX1110, XDS02084
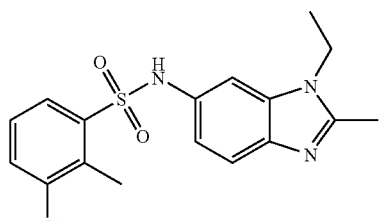
STX1111, XDS02085
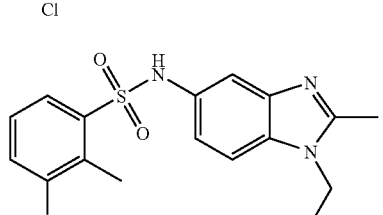
STX1119, XDS02100
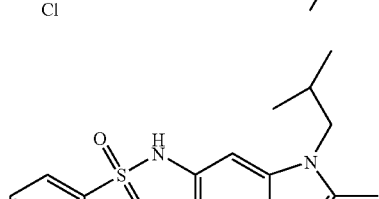
STX1120, XDS02101
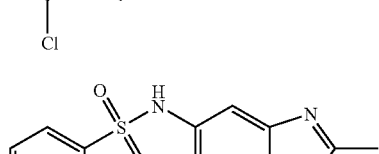
STX997, XDS02015
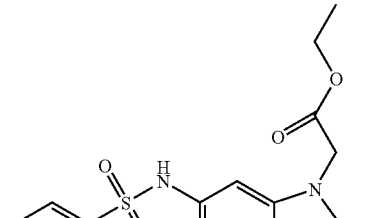
STX978, XDS02017
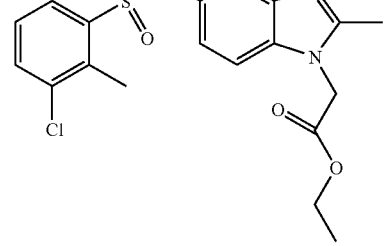

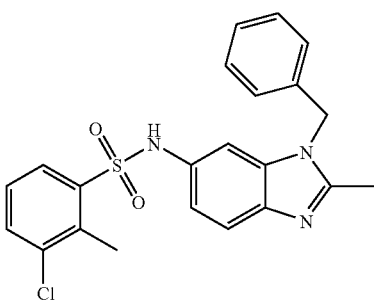

STX1117, XDS02098

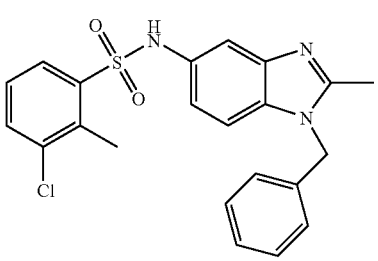

STX1118, XDS02099

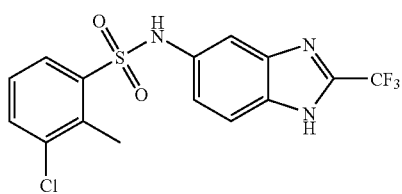

STX879, XDS01173

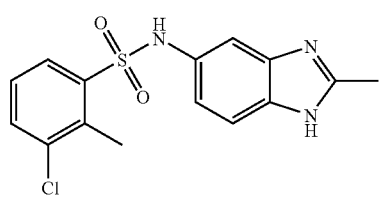

STX985, XDS02026

Preparation of 1-Alkyl-5-amino-2-methyl benzimidazole and 1-alkyl-6-amino-2-methylbenzimidazole To a solution of 5-nitrobenzimidazole (1.0 g, 5.6 mmol) in acetone (50 mL) was added potassium carbonate (1.0 g), followed by alkyl halide (1.2-1.5 equivalents). The mixture was stirred under nitrogen at rt, then partitioned between ethyl acetate and water after TLC showed completion of the reaction. The organic phase was washed with brine, dried over sodium sulphate and concentrated in vacuo to give a mixture of 1-alkyl-5-nitro-2-methylbenzimidazole and 1-alkyl-6-nitro-2-methylbenzimidazole, which were dissolved in ethanol-THF (100 mL, 2:1) and hydrogenated over 5% Pd—C under atmosphere pressure for 8 h. After filtration through Celite®, the filtrate was evaporated to give a yellow solid that was separated with flash chromatography (Methanol-DCM gradient elution). 1-Alkyl-5-aminobenzimidazole and 1-alkyl-6-aminobenzimidazole were obtained as yellow solid or thick syrup.

5-Amino-1,2-dimethylbenzimidazole (XDS01191B, XDS02082B)

Yellow solid, mp 126-127° C. (lit. 128° C., [23]). TLC single spot at $R_f$ 0.30 (5% methanol/DCM); $^1$H NMR (270 MHz, DMSO): δ 7.08 (1H, d, J=8.7 Hz, 7-H), 7.65 (1H, d, J=1.5 Hz, 4-H), 6.50 (1H, dd, J=8.7, 1.5 Hz, 6-H), 4.63 (2H, broad, NH$_2$), 3.58 (3H, s, NCH$_3$), 2.39 (3H, s, CH$_3$).

6-Amino-1,2-dimethylbenzimidazole (XDS01191A, XDS02082A)

Yellow solid. TLC single spot at $R_f$ 10.33 (5% methanol/DCM); $^1$H NMR (270 MHz, DMSO): δ 7.13 (1H, d, J=8.4 Hz, 4-H), 6.48 (1H, d, J=2.0 Hz, 7-H), 6.43 (1H, dd, J=8.4, 2.0 Hz, 5-H), 4.83 (2H, broad, NH$_2$), 3.53 (3H, s, NCH$_3$), 2.39 (3H, s, CH$_3$).

5-Amino-1-ethyl-2-methylbenzimidazole (XDS02079B)

Yellow syrup. TLC single spot at $R_f$, 0.27 (5% methanol/DCM); $^1$H NMR (270 MHz, DMSO): δ 7.12 (1H, d, J=8.3 Hz, 7-H), 6.68 (1H, d, J=2.0 Hz, 4-H), 6.51 (1H, dd, J=8.3, 2.0 Hz, 6-H), 4.68 (2H, broad, NH$_2$), 4.08 (2H, q, J=7.2 Hz, NCH$_2$), 2.43 (3H, s, CH$_3$), 1.24 (3H, t, J=7.2 Hz, CH$_3$); APCI-MS 175 (M$^+$).

6-Amino-1-ethyl-2-methylbenzimidazole (XDS02079A)

Yellow solid. TLC single spot at $R_f$ 10.30 (5% methanol/DCM); $^1$H NMR (270 MHz, DMSO): δ 7.16 (1H, d, J=8.4 Hz, 4-H), 6.68 (1H, d, J=1.7 Hz, 7-H), 6.46 (1H, dd, J=8.4, 1.7 Hz, 5-H), 4.85 (2H, broad, NH$_2$), 4.02 (2H, q, J=7.9 Hz, NCH$_2$), 2.42 (3H, s, CH$_3$), 1.24 (3H, t, J=7.9 Hz, CH$_3$); APCI-MS 175 (M$^+$).

5-Amino-1-i-butyl-2-methylbenzimidazole (XDS02093B)

Yellow syrup. TLC single spot at $R_f$ 10.42 (10% methanol/DCM); $^1$H NMR (400 MHz, DMSO): δ 7.08 (1H, d, J=8.5 Hz, 7-H), 6.65 (1H, d, J=1.9 Hz, 4-H), 6.48 (1H, dd, J=8.5, 1.9 Hz, 6-H), 4.63 (2H, broad, NH$_2$), 3.82 (2H, d, J=7.4 Hz, NCH$_2$), 2.41 (3H, s, CH$_3$), 2.07 (1H, m, CH), 0.84 (6H, d, J=7.0 Hz, 2×CH$_3$); APCI-MS 204 (MH$^+$)

6-Amino-1-i-butyl-2-methylbenzimidazole (XDS02093A)

Yellow solid. TLC single spot at $R_f$ 0.45 (10% methanol/DCM); $^1$H NMR (270 MHz, DMSO): δ 7.15 (1H, d, J=8.2 Hz, 4-H), 6.62 (1H, d, J=1.6 Hz, 7-H), 6.44 (1H, dd, J=8.2, 1.8 Hz, 5-H), 4.83 (2H, broad, NH$_2$), 3.79 (2H, d, J=7.7 Hz, NCH$_2$), 2.41 (3H, s, CH$_3$), 2.10 (1H, m, CH), 0.87 (6H, d, J=6.6 Hz, 2×CH$_3$); APCI-MS 204 (MH$^+$)

(5-Aminobenzoimidazol-1-yl)acetic acid ethyl ester (XDS02012B)

Yellow solid. TLC single spot at $R_f$ 0.36 (5% methanol/DCM); $^1$H NMR (270 MHz, DMSO): δ 7.08 (1H, d, J=8.4 Hz, 7-H), 6.69 (1H, d, J=2.2 Hz, 4-H), 6.49 (1H, dd, J=8.4, 2.2 Hz, 6-H), 5.02 (2H, s, NCH$_2$), 4.68 (2H, s, NH$_2$), 4.16 (2H, q, J=7.2 Hz, CH$_2$), 2.36 (3H, s, CH$_3$), 1.21 (3H, t, J=7.2 Hz, CH$_3$); APCI-MS 234 (MH$^+$).

(6-Aminobenzoimidazol-1-yl)-acetic acid ethyl ester (XDS02012A)

Yellow solid. TLC single spot at R$_f$ 0.40 (5% methanol/DCM); $^1$H NMR (270 MHz, DMSO): δ 7.17 (1H, d, J=9.0 Hz, 4-H), 6.45-6.48 (2H, m, 5 and 7-H), 4.95 (2H, s, NCH$_2$), 4.87 (2H, s, NH$_2$), 4.17 (2H, q, J=7.1 Hz, CH$_2$), 2.36 (3H, s, CH$_3$), 1.22 (3H, t, J=7.1 Hz, CH$_3$); APCI-MS 234 (MH$^+$).

5-Amino-1-benzyl-2-methylbenzimidazole (XDS02086B)

Yellow syrup. TLC single spot at R$_f$ 0.27 (5% methanol/DCM); $^1$H NMR (400 MHz, DMSO): δ 7.26-7.32 (2H, m, ArH), 7.23 (1H, tt, J=7.5, 2.3 Hz, ArH), 7.05-7.09 (3H, m, ArH), 6.69 (1H, d, J=2.3 Hz, 4-H), 6.46 (1H, dd, J=8.2, 2.3 Hz, 6-H), 5.30 (2H, s, CH$_2$), 4.68 (2H, broad, NH$_2$), 2.40 (3H, s, CH$_3$); APCI-MS 238 (MH$^+$).

6-Amino-1-benzyl-2-methylbenzimidazole (XDS02086A)

Yellow solid. TLC single spot at R$_f$ 0.30 (5% methanol/DCM); $^1$H NMR (400 MHz, DMSO): δ 7.28-7.32 (2H, m, ArH), 7.23 (1H, tt, J=7.5, 2.3 Hz, ArH), 7.17 (1H, d, J=8.2, Hz, ArH), 7.06 (2H, m ArH), 6.43-6.46 (2H, m, ArH), 5.26 (2H, s, CH$_2$), 4.63 (2H, s, NH$_2$), 2.40 (3H, s, CH$_3$); APCI-MS 238 (MH$^+$).

Preparation of
5-amino-4-chloro-1,2-dimethylbenzimidazole (XDS02096A)

To a solution of 5-amino-1,2-dimethylbenzimidazole (600 mg, 3.73 mmol) in IPA (15 mL) was added N-chlorosuccinimide (548 mg, 4.10 mmol). The mixture was stirred at rt for 20 min, diluted with DCM (80 mL) and washed with 5% sodium bicarbonate and brine. The dark brown solution was dried over sodium sulphate and concentrated in vacuo to give a brown residue, which was subjected to flash chromatography (methanol-DCM gradient elution). Yellow solid (220 mg, 33%) was obtained. TLC single spot at R$_f$ 10.69 (10% methanol/DCM); $^1$H NMR (270 MHz, DMSO): δ 7.16 (1H, d, J=7.9 Hz, ArH), 6.72 (1H, d, J=7.9, Hz, ArH), 4.90 (2H, s, NH$_2$), 3.64 (3H, s, NCH$_3$), 2.40 (3H, s, CH$_3$); APCI-MS 196 (MH$^+$)

General method for synthesis of N-benzimidazole arylsulphonamide derivatives

To a solution arylsulphonyl chloride (1.1 eq.) in DCM were added pyridine (2.2 eq.) and catalytic amount of DMAP, followed by the corresponding amine (1 eq.). The reaction mixture was stirred at rt under nitrogen for 4-16 h, then partitioned between ethyl acetate and 5% sodium bicarbonate after TLC showed completion of the reaction. The organic layer was washed with brine, dried over sodium sulphate, and concentrated in vacuo to give crude product as solid or thick syrup. The compound was then purified by flash chromatography (Methanol-DCM gradient elution) to give desired arylsulphonamide as crystalline solid. Yield ranges from 50-80%.

3-Chloro-N-(1,2-dimethyl-1H-benzoimidazol-6-yl)-2-methylbenzenesulphonamide (STX975, XDS02001)

White crystalline solid. Mp 265-266° C.; TLC single spot at R$_f$ 0.43 (5% methanol/DCM); HPLC purity >99% (t$_R$ 2. min in 10% water-methanol); $^1$H NMR (270 MHz, DMSO): δ 10.4 (1H, s, NH), 7.84 (1H, d, J=7.9 Hz, ArH), 7.67 (1H, d, J=7.9 Hz, ArH), 7.34 (1H, d, J=8.2 Hz, ArH), 7.32 (1H, t, J=7.9 Hz, ArH), 7.14 (1H, d, J=2 Hz, ArH), 6.80 (1H, dd, J=8.2, 2.0 Hz, ArH), 3.61 (3H, s, NCH$_3$), 2.64 (3H, s, CH$_3$), 2.46 (3H, s, CH$_3$); APCI-MS 348 (M–H$^+$); FAB-HRMS calcd for C$_{16}$H$_{17}$ClN$_3$O$_2$S (MH$^+$) 350.0730, found 350.0749.

3-Chloro-N-(1,2-dimethyl-1H-benzoimidazol-5-yl)-2-methylbenzenesulphonamide (STX976, XDS02003)

White crystalline solid. Mp 283-283.5° C.; TLC single spot at R$_f$ 0.38 (5% methanol/DCM); HPLC purity >99% (t$_R$ 2.0 min in 10% water-methanol); $^1$H NMR (270 MHz, DMSO): δ 10.3 (1H, s, NH), 7.77 (1H, d, J=7.6 Hz, ArH), 7.66 (1H, d, J=7.6 Hz, ArH), 7.32 (1H, d, J=8.4 Hz, ArH), 7.30 (1H, t, J=7.6 Hz, ArH), 7.16 (1H, d, J=2 Hz, ArH), 6.90 (1H, dd, J=8.4, 2.0 Hz, ArH), 3.64 (3H, s, NCH$_3$), 2.64 (3H, s, CH$_3$), 2.44 (3H, s, CH$_3$); APCI-MS 348 (M–H$^+$); FAB-HRMS calcd for C$_{16}$H$_{17}$ClN$_3$O$_2$S (MH$^+$) 350.0730, found 350.0747.

3-Chloro-N-(4-chloro-1,2-dimethyl-1H-benzoimidazol-5-yl)-2-methylbenzenesulphonamide (STX1121, XDS02102B)

Off-white crystalline solid. TLC single spot at R$_f$ 0.50 (10% methanol/DCM); HPLC purity 95% (t$_R$ 2.1 min in 20% water-methanol); $^1$H NMR (270 MHz, DMSO): δ 10.1 (1H, s, NH), 7.70 (1H, dd, J=7.7, 1.7 Hz, ArH), 7.56 (1H, dd, J=7.8, 1.7 Hz, ArH), 7.39 (1H, d, J=8.2 Hz, ArH), 7.25 (1H, t, J=7.7 Hz, ArH), 7.04 (1H, d, J=8.2 Hz, ArH), 3.69 (3H, s, NCH$_3$), 2.67 (3H, s, CH$_3$), 2.51 (3H, s, CH$_3$); APCI-MS 384 (MH$^+$).

N-(1,2-Dimethyl-1H-benzoimidazol-5-yl)-4-propylbenzenesulphonamide (STX1112, XDS02088)

White crystalline solid. TLC single spot at R$_f$ 10.38 (5% methanol/DCM); HPLC purity >99% (t$_R$ 2.1 min in 20% water-methanol); $^1$H NMR (270 MHz, DMSO): δ 9.90 (1H, s, NH), 7.58 (2H, d, J=8.3 Hz, ArH), 7.29-7.32 (3H, m, ArH), 7.17 (1H, d, J=1.5 Hz, ArH), 6.91 (1H, dd, J=8.6, 2.0 Hz, ArH), 3.64 (3H, s, NCH$_3$), 2.55 (2H, m, CH$_2$), 2.50 (3H, s, CH$_3$), 1.55 (2H, sextet, J=7.6 Hz, CH$_2$), 0.84 (3H, t, J=7.6 Hz, CH$_3$); APCI-MS 344 (MH$^+$).

2,5-Dichloro-N-(1,2-dimethyl-1H-benzoimidazol-5-yl)-benzenesulphonamide (STX1113, XDS02089)

White crystalline solid. TLC single spot at R$_f$ 0.67 (10% methanol/DCM); HPLC purity 99% (t$_R$ 2.0 min in 20% water-methanol); $^1$H NMR (270 MHz, DMSO): δ 10.5 (1H, s, NH), 7.84 (1H, t, J=1.4 Hz, ArH), 7.68 (2H, d, J=2.0 Hz, ArH), 7.35 (1H, d, J=8.5 Hz, ArH), 7.21 (1H, d, J=2.0 Hz, ArH), 6.97 (1H, dd, J=8.2, 2.0 Hz, ArH), 3.64 (3H, s, NCH$_3$), 2.45 (3H, s, CH$_3$); APCI-MS 370 (MH$^+$).

2,4-Dichloro-N-(1,2-dimethyl-1H-benzoimidazol-5-yl)-benzenesulphonamide (STX1114, XDS02090)

Off-white crystalline solid. TLC single spot at $R_f$ 0.59 (10% methano/DCM); HPLC purity >99% ($t_R$ 2.0 min in 20% water-methanol); $^1$H NMR (270 MHz, DMSO): δ 10.4 (1H, s, NH), 7.88 (1H, d, J=8.7 Hz, ArH), 7.84 (2H, d, J=1.9 Hz, ArH), 7.52 (1H, dd, J=8.7, 1.9 Hz, ArH), 7.33 (1H, d, J=8.5 Hz, ArH), 7.20 (1H, d, J=1.7 Hz, ArH), 6.95 (1H, dd, J=8.7, 1.7 Hz, ArH), 3.63 (3H, s, NCH$_3$), 2.45 (3H, s, CH$_3$); APCI-MS 370 (MH$^+$).

4-Bromo-N-(1,2-dimethyl-1H-benzoimidazol-5-yl)-2-methylbenzenesulphonamide (STX1115, XDS02091)

White crystalline solid. TLC single spot at $R_f$ 0.67 (10% methano/DCM); HPLC purity >99% ($t_R$ 2.1 min in 20% water-methanol); $^1$H NMR (270 MHz, DMSO): δ 10.1 (1H, s, NH), 7.62-7.69 (2H, m, ArH), 7.50 (1H, dd, J=8.5, 2.2 Hz, ArH), 7.32 (1H, d, J=8.5 Hz, ArH), 7.14 (1H, d, J=1.9 Hz, ArH), 6.89 (1H, dd, J=8.5, 1.9 Hz, ArH), 3.63 (3H, s, NCH$_3$), 2.55 (3H, s, CH$_3$), 2.45 (3H, s, CH$_3$); APCI-MS 394 (MH$^+$).

N-(1,2-Dimethyl-1H-benzoimidazol-5-yl)-4-phenyl-benzenesulphonamide (STX1116, XDS02092)

White crystalline solid. TLC single spot at $R_f$ 0.72 (5% methanol/DCM); HPLC purity >99% ($t_R$ 2.1 min in 20% water-methanol); $^1$H NMR (270 MHz, DMSO): δ 10.0 (1H, s, NH), 7.67-7.82 (6H, m, ArH), 7.41-7.50 (3H, m, ArH), 7.33 (1H, d, J=8.5 Hz, ArH), 7.22 (1H, d, J=1.9 Hz, ArH), 6.95 (1H, dd, J=8.5, 1.9 Hz, ArH), 3.64 (3H, s, NCH$_3$), 2.44 (3H, s, CH$_3$); APCI-MS 378 (MH$^+$).

3-Chloro-N-(1-ethyl-2-methyl-1H-benzoimidazol-6-yl)-2-methylbenzenesulphonamide (STX1110, XDS02084)

Off-white solid. TLC single spot at $R_f$ 0.45 (8% methanol/DCM); HPLC purity >99% ($t_R$ 2.2 min in 20% water-methanol); $^1$H NMR (270 MHz, DMSO): δ 10.4 (1H, s, NH), 7.84 (1H, d, J=7.9 Hz, ArH), 7.67 (1H, d, J=7.8 Hz, ArH), 7.35 (1H, d, J=8.5 Hz, ArH), 7.32 (1H, t, J=7.9 Hz, ArH), 7.10 (1H, d, J=2.2 Hz, ArH), 6.82 (1H, dd, J=8.5, 2.1 Hz, ArH), 4.09 (2H, q, J=7.1 Hz, CH$_2$), 2.61 (3H, s, CH$_3$), 2.46 (3H, s, CH$_3$), 1.18 (3H, t, J=7.1 Hz, CH$_3$); APCI-MS 364 (MH$^+$).

3-Chloro-N-(1-ethyl-2-methyl-1H-benzoimidazol-5-yl)-2-methylbenzenesulphonamid (STX1111, XDS02085)

Off-white solid. TLC single spot at $R_f$ 0.42 (8% methanol/DCM); HPLC purity >99% ($t_R$ 2.2 min in 20% water-methanol); $^1$H NMR (270 MHz, DMSO): δ 10.3 (1H, s, NH), 7.78 (1H, d, J=7.9 Hz, ArH), 7.66 (1H, d, J=7.9 Hz, ArH), 7.36 (1H, d, J=8.2 Hz, ArH), 7.32 (1H, t, J=7.9 Hz, ArH), 7.16 (1H, d, J=1.9 Hz, ArH), 6.90 (1H, dd, J=7.9, 2.0 Hz, ArH), 4.12 (2H, q, J=7.1 Hz, CH$_2$), 2.64 (3H, s, CH$_3$), 2.46 (3H, s, CH$_3$), 1.23 (3H, t, J=7.1 Hz, CH$_3$); APCI-MS 364 (MH$^+$).

3-Chloro-N-(1-isobutyl-2-methyl-1H-benzoimidazol-6-yl)-2-methyl benzenesulphonamide (STX1119, XDS02100)

Off-white solid. TLC single spot at $R_f$ 0.57 (8% methanol/DCM); HPLC purity 99% ($t_R$ 2.2 min in 20% water-methanol); $^1$H NMR (270 MHz, DMSO): δ 10.4 (1H, s, NH), 7.80 (1H, d, J=8.9 Hz, ArH), 7.66 (1H, d, J=8.8 Hz, ArH), 7.36 (1H, d, J=8.5 Hz, ArH), 7.29 (1H, t, J=7.9 Hz, ArH), 7.03 (1H, d, J=1.9 Hz, ArH), 6.84 (1H, dd, J=8.5, 1.8 Hz, ArH), 3.85 (2H, d, J=7.2 Hz, NCH$_2$), 2.61 (3H, s, CH$_3$), 2.45 (3H, s, CH$_3$), 1.91 (1H, m, CH), 0.81 (6H, d, J=7.0 Hz, 2×CH$_3$); APCI-MS 392 (MH$^+$).

3-Chloro-N-(1-isobutyl-2-methyl-1H-benzoimidazol-5-yl)-2-methylbenzenesulphonamide (STX1120, XDS02101)

Off-white solid. TLC single spot at $R_f$ 0.52 (8% methanol/DCM); HPLC purity 99% ($t_R$ 2.3 min in 20% water-methanol); $^1$H NMR (270 MHz, DMSO): δ 10.3 (1H, s, NH), 7.80 (1H, d, J=7.9 Hz, ArH), 7.68 (1H, d, J=7.9 Hz, ArH), 7.38 (1H, d, J=8.8 Hz, ArH), 7.33 (1H, t, J=7.9 Hz, ArH), 7.16 (1H, d, J=1.9 Hz, ArH), 6.90 (1H, dd, j=8.7, 1.9 Hz, ArH), 3.91 (2H, d, J=7.3 Hz, NCH$_2$), 2.62 (3H, s, CH$_3$), 2.47 (3H, s, CH$_3$), 2.05 (1H, m, CH), 0.83 (6H, d, J=7.0 Hz, 2×CH$_3$); APCI-MS 392 (MH$^+$).

[6-(3-Chloro-2-methylbenzenesulphonylamino)-2-methylbenzoimidazol-1-yl]-acetic acid ethyl ester (STX977, XDS02015)

Off-white solid. TLC single spot at $R_f$ 0.46 (6% methanol/DCM); HPLC purity >99% ($t_R$ 2.0 min in 10% water-methanol); $^1$H NMR (270 MHz, DMSO): δ 10.4 (1H, s, NH), 7.82 (1H, d, J=8.0 Hz, ArH), 7.67 (1H, d, J=8.0 Hz, ArH), 7.37 (1H, d, J=8.5 Hz, ArH), 7.30 (1H, t, J=8.0 Hz, ArH), 7.11 (1H, d, J=2.0 Hz, ArH), 6.83 (1H, dd, J=8.5, 2.0 Hz, ArH), 5.09 (2H, s, NCH$_2$), 4.16 (2H, q, J=7.1 Hz, CH$_2$), 2.62 (3H, s, CH$_3$), 2.45 (3H, s, CH$_3$), 1.21 (3H, t, J=7.1 Hz, CH$_3$); APCI-MS 420 (M–H$^+$); FAB-HRMS calcd for C$_{19}$H$_{21}$ClN$_3$O$_4$S (MH$^+$) 422.0941, found 422.0942.

[5-(3-Chloro-2-methylbenzenesulphonylamino)-2-methylbenzoimidazol-1-yl]-acetic acid ethyl ester (STX978, XDS02017)

Off-white solid. TLC single spot at $R_f$ 0.40 (6% methanol/DCM); HPLC purity 99% ($t_R$ 2.0 min in 10% water-methanol); $^1$H NMR (270 MHz, DMSO): δ 10.3 (1H, s, NH), 7.80 (1H, d, J=7.9 Hz, ArH), 7.67 (1H, d, J=7.9 Hz, ArH), 7.29-7.34 (2H, m, ArH), 7.18 (1H, d, J=1.7 Hz, ArH), 6.90 (1H, dd, J=8.6, 1.7 Hz, ArH), 5.11 (2H, s, NCH$_2$), 4.15 (2H, q, J=7.1 Hz, CH$_2$), 2.64 (3H, s, CH$_3$), 2.40 (3H, s, CH$_3$), 1.19 (3H, t, J=7.1 Hz, CH$_3$); APCI-MS 420 (M–H$^+$); FAB-HRMS calcd for C$_{19}$H$_{21}$ClN$_3$O$_4$S (MH$^+$) 422.0941, found 422.0944.

3-Chloro-N-(1-benzyl-2-methyl-1H-benzoimidazol-6-yl)-2-methylbenzenesulphonamide (STX1117, XDS02098)

Off-white solid. TLC single spot at $R_f$ 0.70 (10% methanol/DCM); HPLC purity 99% ($t_R$ 2.2 min in 20% water-methanol); $^1$H NMR (270 MHz, DMSO): δ 10.4 (1H, s, NH), 7.66 (1H, d, J=7.9 Hz, ArH), 7.64 (1H, d, J=7.9 Hz, ArH), 7.30-7.39 (4H, m, ArH), 7.21 (1H, t, J=7.9 Hz, ArH), 7.11 (1H, d, J=2.0 Hz, ArH), 7.02-7.06 (2H, m, ArH), 6.83 (1H, dd, J=7.9, 2.0 Hz, ArH), 5.34 (2H, s, NCH$_2$), 2.58 (3H, s, CH$_3$), 2.45 (3H, s, CH$_3$); APCI-MS 426 (MH$^+$).

3-Chloro-N-(1-benzyl-2-methyl-1H-benzoimidazol-5-yl)-2-methylbenzenesulphonamide (STX1118, XDS02099)

Off-white solid. TLC single spot at $R_f$ 10.65 (10% methanol/DCM); HPLC purity 99% ($t_R$ 2.2 min in 10% water-methanol); $^1$H NMR (270 MHz, DMSO): δ 10.3 (1H, s, NH), 7.80 (1H, d, J=7.9 Hz, ArH), 7.67 (1H, d, J=7.9 Hz, ArH), 7.25-7.35 (5H, m, ArH), 7.19 (1H, d, J=1.9 Hz, ArH), 7.06-7.09 (2H, m, ArH), 6.87 (1H, dd, J=8.5, 1.9 Hz, ArH), 5.38 (2H, s, NCH$_2$), 2.62 (3H, s, CH$_3$), 2.45 (3H, s, CH$_3$); APCI-MS 426 (MH$^+$).

3-Chloro-N-(2-trifluoromethyl-1H-benzoimidazol-5-yl)-2-methylbenzenesulphonamide (STX879, XDS01173)

White crystalline solid. TLC single spot at $R_f$ 0.58 (20% ethyl acetate/DCM); HPLC purity 99% ($t_R$ 2.4 min in 20% water-methanol); $^1$H NMR (270 MHz, DMSO): δ 13.9 (1H, s, NH), 10.7 (1H, s, NH), 7.85 (1H, d, J=8.0 Hz, ArH), 7.68 (1H, d, J=8.0 Hz, ArH), 7.60 (1H, d broad, J=8.1 Hz, ArH), 7.34 (2H, m, ArH), 7.10 (1H, d, J=8.3 Hz, ArH), 2.64 (3H, s, CH$_3$); APCI-MS 388 (M–H$^+$); FAB-HRMS calcd for C$_{15}$H$_{12}$ClF$_3$N$_3$O$_2$S (MH$^+$) 390.0291, found 390.0291.

Preparation of 3-chloro-N-(2-methyl-1H-benzoimidazol-5-yl)-2-methylbenzenesulphonamide (STX985, XDS02026)

The coupling reaction of 3-chloro-2-methylbenzenesulphonyl chloride (2 eq.) with 2-methylbenzimidazole (1 eq.) under the condition described above yielded a mixture of 3-chloro-N-[1-(3-chloro-2-methylbenzenesulphonyl)-2-methyl-1H-benzoimidazol-5-yl]-2-methyl-benzenesulphonamide and 3-chloro-N-[1-(3-chloro-2-methylbenzenesulphonyl)-2-methyl-1H-benzoimidazol-6-yl]-2-methyl-benzenesulphonamide in 1:1 ratio as judged by $^1$HNMR. $^1$H NMR (270 MHz, DMSO): δ 10.7 (2H, s, 2×NH), 7.86-7.96 (3H, m, ArH), 7.65-7.78 (5H, m, ArH), 7.52-7.58 (5H, m, ArH), 7.25-7.40 (3H, m, ArH), 7.07 (2H, t, J=8.2 Hz, ArH), 2.61 (3H, s, CH$_3$), 2.58 (3H, s, CH$_3$), 2.54 (6H, s, 2×CH$_3$), 2.39 (3H, s, CH$_3$), 2.33 (3H, s, CH$_3$). The mixture (200 mg) was dissolved in THF (15 mL), N-hydroxybenzotriazole (200 mg) was added. After stirred at rt for 48 h, the mixture was partitioned between ethyl acetate and 5% sodium bicarbonate. The organic phase was washed with brine, dried over sodium sulphate and concentrate in vacuo to give a yellow residue, which was purified with flash chromatography (methanol/DCM gradient elution). Off white amorphous powder was obtained. TLC single spot at $R_f$ 10.38 (10% methanol/DCM); HPLC purity 99% ($t_R$ 2.0 min in 10% water-methanol); $^1$H NMR (270 MHz, DMSO): δ 12.1 (1H, s, NH), 10.3 (1H, s, NH), 7.78 (1H, d, J=7.9 Hz, ArH), 7.68 (1H, d, J=7.9 Hz, ArH), 7.29-7.35 (2H, m, ArH), 7.12 (1H, s, ArH), 6.83 (1H, dd, J=8.4, 1.8 Hz, ArH), 2.63 (3H, s, CH$_3$), 2.41 (3H, s, CH$_3$); APCI-MS 334 (M–H$^+$); FAB-HRMS calcd for C$_{15}$H$_{15}$ClN$_3$O$_2$S (MH$^+$) 336.0573, found 336.0583.

Synthesis of N-Benzimidazole Arylsulphonamide Derivatives

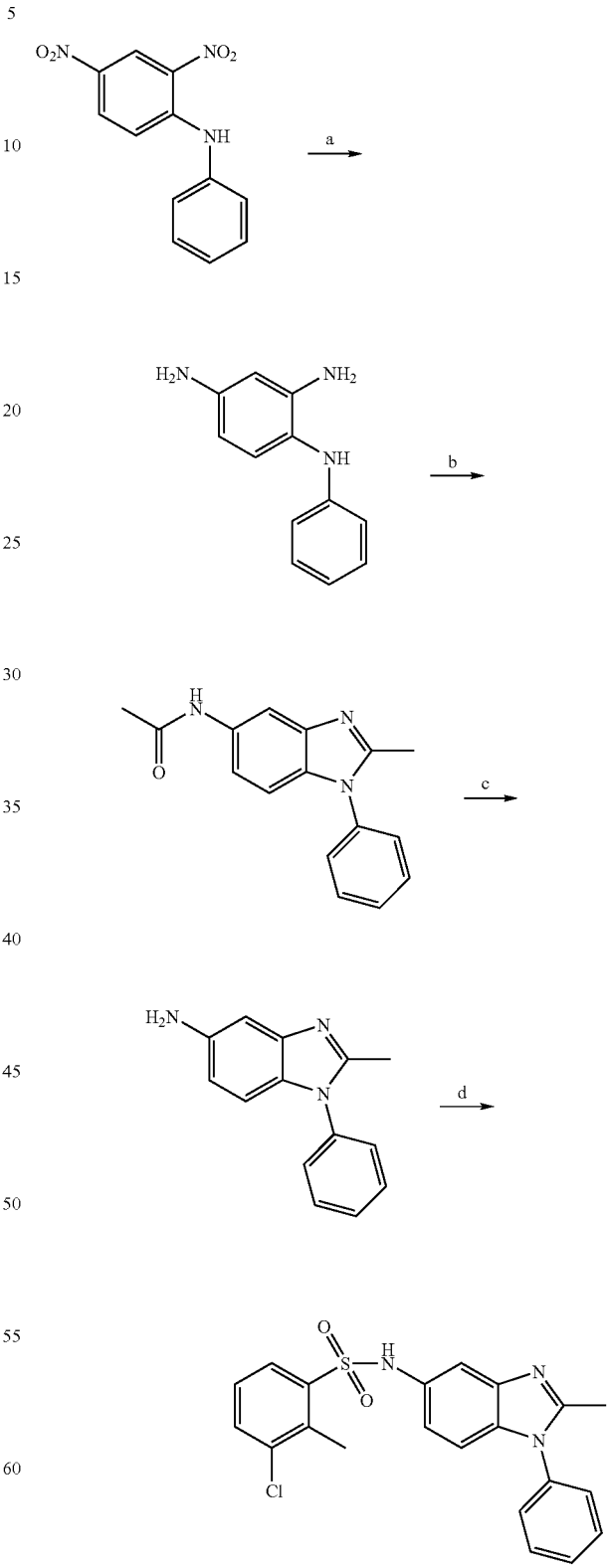

STX1140, XDS02110

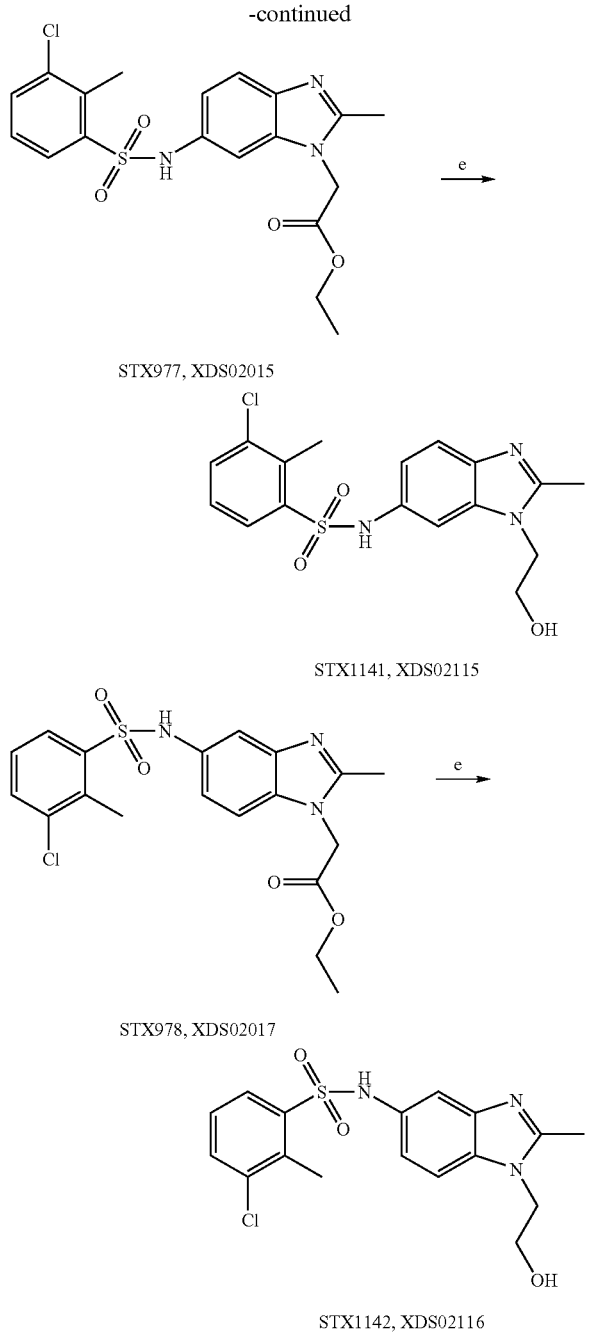

STX977, XDS02015

STX1141, XDS02115

STX978, XDS02017

STX1142, XDS02116 a) Raney-Ni, NH$_2$NH$_2$·H$_2$O, ethanol, rt
b) Ac$_2$O, AcOH, 80° C.
c) 6N HCl, 75° C.
d) 3-Cl-2-Me-benzenesulphonyl chloride, DCM, Pyridine
e) LiAlH4, THF, 0° C.

N'-Phenyl-benzene-1,2,4-triamine

To a solution of 2,4-dinitrophenylamine (1.5 g, 5.8 mmol) in ethanol-THF (150:50 mL) were added hydrazine hydrate (2 mL, 65 mmol) and Raney Nickel (2.0 g). The reaction mixture was stirred at rt for 20 min, filtered through Celite. Evaporation of the solvent gave a black residue, which was purified by flash chromatography (methanol-DCM gradient elution). A black crystalline solid (1.0 g, 87%) was obtained. Mp 128-129° C.; TLC single spot at R$_f$ 10.46 (8% methanol/DCM); $^1$H NMR (270 MHz, DMSO): δ 7.25 (2H, t, J=7.5 Hz, ArH), 6.73 (1H, s, NH), 6.61 (1H, d, J=8.3 Hz, ArH), 6.49-6.55 (3H, m, ArH), 5.99 (1H, d, J=2.5 Hz, ArH), 5.83 (1H, dd, J=8.2, 2.5 Hz, ArH), 4.66 (2H, s, NH$_2$), 4.44 (2H, s, NH$_2$); APCI-MS 198 (M–H$^+$).

N-(2-Methyl-1-phenyl-1H-benzimidazol-5-yl)-acetamide

N$^1$-Phenyl-benzene-1,2,4-triamine (800 mg, 4 mmol) was dissolved in acetic acid (10 mL), acetic anhydride (1.0 mL) was added to the solution. The mixture was stirred at 80° C. for 6 h, cooled to rt and neutralized with 5% sodium carbonate, then extracted with ethyl acetate. The organic phase was washed with brine, dried over magnesium sulphate and concentrated to give a residue, which was crystallized from ethanol. A brown crystalline solid (0.85 g, 80%) was obtained. Mp 231-232° C.; TLC single spot at R$_f$ 0.39 (10% methanol/DCM); $^1$H NMR (270 MHz, DMSO): δ 9.92 (1H, s, NH), 7.97 (1H, d, J=1.6 Hz, ArH), 7.51-7.67 (5H, m, ArH), 7.31 (1H, dd, J=8.3, 1.9 Hz, ArH), 7.04 (1H, d, J=8.3 Hz, ArH), 2.41 (3H, s, CH$_3$), 2.05 (3H, s, CH$_3$); APCI-MS 264 (M–H$^+$).

2-Methyl-1-phenyl-1H-benzoimidazol-5-ylamine

The solution of N-(2-methyl-1-phenyl-1H-benzimidazol-5-yl)-acetamide (800 mg, 3 mmol) in 6N HCl (5 mL) was stirred at 75° C. for 3 h, cooled to rt and neutralized with sodium carbonate to pH 7, then extracted with ethyl acetate. The organic phase was washed with brine, dried over magnesium sulphate and concentrated to give a dark brown solid (600 mg, 90%). Mp 145-146° C.; TLC single spot at R$_f$ 0.47 (10% methanol/DCM); $^1$H NMR (270 MHz, DMSO): δ 7.58-7.64 (2H, m, ArH), 7.46-7.53 (3H, m, ArH), 6.82 (1H, d, J=8.5 Hz, ArH), 6.76 (1H, d, J=1.9 Hz, ArH), 6.51 (1H, dd, J=8.5, 1.9 Hz, ArH), 4.78 (2H, s, NH$_2$), 2.36 (3H, s, CH$_3$); APCI-MS 223 (M$^+$).

3-Chloro-2-methyl-N-(2-methyl-1-phenyl-1H-benzoimidazol-5-yl)-benzenesulphonamide (STX1140, XDS02110)

The compound was prepared with general method of benzenesulphonamide formation. Light pink crystalline solid was obtained. Mp 254-256° C.; TLC single spot at R$_f$ 0.62 (8% methanol/DCM); HPLC purity >99% (t$_R$ 2.6 min in 20% water-methanol); $^1$H NMR (270 MHz, DMSO): δ 10.4 (1H, s, NH), 7.83 (1H, dd, J=8.6, 1.8 Hz, ArH), 7.69 (1H, dd, J=8.6, 1.7 Hz, ArH), 7.58-7.63 (5H, m, ArH), 7.34 (1H, t, J=8.0 Hz, ArH), 7.28 (1H, d, J=1.9 Hz, ArH), 6.90-7.00 (2H, m, ArH), 2.66 (3H, s, CH$_3$), 2.36 (3H, s, CH$_3$); APCI-MS 412 (MH$^+$).

3-Chloro-N-[1-(2-hydroxyethyl)-2-methyl-1H-benzoimidazol-6-yl]-2-methyl-benzenesulfonamide (STX1141, XDS02115)

To a solution of [6-(3-Chloro-2-methyl-benzenesulfonylamino)-2-methyl-benzoimidazol-1-yl]-acetic acid ethyl ester (100 mg, 0.237 mmol) in anhydrous THF (10 mL) was added LiAlH$_4$ (54 mg, 1.42 mmol) at 0° C. The mixture was stirred at 0° C. for 0.5 h, quenched with saturated ammonium chloride solution, neutralized with 6N HCl and extracted with ethyl acetate. The organic phase was washed with brine, dried over sodium sulphate and concentrated in vacuo to give a light pink crystalline solid (82 mg, 91%). Mp 213-214.5° C.; TLC single spot at R$_f$ 0.39 (12% methanol/DCM); HPLC purity >99% (t$_R$ 2.0 min in 20% water-methanol); $^1$H NMR (270

MHz, DMSO): δ 10.4 (1H, s, NH), 7.84 (1H, d, J=7.7 Hz, ArH), 7.67 (1H, d, J=7.9 Hz, ArH), 7.28-7.35 (2H, m, ArH), 7.15 (1H, d, J=1.9 Hz, ArH), 6.80 (1H, dd, J=8.5, 1.9 Hz, ArH), 4.94 (1H, t, J=5.2 Hz, OH), 4.10 (2H, t, J=5.0 Hz, $NCH_2$), 3.59 (2H, q, J=5.2 Hz, $CH_2$), 2.51 (3H, s, $CH_3$), 2.47 (3H, s, $CH_3$); APCI-MS 380 ($MH^+$).

3-Chloro-N-[1-(2-hydroxy-ethyl)-2-methyl-1H-benzoimidazol-5-yl]-2-methyl-benzenesulfonamide (STX1142, XDS02116)

The compound was prepared as above from [5-(3-Chloro-2-methyl-benzenesulfonylamino)-2-methyl-benzoimidazol-1-yl]-acetic acid ethyl ester (35 mg, 0.083 mmol). White crystalline solid (22 mg, 89%) was obtained. Mp 245-247° C.; TLC single spot at $R_f$ 0.38 (12% methanol/DCM); HPLC purity >99% ($t_R$ 2.0 min in 20% water-methanol); $^1$H NMR (270 MHz, DMSO): δ 10.3 (1H, s, NH), 7.79 (1H, d, J=8.0 Hz, ArH), 7.67 (1H, d, J=8.0 Hz, ArH), 7.29-7.35 (2H, m, ArH), 7.16 (1H, s, ArH), 6.89 (1H, d, J=8.5, ArH), 4.90 (1H, t, J=5.0 Hz, OH), 4.14 (2H, t, J=5.0 Hz, $NCH_2$), 3.63 (2H, q, J=5.2 Hz, $CH_2$), 2.65 (3H, s, $CH_3$), 2.48 (3H, s, $CH_3$); APCI-MS 380 ($MH^+$).

Synthesis of Benzoxazole Derivatives

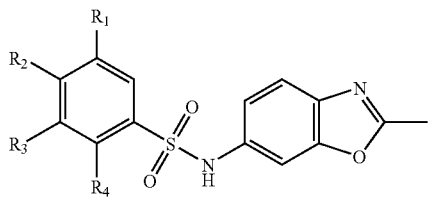

STX 839: $R_1$=$R_2$=H, $R_3$=Cl, $R_4$=Me
STX 840: $R_1$=$R_3$=$R_4$=H, $R_2$=n-propyl
STX 841: $R_1$=$R_4$=Cl, $R_2$=$R_3$=H

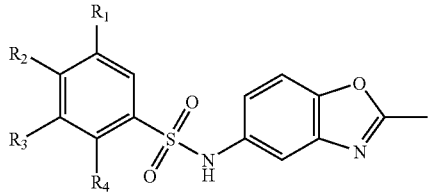

STX 842: $R_1$=$R_2$=H, $R_3$=Cl, $R_4$=Me
STX 843: $R_1$=$R_3$=$R_4$=H, $R_2$=n-propyl
STX 846: $R_1$=$R_4$=Cl, $R_2$=$R_3$=H

Synthesis of 3-chloro-2-methyl-N-(2-methyl-benzooxazol-6-yl)-benzenesulfonamide, STX 839 (KRB01009)

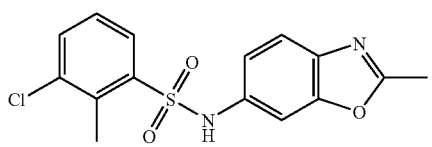

To a solution of 3-chloro-2-methylbenzenesulphonyl chloride (163 mg, 0.723 mmol) in dichloromethane (3 mL) was added pyridine (140 μL, 1.72 mmol) and the mixture was stirred under $N_2$ for 5 min, after which time 6-amino-2-methylbenzoxazole (102 mg, 0.688 mmol) was added. The resulting mixture was stirred for 1 h at room temperature, then saturated $NaHCO_3$ solution was added (8 mL) and the mixture was extracted into ethyl acetate (15 mL). The organic phase was washed with brine, dried ($Na_2SO_4$), filtered and evaporated to give a residue that was purified using flash chromatography to afford a white solid (151 mg, 65%), single spot at $R_f$ 10.50 (60:40 hexane:ethyl acetate). mp 127.1-127.5° C., HPLC purity 97% ($t_R$ 2.05 min in 10% water-acetonitrile). $^1$H NMR ($CDCl_3$): δ 7.85 (1H, dd, J=8.1, 1.1 Hz), 7.53 (1H, dd, J=8.1, 1.3 Hz), 7.45 (1H, d, J=8.4 Hz), 7.27 (1H, d, J=2.2 Hz), 7.17 (1H, t, J=7.9 Hz), 6.93 (1H, s, N—H), 6.86 (1H, dd, J=8.4, 2.2 Hz), 2.71 (3H, s), 2.58 (3H, s). LCMS: 335.14 (M−). FAB-MS ($MH^+$, $C_{15}H_{13}ClN_2O_3S$): calcd 337.0413, found 337.0406.

Synthesis of N-(2-methyl-benzooxazol-6-yl)-4-propyl-benzenesulfonamide, STX 840 (KRB01010)

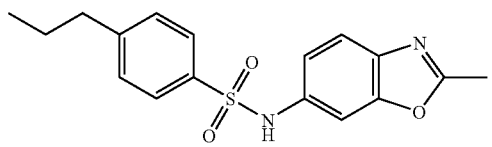

To a solution of 4n-propylbenzenesulphonyl chloride (163 mg, 0.744 mmol) in dichloromethane (3 mL) was added pyridine (140 μL, 1.72 mmol) and the mixture was stirred under $N_2$ for 5 min, after which time 6-amino-2-methylbenzoxazole (105 mg, 0.709 mmol) was added. The resulting mixture was stirred for 1 h at room temperature, then saturated $NaHCO_3$ solution was added (8 mL) and the mixture was extracted into ethyl acetate (15 mL). The organic phase was washed with brine, dried ($Na_2SO_4$), filtered and evaporated to give a residue that was purified using flash chromatography to afford a pale pink solid (164 mg, 70%), single spot at $R_f$ 0.49 (60:40 hexane:ethyl acetate). mp 101.7-102.3° C., HPLC purity 99% ($t_R$ 2.02 min in 10% water-acetonitrile). $^1$H NMR ($CDCl_3$): δ 7.61 (2H, m), 7.43 (1H, d, J=8.4 Hz), 7.37 (1H, d, J=1.8 Hz), 7.19 (2H, m), 6.83 (2H, m), 2.57 (5H, m), 1.58 (2H, sextet, J=7.3 Hz), 0.88 (3H, t, J=7.3 Hz). LCMS: 329.21 (M−). FAB-MS (MH+, $C_{17}H_{18}N_2O_3S$): calcd 331.1116, found 331.1107.

Synthesis of 2,5-dichloro-(2-methyl-benzooxazol-6-yl)-benzenesulfonamide, STX 841 (KRB01011)

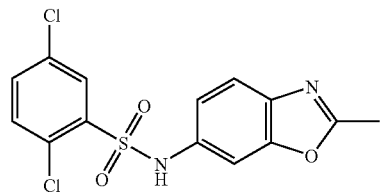

To a solution of 2,5-dichlorobenzenesulphonyl chloride (174 mg, 0.709 mmol) in dichloromethane (3 mL) was added pyridine (140 μL, 1.72 mmol) and the mixture was stirred under N₂ for 5 min, after which time 6-amino-2-methylbenzoxazole (100 mg, 0.675 mmol) was added. The resulting mixture was stirred for 1 h at room temperature, then saturated NaHCO₃ solution was added (8 mL) and the mixture was extracted into ethyl acetate (15 mL). The organic phase was washed with brine, dried (Na₂SO₄), filtered and evaporated to give a residue that was purified using flash chromatography to afford a white solid (154 mg, 64%), single spot at $R_f$ 10.50 (60:40 hexane:ethyl acetate). mp 167.0-167.3° C., HPLC purity 97% ($t_R$ 1.97 min in 10% water-acetonitrile). ¹H NMR (CDCl₃): δ 7.93 (1H, d, J=2.3 Hz), 7.47 (1H, d, J=8.6 Hz), 7.46-7.40 (4H, m), 7.00 (1H, dd, J=8.6, 2.0 Hz), 2.61 (3H, s). LCMS: 355.07 (M−). FAB-MS (MH+, C₁₄H₁₀Cl₂N₂O₃S): calcd 356.9867, found 356.9875.

Synthesis of 3-chloro-2-methyl-N-(2-methyl-benzooxazol-5-yl)-benzenesulfonamide, STX 842 (KRB01014)

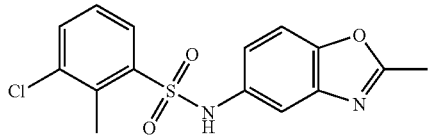

To a solution of 3-chloro-2-methylbenzenesulphonyl chloride (96 mg, 0.43 mmol) in dichloromethane (2 mL) was added pyridine (80 µL, 1.0 mmol) and the mixture was stirred under N₂ for 5 min, after which time 5-amino-2-methylbenzoxazole (60 mg, 0.40 mmol) was added. The resulting mixture was stirred for 1 h at room temperature, then saturated NaHCO₃ solution was added (8 mL) and the mixture was extracted into ethyl acetate (15 mL). The organic phase was washed with brine, dried (Na₂SO₄), filtered and evaporated to give a residue that was purified using flash chromatography to afford a white solid (89 mg, 64%), single spot at $R_f$ 0.52 (1:1 hexane:ethyl acetate). mp 180.2-180.5° C., HPLC purity 99% ($t_R$ 2.32 min in 10% water-acetonitrile). ¹H NMR (CDCl₃): δ 7.82 (1H, dd, J=8.1, 1.1 Hz), 7.52 (1H, dd, J=7.7, 1.1 Hz), 7.32 (1H, d, 8.4 Hz), 7.25 (1H, d, J=2.9 Hz (overlap with CHCl₃)), 7.14 (1H, t, J=8.1 Hz), 6.99 (1H, dd, J=8.4, 2.2 Hz), 6.67 (1H, s, N—H), 2.71 (3H, s), 2.58 (3H, s). LCMS: 335.01 (M−). FAB-MS (MH+, C₁₅H₁₃ClN₂O₃S): calcd 337.0413, found 337.0420.

Synthesis of N-(2-methyl-benzooxazol-5-yl)-4-propyl-benzenesulfonamide, STX 843 (KRB01015)

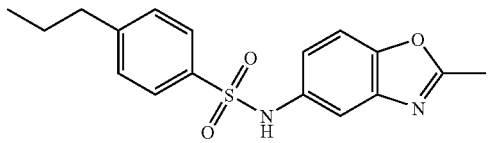

To a solution of 4n-propylbenzenesulphonyl chloride (93 mg, 0.43 mmol) in dichloromethane (2 mL) was added pyridine (80 µL, 1.0 mmol) and the mixture was stirred under N₂ for 5 min, after which time 5-amino-2-methylbenzoxazole (60 mg, 0.40 mmol) was added. The resulting mixture was stirred for 1 h at room temperature, then saturated NaHCO₃ solution was added (8 mL) and the mixture was extracted into ethyl acetate (15 mL). The organic phase was washed with brine, dried (Na₂SO₄), filtered and evaporated to give a residue that was purified using flash chromatography to afford a pale pink oil (112 mg, 85%), single spot at $R_f$ 0.53 (1:1 hexane:ethyl acetate). HPLC purity 99+% ($t_R$ 2.38 min in 10% water-acetonitrile) ¹H NMR (CDCl₃): δ 7.64 (2H, dt, J=8.1, 1.8 Hz), 7.31 (2H, m), 7.18 (2H, d, J=8.4 Hz), 7.06 (1H, dd, J=8.6, 2.4 Hz), 2.59 (5H, m), 1.58 (2H, sextet, J=7.3 Hz), 0.89 (3H, t, J=7.3 Hz). LCMS: 329.15 (M−). FAB-MS (MH⁺, C₁₇H₁₈N₂O₃S): calcd 331.1116, found 331.1118.

Synthesis of 2,5-dichloro-N-(2-methyl-benzooxazol-5-yl)-benzenesulfonamide, STX 846 (KRB01016)

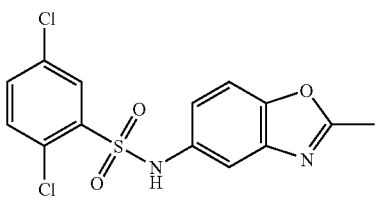

To a solution of 2,5-dichlorobenzenesulphonyl chloride (52 mg, 0.21 mmol) in dichloromethane (1.5 mL) was added pyridine (40 µL, 0.5 mmol) and the mixture was stirred under N₂ for 5 min, after which time 5-amino-2-methylbenzoxazole (30 mg, 0.20 mmol) was added. The resulting mixture was stirred for 1 h at room temperature, then saturated NaHCO₃ solution was added (8 mL) and the mixture was extracted into ethyl acetate (15 mL). The organic phase was washed with brine, dried (Na₂SO₄), filtered and evaporated to give a residue that was purified using flash chromatography to afford a pale pink solid (45 mg, 63%), single spot at $R_f$ 0.53 (1:1 hexane:ethyl acetate). mp 193.5-193.9° C., HPLC purity 98% ($t_R$ 2.27 min in 10% water-acetonitrile). ¹H NMR (CDCl₃): δ 7.86 (1H, d, J=2.2 Hz), 7.39 (4H, m), 7.12 (1H, dd, J=8.4, 1.8 Hz), 2.58 (3H, s). LCMS: 355.07 (M−). FAB-MS (MH+, C₁₄H₁₀Cl₂N₂O₃S): calcd 356.9867, found 356.9878.

All publications mentioned in this specification are herein incorporated by reference. Various modifications and variations of the described methods and system of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention which are obvious to those skilled in chemistry or related fields are intended to be within the scope of the following claims.

REFERENCES

1. Hammond, G H (1990): Molecular properties of corticosteroid binding globulin and sex-steroid binding proteins. Endocr. Rev. 11, 65-79.
2. Gomez-Sanchez E P, Gomex-Sanchez C E (1997): First there was one, then two . . . why not more 11 β-Hydroxysteroid Dehydrogenases? Endocrinology vol. 138, 12.
3. Krozowski Z S, Funder J W (1983): Renal mineralocorticosterone receptors and hippocampal corticosterone binding species have identical intrinsic steroid specificity Proc. Natl. Sci. USA 80: 6056-6060
4. Ulick S, Levine L S, Gunczler P, Zanconato G, Ramirez L C, Rauh W, Rosler A, Bradlow H L, Mew M I (1979): A syndrome of apparent mineralocorticoid excess associated with defects in the peripheral metabolism of cortisol. J. Clin. Endo. And Metab. 49: 757-764.
5. Edwards C R W, Stewart P M, Burt D, Brett L, McIntyre M A, Sutanto W S, Kloet E R, Monder C (1998): Localisation of 11 β-HSD-tissue specific protector of the mineralocorticoid receptor. Lancet 2: 986-989.
6. Moore C C D, Melloh S H, Murai I, Siiteri P K, Miller W L (1993): Structure and function of the hepatic form of 11 β-HSD in the squirrel monkey, an animal model of glucocorticoid resistance. Endocrinology 133: 368-375.
7. Kotelevtsev Y V, Larnieson P M, Best R, Stewart F, Edwards C R W, Seckl J R, Mullins I (1996): Inactivation of 11 β-HSD type 1 by gene targeting in mice. Endocrinology Res. 22: 791-792.
8. Ricketts M L, Verhaeg J M, Bujalska I, Howie A J, Rainey W E, Stewart P M (1998): Immunohistochemicallocalisation of type 1 11 β-HSD in human tissues. I. Clin. Endoc. Metab. 83: 1325-1335.
9. Stewart P M, Sheppard M C (1992): Novel aspects of hormone action: intracellular ligand supply and its control by a series of tissue specific enzymes. Molecular and Cellular Endocrinology 83: C13-C18.
10. Seckl J R, Chapman K E (1997): The 11 β-HSD system, a determinant of glucocorticoid and mineralocorticoid action. Medical and physiological aspects. European I. Biochem. 249: 361-364.
11. Maser E (1998): 11 β-HSD responsible for carbonyl reduction of the tobacco-specific nitrosoamine in mouse lung microsomes. Cancer Res. 58: 2996-3003.
12. Walker B R, Stewart P M, Shackleton C H L, Padfield P L, Edwards C R W (1993): Deficient inactivation of cortisol by 11 β-HSD in essential hypertension. Clin. Endocr. 38: 221-227.
13. Daynes R A, Araneo B A (1998): Contrasting effects of glucocorticoids on the capacity of T-cells to produce the growth factors interleukin-2 and interleukin-4. Eur. J. Immunol. 19: 2319-2324.
14. Bradford M M (1976): A rapid and sensitive method for the quantitation of microgram quantities of protein utilizing the principle of protein-dye binding. Anal. Biochem. 72: 248-254.
15. Barf, T. et al., (2002), Arylsulfonamidothiazoles as a new class of potential antidiabetic drugs. Discovery of potent and selective inhibitors of the 11β-Hydroxysteroid Dehydrogenase Type 1. J. Med. Chem., 45, 3813-3815.
16. Stewart, P. M. and Mason, J. I., (1995), Cortisol to cortisone: Glucocorticoid to mineralocortcoid. Steriods, 60, 143-146.
17. Escher, G. et al., (1995), Furosemide inhibits 11-Hydroxysteroid Dehydrogenase in vitro and in vivo. Endocrinology, 136, 1759-1765.
18. Hult, M. et. al., (1998), Selective inhibition of human type 1 11β-hydroxysteroid dehydrogenase by synthetic steroids and xenobiotics. FEBS Letters, 441, 25-28.
19. Diederich, S. et al., (2002), In the search for specific inhibitors of human 11-hydroxysteroid-dehydrogenase (11β-HSDs): chenodeoxycholic acid selectively inhibits 11β-HSD-1. Eur. J. Endocrinol., 142, 200-207.
20. Takahashi; Okada; Yakugaku Zasshi; 73; 1953; 802, 804; Chem. Abstr.; 1954; 9364.
21. Hunt, Richard el. al. J Chem Soc C, 1966, 344, 184-185.
22. DeGraw, Joseph and Goodman, Leon; *J. Med. Chem.*; 7; 1964; 213.
23. Fries, et. al.; Justus Liebigs Ann. Chem.; 454; 1927; 204.

The invention claimed is:

1. A method of treating a condition or disease associated with 11β-HSD selected from the group consisting of diabetes, obesity; hypertension; glaucoma; arthritis; asthma; osteroporosis; intra-uterine growth retardation; apparent mineralocorticoid excess syndrome (AME); polycystic ovary syndrome (PCOS; hirsutism); acne; oligo- or amenorrhea; adrenal cortical ademoma and carcinoma; Cushing's syndrome; artheroscelerosis; myocardial infarction; insulin resistance; congnitive impairment; breast cancer; and endometrial cancer, comprising administering an effective amount of a compound to an individual in need thereof wherein the compound is a compound having Formula III

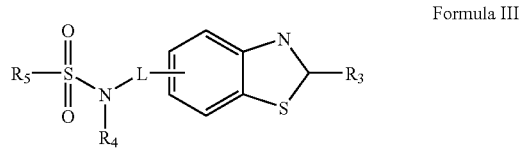

Formula III wherein $R_4$ is selected from H and hydrocarbyl,
$R_5$ is a hydrocarbyl group and L is an optional linker group,
wherein $R_3$ is H or a substituent
and wherein X is selected from S, O, $NR_6$ and $C(R_7)(R_8)$,
wherein $R_6$ is selected from H and hydrocarbyl groups,
wherein each of $R_7$ and $R_6$ are independently selected from H and hydrocarbyl groups.

2. A method according to claim 1 wherein the compound is a compound having Formula IV

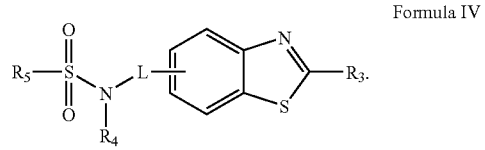

Formula IV

3. A method according to claim 1 wherein the compound is a compound having Formula V

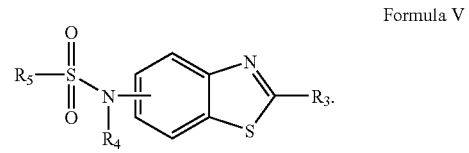

Formula V

4. A method according to claim 1 wherein the compound is a compound having Formula VI

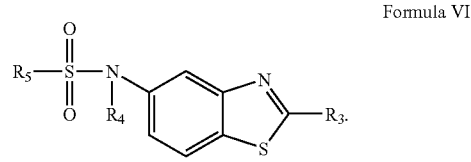

Formula VI

5. A method according to claim 1 wherein the compound is a compound having Formula VII

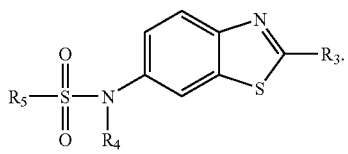

Formula VII

6. A method according to any one of the preceding claims wherein $R_3$ is selected from H, hydrocarbyl, —S-hydrocarbyl, —S—H, halogen and $N(R_9)(R_{10})$, wherein each of $R_9$ and $R_{10}$ are independently selected from H and hydrocarbyl groups.

7. A method according to claim 6 wherein $R_3$ is selected from H and $C_1$-$C_{10}$ alkyl groups, such as $C_1$-$C_6$ alkyl group, and $C_1$-$C_3$ alkyl group.

8. A method according to claim 7 wherein $R_3$ is —$CH_3$.

9. A method according to claim 1 wherein the compound is a compound having Formula VIII

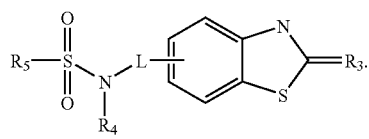

Formula VIII

10. A method to according to claim 1 wherein the compound is a compound having Formula IX

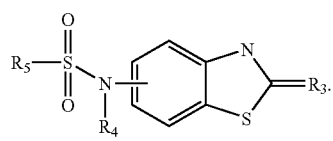

Formula IX

11. A method to according to claim 1 wherein the compound is a compound having Formula X

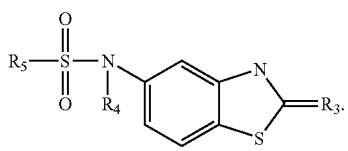

Formula X

12. A method according to claim 1 wherein the compound is a compound having Formula XI

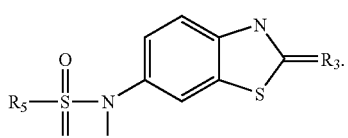

Formula XI

13. A method according to any one of claims 9 to 12 wherein $R_3$ is selected from O, hydrocarbyl, and $N(R_9)$ wherein $R_9$ is selected from H and hydrocarbyl groups.

14. A method according to claim 13 wherein $R_3$ is selected from O, $C_1$-$C_{10}$ alkenyl groups, such as $C_1$-$C_6$ alkenyl group, and $C_1$-$C_3$ alkenyl group, NH and N—$C_1$-$C_{10}$ alkyl groups, such as N—$C_1$-$C_6$ alkyl group, and N—$C_1$-$C_3$ alkyl groups.

15. A method according to claim 1 wherein $R_4$ is selected from H and $C_1$-$C_{10}$ alkyl groups, such as $C_1$-$C_6$ alkyl group, and $C_1$-$C_3$ alkyl group.

16. A method according to claim 15 wherein $R_4$ is H.

17. A method according to claim 1 wherein $R_5$ is a substituted ring.

18. A method according to claim 1 wherein $R_5$ is a carbocyclic ring.

19. A method according to claims 1 wherein $R_5$ is a six membered ring.

20. A method according to claim 1 wherein $R_5$ is an aryl ring.

21. A method according to claim 1 wherein $R_5$ is a group having the formula

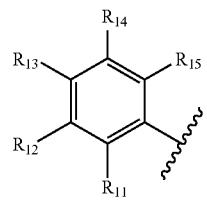

wherein each of $R_{11}$, $R_{12}$, $R_{13}$, $R_{14}$ and $R_{15}$ are independently selected from H, halogen, and hydrocarbyl groups.

22. A method according to claim 21 wherein each of $R_{11}$, $R_{12}$, $R_{13}$, $R_{14}$ and $R_{15}$ are Independently selected from H, halogen, alkyl, phenyl, O-alkyl, O-phenyl, nitrile, haloalkyl, carboxyalkyl, —$CO_2H$, $CO_2$alkyl, and NH-acetyl groups.

23. The method according to claim 1 wherein the condition or disease is diabetes or obesity.

24. The method according to claim 1 wherein the condition or disease is hypertension.

25. The method according to claim 1 wherein the condition or disease is arthritis or asthma.

26. The method according to claim 1 wherein the condition or disease is osteoporosis.

27. The method according to claim 1 wherein the 11β-HSD is 11β-HSD Type 1.

28. The method according to claim 1 wherein the 11β-HSD is 11β-HSD Type 2.

* * * * *